US012611458B2

(12) United States Patent
Garrison et al.

(10) Patent No.: US 12,611,458 B2
(45) Date of Patent: Apr. 28, 2026

(54) CHIMERIC RECEPTORS AND METHODS OF USE THEREOF

(71) Applicant: SENTI BIOSCIENCES, INC., South San Francisco, CA (US)

(72) Inventors: Brian Scott Garrison, San Jose, CA (US); Michelle Elizabeth Hung, South San Francisco, CA (US); Nicholas Frankel, San Francisco, CA (US)

(73) Assignee: Senti Biosciences, Inc., South San Francisco, CA (US)

( * ) Notice: Subject to any disclaimer, the term of this patent is extended or adjusted under 35 U.S.C. 154(b) by 571 days.

(21) Appl. No.: 18/300,981

(22) Filed: Apr. 14, 2023

(65) Prior Publication Data

US 2023/0372486 A1     Nov. 23, 2023

Related U.S. Application Data

(63) Continuation of application No. PCT/US2021/055302, filed on Oct. 15, 2021.

(60) Provisional application No. 63/151,483, filed on Feb. 19, 2021, provisional application No. 63/092,736, filed on Oct. 16, 2020.

(51) Int. Cl.
| | |
|---|---|
| *A61K 40/42* | (2025.01) |
| *A61K 40/11* | (2025.01) |
| *A61K 40/15* | (2025.01) |
| *A61K 40/22* | (2025.01) |
| *A61K 40/31* | (2025.01) |
| *A61P 35/02* | (2006.01) |
| *C07K 14/705* | (2006.01) |
| *C07K 14/725* | (2006.01) |
| *C07K 16/30* | (2006.01) |
| *C12N 5/0783* | (2010.01) |

(52) U.S. Cl.
CPC .......... *A61K 40/4257* (2025.01); *A61K 40/11* (2025.01); *A61K 40/15* (2025.01); *A61K 40/22* (2025.01); *A61K 40/31* (2025.01); *A61K 40/4202* (2025.01); *A61K 40/4214* (2025.01); *A61K 40/4251* (2025.01); *A61P 35/02* (2018.01); *C07K 14/70503* (2013.01); *C07K 14/7051* (2013.01); *C07K 14/70521* (2013.01); *C07K 16/3092* (2013.01); *C12N 5/0636*

(2013.01); *A61K 2239/28* (2023.05); *A61K 2239/29* (2023.05); *A61K 2239/48* (2023.05); *C07K 2317/622* (2013.01); *C07K 2319/03* (2013.01); *C07K 2319/33* (2013.01)

(58) Field of Classification Search
None
See application file for complete search history.

(56) References Cited

U.S. PATENT DOCUMENTS

2007/0044171 A1 *     2/2007     Kovalic ............ C12N 15/8255
                                                                              536/23.6

FOREIGN PATENT DOCUMENTS

| | | |
|---|---|---|
| CA | 3133333 A1 | 4/2020 |
| WO | WO2020065406 A2 | 4/2020 |
| WO | WO-2021157601 A1 * | 8/2021 ......... C07K 16/2803 |
| WO | WO2021168298 A1 | 8/2021 |

OTHER PUBLICATIONS

Samulowitz, et al., "Human Endomucin: Distribution Pattern, Expression on High Endothelial Venules, and Decoration with the MECA-79 Epitope," American Journal of Pathology, vol. 160, No. 5, May 2002, pp. 1669-1681.
Notice of Reasons for Rejection for JP2023-523050 mailed Sep. 8, 2025, 9 pages.
Extended European Search Report for EP21881235.2 mailed Oct. 11, 2024, 8 pages.
Office Action and Search Report for TW110138533 mailed Apr. 11, 2025, 18 pages.
International Search Report and Written Opinion for PCT/US2021/055302 mailed Mar. 24, 2022, 14 pages.

* cited by examiner

*Primary Examiner* — Julie Wu
*Assistant Examiner* — Amy M. Chattin
(74) *Attorney, Agent, or Firm* — DLA Piper LLP (US)

(57) ABSTRACT

Provided herein are EMCN-specific antigen-binding domains, and chimeric proteins including the EMCN-specific antigen-binding. Also provided herein are cells, nucleic acids, vectors, compositions, and methods directed to proteins including the EMCN-specific antigen-binding domains.

19 Claims, 16 Drawing Sheets

Specification includes a Sequence Listing.

Antibody-1(Light) – CDR annotation with Chothia scheme

| 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|----|----|----|----|----|----|----|----|----|----|----|----|----|
| D | I | V | M | T | Q | T | P | P | S | L | S | V | A | L | G | Q | S | V | S | I | S |

LFR1

| 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|----|----|----|----|----|----|----|----|----|----|----|----|----|----|----|----|----|----|----|----|----|----|
| C | K | S | S | Q | S | L | V | A | S | D | E | N | T | Y | L | N | W | L | L | Q | S |

CDR-L1　LFR2

| 45 | 46 | 47 | 48 | 49 | 50 | 51 | 52 | 53 | 54 | 55 | 56 | 57 | 58 | 59 | 60 | 61 | 62 | 63 | 64 | 65 | 66 |
|----|----|----|----|----|----|----|----|----|----|----|----|----|----|----|----|----|----|----|----|----|----|
| P | G | R | S | P | K | R | L | I | Y | Q | V | S | K | L | D | S | G | V | P | D | R |

LFR2　CDR-L2　LFR3

| 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|----|----|----|----|----|----|----|----|----|----|----|----|----|----|----|----|----|----|----|----|----|----|----|
| F | S | G | S | G | S | E | K | D | F | T | L | K | I | S | R | V | E | A | E | D | L |

LFR3

| 89 | 90 | 91 | 92 | 93 | 94 | 95 | 96 | 97 | 98 | 99 | 100 | 101 | 102 | 103 | 104 | 105 | 106 | 107 | 108 | 109 | 110 |
|----|----|----|----|----|----|----|----|----|----|----|-----|-----|-----|-----|-----|-----|-----|-----|-----|-----|-----|
| G | V | Y | Y | C | L | Q | G | I | H | L | P | W | T | F | G | G | G | T | K | L | E |

LFR3　CDR-L3　LFR4

| 111 | 112 |
|-----|-----|
| L | K |

LFR4

FIG. 1

Antibody-1(Heavy) – CDR annotation with Chothia scheme

HFR1

| 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|----|----|----|----|----|----|----|----|----|----|----|----|----|
| Q | V | Q | L | K | E | S | G | P | G | L | V | Q | P | S | Q | T | L | S | L | T | C |

HFR1 / CDR-H1 / HFR2

| 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|----|----|----|----|----|----|----|----|----|----|----|----|----|----|----|----|----|----|----|----|----|----|
| T | V | S | G | F | S | L | V | R | Y | D | M | H | W | V | R | Q | P | P | G | Q | G |

HFR2 / CDR-H2 / HFR3

| 45 | 46 | 47 | 48 | 49 | 50 | 51 | 52 | 53 | 54 | 55 | 56 | 57 | 58 | 59 | 60 | 61 | 62 | 63 | 64 | 65 | 66 |
|----|----|----|----|----|----|----|----|----|----|----|----|----|----|----|----|----|----|----|----|----|----|
| L | E | W | M | G | V | I | W | G | N | G | N | T | H | Y | H | S | A | L | K | S | R |

HFR3 / CDR-H3

| 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|----|----|----|----|----|----|----|----|----|----|----|----|----|----|----|----|----|----|----|----|----|----|
| L | S | I | S | R | D | T | S | K | S | Q | V | F | L | K | M | N | S | L | Q | T | E |

CDR-H3 / HFR4

| 89 | 90 | 91 | 92 | 93 | 94 | 95 | 96 | 97 | 98 | 99 | 100 | 101 | 102 | 103 | 104 | 105 | 106 | 107 | 108 | 109 | 110 |
|----|----|----|----|----|----|----|----|----|----|----|-----|-----|-----|-----|-----|-----|-----|-----|-----|-----|-----|
| D | T | A | I | Y | F | C | T | L | R | I | K | D | W | G | P | G | T | M | V | T | V |

HFR4

| 111 | 112 |
|-----|-----|
| S | S |

FIG. 2

Expression of aCAR+iCAR+ cells

Expression breakdown

CHIMERIC RECEPTORS AND METHODS OF USE THEREOF

CROSS REFERENCE TO RELATED APPLICATIONS

This application is a continuation of International Application No. PCT/US2021/055302, filed Oct. 15, 2021, which claims the benefit of U.S. Provisional Application Nos. 63/151,483 filed Feb. 19, 2021, and 63/092,736 filed Oct. 16, 2020, each of which is hereby incorporated in its entirety by reference for all purposes.

SEQUENCE LISTING

The instant application contains a Sequence Listing which has been submitted via Patent Center and is hereby incorporated by reference in its entirety. Said .xml copy, created on Jul. 19, 2023, is named STB-022WOC1, and is 166,331 bytes in size.

BACKGROUND

Chimeric antigen receptor (CAR) based adoptive cell therapies used to redirect the specificity and function of immunoresponsive cells, such as T cells, have shown efficacy in patients with lymphoid malignancies (Pule et al., *Nat. Med.* (14):1264-1270 (2008); Maude et al., *N Engl J Med.* (371):1507-17 (2014); Brentjens et al., *Sci Transl Med.* (5):177ra38 (2013)). CAR T cells have been shown to induce complete remission in patients with CD19-expressing malignancies for whom chemotherapies have led to drug resistance and tumor progression. The success of CD19 CAR therapy provides optimism for treating other hematological malignancies, such as acute myeloid leukemia (AML). Acute myeloid leukemia is the most common acute leukemia in adults. AML is a cancer of the myeloid line of blood cells and is characterized by the rapid growth of abnormal cells that build up in the bone marrow and blood and interfere with normal blood cells. Sometimes, AML can spread to the brain, skin, or gums. The standard chemotherapy treatments for AML have not changed substantially over the past 40 years (Pulte et al., 2008), and overall survival remains very poor.

One challenge to developing CAR therapy for AML is the lack of suitable targets. The ability to identify appropriate CAR targets is important to effectively targeting and treating the tumor without damaging normal cells that express the same target antigen. Thus, there remains a need for CAR-T cell-based AML therapies that target AML cells without targeting normal cells or tissues.

SUMMARY

Provided for herein is a chimeric protein comprising an antigen-binding domain specific for endomucin (EMCN) and a heterologous molecule or moiety, wherein the antigen-binding domain comprises a heavy chain variable (VH) region and a light chain variable (VL) region, wherein: (a) the VH comprises: a heavy chain complementarity determining region 1 (CDR-H1) having the amino acid sequence of RYDMH (SEQ ID NO: 102), a heavy chain complementarity determining region 2 (CDR-H2) having the amino acid sequence of VIWGNGNTHYHSALKS (SEQ ID NO: 103), and a heavy chain complementarity determining region 3 (CDR-H3) having the amino acid sequence of RIKD (SEQ ID NO: 4), and the VL comprises: a light chain complementarity determining region 1 (CDR-L1) having the amino acid sequence of KSSQSLVASDENTYLN (SEQ ID NO: 10), a light chain complementarity determining region 2 (CDR-L2) having the amino acid sequence of QVSKLDS (SEQ ID NO: 11), and a light chain complementarity determining region 3 (CDR-L3) having the amino acid sequence of LQGIHLPWT (SEQ ID NO: 12), and wherein the amino acid sequences of the CDR-H1, the CDR-H2, the CDR-H3, the CDR-L1, the CDR-L2, and the CDR-L3 of the reference antibody are defined based on the Kabat numbering scheme; (b) the VH comprises: a heavy chain complementarity determining region 1 (CDR-H1) having the amino acid sequence of GFSLSRY (SEQ ID NO: 2), a heavy chain complementarity determining region 2 (CDR-H2) having the amino acid sequence of WGNGN (SEQ ID NO: 3), and a heavy chain complementarity determining region 3 (CDR-H3) having the amino acid sequence of RIKD (SEQ ID NO: 4), and the VL comprises: a light chain complementarity determining region 1 (CDR-L1) having the amino acid sequence of KSSQSLVASDENTYLN (SEQ ID NO: 10), a light chain complementarity determining region 2 (CDR-L2) having the amino acid sequence of QVSKLDS (SEQ ID NO: 11), and a light chain complementarity determining region 3 (CDR-L3) having the amino acid sequence of LQGIHLPWT (SEQ ID NO: 12), wherein the amino acid sequences of the CDR-H1, the CDR-H2, the CDR-H3, the CDR-L1, the CDR-L2, and the CDR-L3 of the reference antibody are defined based on the Chothia numbering scheme; or (c) the VH comprises: a heavy chain complementarity determining region 1 (CDR-H1) contained within the VH region amino acid sequence of SEQ ID NO: 1, a heavy chain complementarity determining region 2 (CDR-H2) contained within the VH region amino acid sequence of SEQ ID NO: 1, and a heavy chain complementarity determining region 3 (CDR-H3) contained within the VH region amino acid sequence of SEQ ID NO: 1, and the VL comprises: a light chain complementarity determining region 1 (CDR-L1) are contained within the VL region amino acid sequence of SEQ ID NO: 9, a light chain complementarity determining region 2 (CDR-L2) are contained within the VL region amino acid sequence of SEQ ID NO: 9, and a light chain complementarity determining region 3 (CDR-L3) are contained within the VL region amino acid sequence of SEQ ID NO: 9, and optionally wherein the amino acid sequences of the CDR-H1, the CDR-H2, the CDR-H3, the CDR-L1, the CDR-L2, and the CDR-L3 of the reference antibody are defined based on the Kabat or Chothia numbering scheme.

In some aspects, the antigen-binding domain comprises a heavy chain variable (VH) region and a light chain variable (VL) region, wherein the VH comprises: a heavy chain complementarity determining region 1 (CDR-H1) having the amino acid sequence of RYDMH (SEQ ID NO: 102), a heavy chain complementarity determining region 2 (CDR-H2) having the amino acid sequence of VIWGNGNTHYHSALKS (SEQ ID NO: 103), and a heavy chain complementarity determining region 3 (CDR-H3) having the amino acid sequence of RIKD (SEQ ID NO: 4), and the VL comprises: a light chain complementarity determining region 1 (CDR-L1) having the amino acid sequence of KSSQSLVASDENTYLN (SEQ ID NO: 10), a light chain complementarity determining region 2 (CDR-L2) having the amino acid sequence of QVSKLDS (SEQ ID NO: 11), and a light chain complementarity determining region 3 (CDR-L3) having the amino acid sequence of LQGIHLPWT (SEQ ID NO: 12), and wherein the amino acid sequences of the CDR-H1, the CDR-H2, the CDR-H3, the CDR-L1, the CDR-L2, and the CDR-L3 of the reference antibody are defined based on the Kabat numbering scheme.

In some aspects, the antigen-binding domain comprises a heavy chain variable (VH) region and a light chain variable (VL) region, wherein the VH comprises: a heavy chain complementarity determining region 1 (CDR-H1) having the amino acid sequence of GFSLSRY (SEQ ID NO: 2), a heavy chain complementarity determining region 2 (CDR-H2) having the amino acid sequence of WGNGN (SEQ ID NO: 3), and a heavy chain complementarity determining region 3 (CDR-H3) having the amino acid sequence of RIKD (SEQ ID NO: 4), and the VL comprises: a light chain complementarity determining region 1 (CDR-L1) having the amino acid sequence of KSSQSLVASDENTYLN (SEQ ID NO: 10), a light chain complementarity determining region 2 (CDR-L2) having the amino acid sequence of QVSKLDS (SEQ ID NO: 11), and a light chain complementarity determining region 3 (CDR-L3) having the amino acid sequence of LQGIHLPWT (SEQ ID NO: 12), wherein the amino acid sequences of the CDR-H1, the CDR-H2, the CDR-H3, the CDR-L1, the CDR-L2, and the CDR-L3 of the reference antibody are defined based on the Chothia numbering scheme.

In some aspects, the antigen-binding domain comprises a heavy chain variable (VH) region and a light chain variable (VL) region, wherein the VH comprises: a heavy chain complementarity determining region 1 (CDR-H1) contained within the VH region amino acid sequence of SEQ ID NO: 1, a heavy chain complementarity determining region 2 (CDR-H2) contained within the VH region amino acid sequence of SEQ ID NO: 1, and a heavy chain complementarity determining region 3 (CDR-H3) contained within the VH region amino acid sequence of SEQ ID NO: 1, and the VL comprises: a light chain complementarity determining region 1 (CDR-L1) are contained within the VL region amino acid sequence of SEQ ID NO: 9, a light chain complementarity determining region 2 (CDR-L2) are contained within the VL region amino acid sequence of SEQ ID NO: 9, and a light chain complementarity determining region 3 (CDR-L3) are contained within the VL region amino acid sequence of SEQ ID NO: 9, and optionally wherein the amino acid sequences of the CDR-H1, the CDR-H2, the CDR-H3, the CDR-L1, the CDR-L2, and the CDR-L3 of the reference antibody are defined based on the Kabat or Chothia numbering scheme.

In some aspects, the VH region comprises the amino acid sequence of SEQ ID NO: 1. In some aspects, the VL region comprises the amino acid sequence of SEQ ID NO: 9.

In some aspects, the antigen-binding domain comprises a single chain variable fragment (scFv). In some aspects, the VH and VL of the scFv are separated by a peptide linker. In some aspects, the antigen-binding domain comprises the structure VH-L-VL or VL-L-VH, wherein VH is the heavy chain variable domain, L is the peptide linker, and VL is the light chain variable domain. In some aspects, the scFv comprises an amino acid sequence selected from the group consisting of: SEQ ID Nos: 17-22.

In some aspects, the chimeric protein is a chimeric antigen receptor (CAR), and wherein the heterologous molecule or moiety comprises a polypeptide selected from the group consisting of: a transmembrane domain, one or more intracellular signaling domains, a hinge domain, a spacer region, one or more peptide linkers, and combinations thereof.

In some aspects, the CAR is an inhibitory CAR comprising one or more intracellular inhibitory domains that inhibit an immune response. In some aspects, the intracellular inhibitory domain comprises an enzymatic inhibitory domain or an intracellular inhibitory co-signaling domain.

Also provided herein is an engineered nucleic acid encoding the chimeric protein as previously described.

Also provided herein is an expression vector comprising an engineered nucleic acid as previously described.

Also provided herein is an isolated cell comprising an engineered nucleic acid as previously described.

Also provided herein is a population of engineered cells expressing an engineered nucleic acid or an expression vector as previously described.

In some aspects, the isolated cell or population of cells further comprises one or more tumor-targeting chimeric receptors expressed on the cell surface. In some aspects, the one or more tumor-targeting chimeric receptors is a chimeric antigen receptor (CAR) or an engineered T cell receptor.

In some aspects, the cell or population of cells is selected from the group consisting of: a T cell, a CD8+ T cell, a CD4+ T cell, a gamma-delta T cell, a cytotoxic T lymphocyte (CTL), a regulatory T cell, a viral-specific T cell, a Natural Killer T (NKT) cell, a Natural Killer (NK) cell, a B cell, a tumor-infiltrating lymphocyte (TIL), an innate lymphoid cell, a mast cell, an eosinophil, a basophil, a neutrophil, a myeloid cell, a macrophage, a monocyte, a dendritic cell, an erythrocyte, a platelet cell, a human embryonic stem cell (ESC), an ESC-derived cell, a pluripotent stem cell, a mesenchymal stromal cell (MSC), an induced pluripotent stem cell (iPSC), and an iPSC-derived cell.

Also provided herein is a pharmaceutical composition comprising an effective amount of a cell or population of engineered cells of as previously described and a pharmaceutically acceptable carrier, pharmaceutically acceptable excipient, or a combination thereof.

Also provided herein is a method of stimulating a cell-mediated immune response to a tumor cell in a subject, the method comprising administering to a subject having a tumor a therapeutically effective dose of any of the cells as previously described or a composition of as previously described.

Also provided herein is a method of treating a subject having a tumor, the method comprising administering a therapeutically effective dose of any of the cells as previously described or the composition of as previously described.

Also provided for herein is a chimeric protein comprising an antigen-binding domain specific for endomucin (EMCN) and a heterologous molecule or moiety, wherein the antigen-binding domain comprises a heavy chain variable (VH) region and a light chain variable (VL) region, and wherein the VH comprises a heavy chain complementarity determining region 3 (CDR-H3) having the amino acid sequence of RIKD (SEQ ID NO:4).

Also provided for herein is a chimeric protein comprising an antigen-binding domain specific for endomucin (EMCN) and a heterologous molecule or moiety, wherein the antigen-binding domain comprises a heavy chain variable (VH) region and a light chain variable (VL) region, wherein the VH comprises a heavy chain complementarity determining region 1 (CDR-H1), a heavy chain complementarity determining region 2 (CDR-H2), and a heavy chain complementarity determining region 3 (CDR-H3), and wherein the amino acid sequences of CDR-H1, CDR-H2, and CDR-H3 are contained within the VH region amino acid sequence of SEQ ID NO:1.

Also provided for herein is a chimeric protein comprising an antigen-binding domain specific for endomucin (EMCN) and a heterologous molecule or moiety, wherein the antigen-binding domain comprises a heavy chain variable (VH) region and a light chain variable (VL) region, and wherein the VH comprises: (a) a heavy chain complementarity determining region 1 (CDR-H1) having the amino acid sequence of GFSLSRY (SEQ ID NO:2), a heavy chain complementarity determining region 2 (CDR-H2) having the amino acid sequence of WGNGN (SEQ ID NO:3), and a heavy chain complementarity determining region 3 (CDR-H3) having the amino acid sequence of RIKD (SEQ ID NO:4), or (b) a heavy chain complementarity determining region 1 (CDR-H1) having the amino acid sequence of RYDMH (SEQ ID NO: 102), a heavy chain complementarity determining region 2 (CDR-H2) having the amino acid sequence of VIWGNGNTHYHSALKS (SEQ ID NO: 103), and a heavy chain complementarity determining region 3 (CDR-H3) having the amino acid sequence of RIKD (SEQ ID NO: 4).

In some aspects, the VL comprises a light chain complementarity determining region 1 (CDR-L1), a light chain complementarity determining region 2 (CDR-L2), and a light chain complementarity determining region 3 (CDR-L3), wherein the amino acid sequences of CDR-L1, CDR-L2, and CDR-L3 are contained within the VL region amino acid sequence of SEQ ID NO:9. In some aspects, the amino acid sequences of the CDR-L1, the CDR-L2, and the CDR-L3 of the reference antibody are defined based on the Kabat numbering scheme. In some aspects, the amino acid sequences of the CDR-L1, the CDR-L2, and the CDR-L3 of the reference antibody are defined based on the Chothia numbering scheme. In some aspects, the VL comprises: a light chain complementarity determining region 1 (CDR-L1) having the amino acid sequence of KSSQSLVASDENTYLN (SEQ ID NO:10), a light chain complementarity determining region 2 (CDR-L2) having the amino acid sequence of QVSKLDS (SEQ ID NO:11), and a light chain complementarity determining region 3 (CDR-L3) having the amino acid sequence of LQGIHLPWT (SEQ ID NO:12).

Also provided for herein is a chimeric protein comprising an antigen-binding domain specific for endomucin (EMCN) and a heterologous molecule or moiety, wherein the antigen-binding domain comprises a heavy chain variable (VH) region and a light chain variable (VL) region, wherein the VL comprises a light chain complementarity determining region 1 (CDR-L1), a light chain complementarity determining region 2 (CDR-L2), and a light chain complementarity determining region 3 (CDR-L3), and wherein the amino acid sequences of CDR-L1, CDR-L2, and CDR-L3 are contained within the VL region amino acid sequence of SEQ ID NO:9. In some aspects, the amino acid sequences of the CDR-L1, the CDR-L2, and the CDR-L3 of the reference antibody are defined based on the Kabat numbering scheme. In some aspects, the amino acid sequences of the CDR-L1, the CDR-L2, and the CDR-L3 of the reference antibody are defined based on the Chothia numbering scheme.

Also provided for herein is a chimeric protein comprising an antigen-binding domain specific for endomucin (EMCN) and a heterologous molecule or moiety, wherein the antigen-binding domain comprises a heavy chain variable (VH) region and a light chain variable (VL) region, and wherein the VL comprises: a light chain complementarity determining region 1 (CDR-L1) having the amino acid sequence of KSSQSLVASDENTYLN (SEQ ID NO:10), a light chain complementarity determining region 2 (CDR-L2) having the amino acid sequence of QVSKLDS (SEQ ID NO:11), and a light chain complementarity determining region 3 (CDR-L3) having the amino acid sequence of LQGIHLPWT (SEQ ID NO:12).

In some aspects, the VH comprises a heavy chain complementarity determining region 1 (CDR-H1), a heavy chain complementarity determining region 2 (CDR-H2), and a heavy chain complementarity determining region 3 (CDR-H3), wherein the amino acid sequences of CDR-H1, CDR-H2, and CDR-H3 are contained within the VH region amino acid sequence of SEQ ID NO:1. In some aspects, the VH comprises: a heavy chain complementarity determining region 1 (CDR-H1) having the amino acid sequence of GFSLSRY (SEQ ID NO:2), a heavy chain complementarity determining region 2 (CDR-H2) having the amino acid sequence of WGNGN (SEQ ID NO:3), and a heavy chain complementarity determining region 3 (CDR-H3) having the amino acid sequence of RIKD (SEQ ID NO:4). In some aspects, the VH comprises: a heavy chain complementarity determining region 1 (CDR-H1) having the amino acid sequence of RYDMH (SEQ ID NO: 102), a heavy chain complementarity determining region 2 (CDR-H2) having the amino acid sequence of VIWGNGNTHYHSALKS (SEQ ID NO: 103), and a heavy chain complementarity determining region 3 (CDR-H3) having the amino acid sequence of RIKD (SEQ ID NO: 4).

Also provided for herein is a chimeric protein comprising an antigen-binding domain specific for endomucin (EMCN) and a heterologous molecule or moiety, wherein the antigen-binding domain comprises a heavy chain variable (VH) region and a light chain variable (VL) region, wherein the VH comprises: (a) a heavy chain complementarity determining region 1 (CDR-H1) having the amino acid sequence of GFSLSRY (SEQ ID NO:2), a heavy chain complementarity determining region 2 (CDR-H2) having the amino acid sequence of WGNGN (SEQ ID NO:3), and a heavy chain complementarity determining region 3 (CDR-H3) having the amino acid sequence of RIKD (SEQ ID NO:4), or (b) a heavy chain complementarity determining region 1 (CDR-H1) having the amino acid sequence of RYDMH (SEQ ID NO: 102), a heavy chain complementarity determining region 2 (CDR-H2) having the amino acid sequence of VIWGNGNTHYHSALKS (SEQ ID NO: 103), and a heavy chain complementarity determining region 3 (CDR-H3) having the amino acid sequence of RIKD (SEQ ID NO: 4), and wherein the VL comprises: a light chain complementarity determining region 1 (CDR-L1) having the amino acid sequence of KSSQSLVASDENTYLN (SEQ ID NO:10), a light chain complementarity determining region 2 (CDR-L2) having the amino acid sequence of QVSKLDS (SEQ ID NO:11), and a light chain complementarity determining region 3 (CDR-L3) having the amino acid sequence of LQGIHLPWT (SEQ ID NO:12).

In some aspects, the VH region comprises an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO:1. In some aspects, the VH region comprises the amino acid sequence of SEQ ID NO:1.

In some aspects, the VL region comprises an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO:9. In some aspects, the VL region comprises the amino acid sequence of SEQ ID NO:9.

Also provided for herein is a chimeric protein comprising an antigen-binding domain specific for endomucin (EMCN) and a heterologous molecule or moiety, wherein the antigen-binding domain comprises a heavy chain variable (VH)

region and a light chain variable (VL) region, and wherein the VH comprises an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO:1. In some aspects, the VH region comprises the amino acid sequence of SEQ ID NO:1. In some aspects, the VL region comprises an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO:9. In some aspects, the VL region comprises the amino acid sequence of SEQ ID NO:9.

Also provided for herein is a chimeric protein comprising an antigen-binding domain specific for endomucin (EMCN) and a heterologous molecule or moiety, wherein the antigen-binding domain comprises an antibody or antigen-binding fragment thereof, wherein the antibody or antigen-binding fragment thereof comprises a heavy chain variable (VH) region and a light chain variable (VL) region, and wherein the VL comprises an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO:9. In some aspects, the VL region comprises the amino acid sequence of SEQ ID NO:9. In some aspects, the VH region comprises the amino acid sequence of SEQ ID NO:1.

Also provided for herein is a chimeric protein comprising an antigen-binding domain specific for endomucin (EMCN) and a heterologous molecule or moiety, wherein the antigen-binding domain competes with a reference antibody or antigen-binding fragment thereof for binding to EMCN, wherein the reference antibody or antigen-binding fragment thereof comprises a heavy chain variable (VH) region and a light chain variable (VL) region, wherein the VH comprises: a heavy chain complementarity determining region 1 (CDR-H1) having the amino acid sequence of GFSLSRY (SEQ ID NO:2), a heavy chain complementarity determining region 2 (CDR-H2) having the amino acid sequence of WGNGN (SEQ ID NO:3), and a heavy chain complementarity determining region 3 (CDR-H3) having the amino acid sequence of RIKD (SEQ ID NO:4), and wherein the VL comprises: a light chain complementarity determining region 1 (CDR-L1) having the amino acid sequence of KSSQSLVASDEN-TYLN (SEQ ID NO:10), a light chain complementarity determining region 2 (CDR-L2) having the amino acid sequence of QVSKLDS (SEQ ID NO:11), and a light chain complementarity determining region 3 (CDR-L3) having the amino acid sequence of LQGIHLPWT (SEQ ID NO:12).

Also provided for herein is a chimeric protein comprising an antigen-binding domain specific for endomucin (EMCN) and a heterologous molecule or moiety, wherein the antigen-binding domain binds essentially the same EMCN epitope as a reference antibody or antigen-binding fragment thereof, wherein the reference antibody or antigen-binding fragment thereof comprises a heavy chain variable (VH) region and a light chain variable (VL) region, wherein the VH comprises: a heavy chain complementarity determining region 1 (CDR-H1) having the amino acid sequence of GFSLSRY (SEQ ID NO:2), a heavy chain complementarity determining region 2 (CDR-H2) having the amino acid sequence of WGNGN (SEQ ID NO:3), and a heavy chain complementarity determining region 3 (CDR-H3) having the amino acid sequence of RIKD (SEQ ID NO:4), and wherein the VL comprises: a light chain complementarity determining region 1 (CDR-L1) having the amino acid sequence of KSSQSLVASDEN-TYLN (SEQ ID NO:10), a light chain complementarity determining region 2 (CDR-L2) having the amino acid sequence of QVSKLDS (SEQ ID NO:11), and a light chain complementarity determining region 3 (CDR-L3) having the amino acid sequence of LQGIHLPWT (SEQ ID NO:12).

Also provided for herein is a chimeric protein comprising an antigen-binding domain specific for endomucin (EMCN) and a heterologous molecule or moiety, wherein the antigen-binding domain binds an epitope of human EMCN that is the same as the EMCN epitope bound by a reference antibody or antigen-binding fragment thereof, wherein the reference antibody or antigen-binding fragment thereof comprises a heavy chain variable (VH) region and a light chain variable (VL) region, wherein the VH comprises: a heavy chain complementarity determining region 1 (CDR-H1) having the amino acid sequence of GFSLSRY (SEQ ID NO:2), a heavy chain complementarity determining region 2 (CDR-H2) having the amino acid sequence of WGNGN (SEQ ID NO:3), and a heavy chain complementarity determining region 3 (CDR-H3) having the amino acid sequence of RIKD (SEQ ID NO:4), and wherein the VL comprises: a light chain complementarity determining region 1 (CDR-L1) having the amino acid sequence of KSSQSLVASDEN-TYLN (SEQ ID NO:10), a light chain complementarity determining region 2 (CDR-L2) having the amino acid sequence of QVSKLDS (SEQ ID NO:11), and a light chain complementarity determining region 3 (CDR-L3) having the amino acid sequence of LQGIHLPWT (SEQ ID NO:12). In some aspects, the VH region of the reference antibody or antigen-binding fragment thereof comprises the amino acid sequence of SEQ ID NO:1. In some aspects, the VL region of the reference antibody or antigen-binding fragment thereof comprises the amino acid sequence of SEQ ID NO:9.

In some aspects, the antigen-binding domain comprises a F(ab) fragment, a F(ab') fragment, or a single chain variable fragment (scFv). In some aspects, the antibody or antigen-binding fragment thereof comprises a single chain variable fragment (scFv).

In some aspects, the VH and VL of the scFv are separated by a peptide linker. In some aspects, the antigen-binding domain comprises the structure VH-L-VL or VL-L-VH, wherein VH is the heavy chain variable domain, L is the peptide linker, and VL is the light chain variable domain. In some aspects, the peptide linker comprises an amino acid sequence selected from the group consisting of: SEQ ID Nos:23-39.

In some aspects, the scFv comprises an amino acid sequence selected from the group consisting of: SEQ ID Nos:17-22.

In some aspects, the chimeric protein is an antibody-drug conjugate, and wherein the heterologous molecule or moiety comprises a therapeutic agent.

In some aspects, the chimeric protein is a chimeric antigen receptor (CAR), and wherein the heterologous molecule or moiety comprises a polypeptide selected from the group consisting of: a transmembrane domain, one or more intracellular signaling domains, a hinge domain, a spacer region, one or more peptide linkers, and combinations thereof. In some aspects, the CAR comprises a transmembrane domain. In some aspects, the CAR comprises one or more intracellular signaling domains. In some aspects, the CAR is an activating CAR comprising one or more intracellular signaling domains that stimulate an immune response. In some aspects, the CAR is an inhibitory CAR comprising one or more intracellular inhibitory domains that inhibit an immune response. In some aspects, the intracellular inhibitory domain comprises an enzymatic inhibitory domain. In some aspects, the intracellular inhibitory domain comprises an intracellular inhibitory co-signaling domain. In some aspects, the CAR comprises a spacer region between the antigen-binding domain and the transmembrane domain. In some aspects, the spacer region has an amino acid sequence selected from the group consisting of SEQ ID NOs:40-48.

Also provided herein is a single chain variable fragment (scFv) specific for endomucin (EMCN), comprising a heavy chain variable (VH) region and a light chain variable (VL) region, wherein the VH comprises a heavy chain complementarity determining region 3 (CDR-H3) having the amino acid sequence of RIKD (SEQ ID NO: 4).

Also provided herein is a single chain variable fragment (scFv) specific for endomucin (EMCN), wherein the antigen-binding domain comprises a heavy chain variable (VH) region and a light chain variable (VL) region, wherein the VH comprises a heavy chain complementarity determining region 1 (CDR-H1), a heavy chain complementarity determining region 2 (CDR-H2), and a heavy chain complementarity determining region 3 (CDR-H3), and wherein the amino acid sequences of CDR-H1, CDR-H2, and CDR-H3 are contained within the VH region amino acid sequence of SEQ ID NO: 1. In some aspects, the amino acid sequences of the CDR-H1, the CDR-H2, and the CDR-H3 of the reference antibody are defined based on the Kabat numbering scheme. In some aspects, the amino acid sequences of the CDR-H1, the CDR-H2, and the CDR-H3 of the reference antibody are defined based on the Chothia numbering scheme.

Also provided herein is a single chain variable fragment (scFv) specific for endomucin (EMCN), wherein the antigen-binding domain comprises a heavy chain variable (VH) region and a light chain variable (VL) region, and wherein the VH comprises: (a) a heavy chain complementarity determining region 1 (CDR-H1) having the amino acid sequence of RYDMH (SEQ ID NO: 102), a heavy chain complementarity determining region 2 (CDR-H2) having the amino acid sequence of VIWGNGNTHYHSALKS (SEQ ID NO: 103), and a heavy chain complementarity determining region 3 (CDR-H3) having the amino acid sequence of RIKD (SEQ ID NO: 4), wherein the amino acid sequences of the CDR-H1, the CDR-H2, the CDR-H3, the CDR-L1, the CDR-L2, and the CDR-L3 of the reference antibody are defined based on the Kabat numbering scheme; or (b) a heavy chain complementarity determining region 1 (CDR-H1) having the amino acid sequence of GFSLSRY (SEQ ID NO: 2), a heavy chain complementarity determining region 2 (CDR-H2) having the amino acid sequence of WGNGN (SEQ ID NO: 3), and a heavy chain complementarity determining region 3 (CDR-H3) having the amino acid sequence of RIKD (SEQ ID NO: 4), wherein the amino acid sequences of the CDR-H1, the CDR-H2, the CDR-H3, the CDR-L1, the CDR-L2, and the CDR-L3 of the reference antibody are defined based on the Chothia numbering scheme.

In some aspects, the VL of the scFv comprises a light chain complementarity determining region 1 (CDR-L1), a light chain complementarity determining region 2 (CDR-L2), and a light chain complementarity determining region 3 (CDR-L3), wherein the amino acid sequences of CDR-L1, CDR-L2, and CDR-L3 are contained within the VL region amino acid sequence of SEQ ID NO: 9.

In some aspects, the VL of the scFv comprises: a light chain complementarity determining region 1 (CDR-L1) having the amino acid sequence of KSSQSLVASDENTYLN (SEQ ID NO: 10), a light chain complementarity determining region 2 (CDR-L2) having the amino acid sequence of QVSKLDS (SEQ ID NO: 11), and a light chain complementarity determining region 3 (CDR-L3) having the amino acid sequence of LQGIHLPWT (SEQ ID NO: 12).

Also provided herein is a single chain variable fragment (scFv) specific for endomucin (EMCN), wherein the antigen-binding domain comprises a heavy chain variable (VH) region and a light chain variable (VL) region, wherein the VL comprises a light chain complementarity determining region 1 (CDR-L1), a light chain complementarity determining region 2 (CDR-L2), and a light chain complementarity determining region 3 (CDR-L3), and wherein the amino acid sequences of CDR-L1, CDR-L2, and CDR-L3 are contained within the VL region amino acid sequence of SEQ ID NO: 9. In some aspects, the amino acid sequences of the CDR-H1, the CDR-H2, the CDR-H3, the CDR-L1, the CDR-L2, and the CDR-L3 of the reference antibody are defined based on the Kabat numbering scheme. In some aspects, the amino acid sequences of the CDR-H1, the CDR-H2, the CDR-H3, the CDR-L1, the CDR-L2, and the CDR-L3 of the reference antibody are defined based on the Chothia numbering scheme.

Also provided herein is a single chain variable fragment (scFv) specific for endomucin (EMCN), wherein the antigen-binding domain comprises a heavy chain variable (VH) region and a light chain variable (VL) region, and wherein the VL comprises: a light chain complementarity determining region 1 (CDR-L1) having the amino acid sequence of KSSQSLVASDENTYLN (SEQ ID NO: 10), a light chain complementarity determining region 2 (CDR-L2) having the amino acid sequence of QVSKLDS (SEQ ID NO: 11), and a light chain complementarity determining region 3 (CDR-L3) having the amino acid sequence of LQGIHLPWT (SEQ ID NO: 12).

In some aspects, the VH of the scFv comprises a heavy chain complementarity determining region 1 (CDR-H1), a heavy chain complementarity determining region 2 (CDR-H2), and a heavy chain complementarity determining region 3 (CDR-H3), wherein the amino acid sequences of CDR-H1, CDR-H2, and CDR-H3 are contained within the VH region amino acid sequence of SEQ ID NO: 1. In some aspects, the amino acid sequences of the CDR-H1, the CDR-H2, and the CDR-H3 of the reference antibody are defined based on the Kabat numbering scheme. In some aspects, the amino acid sequences of the CDR-H1, the CDR-H2, and the CDR-H3 of the reference antibody are defined based on the Chothia numbering scheme.

In some aspects, the VH of the scFv comprises: a heavy chain complementarity determining region 1 (CDR-H1) having the amino acid sequence of GFSLSRY (SEQ ID NO: 2), a heavy chain complementarity determining region 2 (CDR-H2) having the amino acid sequence of WGNGN (SEQ ID NO: 3), and a heavy chain complementarity determining region 3 (CDR-H3) having the amino acid sequence of RIKD (SEQ ID NO: 4).

In some aspects, the VH of the scFv comprises: or a heavy chain complementarity determining region 1 (CDR-H1) having the amino acid sequence of RYDMH (SEQ ID NO: 102), a heavy chain complementarity determining region 2 (CDR-H2) having the amino acid sequence of VIWGNG-NTHYHSALKS (SEQ ID NO: 103), and a heavy chain complementarity determining region 3 (CDR-H3) having the amino acid sequence of RIKD (SEQ ID NO: 4).

Also provided herein is a single chain variable fragment (scFV) specific for endomucin (EMCN), wherein the antigen-binding domain comprises a heavy chain variable (VH) region and a light chain variable (VL) region, wherein the VH comprises: (a) a heavy chain complementarity determining region 1 (CDR-H1) having the amino acid sequence of GFSLSRY (SEQ ID NO: 2), a heavy chain complementarity determining region 2 (CDR-H2) having the amino acid sequence of WGNGN (SEQ ID NO: 3), and a heavy chain complementarity determining region 3 (CDR-H3) having the amino acid sequence of RIKD (SEQ ID NO: 4), or (b) a heavy chain complementarity determining region 1 (CDR-H1) having the amino acid sequence of RYDMH (SEQ ID NO: 102), a heavy chain complementarity determining region 2 (CDR-H2) having the amino acid sequence of VIWGNGNTHYHSALKS (SEQ ID NO: 103), and a heavy chain complementarity determining region 3 (CDR-H3) having the amino acid sequence of RIKD (SEQ ID NO: 4), and wherein the VL comprises: a light chain complementarity determining region 1 (CDR-L1) having the amino acid sequence of KSSQSLVASDENTYLN (SEQ ID NO: 10), a light chain complementarity determining region 2 (CDR-L2) having the amino acid sequence of QVSKLDS (SEQ ID NO: 11), and a light chain complementarity determining region 3 (CDR-L3) having the amino acid sequence of LQGIHLPWT (SEQ ID NO: 12).

In some aspects, the VH of the scFv comprises an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO: 1.

In some aspects, the VH of the scFv comprises the amino acid sequence of SEQ ID NO: 1.

In some aspects, the VL of the scFv comprises an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO: 9.

In some aspects, the VL of the scFv comprises the amino acid sequence of SEQ ID NO: 9.

Also provided herein is a single chain variable fragment (scFV) specific for endomucin (EMCN), wherein the antigen-binding domain comprises a heavy chain variable (VH) region and a light chain variable (VL) region, and wherein the VH comprises an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO: 1.

In some aspects, the VH region of the scFv comprises the amino acid sequence of SEQ ID NO: 1.

In some aspects, the VL region of the scFv comprises an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO: 9.

In some aspects, the VL region of the scFv comprises the amino acid sequence of SEQ ID NO: 9.

Also provided herein is a single chain variable fragment (scFV) comprising an antigen-binding domain specific for endomucin (EMCN), wherein the antigen-binding domain comprises an antibody or antigen-binding fragment thereof, wherein the antibody or antigen-binding fragment thereof comprises a heavy chain variable (VH) region and a light chain variable (VL) region, and wherein the VL comprises an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO: 9.

In some aspects, the VH region of the scFv comprises the amino acid sequence of SEQ ID NO: 1.

Also provided herein is a single chain variable fragment (scFV) comprising an antigen-binding domain specific for endomucin (EMCN), wherein the antigen-binding domain competes with a reference antibody or antigen-binding fragment thereof for binding to EMCN, wherein the reference antibody or antigen-binding fragment thereof comprises a heavy chain variable (VH) region and a light chain variable (VL) region, wherein the VH comprises: a heavy chain complementarity determining region 1 (CDR-H1) having the amino acid sequence of GFSLSRY (SEQ ID NO: 2), a heavy chain complementarity determining region 2 (CDR-H2) having the amino acid sequence of WGNGN (SEQ ID NO: 3), and a heavy chain complementarity determining region 3 (CDR-H3) having the amino acid sequence of RIKD (SEQ ID NO: 4), and wherein the VL comprises: a light chain complementarity determining region 1 (CDR-L1) having the amino acid sequence of KSSQSLVASDENTYLN (SEQ ID NO: 10), a light chain complementarity determining region 2 (CDR-L2) having the amino acid sequence of QVSKLDS (SEQ ID NO: 11), and a light chain complementarity determining region 3 (CDR-L3) having the amino acid sequence of LQGIHLPWT (SEQ ID NO: 12), wherein the amino acid sequences of the CDR-H1, the CDR-H2, the CDR-H3, the CDR-L1, the CDR-L2, and the CDR-L3 of the reference antibody are defined based on the Chothia annotation and numbering scheme.

Also provided herein is a single chain variable fragment (scFV) comprising an antigen-binding domain specific for endomucin (EMCN), wherein the antigen-binding domain binds essentially the same EMCN epitope as a reference antibody or antigen-binding fragment thereof, wherein the reference antibody or antigen-binding fragment thereof comprises a heavy chain variable (VH) region and a light chain variable (VL) region, wherein the VH comprises: a heavy chain complementarity determining region 1 (CDR-H1) having the amino acid sequence of GFSLSRY (SEQ ID NO: 2), a heavy chain complementarity determining region 2 (CDR-H2) having the amino acid sequence of WGNGN (SEQ ID NO: 3), and a heavy chain complementarity determining region 3 (CDR-H3) having the amino acid sequence of RIKD (SEQ ID NO: 4), and wherein the VL comprises: a light chain complementarity determining region 1 (CDR-L1) having the amino acid sequence of KSSQSLVASDENTYLN (SEQ ID NO: 10), a light chain complementarity determining region 2 (CDR-L2) having the amino acid sequence of QVSKLDS (SEQ ID NO: 11), and a light chain complementarity determining region 3 (CDR-L3) having the amino acid sequence of LQGIHLPWT (SEQ ID NO: 12), wherein the amino acid sequences of the CDR-H1, the CDR-H2, the CDR-H3, the CDR-L1, the CDR-L2, and the CDR-L3 of the reference antibody are defined based on the Chothia annotation and numbering scheme.

In some aspects, an scFv as previously described comprises an amino acid sequence selected from the group consisting of SEQ ID NOs: 17-22.

Also provided herein is a single chain variable fragment (scFV) comprising an antigen-binding domain specific for endomucin (EMCN), wherein the antigen-binding domain binds an epitope of human EMCN that is the same as the EMCN epitope bound by a reference antibody or antigen-binding fragment thereof, wherein the reference antibody or antigen-binding fragment thereof comprises a heavy chain variable (VH) region and a light chain variable (VL) region, wherein the VH comprises: a heavy chain complementarity determining region 1 (CDR-H1) having the amino acid sequence of GFSLSRY (SEQ ID NO: 2), a heavy chain complementarity determining region 2 (CDR-H2) having the amino acid sequence of WGNGN (SEQ ID NO: 3), and a heavy chain complementarity determining region 3 (CDR-H3) having the amino acid sequence of RIKD (SEQ ID NO: 4), and wherein the VL comprises: a light chain complementarity determining region 1 (CDR-L1) having the amino acid sequence of KSSQSLVASDENTYLN (SEQ ID NO: 10), a light chain complementarity determining region 2 (CDR-L2) having the amino acid sequence of QVSKLDS (SEQ ID NO: 11), and a light chain complementarity determining region 3 (CDR-L3) having the amino acid sequence of LQGIHLPWT (SEQ ID NO: 12), wherein the amino acid sequences of the CDR-H1, the CDR-H2, the CDR-H3, the CDR-L1, the CDR-L2, and the CDR-L3 of the reference antibody are defined based on the Chothia annotation and numbering scheme.

In some aspects, the VH region of the reference antibody or antigen-binding fragment thereof comprises the amino acid sequence of SEQ ID NO: 1.

In some aspects, the VL region of the reference antibody or antigen-binding fragment thereof comprises the amino acid sequence of SEQ ID NO: 9.

Also provided for herein is a composition comprising any of the chimeric proteins or scFvs provided herein and a pharmaceutically acceptable carrier, pharmaceutically acceptable excipient, or a combination thereof.

Also provided for herein is an engineered nucleic acid encoding any of the chimeric proteins or scFvs provided herein. Also provided for herein is an expression vector comprising any of the engineered nucleic acids provided herein.

Also provided for herein is a composition comprising any of the engineered nucleic acids provided herein or any of the expression vectors provided herein, and a pharmaceutically acceptable carrier, pharmaceutically acceptable excipient, or a combination thereof.

Also provided for herein is a method of making an engineered cell, comprising transducing an isolated cells with any of the engineered nucleic acids provided herein or any of the expression vectors provided herein.

Also provided for herein is an engineered cell produced by any of the methods provided herein.

Also provided for herein is an isolated cell comprising any of the engineered nucleic acids provided herein, any of the expression vectors provided herein, or any of the compositions provided herein.

Also provided for herein is a population of engineered cells expressing any of the engineered nucleic acids provided herein, any of the expression vectors provided herein.

Also provided for herein is an isolated cell or population of cells comprising any of the chimeric proteins or scFvs provided herein.

Also provided for herein is a population of engineered cells expressing any of the chimeric proteins provided herein. In some aspects, the chimeric protein is recombinantly expressed. In some aspects, the chimeric protein is expressed from a vector or a selected locus from the genome of the cell. In some aspects, the cell or population of cells further comprises one or more tumor-targeting chimeric receptors expressed on the cell surface. In some aspects, each of the one or more tumor-targeting chimeric receptors is a chimeric antigen receptors (CAR) or an engineered T cell receptor. In some aspects, the cell or population of cells is selected from the group consisting of: a T cell, a CD8+ T cell, a CD4+ T cell, a gamma-delta T cell, a cytotoxic T lymphocyte (CTL), a regulatory T cell, a viral-specific T cell, a Natural Killer T (NKT) cell, a Natural Killer (NK) cell, a B cell, a tumor-infiltrating lymphocyte (TIL), an innate lymphoid cell, a mast cell, an eosinophil, a basophil, a neutrophil, a myeloid cell, a macrophage, a monocyte, a dendritic cell, an erythrocyte, a platelet cell, a human embryonic stem cell (ESC), an ESC-derived cell, a pluripotent stem cell, a mesenchymal stromal cell (MSC), an induced pluripotent stem cell (iPSC), and an iPSC-derived cell. In some aspects, the cell is autologous. In some aspects, the cell is allogeneic.

Also provided for herein is a pharmaceutical composition comprising an effective amount of any of the cells or population of engineered cells provided herein and a pharmaceutically acceptable carrier, pharmaceutically acceptable excipient, or a combination thereof.

Also provided for herein is a pharmaceutical composition comprising an effective amount of genetically modified cells expressing any of the chimeric proteins provided herein and a pharmaceutically acceptable carrier, pharmaceutically acceptable excipient, or a combination thereof. In some aspects, the pharmaceutical composition is for treating and/or preventing a tumor.

Also provided for herein is a method of treating a subject in need thereof, the method comprising administering a therapeutically effective dose of any of the compositions provided herein, or any of the cells provided herein.

Also provided for herein is a method of stimulating a cell-mediated immune response to a tumor cell in a subject, the method comprising administering to a subject having a tumor a therapeutically effective dose of any of the compositions provided herein, or any of the cells provided herein.

Also provided for herein is a method of treating a subject having a tumor, the method comprising administering a therapeutically effective dose of any of the compositions provided herein, or any of the cells provided herein.

In some aspects, the method includes administering a composition comprising an immunocompetent cell or population of cells expressing an inhibitory as described herein, and the cell or population of cells further express one or more tumor-targeting chimeric receptors. In some aspects, the method results in reduced off-target effects as compared to a method of administering an equivalent composition including a cell or population of cells comprising the one or more tumor-targeting chimeric receptors but lacking the inhibitory CAR.

Also provided for herein is a kit for treating and/or preventing a tumor, comprising any of the chimeric proteins provided herein. In some aspects, the kit further comprises written instructions for using the chimeric protein for producing one or more antigen-specific cells for treating and/or preventing a tumor in a subject.

Also provided for herein is a kit for treating and/or preventing a tumor, comprising any of the cells or population of cells provided herein. In some aspects, the kit further comprises written instructions for using the cell for treating and/or preventing a tumor in a subject.

Also provided for herein is a kit for treating and/or preventing a tumor, comprising any of the isolated nucleic acids provided herein. In some aspects, the kit further comprises written instructions for using the nucleic acid for producing one or more antigen-specific cells for treating and/or preventing a tumor in a subject.

Also provided for herein is a kit for treating and/or preventing a tumor, comprising any of the vectors provided herein. In some aspects, the kit further comprises written instructions for using the vector for producing one or more antigen-specific cells for treating and/or preventing a tumor in a subject.

Also provided for herein is a kit for treating and/or preventing a tumor, comprising any of the compositions provided herein. In some aspects, the kit further comprises written instructions for using the composition for treating and/or preventing a tumor in a subject.

BRIEF DESCRIPTION OF THE DRAWINGS

These and other features, aspects, and advantages of the present disclosure will become better understood with regard to the following description, and accompanying drawings.

FIG. 1. Sequencing results for the light-chain variable regions of Antibody-1 (Ab1) using Chothia naming scheme. (FIG. 1 contains SEQ ID NO:9)

FIG. 2. Sequencing results for the heavy-chain variable regions of Antibody-1 (Ab1) using Chothia naming scheme. (FIG. 2 contains SEQ ID NO:1)

DETAILED DESCRIPTION

Figure 3A:
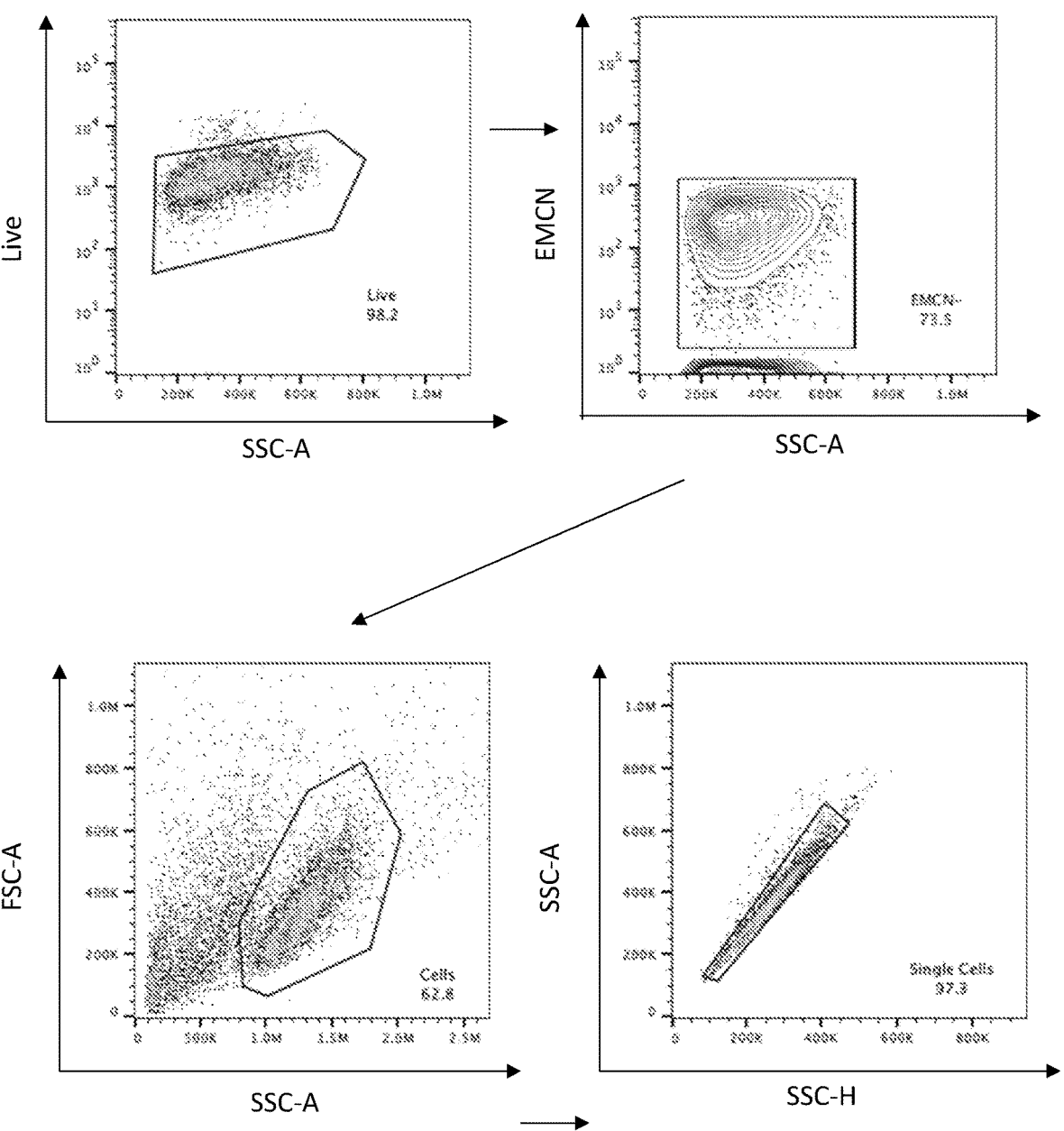
FIG. 3A. Gating strategy for establishing EMCN expression baseline.

The practice of the present disclosure will employ, unless otherwise indicated, conventional methods of molecular biology, chemistry, biochemistry, virology, and immunology, within the skill of the art. Such techniques are explained fully in the literature. See, e.g., Hepatitis C Viruses: Genomes and Molecular Biology (S. L. Tan ed., Taylor & Francis, 2006); Fundamental Virology, $3^{rd}$ Edition, vol. I & II (B. N. Fields and D. M. Knipe, eds.); Handbook of Experimental Immunology, Vols. I-IV (D. M. Weir and C. C. Blackwell eds., Blackwell Scientific Publications); A. L. Lehninger, Biochemistry (Worth Publishers, Inc., current addition); Sambrook, et al., Molecular Cloning: A Laboratory Manual ($3^{rd}$ Edition, 2001); Methods In Enzymology (S. Colowick and N. Kaplan eds., Academic Press, Inc.).

Definitions

Unless otherwise defined, all terms of art, notations and other scientific terminology used herein are intended to have the meanings commonly understood by those of skill in the art. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., Molecular Cloning: A Laboratory Manual 4th ed. (2012) Cold Spring Harbor Laboratory Press, Cold Spring Harbor, NY. As appropriate, procedures involving the use of commercially available kits and reagents are generally carried out in accordance with manufacturer-defined protocols and conditions unless otherwise noted.

As used herein, the singular forms "a," "an," and "the" include the plural referents unless the context clearly indicates otherwise. The terms "include," "such as," and the like are intended to convey inclusion without limitation, unless otherwise specifically indicated.

As used herein, the term "comprising" also specifically includes embodiments "consisting of" and "consisting essentially of" the recited elements, unless specifically indicated otherwise.

The term "about" indicates and encompasses an indicated value and a range above and below that value. In certain embodiments, the term "about" indicates the designated value±10%, ±5%, or ±1%. In certain embodiments, where applicable, the term "about" indicates the designated value(s)±one standard deviation of that value(s).

As used herein, the term "stimulating a cell-mediated immune response" or "stimulating an immune response" refers to generating a signal that results in an immune response by one or more cell types or cell populations. Immunostimulatory activity may include pro-inflammatory activity. In various embodiments, the immune response occurs after immune cell (e.g., T-cell or NK cell) activation or concomitantly mediated through receptors including, but not limited to, CD28, CD137 (4-1BB), OX40, CD40 and ICOS, and their corresponding ligands, including B7-1, B7-2, OX-40L, and 4-1BBL. Such polypeptides may be present in the tumor microenvironment and can activate immune responses to neoplastic cells. In various embodiments, promoting, stimulating, or otherwise agonizing pro-inflammatory polypeptides and/or their ligands may enhance the immune response of an immunoresponsive cell. Without being bound to a particular theory, receiving multiple stimulatory signals (e.g., co-stimulation) is important to mount a robust and long-term cell-mediated immune response, such as a T cell mediated immune response where T cells can become inhibited and unresponsive to antigen (also referred to as "T cell anergy") in the absence of co-stimulatory signals. While the effects of the variety of co-stimulatory signals, particularly in combination with one another, can vary and remain only partially understood, co-stimulation generally results in increasing gene expression in order to generate long-lived, proliferative, and apoptotic resistant cells, such as T cells or NK cells, that robustly respond to antigen, for example in meditating complete and/or sustained eradication of targets cells expressing a cognate antigen.

As used herein, the term "chimeric antigen receptor" or alternatively a "CAR" refers to a recombinant polypeptide construct comprising at least an extracellular antigen-binding domain, a transmembrane domain and a cytoplasmic signaling domain (also referred to herein as "an intracellular signaling domain") comprising a functional signaling domain.

As used herein, the term "activating CAR" or "aCAR" refers to CAR constructs/architectures capable of inducing signal transduction or changes in protein expression in the activating CAR-expressing cell that intitiate, activate, stimulate, or increase an immune response upon binding to a cognate aCAR ligand.

As used herein, the term "inhibitory CAR" or "iCAR" refers to CAR constructs/architectures capable of inducing signal transduction or changes in protein expression in the inhibitory CAR-expressing cell that prevent, attenuate, inhibit, reduce, decrease, inhibit, or suppress an immune response upon binding to a cognate iCAR ligand, such as reduced activation of immunoresponsive cells receiving or having received one or more stimulatory signals, including co-stimulatory signals.

As used herein, the term "intracellular signaling domain" refers to the functional portion of a protein which acts by transmitting information within the cell to regulate cellular activity via defined signaling pathways by generating second messengers or functioning as effectors by responding to such messengers.

As used herein, the term "extracellular antigen-binding domain" or "antigen-binding domain" (ABD) refers to a polypeptide sequence or polypeptide complex that specifically recognizes or binds to a given antigen or epitope, such as the polypeptide sequence or polypeptide complex portion of the chimeric proteins described herein that provide the EMCN-specific binding. An ABD (or antibody, antigen-binding fragment, and/or the chimeric protein including the same) is said to "recognize" the epitope (or more generally, the antigen) to which the ABD specifically binds, and the epitope is said to be the "recognition specificity" or "binding specificity" of the ABD. The ABD is said to bind to its specific antigen or epitope with a particular affinity. As described herein, "affinity" refers to the strength of interaction of non-covalent intermolecular forces between one molecule and another. The affinity, i.e., the strength of the interaction, can be expressed as a dissociation equilibrium constant (KD), wherein a lower KD value refers to a stronger interaction between molecules. KD values of antibody constructs are measured by methods well known in the art including, but not limited to, bio-layer interferometry (e.g. Octet/FORTEBIO®), surface plasmon resonance (SPR) technology (e.g. Biacore®), and cell binding assays (e.g., Flow-cytometry). Specific binding, as assessed by affinity, can refer to a binding molecule with an affinity between an ABD and its cognate antigen or epitope in which the KD value is below $10^{-6}$M, $10^{-7}$M, $10^{-8}$M, $10^{-9}$M, or $10^{-10}$M. Specific binding can also include recognition and binding of a biological molecule of interest (e.g., a polypeptide) while not specifically recognizing and binding other molecules in a sample, for example, a biological sample, which naturally includes a polypeptide of the present disclosure. In certain embodiments, specific binding refers to binding between an ABD, antibody, or antigen-binding fragment to an epitope or antigen or antigenic determinant in such a manner that binding can be displaced or competed with a second preparation of identical or similar epitope, antigen or antigenic determinant.

An ABD can be an antibody. The term "antibody," as used herein, refers to a protein, or polypeptide sequence derived from an immunoglobulin molecule which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules.

An ABD can be an antigen-binding fragment of an antibody. As used herein, the term "antigen-binding fragment" refers to at least one portion of an intact antibody, or recombinant variants thereof, that is sufficient to confer recognition and specific binding of the antigen-binding fragment to a target, such as an antigen or epitope. Examples of antigen-binding fragments include, but are not limited to, Fab, Fab', F(ab')$_2$, Fv, scFv, linear antibodies, single domain antibodies such as sdAb (either VL or VH), camelid VHH domains, and multi-specific antibodies formed from antigen-binding fragments such as a bivalent fragment comprising two Fab fragments linked by a disulfide bridge at the hinge region, and an isolated CDR or other epitope binding fragments of an antibody. An antigen-binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23: 1126-1 136, 2005). Antigen binding fragments can also be grafted into scaffolds based on polypeptides such as a fibronectin type III (Fn3)(see U.S. Pat. No. 6,703,199, which describes fibronectin polypeptide minibodies).

The number of ABDs in a binding molecule, such as the chimeric proteins described herein, defines the "valency" of the binding molecule. A binding molecule having a single ABD is "monovalent". A binding molecule having a plurality of ABDs is said to be "multivalent". A multivalent binding molecule having two ABDs is "bivalent." A multivalent binding molecule having three ABDs is "trivalent." A multivalent binding molecule having four ABDs is "tetravalent." In various multivalent embodiments, all of the plurality of ABDs have the same recognition specificity and can be referred to as a "monospecific multivalent" binding molecule. In other multivalent embodiments, at least two of the plurality of ABDs have different recognition specificities. Such binding molecules are multivalent and "multispecific." In multivalent embodiments in which the ABDs collectively have two recognition specificities, the binding molecule is "bispecific." In multivalent embodiments in which the ABDs collectively have three recognition specificities, the binding molecule is "trispecific." In multivalent embodiments in which the ABDs collectively have a plurality of recognition specificities for different epitopes present on the same antigen, the binding molecule is "multi-paratopic." Multivalent embodiments in which the ABDs collectively recognize two epitopes on the same antigen are "biparatopic."

In various multivalent embodiments, multivalency of the binding molecule improves the avidity of the binding molecule for a specific target. As described herein, "avidity" refers to the overall strength of interaction between two or more molecules, e.g. a multivalent binding molecule for a specific target, wherein the avidity is the cumulative strength of interaction provided by the affinities of multiple ABDs. Avidity can be measured by the same methods as those used to determine affinity, as described above. In certain embodiments, the avidity of a binding molecule for a specific target is such that the interaction is a specific binding interaction, wherein the avidity between two molecules has a KD value below $10^{-6}$M, $10^{-7}$M, $10^{-8}$M, $10^{-9}$M, or $10^{-10}$M. In certain embodiments, the avidity of a binding molecule for a specific target has a KD value such that the interaction is a specific binding interaction, wherein the one or more affinities of individual ABDs do not have has a KD value that qualifies as specifically binding their respective antigens or epitopes on their own. In certain embodiments, the avidity is the cumulative strength of interaction provided by the affinities of multiple ABDs for separate antigens on a shared specific target or complex, such as separate antigens found on an individual cell. In certain embodiments, the avidity is the cumulative strength of interaction provided by the affinities of multiple ABDs for separate epitopes on a shared individual antigen.

As used herein, the term "single-chain variable fragment" or "scFv" refers to a fusion protein comprising at least one antigen-binding fragment comprising a variable region of a light chain and at least one antigen-binding fragment comprising a variable region of a heavy chain, wherein the light and heavy chain variable regions are contiguously linked via a short flexible polypeptide linker, capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

As used herein, "variable region" refers to a variable sequence that arises from a recombination event, for example, following V, J, and/or D segment recombination in an immunoglobulin gene in a B cell or T cell receptor (TCR) gene in a T cell. In immunoglobulin genes, variable regions are typically defined from the antibody chain from which they are derived, e.g., VH refers to the variable region of an antibody heavy chain and VL refers to the variable region of an antibody light chain. A select VH and select VL can associate together to form an antigen-binding domain that confers antigen specificity and binding affinity.

The term "complementarity determining region" or "CDR," as used herein, refers to the sequences within antibody variable regions VH and VL which confer antigen specificity and binding affinity. For example, in general, there are three CDRs in each heavy chain variable region (e.g., HCDR1, HCDR2, and HCDR3) and three CDRs in each light chain variable region (LCDR1, LCDR2, and LCDR3). The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al, (1997) JMB 273, 927-948 ("Chothia" numbering scheme), or a combination thereof. Under the Kabat numbering scheme, in some embodiments, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under the Chothia numbering scheme, in some embodiments, the CDR amino acids in the VH are numbered 26-32 (HCDR1), 52-56 (HCDR2), and 95-102 (HCDR3); and the CDR amino acid residues in the VL are numbered 26-32 (LCDR1), 50-52 (LCDR2), and 91-96 (LCDR3). In a combined Kabat and Chothia numbering scheme, in some embodiments, the CDRs correspond to the amino acid residues that are part of a Kabat CDR, a Chothia CDR, or both. For instance, in some embodiments, the CDRs correspond to amino acid residues 26-35 (HCDR1), 50-65 (HCDR2), and 95-102 (HCDR3) in a VH, e.g., a mammalian VH, e.g., a human VH; and amino acid residues 24-34 (LCDR1), 50-56 (LCDR2), and 89-97 (LCDR3) in a VL, e.g., a mammalian VL, e.g., a human VL. In a variety of embodiments, the CDRs are mammalian sequences, including, but not limited to, mouse, rat, hamster, rabbit, camel, donkey, goat, and human sequences. In a preferred embodiment, the CDRs are human sequences. In various embodiments, the CDRs are naturally occurring sequences.

The term "framework region" or "FR," as used herein, refers to the generally conserved sequences within antibody variable regions VH and VL that act as a scaffold for interspersed CDRs, typically in a FR1-CDR1-FR2-CDR2-FR3-CDR3-FR4 arrangement (from N-terminus to C-terminus). In a variety of embodiments, the FRs are mammalian sequences, including, but not limited to mouse, rat, hamster, rabbit, camel, donkey, goat, and human sequences. In specific embodiments, the FRs are human sequences. In various embodiments, the FRs are naturally occurring sequences. In various embodiments, the FRs are synthesized sequences including, but not limited, rationally designed sequences.

As used herein, the term "antibody heavy chain" refers to the larger of the two types of polypeptide chains present in antibody molecules in their naturally occurring conformations, and which normally determines the class to which the antibody belongs.

As used herein, the term "antibody light chain" refers to the smaller of the two types of polypeptide chains present in antibody molecules in their naturally occurring conformations. Kappa (κ) and lambda (λ) light chains refer to the two major antibody light chain isotypes.

As used herein, the term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

As used herein, the term "antigen" or "Ag" refers to a molecule that provokes an immune response. This immune response may involve either antibody production, or the activation of specific immunologically competent cells, or both. The skilled artisan will understand that any macro-molecule, including virtually all proteins or peptides, can serve as an antigen.

As used herein, the term "anti-tumor effect" or "anti-tumor activity" refers to a biological effect which can be manifested by various means, including but not limited to, e.g., a decrease in tumor volume, a decrease in the number of tumor cells, a decrease in the number of metastases, an increase in life expectancy, decrease in tumor cell prolifera-tion, decrease in tumor cell survival, or amelioration of various physiological symptoms associated with the cancer-ous condition. An "anti-tumor effect" can also be manifested by the ability of the peptides, polynucleotides, cells and antibodies of the present disclosure in prevention of the occurrence of tumor in the first place, such as in a prophy-lactic therapy or treatment.

As used herein, the term "autologous" refers to any material derived from the same subject to whom it is later to be re-introduced into the subject.

As used herein, the term "allogeneic" refers to any material derived from a different animal of the same species as the subject to whom the material is introduced. Two or more subjects are said to be allogeneic to one another when the genes at one or more loci are not identical. In some embodiments, allogeneic material from individuals of the same species may be sufficiently genetically distinct, e.g., at particular genes such as MHC alleles, to interact antigeni-cally. In some embodiments, allogeneic material from indi-viduals of the same species may be sufficiently genetically similar, e.g., at particular genes such as MHC alleles, to not interact antigenically.

Isolated nucleic acid molecules of the present disclosure include any nucleic acid molecule that encodes a polypep-tide of the present disclosure, or fragment thereof. Such nucleic acid molecules need not be 100% homologous or identical with an endogenous nucleic acid sequence, but will typically exhibit substantial identity. Nucleic acids having "substantial identity" or "substantial homology" to an endogenous sequence are typically capable of hybridizing with at least one strand of a double-stranded nucleic acid molecule. As used herein, "hybridize" refers to pairing to form a double-stranded molecule between complementary polynucleotide sequences (e.g., a gene described herein), or portions thereof, under various conditions of stringency. For example, stringent salt concentration may be less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide or at least about 50% formamide. Stringent temperature conditions will ordinarily include temperatures of at least about 30° C., at least about 37° C., or at least about 42° C. Varying additional parameters, such as hybridization time, the concentration of detergent, e.g., sodium dodecyl sulfate (SDS), and the inclusion or exclu-sion of carrier DNA, are well known to those skilled in the art. Various levels of stringency may be accomplished by combining these various conditions as needed.

By "substantially identical" or "substantially homolo-gous" is meant a polypeptide or nucleic acid molecule exhibiting at least about 50% homologous or identical to a reference amino acid sequence (for example, any one of the amino acid sequences described herein) or nucleic acid sequence (for example, any one of the nucleic acid sequences described herein). Preferably, such a sequence is at least about 60%, about 80%, about 85%, about 90%, about 95%, about 99%, or about 100% homologous or identical at the amino acid level or nucleic acid to the sequence used for comparison. Sequence identity is typically measured using sequence analysis software (for example, Sequence Analysis Software Package of the Genetics Computer Group, Uni-versity of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

As used herein, the term "encoding" refers to the inherent property of specific sequences of nucleotides in a polynucle-otide, such as a gene, a cDNA, or an mRNA, to serve as templates for synthesis of other polymers and macromol-ecules in biological processes having either a defined sequence of nucleotides (e.g., rRNA, tRNA and mRNA) or a defined sequence of amino acids and the biological prop-erties resulting therefrom. Thus, a gene, cDNA, or RNA, encodes a protein if transcription and translation of mRNA corresponding to that gene produces the protein in a cell or other biological system. Both the coding strand, the nucleo-tide sequence of which is identical to the mRNA sequence and is usually provided in sequence listings, and the non-coding strand, used as the template for transcription of a gene or cDNA, can be referred to as encoding the protein or other product of that gene or cDNA. Unless otherwise specified, a "nucleotide sequence encoding an amino acid sequence" includes all nucleotide sequences that are degen-erate versions of each other and that encode the same amino acid sequence. The phrase nucleotide sequence that encodes a protein or an RNA may also include introns to the extent that the nucleotide sequence encoding the protein may in some version contain an intron(s).

As used herein, the term "ligand" refers to a molecule that binds to a receptor. In particular, the ligand binds a receptor on another cell, allowing for cell-to-cell recognition and/or interaction.

The terms "effective amount" and "therapeutically effec-tive amount" are used interchangeably herein, and refer to an amount of a compound, formulation, material, or composi-tion, as described herein effective to achieve a particular biological result. In some embodiments, an "effective amount" or a "therapeutically effective amount" is an amount sufficient to arrest, ameliorate, or inhibit the con-tinued proliferation, growth, or metastasis of a disease or disorder of interest, e.g., a myeloid disorder.

As used herein, the term "immunoresponsive cell" refers to a cell that functions in an immune response (e.g., an immune effector response) or a progenitor, or progeny thereof. Examples of immune effector cells include, without limitation, alpha/beta T cells, gamma/delta T cells, B cells, natural killer (NK) cells, natural killer T (NKT) cells, mast cells, and myeloid-derived phagocytes.

As used herein, the term "immune effector response" or "immune effector function" refers to a function or response, e.g., of an immunoresponsive cell, that enhances or pro-motes an immune attack of a target cell. For example, an immune effector function or response may refer to a property of a T cell or NK cell that promotes killing or the inhibition of growth or proliferation, of a target cell. In the case of a T cell, primary stimulation and co-stimulation are examples of immune effector function or response.

As used herein, the term "flexible polypeptide linker" or "linker" refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence (Gly-Gly-Gly-Gly-Ser)$_n$ (SEQ ID NO:110) or (Gly-Gly-Gly-Ser)$_n$, (SEQ ID NO:111) where n is a positive integer equal to or greater than 1. For example, n=1, n=2, n=3, n=4, n=5, n=6, n=7, n=8, n=9, or n=10. In some embodiments, the flexible polypeptide linkers include, but are not limited to, Gly$_4$Ser (SEQ ID NO:33) or (Gly$_4$Ser)$_3$ (SEQ ID NO:35). In other embodiments, the linkers include multiple repeats of (Gly$_2$Ser) (SEQ ID NO:23), (GlySer) or (Gly$_3$Ser) (SEQ ID NO:28). In some embodiments, the flexible polypeptide linkers include a Whitlow linker (e.g., GSTSGSGKPGSGEGSTKG [SEQ ID NO:38]). Also included within the scope of the present disclosure are linkers described, for example, in WO2012/138475.

As used herein, the terms "treat", "treatment" and "treating" refer to the reduction or amelioration of the progression, severity and/or duration of a proliferative disorder (e.g., cancer), or the amelioration of one or more symptoms (preferably, one or more discernible symptoms) of a proliferative disorder resulting from the administration of one or more therapies (e.g., one or more therapeutic agents such as a CAR of the present disclosure). In some embodiments, reduction or amelioration refers to the amelioration of at least one measurable physical parameter of a proliferative disorder, such as growth of a tumor, not necessarily discernible by the patient. In other embodiments, the terms "treat", "treatment", and "treating" refer to the inhibition of the progression of a proliferative disorder, either physically by, e.g., stabilization of a discernible symptom, physiologically by, e.g., stabilization of a physical parameter, or both. In some embodiments, reduction or amelioration include reduction or stabilization of tumor size or cancerous cell count.

As used herein, the term "subject" is intended to include living organisms in which an immune response can be elicited (e.g., mammals, human).

Other aspects of the present disclosure are described in the following sections and are within the ambit of the claimed invention.

Other Interpretational Conventions

Ranges recited herein are understood to be shorthand for all of the values within the range, inclusive of the recited endpoints. For example, a range of 1 to 50 is understood to include any number, combination of numbers, or sub-range from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless otherwise indicated, reference to a compound that has one or more stereocenters intends each stereoisomer, and all combinations of stereoisomers, thereof.

Endomucin-Specific Chimeric Proteins and Antigen-Binding Domains

The present disclosure provides antigen-binding domains (e.g., single-chain variable fragments) that bind to endomucin (EMCN), chimeric proteins including antigen-binding domains that bind to EMCN, and nucleic acids encoding such antigen-binding domains and chimeric proteins. Without wishing to be bound by theory, EMCN is a sialoglycoprotein that interferes with assembly of focal adhesion complexes and inhibits interaction between cells and extracellular matrix. In some embodiments, EMCN-specific chimeric proteins bind to human EMCN (e.g., Uniprot Q9ULC0, herein incorporated by reference for all purposes) or an epitope fragment thereof. EMCN can be expressed on hematopoietic stem and progenitor cells (HSPCs). EMCN can be expressed on cells generally considered to be healthy, such as healthy HSPCs. EMCN-specific antibodies have been previously described, including CBFYE-0213, V.7.C7.1, L4B1, L5F12, L10B5, L3F12, L6H3, L6H10 (also referred to herein as Ab1), L9H8, and L10F12, as described in Samulowitz U. et al., Am. J. Path., 2002 May, 160(5): 1669-1681, herein incorporated by reference for all purposes.

The present disclosure provides an EMCN-specific antigen-binding domain having one or more of the amino acid sequences listed in Table A.

In some embodiments, the EMCN-specific antigen-binding domain has a heavy chain variable (VH) region and a light chain variable (VL) region in which the VH includes a heavy chain complementarity determining region 3 (CDR-H3) having the amino acid sequence of RIKD (SEQ ID NO:4). In some embodiments, the EMCN-specific antigen-binding domain has a heavy chain variable (VH) region and a light chain variable (VL) region in which the VH includes a heavy chain complementarity determining region 1 (CDR-H1), a heavy chain complementarity determining region 2 (CDR-H2), and a heavy chain complementarity determining region 3 (CDR-H3) having the amino acid sequences of CDR-H1, CDR-H2, and CDR-H3 contained within the VH region amino acid sequence of SEQ ID NO:1. In some embodiments, the EMCN-specific antigen-binding domain has a heavy chain variable (VH) region and a light chain variable (VL) region in which the VH includes a heavy chain complementarity determining region 1 (CDR-H1) having the amino acid sequence of GFSLSRY (SEQ ID NO:2), a heavy chain complementarity determining region 2 (CDR-H2) having the amino acid sequence of WGNGN (SEQ ID NO:3), and a heavy chain complementarity determining region 3 (CDR-H3) having the amino acid sequence of RIKD (SEQ ID NO:4). In some embodiments, the EMCN-specific antigen-binding domain having the VH sequences above can have a light chain complementarity determining region 1 (CDR-L1), a light chain complementarity determining region 2 (CDR-L2), and a light chain complementarity determining region 3 (CDR-L3), wherein the amino acid sequences of CDR-L1, CDR-L2, and CDR-L3 are contained within the VL region amino acid sequence of SEQ ID NO:9. In some embodiments, the EMCN-specific antigen-binding domain having the VH sequences above can have a heavy chain complementarity determining region 1 (CDR-L1) having the amino acid sequence of KSSQSLV-ASDENTYLN (SEQ ID NO:10), a heavy chain complementarity determining region 2 (CDR-L2) having the amino acid sequence of QVSKLDS (SEQ ID NO:11), and a heavy chain complementarity determining region 3 (CDR-L3) having the amino acid sequence of LQGIHLPWT (SEQ ID NO:12).

In some embodiments, the EMCN-specific antigen-binding domain has a heavy chain variable (VH) region and a light chain variable (VL) region in which the VL includes a light chain complementarity determining region 1 (CDR-L1), a light chain complementarity determining region 2

(CDR-L2), and a light chain complementarity determining region 3 (CDR-L3) having the amino acid sequences of CDR-L1, CDR-L2, and CDR-L3 contained within the VL region amino acid sequence of SEQ ID NO:9. In some embodiments, the EMCN-specific antigen-binding domain has a heavy chain variable (VH) region and a light chain variable (VL) region in which the VL includes a light chain complementarity determining region 1 (CDR-L1) having the amino acid sequence of KSSQSLVASDENTYLN (SEQ ID NO:10), a light chain complementarity determining region 2 (CDR-L2) having the amino acid sequence of QVSKLDS (SEQ ID NO:11), and a light chain complementarity determining region 3 (CDR-L3) having the amino acid sequence of LQGIHLPWT (SEQ ID NO:12). In some embodiments, the EMCN-specific antigen-binding domain having the VL sequences above can have a heavy chain complementarity determining region 1 (CDR-H1), a heavy chain complementarity determining region 2 (CDR-H2), and a heavy chain complementarity determining region 3 (CDR-H3) having the amino acid sequences of CDR-H1, CDR-H2, and CDR-H3 contained within the VH region amino acid sequence of SEQ ID NO:1. In some embodiments, the EMCN-specific antigen-binding domain having the VL sequences above can have a heavy chain complementarity determining region 1 (CDR-H1) having the amino acid sequence of GFSLSRY (SEQ ID NO:2), a heavy chain complementarity determining region 2 (CDR-H2) having the amino acid sequence of WGNGN (SEQ ID NO:3), and a heavy chain complementarity determining region 3 (CDR-H3) having the amino acid sequence of RIKD (SEQ ID NO:4).

In some embodiments, the EMCN-specific antigen-binding domain has a heavy chain variable (VH) region and a light chain variable (VL) region in which; (1) the VH includes a heavy chain complementarity determining region 1 (CDR-H1) having the amino acid sequence of GFSLSRY (SEQ ID NO:2), a heavy chain complementarity determining region 2 (CDR-H2) having the amino acid sequence of WGNGN (SEQ ID NO:3), and a heavy chain complementarity determining region 3 (CDR-H3) having the amino acid sequence of RIKD (SEQ ID NO:4), and (2) the VL includes a light chain complementarity determining region 1 (CDR-L1) having the amino acid sequence of KSSQSLVASDEN-TYLN (SEQ ID NO:10), a light chain complementarity determining region 2 (CDR-L2) having the amino acid sequence of QVSKLDS (SEQ ID NO:11), and a light chain complementarity determining region 3 (CDR-L3) having the amino acid sequence of LQGIHLPWT (SEQ ID NO:12).

In some embodiments, the EMCN-specific antigen-binding domain has a VH region including the amino acid sequence of SEQ ID NO:1. In some embodiments, the EMCN-specific antigen-binding domain has a VH region including an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO:1.

In some embodiments, the EMCN-specific antigen-binding domain has a VL region including the amino acid sequence of SEQ ID NO:9. In some embodiments, the EMCN-specific antigen-binding domain has a VL region including an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO:9.

In some embodiments, the EMCN-specific antigen-binding domain has a (1) VH region including the amino acid sequence of SEQ ID NO:1, and (2) a VL region including an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO:9 or a VL region including the amino acid sequence of SEQ ID NO:9. In some embodiments, the EMCN-specific antigen-binding domain has a (1) VH region including an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO:1, and (2) a VL region including an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO:9 or a VL region including the amino acid sequence of SEQ ID NO:9.

In some embodiments, the EMCN-specific antigen-binding domain has (1) a VL region including the amino acid sequence of SEQ ID NO:9, and (2) a VH region including the amino acid sequence of SEQ ID NO:1 or a VH region including an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO:1. In some embodiments, the EMCN-specific antigen-binding domain has a VL region including an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO:9 and (2) a VH region including the amino acid sequence of SEQ ID NO:1 or a VH region including an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO:1.

In some embodiments, the EMCN-specific antigen-binding domain competes with a reference antibody or antigen-binding fragment thereof having a heavy chain variable (VH) region and a light chain variable (VL) region in which; (1) the VH includes a heavy chain complementarity determining region 1 (CDR-H1) having the amino acid sequence of GFSLSRY (SEQ ID NO:2), a heavy chain complementarity determining region 2 (CDR-H2) having the amino acid sequence of WGNGN (SEQ ID NO:3), and a heavy chain complementarity determining region 3 (CDR-H3) having the amino acid sequence of RIKD (SEQ ID NO:4), and (2) the VL includes a light chain complementarity determining region 1 (CDR-L1) having the amino acid sequence of KSSQSLVASDENTYLN (SEQ ID NO:10), a light chain complementarity determining region 2 (CDR-L2) having the amino acid sequence of QVSKLDS (SEQ ID NO:11), and a light chain complementarity determining region 3 (CDR-L3) having the amino acid sequence of LQGIHLPWT (SEQ ID NO:12).

In some embodiments, the EMCN-specific antigen-binding domain binds the same or essentially the same epitope (e.g., a distinct human EMCN epitope) as a reference antibody or antigen-binding fragment thereof having a heavy chain variable (VH) region and a light chain variable (VL) region in which; (1) the VH includes a heavy chain complementarity determining region 1 (CDR-H1) having the amino acid sequence of GFSLSRY (SEQ ID NO:2), a heavy chain complementarity determining region 2 (CDR-H2) having the amino acid sequence of WGNGN (SEQ ID NO:3), and a heavy chain complementarity determining region 3 (CDR-H3) having the amino acid sequence of RIKD (SEQ ID NO:4), and (2) the VL includes a light chain complementarity determining region 1 (CDR-L1) having the amino acid sequence of KSSQSLVASDENTYLN (SEQ ID NO:10), a light chain complementarity determining region 2 (CDR-L2) having the amino acid sequence of QVSKLDS (SEQ ID NO:11), and a light chain complementarity determining region 3 (CDR-L3) having the amino acid sequence of LQGIHLPWT (SEQ ID NO:12). In some embodiments, the EMCN-specific antigen-binding domain binds the same or essentially the same epitope (e.g., a distinct human EMCN epitope) as a reference antibody or antigen-binding fragment thereof having a VH including the amino acid sequence of SEQ ID NO:1. In some embodiments, the EMCN-specific antigen-binding domain binds the same or essentially the same epitope (e.g., a distinct human EMCN epitope) as a reference antibody or antigen-binding fragment thereof having a VL including the amino acid sequence of SEQ ID NO:9.

The EMCN-specific antigen-binding domain can be in any of the formats described herein, such as a Fab, Fab', F(ab')$_2$, Fv, scFv, linear antibody, single domain antibody such as sdAb (either VL or VH), camelid VHH, and multi-specific formats. In some embodiments, the EMCN-specific antigen-binding domain is in a F(ab) format. In some embodiments, the EMCN-specific antigen-binding domain is in a F(ab') format.

In some embodiments, the EMCN-specific antigen-binding domain is in a single chain variable fragment (scFv) format, including scFv formats having any of the peptide linkers described herein (e.g., see Table 1). In some embodiments, the EMCN-specific antigen-binding domain has the structure VH-L-VL or VL-L-VH, where L is the peptide linker. The present disclosure also provides chimeric proteins, and nucleic acids that encode such chimeric proteins, that include an EMCN-specific antigen-binding domain having one or more of the amino acid sequences listed in Table A. The chimeric proteins may include any of the EMCN-specific antigen-binding domains as previously described.

Chimeric Antigen Receptors (CARs)

Certain aspects of the present disclosure relate to chimeric receptors that have any one of the EMCN-specific antigen-binding domain described herein and are capable of specifically binding to an EMCN protein, an EMCN-derived antigen, or an EMCN-derived epitope. In some embodiments, the chimeric receptor is a chimeric antigen receptor (CAR). In general, CARs are chimeric proteins that include an antigen-binding domain and polypeptide molecules that are heterologous to the antigen-binding domain, such as peptides heterologous to an antibody that an antigen-binding domain may be derived from. Polypeptide molecules that are heterologous to the antigen-binding domain can include, but are not limited to, a transmembrane domain, one or more intracellular signaling domains, a hinge domain, a spacer region, one or more peptide linkers, or combinations thereof.

In some embodiments, CARs are engineered receptors that graft or confer a specificity of interest (e.g., EMCN) onto an immune effector cell. In certain embodiments, CARs can be used to graft the specificity of an antibody onto an immunoresponsive cell, such as a T cell. In some embodiments, CARs of the present disclosure comprise an extracellular antigen-binding domain (e.g., an scFv) fused to a transmembrane domain, fused to one or more intracellular signaling domains.

In some embodiments, the chimeric antigen receptor is an activating chimeric antigen receptor (aCAR and also generally referred to as CAR unless otherwise specified). In some embodiments, binding of the chimeric antigen receptor to its cognate ligand is sufficient to induce activation of the immunoresponsive cell. In some embodiments, binding of the chimeric antigen receptor to its cognate ligand is sufficient to induce stimulation of the immunoresponsive cell. In some embodiments, activation of an immunoresponsive cell results in killing of target cells. In some embodiments, activation of an immunoresponsive cell results in cytokine or chemokine expression and/or secretion by the immunoresponsive cell. In some embodiments, stimulation of an immunoresponsive cell results in cytokine or chemokine expression and/or secretion by the immunoresponsive cell. In some embodiments, stimulation of an immunoresponsive cell induces differentiation of the immunoresponsive cell. In some embodiments, stimulation of an immunoresponsive cell induces proliferation of the immunoresponsive cell. In some embodiments, activation and/or stimulation of the immunoresponsive cell can be combinations of the above responses.

A CAR of the present disclosure may be a first, second, or third generation CAR. "First generation" CARs comprise a single intracellular signaling domain, generally derived from a T cell receptor chain. "First generation" CARs generally have the intracellular signaling domain from the CD3-zeta (CD3ζ) chain, which is the primary transmitter of signals from endogenous TCRs. "First generation" CARs can provide de novo antigen recognition and cause activation of both CD4$^+$ and CD8$^+$ T cells through their CD3ζ chain signaling domain in a single fusion molecule, independent of HLA-mediated antigen presentation. "Second generation" CARs add a second intracellular signaling domain from one of various co-stimulatory molecules (e.g., CD28, 4-1BB, ICOS, OX40) to the cytoplasmic tail of the CAR to provide additional signals to the T cell. "Second generation" CARs provide both co-stimulation (e.g., CD28 or 4-1BB) and activation (CD3ζ). Preclinical studies have indicated that "Second Generation" CARs can improve the anti-tumor activity of immunoresponsive cell, such as a T cell. "Third generation" CARs have multiple intracellular co-stimulation signaling domains (e.g., CD28 and 4-1BB) and an intracellular activation signaling domain (CD3ζ).

In some embodiments, the chimeric antigen receptor is a chimeric inhibitory receptor (iCAR). In some embodiments, the one or more chimeric inhibitory receptors bind antigens that are expressed on a non-tumor cell derived from a tissue selected from the group consisting of brain, neuronal tissue, endocrine, bone, bone marrow, immune system, endothelial tissue, muscle, lung, liver, gallbladder, pancreas, gastrointestinal tract, kidney, urinary bladder, male reproductive organs, female reproductive organs, adipose, soft tissue, and skin.

In some embodiments, a chimeric inhibitory receptor (e.g. an EMCN-specific chimeric inhibitory receptor) may be used, for example, with one or more activating chimeric receptors (e.g., activating chimeric TCRs or CARs) expressed on a cell of the present disclosure (e.g., an immunoresponsive cell) as NOT-logic gates to control, modulate, or otherwise inhibit one or more activities of the one or more activating chimeric receptors. For instance, if a healthy cell expresses both an antigen that is recognized by a tumor-targeting chimeric receptor and an antigen that is recognized by a chimeric inhibitory receptor, an immunoresponsive cell expressing the tumor-associated antigen may bind to the healthy cell. In such a case, the inhibitory chimeric antigen will also bind its cognate ligand on the healthy cell and the inhibitory function of the chimeric inhibitory receptor will reduce, decrease, prevent, or inhibit the activation of the immunoresponsive cell via the tumor-targeting chimeric receptor ("NOT-logic gating"). In some embodiments, a chimeric inhibitory receptor of the present disclosure may inhibit one or more activities of a cell of the present disclosure (e.g., an immunoresponsive cell). In some embodiments, an immunoresponsive cell may comprise one or more tumor-targeting chimeric receptors and one or more chimeric inhibitory receptors that targets an antigen that is not expressed, or generally considered to be expressed, on the tumor (e.g., EMCN). Combinations of tumor-targeting chimeric receptors and chimeric inhibitory receptors in the same immunoresponsive cell may be used to reduce on-target off-tumor toxicity.

In some embodiments, the extracellular antigen-binding domain of a CAR of the present disclosure binds to one or more antigens (e.g., EMCN) with a dissociation constant $(K_d)$ of about $2\times10^{-7}$ M or less, about $1\times10^{-7}$ M or less, about $9\times10^{-8}$ M or less, about $1\times10^{-8}$ M or less, about $9\times10^{-9}$ M or less, about $5\times10^{-9}$ M or less, about $4\times10^{-9}$ M or less, about $3\times10^{-9}$ M or less, about $2\times10^{-9}$ M or less, or about $1\times10^{-9}$ M or less. In some embodiments, the $K_d$ ranges from about is about $2\times10^{-7}$ M to about $1\times10^{-9}$ M.

Binding of the extracellular antigen-binding domain of a CAR of the present disclosure can be determined by, for example, an enzyme-linked immunosorbent assay (ELISA), a radioimmunoassay (RIA), FACS analysis, a bioassay (e.g., growth inhibition), bio-layer interferometry (e.g. Octet/FORTEBIO®), surface plasmon resonance (SPR) technology (e.g. Biacore®), or a Western Blot assay. Each of these assays generally detect the presence of protein-antibody complexes of particular interest by employing a labeled reagent (e.g., an antibody or scFv) specific for the complex of interest. For example, the scFv can be radioactively labeled and used in an RIA assay. The radioactive isotope can be detected by such means as the use of a $\gamma$ counter or a scintillation counter or by autoradiography. In certain embodiments, the extracellular antigen-binding domain of the CAR is labeled with a fluorescent marker. Non-limiting examples of fluorescent markers include green fluorescent protein (GFP), blue fluorescent protein (e.g., EBFP, EBFP2, Azurite, and mKalamal), cyan fluorescent protein (e.g., ECFP, Cerulean, and CyPet), and yellow fluorescent protein (e.g., YFP, Citrine, Venus, and YPet). In certain embodiments, the extracellular antigen-binding domain of the CAR is labeled with a secondary antibody specific for the extracellular antigen-binding domain and wherein the secondary antibody is labeled (e.g., radioactively or with a fluorescent marker).

In some embodiments, CARs of the present disclosure comprise an extracellular antigen-binding domain that binds to EMCN (e.g., a EMCN protein, a EMCN-derived antigen, or an EMCN-derived epitope), a transmembrane domain, and one or more intracellular signaling domains. In some embodiments, the extracellular antigen-binding domain comprises an scFv. In some embodiments, the extracellular antigen-binding domain comprises a Fab fragment, which may be crosslinked. In certain embodiments, the extracellular binding domain is a F(ab)₂ fragment.

Extracellular Antigen-Binding Domain

The extracellular antigen-binding domain of a CAR of the present disclosure specifically binds to EMCN (e.g., an EMCN protein, an EMCN-derived antigen, or an EMCN-derived epitope). In certain embodiments, the extracellular antigen-binding domain binds to EMCN expressed on a hematopoietic stem cell. In certain embodiments, the extracellular antigen-binding domain binds to EMCN expressed on cells generally considered to be healthy, such as healthy HSPCs. In some embodiments, EMCN is human EMCN.

Antigen-binding domains of the present disclosure can include any domain that binds to the antigen including, without limitation, a monoclonal antibody, a polyclonal antibody, a recombinant antibody, a bispecific antibody, a conjugated antibody, a human antibody, a humanized antibody, and a functional fragment thereof, including but not limited to a single-domain antibody (sdAb) such as a heavy chain variable domain (VH), a light chain variable domain (VL) and a variable domain (VHH) of camelid derived nanobody, and to an alternative scaffold known in the art to function as antigen-binding domain, such as a recombinant fibronectin domain, a T cell receptor (TCR), a recombinant TCR with enhanced affinity, or a fragment thereof, e.g., single chain TCR, and the like. In some instances, it is beneficial for the antigen-binding domain to be derived from the same species in which the CAR will ultimately be used in.

In some embodiments, the extracellular antigen-binding domain comprises an antibody. In certain embodiments, the antibody is a human antibody. In certain embodiments, the antibody is a chimeric antibody. In some embodiments, the extracellular antigen-binding domain comprises an antigen-binding fragment of an antibody.

In some embodiments, the extracellular antigen-binding domain comprises a F(ab) fragment. In certain embodiments, the extracellular antigen-binding domain comprises a F(ab') fragment.

In some embodiments, the extracellular antigen-binding domain comprises an scFv. In some embodiments, the extracellular antigen-binding domain comprises two single chain variable fragments (scFvs). In some embodiments, each of the two scFvs binds to a distinct epitope on the same antigen. In some embodiments, the extracellular antigen-binding domain comprises a first scFv and a second scFv. In some embodiments, the first scFv and the second scFv bind distinct epitopes on the same antigen. In certain embodiments, the scFv is a mammalian scFv. In certain embodiments, the scFv is a chimeric scFv. In certain embodiments, the scFv comprises a heavy chain variable domain (VH) and a light chain variable domain (VL).

In certain embodiments, the VH and VL are separated by a peptide linker. In certain embodiments, the peptide linker comprises any of the amino acid sequences shown in Table 1. In certain embodiments, the scFv comprises the structure VH-L-VL or VL-L-VH, wherein VH is the heavy chain variable domain, L is the peptide linker, and VL is the light chain variable domain. In some embodiments, each of the one or more scFvs comprises the structure VH-L-VL or VL-L-VH, wherein VH is the heavy chain variable domain, L is the peptide linker, and VL is the light chain variable domain. When there are two or more scFv linked together, each scFv can be linked to the next scFv with a peptide linked. In some embodiments, each of the one or more scFvs is separated by a peptide linker.

TABLE 1

| Peptide Linkers | | |
| --- | --- | --- |
| Linker | Amino Acid Sequence | SEQ ID NO: |
| (G₂S)₁ scFv linker | GGS | 23 |
| (G₂S)₂ scFv linker | GGSGGS | 24 |
| (G₂S)₃ scFv linker | GGSGGSGGS | 25 |

TABLE 1-continued

Peptide Linkers

| Linker | Amino Acid Sequence | SEQ ID NO: |
|---|---|---|
| $(G_2S)_4$ scFv linker | GGSGGSGGSGGS | 26 |
| $(G_2S)_5$ scFv linker | GGSGGSGGSGGSGGS | 27 |
| $(G_3S)_1$ scFv linker | GGGS | 28 |
| $(G_3S)_2$ scFv linker | GGGSGGGS | 29 |
| $(G_3S)_3$ scFv linker | GGGSGGGSGGGS | 30 |
| $(G_3S)_4$ scFv linker | GGGSGGGSGGGSGGGS | 31 |
| $(G_3S)_5$ scFv linker | GGGSGGGSGGGSGGGSGGGS | 32 |
| $(G_4S)_1$ linker | GGGGS | 33 |
| $(G_4S)_2$ linker | GGGGSGGGGS | 34 |
| $(G_4S)_3$ linker | GGGGSGGGGSGGGGS | 35 |
| $(G_4S)_4$ linker | GGGGSGGGGSGGGGSGGGGS | 36 |
| $(G_4S)_5$ linker | GGGGSGGGGSGGGGSGGGGSGGGGS | 37 |
| Whitlow linker | GSTSGSGKPGSGEGSTKG | 38 |
| scFv linker 2 | EAAAKEAAAKEAAAKEAAAK | 39 |

In some embodiments, the immune effector cell comprises a first chimeric receptor and a second chimeric receptor. The antigen-binding domain of the first chimeric receptor and the antigen-binding domain of the second chimeric receptor can be an appropriate antigen-biding domain described herein or known in the art. For example, the first or second antigen-binding domain can be one or more antibodies, antigen-binding fragments of an antibody, F(ab) fragments, F(ab') fragments, single chain variable fragments (scFvs), or single-domain antibodies (sdAbs). In some embodiments, the antigen-binding domain of the first chimeric receptor and/or the second chimeric receptor comprises two single chain variable fragments (scFvs). In some embodiments, each of the two scFvs binds to a distinct epitope on the same antigen. In some embodiments, the antigen-binding domain of the first chimeric receptor can be specific for EMCN and the chimeric receptor can be specific for a second distinct antigen, such as a cancer antigen (e.g., an antigen expressed on a myeloid cell, such as an AML cell).

In some embodiments, the extracellular antigen-binding domain comprises a single-domain antibody (sdAb). In certain embodiments, the sdAb is a humanized sdAb. In certain embodiments, the sdAb is a chimeric sdAb.

In some embodiments, a CAR of the present disclosure may comprise two or more antigen-binding domains, three or more antigen-binding domains, four or more antigen-binding domains, five or more antigen-binding domains, six or more antigen-binding domains, seven or more antigen-binding domains, eight or more antigen-binding domains, nine or more antigen-binding domains, or ten or more antigen-binding domains. In some embodiments, each of the two or more antigen-binding domains binds the same antigen. In some embodiments, each of the two or more antigen-binding domains binds a different epitope of the same antigen. In some embodiments, each of the two or more antigen-binding domains binds a different antigen.

In some embodiments, the CAR comprises two antigen-binding domains. In some embodiments, the two antigen-binding domains are attached to one another via a flexible linker. In some embodiments, each of the two-antigen-binding domains may be independently selected from an antibody, an antigen-binding fragment of an antibody, an scFv, a sdAb, a recombinant fibronectin domain, a T cell receptor (TCR), a recombinant TCR with enhanced affinity, and a single chain TCR. In some embodiments, the CAR comprising two antigen-binding domains is a bispecific CAR or a tandem CAR (tanCAR).

In certain embodiments, the bispecific CAR or tanCAR comprises an antigen-binding domain comprising a bispecific antibody or antibody fragment (e.g., scFv). In some embodiments, within each antibody or antibody fragment (e.g., scFv) of a bispecific antibody molecule, the VH can be upstream or downstream of the VL. In some embodiments, the upstream antibody or antibody fragment (e.g., scFv) is arranged with its VH ($VH_1$) upstream of its VL ($VL_1$) and the downstream antibody or antibody fragment (e.g., scFv) is arranged with its VL ($VL_2$) upstream of its VH ($VH_2$), such that the overall bispecific antibody molecule has the arrangement $VH_1$-$VL_1$-$VL_2$-$VH_2$. In other embodiments, the upstream antibody or antibody fragment (e.g., scFv) is arranged with its VL ($VL_1$) upstream of its VH ($VH_1$) and the downstream antibody or antibody fragment (e.g., scFv) is arranged with its VH ($VH_2$) upstream of its VL ($VL_2$), such that the overall bispecific antibody molecule has the arrangement $VL_1$ $VH_1$-$VH_2$-$VL_2$. In some embodiments, a linker is disposed between the two antibodies or antibody fragments (e.g., scFvs), for example, between $VL_1$ and $VL_2$ if the construct is arranged as $VH_1$-$VL_1$-$VL_2$-$VH_2$, or between $VH_1$ and $VH_2$ if the construct is arranged as $VL_1$-$VH_1$-$VH_2$-$VL_2$. The linker may be a linker as described herein, e.g., a $(Gly_4$-Ser)n linker, wherein n is 1, 2, 3, 4, 5, or 6. In general, the linker between the two scFvs should be long enough to avoid mispairing between the domains of the two scFvs. In some embodiments, a linker is disposed between the VL and VH of the first scFv. In some embodiments, a linker is disposed between the VL and VH of the second scFv. In constructs that have multiple linkers, any two or more of the linkers may be the same or different. Accordingly, in some embodiments, a bispecific CAR or tanCAR comprises VLs, VHs, and may further comprise one or more linkers in an arrangement as described herein.

In some embodiments, chimeric receptors comprise a bivalent CAR. In some embodiments, the bivalent CAR is an EMCN bivalent CAR. In some embodiments, the bivalent EMCN CAR comprises one or more of the anti-EMCN sequences shown in Table A. In some embodiments, the ABDs of the bivalent EMCN CAR each comprises the same ABD.

In some embodiments, chimeric receptors comprise a bicistronic chimeric antigen receptor. In some embodiments, the bicistronic chimeric antigen receptor comprises an EMCN CAR. In some embodiments, the bicistronic EMCN CAR comprises one or more of the anti-EMCN sequences shown in Table A.

Transmembrane Domain

In some embodiments, the transmembrane domain of a CAR of the present disclosure (e.g. the EMCN-specific CARs described herein) comprises a hydrophobic alpha helix that spans at least a portion of a cell membrane. It has been shown that different transmembrane domains can result in different receptor stability. After antigen recognition, receptors cluster and a signal is transmitted to the cell. In some embodiments, the transmembrane domain of a CAR of the present disclosure can comprise the transmembrane domain of a CD8 polypeptide, a CD28 polypeptide, a CD3-zeta polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, a BTLA polypeptide, a LIR-1 (LILRB1) polypeptide, or can be a synthetic peptide, or any combination thereof.

In some embodiments, the transmembrane domain is derived from a CD8 polypeptide. Any suitable CD8 polypeptide may be used. Exemplary CD8 polypeptides include, without limitation, NCBI Reference Nos. NP_001139345 and AAA92533.1. In some embodiments, the transmembrane domain is derived from a CD28 polypeptide. Any suitable CD28 polypeptide may be used. Exemplary CD28 polypeptides include, without limitation, NCBI Reference Nos. NP_006130.1 and NP_031668.3. In some embodiments, the transmembrane domain is derived from a CD3-zeta polypeptide. Any suitable CD3-zeta polypeptide may be used. Exemplary CD3-zeta polypeptides include, without limitation, NCBI Reference Nos. NP_932170.1 and NP_001106862.1. In some embodiments, the transmembrane domain is derived from a CD4 polypeptide. Any suitable CD4 polypeptide may be used. Exemplary CD4 polypeptides include, without limitation, NCBI Reference Nos. NP_000607.1 and NP_038516.1. In some embodiments, the transmembrane domain is derived from a 4-1BB polypeptide. Any suitable 4-1BB polypeptide may be used. Exemplary 4-1BB polypeptides include, without limitation, NCBI Reference Nos. NP_001552.2 and NP_001070977.1. In some embodiments, the transmembrane domain is derived from an OX40 polypeptide. Any suitable OX40 polypeptide may be used. Exemplary OX40 polypeptides include, without limitation, NCBI Reference Nos. NP_003318.1 and NP_035789.1. In some embodiments, the transmembrane domain is derived from an ICOS polypeptide. Any suitable ICOS polypeptide may be used. Exemplary ICOS polypeptides include, without limitation, NCBI Reference Nos. NP_036224 and NP_059508. In some embodiments, the transmembrane domain is derived from a CTLA-4 polypeptide. Any suitable CTLA-4 polypeptide may be used. Exemplary CTLA-4 polypeptides include, without limitation, NCBI Reference Nos. NP_005205.2 and NP_033973.2. In some embodiments, the transmembrane domain is derived from a PD-1 polypeptide. Any suitable PD-1 polypeptide may be used. Exemplary PD-1 polypeptides include, without limitation, NCBI Reference Nos. NP_005009 and NP_032824. In some embodiments, the transmembrane domain is derived from a LAG-3 polypeptide. Any suitable LAG-3 polypeptide may be used. Exemplary LAG-3 polypeptides include, without limitation, NCBI Reference Nos. NP_002277.4 and NP_032505.1. In some embodiments, the transmembrane domain is derived from a 2B4 polypeptide. Any suitable 2B4 polypeptide may be used. Exemplary 2B4 polypeptides include, without limitation, NCBI Reference Nos. NP_057466.1 and NP_061199.2. In some embodiments, the transmembrane domain is derived from a BTLA polypeptide. Any suitable BTLA polypeptide may be used. Exemplary BTLA polypeptides include, without limitation, NCBI Reference Nos. NP_861445.4 and NP_001032808.2. Any suitable LIR-1 (LILRB1) polypeptide may be used. Exemplary LIR-1 (LILRB1) polypeptides include, without limitation, NCBI Reference Nos. NP_001075106.2 and NP_001075107.2.

In some embodiments, the transmembrane domain comprises a polypeptide comprising an amino acid sequence that is at least 85%, at least 90%, at least 91%, at least 92%, at least 93%, at least 94%, at least 95%, at least 96%, at least 97%, at least 98%, at least 99%, or 100% homologous to the sequence of NCBI Reference No. NP_001139345, AAA92533.1, NP_006130.1, NP_031668.3, NP_932170.1, NP_001106862.1, NP_000607.1, NP_038516.1, NP 001552.2, NP_001070977.1, NP 003318.1, NP_035789.1, NP 036224, NP_059508, NP 005205.2, NP 033973.2, NP_005009, NP 032824, NP_002277.4, NP_032505.1, NP 057466.1, NP_061199.2, NP 861445.4, or NP_001032808.2, or fragments thereof. In some embodiments, the homology may be determined using standard software such as BLAST or FASTA. In some embodiments, the polypeptide may comprise one conservative amino acid substitution, up to two conservative amino acid substitutions, or up to three conservative amino acid substitutions. In some embodiments, the polypeptide can have an amino acid sequence that is a consecutive portion of NCBI Reference No. NP_001139345, AAA92533.1, NP_006130.1, NP 031668.3, NP_932170.1, NP_001106862.1, NP_000607.1, NP 038516.1, NP 001552.2, NP_001070977.1, NP_003318.1, NP_035789.1, NP 036224, NP_059508, NP_005205.2, NP_033973.2, NP_005009, NP 032824, NP 002277.4, NP_032505.1, NP_057466.1, NP_061199.2, NP_861445.4, or NP_001032808.2 that is at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, or at least 240 amino acids in length.

Further examples of suitable polypeptides from which a transmembrane domain may be derived include, without limitation, the transmembrane region(s) of the alpha, beta or zeta chain of the T-cell receptor, CD27, CD3 epsilon, CD45, CD5, CD9, CD16, CD22, CD33, CD37, CD64, CD80, CD86, CD134, CD137, CD154, KIRDS2, CD2, CD27, LFA-1 (CD11a, CD18), GITR, CD40, BAFFR, HVEM (LIGHTR), SLAMF7, NKp80 (KLRF1), NKp44, NKp30, NKp46, CD160, CD19, IL2R beta, IL2R gamma, IL7Rα, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMFI, CD150, IPO-3), BLAME (SLAMF8), SELPLG (CD162), LTBR, PAG/Cbp, NKG2D, and NG2C.

In some embodiments, the transmembrane domain comprises the sequence IYIWAPLAGTCGVLLLSLVIT (SEQ ID NO:82). In some embodiments, the transmembrane domain comprises the sequence IYIWAPLAGTCGVLLLSLVITLYCNHR (SEQ ID NO:83). In some embodiments, the transmembrane domain comprises the sequence IYIWAPLAGTCGVLLLSLVITLYCNHRN (SEQ ID NO:84).

In some aspects, the transmembrane domain further comprises at least a portion of an extracellular domain of the same protein.

Spacer Region

In some embodiments, a CAR of the present disclosure (e.g. the EMCN-specific CARs described herein) can also comprise a spacer region that links the extracellular antigen-binding domain to the transmembrane domain. The spacer region may be flexible enough to allow the antigen-binding domain to orient in different directions to facilitate antigen recognition. In some embodiments, the spacer region may be a hinge from a human protein. For example, the hinge may be a human Ig (immunoglobulin) hinge, including without limitation an IgG4 hinge, an IgG2 hinge, a CD8a hinge, or an IgD hinge. In some embodiments, the spacer region may comprise an IgG4 hinge, an IgG2 hinge, an IgD hinge, a CD28 hinge, a KIR2DS2 hinge, an LNGFR hinge, or a PDGFR-beta extracellular linker. In some embodiments, the spacer region is localized between the antigen-binding domain and the transmembrane domain. In some embodiments, a spacer region may comprise any of the amino acid sequences listed in Table 2, or an amino acid sequence that is at least 90%, at least 91%, at least 92%, at least 93%, at least 94%, at least 95%, at least 96%, at least 97%, at least 98%, or at least 99% identical to any of the amino acid sequences listed in Table 2. In some embodiments, nucleic acids encoding any of the spacer regions of the present disclosure may comprise any of the nucleic acid sequences listed in Table 3, or a nucleic acid sequence that is at least 90%, at least 91%, at least 92%, at least 93%, at least 94%, at least 95%, at least 96%, at least 97%, at least 98%, or at least 99% identical to any of the nucleic acid sequences listed in Table 3.

TABLE 2

Spacer Amino Acid Sequences

| Amino Acid Sequence | SEQ ID NO: | Description |
|---|---|---|
| AAAIEVMYPPPYLDNEKSNGT IIHVKGKHLCPSPLFPGPSKP | 40 | CD28 hinge |
| ESKYGPPCPSCP | 41 | IgG4 minimal hinge |
| ESKYGPPAPSAP | 42 | IgG4 minimal hinge, no disulfides |
| ESKYGPPCPPCP | 43 | IgG4 S228P minimal hinge, enhanced disulfide formation |
| EPKSCDKTHTCP | 44 | IgG1 minimal hinge |
| AAAFVPVFLPAKPTTTPAPRPP TPAPTIASQPLSLRPEACRPAA GGAVHTRGLDFACDIYIWAPLA GTCGVLLLSLVITLYCNHRN | 45 | Extended CD8a hinge |
| ACPTGLYTHSGECCKACNLGEG VAQPCGANQTVCEPCLDSVTFS DVVSATEPCKPCTECVGLQSMS APCVEADDAVCRCAYGYYQDET TGRCEACRVCEAGSGLVFSCQD KQNTVCEECPDGTYSDEADAEC | 46 | LNGFR hinge |
| ACPTGLYTHSGECCKACNLGEG VAQPCGANQTVC | 47 | Truncated LNGFR hinge (TNFR-Cys1) |
| AVGQDTQEVIVVPHSLPFKV | 48 | PDGFR-beta extracellular linker |

36

TABLE 3

Spacer Nucleic Acid Sequences

| Nucleic Acid Sequence | SEQ ID NO: | Description |
|---|---|---|
| GCAGCAGCTATCGAGGTGAT GTATCCTCCGCCCTACCTGG ATAATGAAAAGAGTAATGGG ACTATCATTCATGTAAAAGG GAAGCATCTTTGTCCTTCTC CCCTTTTCCCCGGTCCGTCT AAACCT | 49 | CD28 hinge |
| GAAAGCAAGTACGGTCCACC TTGCCCTAGCTGTCCG | 50 | IgG4 minimal hinge |
| GAATCCAAGTACGGCCCCCC AGCGCCTAGTGCCCCA | 51 | IgG4 minimal hinge, no disulfides |
| GAATCTAAATATGGCCCGCC ATGCCCGCCTTGCCCA | 52 | IgG4 S228P minimal hinge, enhanced disulfide formation |
| GAACCGAAGTCTTGTGATAA AACTCATACGTGCCCG | 53 | IgG1 minimal hinge |
| GCTGCTGCTTTCGTACCCGT GTTCCTCCCTGCTAAGCCTA CGACTACCCCCGCACCGAGA CCACCCACGCCAGCACCCAC GATTGCTAGCCAGCCCCTTA GTTTGCGACCAGAAGCTTGT CGGCCTGCTGCTGGTGGCGC GGTACATACCCGCGGCCTTG ATTTTGCTTGCGATATATAT ATCTGGGCGCCTCTGGCCGG AACATGCGGGGTCCTCCTCC TTTCTCTGGTTATTACTCTC TACTGTAATCACAGGAAT | 54 | Extended CD8a hinge |
| GCCTGCCCGACCGGGCTCTA CACTCATAGCGGGGAATGTT GTAAGGCATGTAACTTGGGT GAGGGCGTCGCACAGCCCTG CGGAGCTAACCAAACAGTGT GCGAACCCTGCCTCGATAGT GTGACGTTCTCTGATGTTGT ATCAGCTACAGAGCCTTGCA AACCATGTACTGAGTGCGTT GGACTTCAGTCAATGAGCGC TCCATGTGTGGAGGCAGATG ATGCGGTCTGTCGATGTGCT TACGGATACTACCAAGACGA GACAACAGGGCGGTGCGAGG CCTGTAGAGTTTGTGAGGCG GGCTCCGGGCTGGTGTTTTC ATGTCAAGACAAGCAAAATA CGGTCTGTGAAGAGTGCCCT GATGGCACCTACTCAGACGA AGCAGATGCAGAATGC | 55 | LNGFR hinge |
| GCCTGCCCTACAGGACTCTA CACGCATAGCGGTGAGTGTT GTAAAGCATGCAACCTCGGG GAAGGTGTAGCCCAGCCATG CGGGGCTAACCAAACCGTTT GC | 56 | Truncated LNGFR hinge (TNFR-Cys1) |
| GCTGTGGGCCAGGACACGCA GGAGGTCATCGTGGTGCCAC ACTCCTTGCCCTTTAAGGTG | 57 | PDGFR-beta extracellular linker |

In some embodiments, the spacer region comprises the sequence shown in SEQ ID NO:40. In some embodiments, the spacer region comprises the sequence shown in SEQ ID NO:41. In some embodiments, the spacer region comprises the sequence shown in SEQ ID NO:42. In some embodiments, the spacer region comprises the sequence shown in SEQ ID NO:43. In some embodiments, the spacer region comprises the sequence shown in SEQ ID NO:44. In some embodiments, the spacer region comprises the sequence shown in SEQ ID NO:45. In some embodiments, the spacer region comprises the sequence shown in SEQ ID NO:46. In some embodiments, the spacer region comprises the sequence shown in SEQ ID NO:47. In some embodiments, the spacer region comprises the sequence shown in SEQ ID NO:48. In some embodiments, the spacer region comprises the sequence shown in SEQ ID NO:49. In some embodiments, the spacer region comprises the sequence TTTPA-PRPPTPAPTIALQPLSLRPEACRPAAGGAVHTRGLD-FACD (SEQ ID NO:85). In some embodiments, the spacer region comprises the sequence ALSNSIMYFSHFVPVFL-PAKPTTTPAPRPPTPAPTIASQPLSLRPEACR-PAAGGAVHTR GLDFACD (SEQ ID NO:86). In some embodiments, the spacer region comprises the sequence FVPVFLPAKPTTTPAPRPPTPAPTIALQPLSLRPEACR-PAAGGAVHTRGLDFACD (SEQ ID NO:87).

In some embodiments, a CAR of the present disclosure may further include a short oligopeptide or polypeptide linker that is between 2 amino acid residues and 10 amino acid residues in length, and that may form the linkage between the transmembrane domain and the cytoplasmic region of the CAR. A non-limiting example of a suitable linker is a glycine-serine doublet. In some embodiments, the linker comprises the amino acid sequence of GGCK-JSGGCKJS (SEQ ID NO:88).

Intracellular Signaling Domains

In some embodiments, a CAR of the present disclosure (e.g. the EMCN-specific CARs described herein) comprises one or more cytoplasmic domains or regions. The cytoplasmic domain or region of the CAR may include an intracellular signaling domain.

Examples of suitable intracellular signaling domains that may be used in CARs of the present disclosure include, without limitation, cytoplasmic sequences of the T cell receptor (TCR) and co-receptors that act in concert to modulate signal transduction following antigen receptor engagement, as well as any derivative or variant of these sequences and any recombinant sequence that has the same functional capability.

Without wishing to be bound by theory, it is believed that signals generated through the TCR alone are insufficient for full activation of the T cell and that a secondary and/or co-stimulatory signal is thus also typically required for full activation. Accordingly, T cell activation may be mediated by two distinct classes of cytoplasmic signaling sequences, those that initiate antigen-dependent primary activation through the TCR (primary intracellular signaling domains) and those that act in an antigen-independent manner to provide a secondary or co-stimulatory signal (secondary cytoplasmic domain, e.g., a co-stimulatory domain). In addition, T cell signaling and function (e.g., an activating signaling cascade) can be negatively regulated by inhibitory receptors present in a T cell through intracellular inhibitory co-signaling domains.

In some embodiments, the intracellular signaling domain of a CAR of the present disclosure can include an inhibitory intracellular signaling domains. Examples of inhibitory intracellular domains that can be used include PD-1, CTLA4, TIGIT, BTLA, and LIR-1 (LILRB1), TIM3, KIR3DL1, NKG2A, LAG3, SLAP1, SLAP2, Dok-1, Dok-2, LAIR1, GRB-2, CD200R, SIRPα, HAVR, GITR, PD-L1, KIR2DL1, KIR2DL2, KIR2DL3, KIR3DL2, CD94, KLRG- 1, CEACAM1, LIR2, LIR3, LIR5, SIGLEC-2, and SIGLEC-10. In some embodiments, the inhibitory intracellular signaling domain includes one or more intracellular inhibitory co-signaling domains. In some embodiments, the one or more intracellular inhibitory co-signaling domains are linked to other domains (e.g., a transmembrane domain) through a peptide linker (e.g., see Table 2) or a spacer or hinge sequence (e.g., see Table 3). In some embodiments, when two or more intracellular inhibitory co-signaling domains are present, the two or more intracellular inhibitory co-signaling domains can be linked through a peptide linker (e.g., see Table 2) or a spacer or hinge sequence (e.g., see Table 3). In some embodiments, the intracellular inhibitory co-signaling domain is an inhibitory domain. In some embodiments, the one or more intracellular inhibitory co-signaling domains of a chimeric protein comprises one or more ITIM-containing protein, or fragment(s) thereof. ITIMs are conserved amino acid sequences found in cytoplasmic tails of many inhibitory immune receptors. Examples of ITIM-containing proteins include PD-1, TIGIT, BTLA, and LIR-1 (LILRB1), TIM3, KIR3DL1, NKG2A, LAG3, LAIR1, SIRPα, KIR2DL1, KIR2DL2, KIR2DL3, KIR3DL2, CD94, KLRG-1, CEACAM1, LIR2, LIR3, LIR5, SIGLEC-2, and SIGLEC-10. In some embodiments, the one or more intracellular inhibitory co-signaling domains comprise one or more non-ITIM scaffold proteins, or a fragment(s) thereof. In some embodiments, the one or more non-ITIM scaffold proteins, or fragments thereof, are selected from GRB-2, Dok-1, Dok-2, SLAP, LAG3, HAVR, GITR, and PD-L1. The inhibitory intracellular signaling domain can further include an enzymatic inhibitory domain. In some embodiments, the enzymatic inhibitory domain comprises an enzyme catalytic domain. In some embodiments, the enzyme catalytic domain is derived from an enzyme selected from the group consisting of: CSK, SHP-1, PTEN, CD45, CD148, PTP-MEG1, PTP-PEST, c-CBL, CBL-b, PTPN22, LAR, PTPH1, SHIP-1, and RasGAP. Examples of enzymatic regulation of signaling is described in more detail in Pavel Otahal et al. (Biochim Biophys Acta. 2011 February; 1813(2):367-76), Kosugi A., et al. (Involvement of SHP-1 tyrosine phosphatase in TCR-mediated signaling pathways in lipid rafts, Immunity, 2001 June; 14(6): 669-80), and Stanford, et al. (Regulation of TCR signaling by tyrosine phosphatases: from immune homeostasis to autoimmunity, Immunology, 2012 September; 137(1): 1-19), each of which is incorporated herein by reference for all purposes.

In some embodiments, the intracellular signaling domain of a CAR of the present disclosure can comprise a primary signaling domain regulates primary activation of the TCR complex either in a stimulatory way or in an inhibitory way. Primary intracellular signaling domains that act in a stimulatory manner may contain signaling motifs which are known as immunoreceptor tyrosine-based activation motifs (ITAMs). Examples of suitable ITAM-containing primary intracellular signaling domains that that may be used in the CARs of the present disclosure include, without limitation, those of CD3-zeta, FcR gamma, FcR beta, CD3 gamma, CD3 delta, CD3 epsilon, CD5, CD22, CD79a, CD79b, CD278 (also known as "ICOS"), FcεRI, DAP10, DAP12, and CD66d.

In some embodiments, a CAR of the present disclosure (e.g. the EMCN-specific CARs described herein) comprises an intracellular signaling domain, e.g., a primary signaling domain of CD3-zeta polypeptide. A CD3-zeta polypeptide of the present disclosure may have an amino acid sequence that is at least 85%, at least 90%, at least 91%, at least 92%, at least 93%, at least 94%, at least 95%, at least 96%, at least 97%, at least 98%, at least 99%, or 100% homologous to the sequence of NCBI Reference No. NP_932170 or NP_001106864.2, or fragments thereof. In some embodiments, the CD3-zeta polypeptide may comprise one conservative amino acid substitution, up to two conservative amino acid substitutions, or up to three conservative amino acid substitutions. In some embodiments, the polypeptide can have an amino acid sequence that is a consecutive portion of NCBI Reference No. NP_932170 or NP_001106864.2 that is at least 20, at least 30, at least 40, at least 50, at least 60, at least 70, at least 80, at least 90, at least 100, at least 110, at least 120, at least 130, at least 140, at least 150, or at least 160, at least 170, or at least 180 amino acids in length.

In other embodiments, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In one embodiment, a primary signaling domain comprises one, two, three, four or more ITAM motifs.

In some embodiments, the intracellular signaling domain of a CAR of the present disclosure can comprise the CD3-zeta signaling domain by itself or it can be combined with any other desired intracellular signaling domain(s) useful in the context of a CAR of the present disclosure. For example, the intracellular signaling domain of the CAR can comprise a CD3-zeta chain portion and a costimulatory signaling domain. The costimulatory signaling domain may refer to a portion of the CAR comprising the intracellular domain of a costimulatory molecule. A costimulatory molecule of the present disclosure is a cell surface molecule other than an antigen receptor or its ligands that may be required for an efficient response of lymphocytes to an antigen. Examples of suitable costimulatory molecules include, without limitation, CD97, CD2, ICOS, CD27, CD154, CD8, OX40, 4-1BB, CD28, ZAP40, CD30, GITR, HVEM, DAP10, DAP12, MyD88, 2B4, CD40, PD-1, lymphocyte function-associated antigen-1 (LFA-1), CD7, LIGHT, NKG2C, B7-H3, and a ligand that specifically binds with CD83, an MHC class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, CDS, ICAM-1, (CD11a/CD18), BAFFR, KIRDS2, SLAMF7, NKp80 (KLRF1), NKp44, NKp30, NKp46, CD19, CD4, IL2R beta, IL2R gamma, IL7R alpha, ITGA4, VLA1, CD49a, ITGA4, IA4, CD49D, ITGA6, VLA-6, CD49f, ITGAD, CDIId, ITGAE, CD103, ITGAL, CD11a, ITGAM, CD11b, ITGAX, CD11c, ITGB1, CD29, ITGB2, CD18, ITGB7, NKG2D, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMFI, CD150, IPO-3), BLAME (SLAMF8), SELPLG (CD162), LTBR, LAT, GADS, SLP-76, PAG/Cbp, CD19a, and the like.

In some embodiments, the intracellular signaling sequences within the cytoplasmic portion of a CAR of the present disclosure may be linked to each other in a random or specified order. In some embodiments, a short oligopeptide or polypeptide linker, for example, between 2 amino acids and 10 amino acids (e.g., 2 amino acids, 3 amino acids, 4 amino acids, 5 amino acids, 6 amino acids, 7 amino acids, 8 amino acids, 9 amino acids, or 10 amino acids) in length may form the linkage between intracellular signaling sequences. In one embodiment, a glycine-serine doublet can be used as a suitable linker. In one embodiment, a single amino acid, e.g., an alanine or a glycine, can be used as a suitable linker.

In some embodiments, the intracellular signaling domain comprises two or more costimulatory signaling domains, e.g., two costimulatory signaling domains, three costimulatory signaling domains, four costimulatory signaling domains, five costimulatory signaling domains, six costimulatory signaling domains, seven costimulatory signaling domains, eight costimulatory signaling domains, nine costimulatory signaling domains, 10 costimulatory signaling domains, or more costimulatory signaling domains. In one embodiment, the intracellular signaling domain comprises two costimulatory signaling domains. In some embodiments, the two or more costimulatory signaling domains are separated by a linker of the present disclosure (e.g., any of the linkers described in Table 1). In one embodiment, the linker is a glycine residue. In another embodiment, the linker is an alanine residue.

In some embodiments, a cell of the present disclosure expresses a CAR that includes an antigen-binding domain that binds a EMCN, a transmembrane domain of the present disclosure, a primary signaling domain, and one or more costimulatory signaling domains.

In some embodiments, a cell of the present disclosure expresses an iCAR that includes an antigen-binding domain that binds EMCN (e.g., an EMCN-specific antigen-binding domain having one or more of the amino acid sequences listed in Table A), a transmembrane domain of the present disclosure, and one or more intracellular inhibitory co-signaling domains. In some embodiments, a cell of the present disclosure expresses (1) a CAR that includes an antigen-binding domain that binds EMCN (e.g., an EMCN-specific antigen-binding domain having one or more of the amino acid sequences listed in Table A), a transmembrane domain of the present disclosure, a primary signaling domain, and one or more costimulatory signaling domains.

In some embodiments, the transmembrane domain is derived from the same protein as one of the one or more intracellular signaling domains. In some embodiments, the CAR is an inhibitory CAR and includes a transmembrane domain and at least one intracellular inhibitory co-signaling domain each derived from a protein selected from PD-1, CTLA4, TIGIT, BTLA, and LIR-1 (LILRB1), TIM3, KIR3DL1, NKG2A, LAG3, SLAP1, SLAP2, Dok-1, Dok-2, LAIR1, GRB-2, CD200R, SIRPα, HAVR, GITR, PD-L1, KIR2DL1, KIR2DL2, KIR2DL3, KIR3DL2, CD94, KLRG-1, CEACAM1, LIR2, LIR3, LIR5, SIGLEC-2, and SIGLEC-10.

In some embodiments, the transmembrane domain is derived from a first protein and the one or more intracellular signaling domains are derived from a second protein that are distinct from the first protein.

Natural Killer Cell Receptor (NKR) CARs

In some embodiments, a CAR of the present disclosure (e.g. the EMCN-specific CARs described herein) comprises one or more components of a natural killer cell receptor (NKR), thereby forming an NKR-CAR. The NKR component may be a transmembrane domain, a hinge domain, or a cytoplasmic domain from any suitable natural killer cell receptor, including without limitation, a killer cell immunoglobulin-like receptor (KIR), such as KIR2DL1, KIR2DL2/L3, KIR2DL4, KIR2DL5A, KIR2DL5B, KIR2DS1, KIR2DS2, KIR2DS3, KIR2DS4, DIR2DS5, KIR3DL1/S1, KIR3DL2, KIR3DL3, KIR2DP1, and KIRS DPI; a natural cytotoxicity receptor (NCR), such as NKp30, NKp44, NKp46; a signaling lymphocyte activation molecule (SLAM) family of immune cell receptor, such as CD48, CD229, 2B4, CD84, NTB-A, CRACC, BLAME, and CD2F-10; an Fc receptor (FcR), such as CD16, and CD64; and an Ly49 receptor, such as LY49A and LY49C. In some embodiments, the NKR-CAR may interact with an adaptor molecule or intracellular signaling domain, such as DAP12. Exemplary configurations and sequences of CARs comprising NKR components are described in International Patent Publication WO2014/145252, published Sep. 18, 2014.

Additional Chimeric Receptor Targets

Certain aspects of the present disclosure relate to chimeric receptors and nucleic acids that encode such chimeric receptors that bind to an antigen of interest in addition to EMCN. Certain aspects of the present disclosure relate to chimeric receptors and cells, such as immunoresponsive cells, that have been genetically modified to express one or more of such chimeric receptors that bind to an antigen of interest in addition to EMCN, and to methods of using such receptors and cells to treat and/or prevent myeloid malignancies, such as AML, and other pathologies where an antigen-specific immune response is desired. Malignant cells have developed a series of mechanisms to protect themselves from immune recognition and elimination. The present disclosure provides immunogenicity within the tumor microenvironment for treating such malignant cells.

In some embodiments, a first chimeric receptor includes an antigen-binding domain that binds EMCN (e.g., an EMCN-specific antigen-binding domain having one or more of the amino acid sequences listed in Table A) and a second chimeric receptor includes an additional antigen-binding domain that binds a second antigen, such as a tumor-associated antigen (e.g., an AML-associated antigen). In some embodiments, a cell can express a first chimeric receptor specific for EMCN (e.g., a CAR including an EMCN-specific antigen-binding domain having one or more of the amino acid sequences listed in Table A) and a second chimeric receptor specific for a second antigen, such as a tumor-associated antigen (e.g., an AML-associated antigen). In some embodiments, a cell can express a first chimeric inhibitory receptor specific for EMCN (e.g., an inhibitory CAR including an EMCN-specific antigen-binding domain having one or more of the amino acid sequences listed in Table A) and a second chimeric receptor specific for a second antigen, such as a tumor-associated antigen (e.g., an AML-associated antigen). For example, a cell (e.g., an immunoresponsive cell) can be engineered to co-expresses or capable of co-expressing an iCAR that includes an antigen-binding domain that binds EMCN (e.g., an EMCN-specific antigen-binding domain having one or more of the amino acid sequences listed in Table A) and an aCAR that targets a tumor-associated antigen (e.g., an AML-associated antigen). Suitable antibodies that bind to an antigen in addition to EMCN include any antibody, whether natural or synthetic, full length or a fragment thereof, monoclonal or polyclonal, that binds sufficiently strongly and specifically to a second antigen, such a tumor-associated antigen (e.g., an AML-associated antigen). In some embodiments, commercially available antibodies may be used for binding to a second antigen, such a tumor-associated antigen (e.g., an AML-associated antigen). The CDRs of the commercially available antibodies are readily accessible by one skilled in the art using conventional sequencing technology. Further, one skilled in the art is able to construct nucleic acids encoding scFvs and chimeric receptors (e.g., CARs and TCRs) based on the CDRs of such commercially available antibodies.

T Cell Receptor (TCR)

Certain aspects of the present disclosure relate to chimeric receptors that specifically bind to a second antigen, such a tumor-associated antigen (e.g., an AML-associated antigen) and the chimeric receptor for the second antigen is an engineered T cell receptor (TCR). TCRs of the present disclosure are disulfide-linked heterodimeric proteins containing two variable chains expressed as part of a complex with the invariant CD3 chain molecules. TCRs are found on the surface of T cells, and are responsible for recognizing antigens as peptides bound to major histocompatibility complex (MHC) molecules. In certain embodiments, a TCR of the present disclosure comprises an alpha chain encoded by TRA and a beta chain encoded by TRB. In certain embodiments, a TCR comprises a gamma chain and a delta chain (encoded by TRG and TRD, respectively).

Each chain of a TCR is composed of two extracellular domains: a variable (V) region and a constant (C) region. The constant region is proximal to the cell membrane, followed by a transmembrane region and a short cytoplasmic tail. The variable region binds to the peptide/MHC complex. Each of the variable regions has three complementarity determining regions (CDRs).

In certain embodiments, a TCR can form a receptor complex with three dimeric signaling modules CD3δ/ε, CD3γ/ε, and CD247ζ/ζ or CD247ζ/η. When a TCR complex engages with its antigen and MHC (peptide/MHC), the T cell expressing the TCR complex is activated.

In some embodiments, a TCR of the present disclosure is a recombinant TCR. In certain embodiments, the TCR is a non-naturally occurring TCR. In certain embodiments, the TCR differs from a naturally occurring TCR by at least one amino acid residue. In some embodiments, the TCR differs from a naturally occurring TCR by at least 2 amino acid residues, at least 3 amino acid residues, at least 4 amino acid residues, at least 5 amino acid residues, at least 6 amino acid residues, at least 7 amino acid residues, at least 8 amino acid residues, at least 9 amino acid residues, at least 10 amino acid residues, at least 11 amino acid residues, at least 12 amino acid residues, at least 13 amino acid residues, at least 14 amino acid residues, at least 15 amino acid residues, at least 20 amino acid residues, at least 25 amino acid residues, at least 30 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues, or more amino acid residues. In certain embodiments, the TCR is modified from a naturally occurring TCR by at least one amino acid residue. In some embodiments, the TCR is modified from a naturally occurring TCR by at least 2 amino acid residues, at least 3 amino acid residues, at least 4 amino acid residues, at least 5 amino acid residues, at least 6 amino acid residues, at least 7 amino acid residues, at least 8 amino acid residues, at least 9 amino acid residues, at least 10 amino acid residues, at least 11 amino acid residues, at least 12 amino acid residues, at least 13 amino acid residues, at least 14 amino acid residues, at least 15 amino acid residues, at least 20 amino acid residues, at least 25 amino acid residues, at least 30 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues, or more amino acid residues.

Chimeric TCRs

In some embodiments, a TCR of the present disclosure comprises one or more antigen-binding domains that may be grafted to one or more constant domain of a TCR chain, for example a TCR alpha chain or TCR beta chain, to create a chimeric TCR that binds specifically to a second antigen of interest, such a tumor-associated antigen (e.g., an AML-associated antigen). Without wishing to be bound by theory, it is believed that chimeric TCRs may signal through the TCR complex upon antigen binding. For example, an antibody or antibody fragment (e.g., scFv) can be grafted to the constant domain, e.g., at least a portion of the extracellular constant domain, the transmembrane domain and the cytoplasmic domain, of a TCR chain, such as the TCR alpha chain and/or the TCR beta chain. As another example, the CDRs of an antibody or antibody fragment may be grafted into a TCR alpha chain and/or beta chain to create a chimeric TCR that binds specifically to a second antigen, such a tumor-associated antigen (e.g., an AML-associated antigen). Such chimeric TCRs may be produced by methods known in the art (e.g., Willemsen R A et al., Gene Therapy 2000; 7:1369-1377; Zhang T et al., Cancer Gene Ther 2004 11: 487-496; and Aggen et al., Gene Ther. 2012 April; 19(4): 365-74).

Immunoresponsive Cells

Certain aspects of the present disclosure relate to a cell, such as an immunoresponsive cell, that has been genetically engineered to comprise one or more chimeric receptors of the present disclosure or one or more nucleic acids encoding such chimeric receptors, and to methods of using such cells for treating myeloid malignancies (e.g., AML).

In some embodiments, the cell is a mammalian cell. In some embodiments, the mammalian cell is a primary cell. In some embodiments, the mammalian cell is a cell line. In some embodiments, the mammalian cell a bone marrow cell, a blood cell, a skin cell, bone cell, a muscle cell, a neuronal cell, a fat cell, a liver cell, or a heart cell. In some embodiments, the cell is a stem cell. Exemplary stem cells include, without limitation embryonic stem cells (ESCs), induced pluripotent stem cells (iPSCs), adult stem cells, and tissue-specific stem cells, such as hematopoietic stem cells (blood stem cells), mesenchymal stem cells (MSC), neural stem cells, epithelial stem cells, or skin stem cells. In some embodiments, the cell is a cell that is derived or differentiated from a stem cell of the present disclosure. In some embodiments, the cell is an immune cell. Immune cells of the present disclosure may be isolated or differentiated from a stem cell of the present disclosure (e.g., from an ESC or iPSC). Exemplary immune cells include, without limitation, T cells (e.g., helper T cells, cytotoxic T cells, memory T cells, regulatory T cells, natural killer T cells, alpha beta T cells, and gamma delta T cells), B cells, natural killer (NK) cells, dendritic cells, myeloid cells, macrophages, and monocytes. In some embodiments, the cell is a neuronal cell. Neuronal cells of the present disclosure may be isolated or differentiated from a stem cell of the present disclosure (e.g., from an ESC or iPSC). Exemplary neuronal cells include, without limitation, neural progenitor cells, neurons (e.g., sensory neurons, motor neurons, cholinergic neurons, GABAergic neurons, glutamatergic neurons, dopaminergic neurons, or serotonergic neurons), astrocytes, oligodendrocytes, and microglia.

In some embodiments, the cell is an immunoresponsive cell. Immunoresponsive cells of the present disclosure may be isolated or differentiated from a stem cell of the present disclosure (e.g., from an ESC or iPSC). Exemplary immunoresponsive cells of the present disclosure include, without limitation, cells of the lymphoid lineage. The lymphoid lineage, comprising B cells, T cells, and natural killer (NK) cells, provides for the production of antibodies, regulation of the cellular immune system, detection of foreign agents in the blood, detection of cells foreign to the host, and the like. Examples of immunoresponsive cells of the lymphoid lineage include, without limitation, T cells, Natural Killer (NK) cells, embryonic stem cells, pluripotent stem cells, and induced pluripotent stem cells (e.g., those from which lymphoid cells may be derived or differentiated). T cells can be lymphocytes that mature in the thymus and are chiefly responsible for cell-mediated immunity. T cells are involved in the adaptive immune system. In some embodiments, T cells of the present disclosure can be any type of T cells, including, without limitation, T helper cells, cytotoxic T cells, memory T cells (including central memory T cells, stem-cell-like memory T cells (or stem-like memory T cells), and two types of effector memory T cells: e.g., $T_{EM}$ cells and $T_{EMRA}$ cells, regulatory T cells (also known as suppressor T cells), natural killer T cells, mucosal associated invariant T cells, and γδ T cells. Cytotoxic T cells (CTL or killer T cells) are a subset of T lymphocytes capable of inducing the death of infected somatic or tumor cells. A patient's own T cells may be genetically modified to target specific antigens through the introduction of one or more chimeric receptors, such as a chimeric TCRs or CARs.

Natural killer (NK) cells can be lymphocytes that are part of cell-mediated immunity and act during the innate immune response. NK cells do not require prior activation in order to perform their cytotoxic effect on target cells.

In some embodiments, an immunoresponsive cell of the present disclosure is a T cell. T cells of the present disclosure may be autologous, allogeneic, or derived in vitro from engineered progenitor or stem cells.

In some embodiments, an immunoresponsive cell of the present disclosure is a universal T cell with deficient TCR-up. Methods of developing universal T cells are described in the art, for example, in Valton et al., Molecular Therapy (2015); 23 9, 1507-1518, and Torikai et al., Blood 2012 119:5697-5705.

In some embodiments, an immunoresponsive cell of the present disclosure is an isolated immunoresponsive cell comprising one or more chimeric receptors of the present disclosure. In some embodiments, the immunoresponsive cell comprises one or more, two or more, three or more, four or more, five or more, six or more, seven or more, eight or more, nine or more, or ten or more chimeric receptors of the present disclosure.

In some embodiments, an immunoresponsive cell is a T cell. In some embodiments, an immunoresponsive cell is a Natural Killer (NK) cell.

In some embodiments, an immunoresponsive cell express or is capable of expressing an immune receptor. Immune receptors generally are capable of inducing signal transduction or changes in protein expression in the immune receptor-expressing cell that results in the modulation of an immune response upon binding to a cognate ligand (e.g., regulate, activate, initiate, stimulate, increase, prevent, attenuate, inhibit, reduce, decrease, inhibit, or suppress an immune response). For example, when CD3 chains present in a TCR/CAR cluster in response to ligand binding, an immunoreceptor tyrosine-based activation motifs (ITAMs)-meditated signal transduction cascade is produced. Specifically, in certain embodiments, when an endogenous TCR, exogenous TCR, chimeric TCR, or a CAR (specifically an activating CAR) binds their respective antigen, a formation of an immunological synapse occurs that includes clustering of many molecules near the bound receptor (e.g. CD4 or CD8, CD3γ/δ/ε/ζ, etc.). This clustering of membrane bound signaling molecules allows for ITAM motifs contained within the CD3 chains to become phosphorylated that in turn can initiate a T cell activation pathway and ultimately activates transcription factors, such as NF-κB and AP-1. These transcription factors are capable of inducing global gene expression of the T cell to increase IL-2 production for proliferation and expression of master regulator T cell proteins in order to initiate a T cell mediated immune response, such as cytokine production and/or T cell mediated killing.

Cells Expressing Multiple Chimeric Receptors

In some embodiments, a cell of the present disclosure (e.g., an immunoresponsive cell) comprises two or more chimeric receptors of the present disclosure. In some embodiments, the cell comprises two or more chimeric receptors, wherein one of the two or more chimeric receptors is a chimeric inhibitory receptor. In some embodiments, the cell comprises three or more chimeric receptors, wherein at least one of the three or more chimeric receptors is a chimeric inhibitory receptor. In some embodiments, the cell comprises four or more chimeric receptors, wherein at least one of the four or more chimeric receptors is a chimeric inhibitory receptor. In some embodiments, the cell comprises five or more chimeric receptors, wherein at least one of the five or more chimeric receptors is a chimeric inhibitory receptor.

In some embodiments, each of the two or more chimeric receptors comprise a different antigen-binding domain, e.g., that binds to the same antigen or to a different antigen. In some embodiments each antigen bound by the two or more chimeric receptors are expressed on the same cell, such as a myeloid cell type (e.g., same AML cell type).

In embodiments where a cell of the present disclosure (e.g., an immunoresponsive cell) expresses two or more distinct chimeric receptors, the antigen-binding domain of each of the different chimeric receptors may be designed such that the antigen-binding domains do not interact with one another. For example, a cell of the present disclosure (e.g., an immunoresponsive cell) expressing a first chimeric receptor (e.g., an EMCN-specific chimeric receptor) and a second chimeric receptor may comprise a first chimeric receptor that comprises an antigen-binding domain that does not form an association with the antigen-binding domain of the second chimeric receptor. For example, the antigen-binding domain of the first chimeric receptor may comprise an antibody fragment, such as an scFv, while the antigen-binding domain of the second chimeric receptor may comprise a VHH.

Without wishing to be bound by theory, it is believed that in cells having a plurality of chimeric membrane embedded receptors that each comprise an antigen-binding domain, interactions between the antigen-binding domains of each of the receptors can be undesirable, because such interactions may inhibit the ability of one or more of the antigen-binding domains to bind their cognate antigens. Accordingly, in embodiments where cells of the present disclosure (e.g., immunoresponsive cells) express two or more chimeric receptors, the chimeric receptors comprise antigen-binding domains that minimize such inhibitory interactions. In one embodiment, the antigen-binding domain of one chimeric receptor comprises an scFv and the antigen-binding domain of the second chimeric receptor comprises a single VH domain, e.g., a camelid, shark, or lamprey single VH domain, or a single VH domain derived from a human or mouse sequence.

In some embodiments, when present on the surface of a cell, binding of the antigen-binding domain of the first chimeric receptor to its cognate antigen (e.g., an EMCN-specific chimeric receptor binding to EMCN) is not substantially reduced by the presence of the second chimeric receptor. In some embodiments, binding of the antigen-binding domain of the first chimeric receptor to its cognate antigen in the presence of the second chimeric receptor is 85%, 90%, 95%, 96%, 97%, 98%, or 99% of binding of the antigen-binding domain of the first chimeric receptor to its cognate antigen in the absence of the second chimeric receptor. In some embodiments, when present on the surface of a cell, the antigen-binding domains of the first chimeric receptor and the second chimeric receptor associate with one another less than if both were scFv antigen-binding domains. In some embodiments, the antigen-binding domains of the first chimeric receptor and the second chimeric receptor associate with one another 85%, 90%, 95%, 96%, 97%, 98%, or 99% less than if both were scFv antigen-binding domains.

Chimeric Inhibitory Receptors

In some embodiments, a cell of the present disclosure (e.g., an immunoresponsive cell) comprises one or more chimeric inhibitory receptors of the present disclosure. In some embodiments, each of the one or more chimeric inhibitory receptors comprises an antigen-binding domain that binds an antigen generally expressed on normal cells (e.g., cells generally considered to be healthy) but not on tumor cells, such as AML cells. In some embodiments, a chimeric inhibitory receptor includes an antigen-binding domain that binds EMCN (e.g., an EMCN-specific antigen-binding domain having one or more of the amino acid sequences listed in Table A).

In some embodiments, the one or more chimeric inhibitory receptors bind antigens that are expressed on a non-tumor cell derived from a tissue selected from the group consisting of brain, neuronal tissue, endocrine, bone, bone marrow, immune system, endothelial tissue, muscle, lung, liver, gallbladder, pancreas, gastrointestinal tract, kidney, urinary bladder, male reproductive organs, female reproductive organs, adipose, soft tissue, and skin.

In some embodiments, a chimeric inhibitory receptor (e.g. an EMCN-specific chimeric inhibitory receptor) may be used, for example, with one or more activating chimeric receptors (e.g., activating chimeric TCRs or CARs) expressed on a cell of the present disclosure (e.g., an immunoresponsive cell) as NOT-logic gates to control, modulate, or otherwise inhibit one or more activities of the one or more activating chimeric receptors. In some embodiments, a chimeric inhibitory receptor of the present disclosure may inhibit one or more activities of a cell of the present disclosure (e.g., an immunoresponsive cell).

In some embodiments, a cell of the present disclosure comprises one or more chimeric inhibitory receptors of the present disclosure and further comprises a tumor-targeting chimeric receptor that binds to one or more tumor-associated antigens. In some embodiments, the one or more tumor-associated antigens include an AML-associated antigen. In some embodiments, the one or more tumor-associated antigens include CD33. In some embodiments, the one or more tumor-associated antigens include FLT3. In some embodiments, the one or more tumor-associated antigens include CD33 and FLT3. Without wishing to be bound by theory, when administering an immunocompetent cell expressing a tumor-targeting chimeric receptor that binds to a tumor-associated antigen, if the tumor-associated antigen is also expressed by healthy cells such as healthy HSPCs, further expressing an EMCN-specific chimeric inhibitory receptor as described herein can reduce off-target effects of the tumor-targeting chimeric receptor. As used herein "off-target effects" refers to killing of off-target cells (i.e., non-tumor cells that also express the tumor-associated antigen) by an immunocompetent cell expressing a tumor-targeting chimeric receptor. In some embodiments, the reduced off-target effects is reduced killing of healthy HSPCs. In some embodiments, the reduced off-target effects are at least 5% less, at least 10% less, at least 15% less, at least 20% less, at least 25% less, at least 30% less, at least 35% less, at least 40% less, at least 45% less, or at least 50% less killing of off-target cells, as compared to an equivalent immunocompetent cell expressing the tumor-targeting antigen but not expressing the chimeric inhibitory receptor as disclosed herein.

Co-Stimulatory Ligands

In some embodiments, a cell of the present disclosure (e.g., an immunoresponsive cell) can further include one or more recombinant or exogenous co-stimulatory ligands. For example, the cell can be further transduced with one or more co-stimulatory ligands, such that the cell co-expresses or is induced to co-express one or more chimeric receptors of the present disclosure (e.g., the EMCN-specific CARs described herein) and one or more co-stimulatory ligands. Without wishing to be bound by theory, it is believed that the interaction between the one or more chimeric receptors and the one or more co-stimulatory ligands may provide a non-antigen-specific signal important for full activation of the cell. Examples of suitable co-stimulatory ligands include, without limitation, members of the tumor necrosis factor (TNF) superfamily, and immunoglobulin (Ig) superfamily ligands. TNF is a cytokine involved in systemic inflammation and stimulates the acute phase reaction. Its primary role is in the regulation of immune cells. Members of TNF superfamily share a number of common features. The majority of TNF superfamily members are synthesized as type II transmembrane proteins (extracellular C-terminus) containing a short cytoplasmic segment and a relatively long extracellular region. Examples of suitable TNF superfamily members include, without limitation, nerve growth factor (NGF), CD40L (CD40L)/CD 154, CD137L/4-1BBL, TNF-a, CD134L/OX40L/CD252, CD27L/CD70, Fas ligand (FasL), CD30L/CD153, tumor necrosis factor beta (TNFP)/ lymphotoxin-alpha (LTa), lymphotoxin-beta (LTP), CD257/B cell-activating factor (B AFF)/Bly s/THANK/ Tall-1, glucocorticoid-induced TNF Receptor ligand (GITRL), and TNF-related apoptosis-inducing ligand (TRAIL), LIGHT (TNFSF 14). The immunoglobulin (Ig) superfamily is a large group of cell surface and soluble proteins that are involved in the recognition, binding, or adhesion processes of cells. These proteins share structural features with immunoglobulins and possess an immunoglobulin domain (fold). Examples of suitable immunoglobulin superfamily ligands include, without limitation, CD80 and CD86, both ligands for CD28, PD-L1/(B7-H1) that ligands for PD-1. In certain embodiments, the one or more co-stimulatory ligands are selected from 4-1BBL, CD80, CD86, CD70, OX40L, CD48, TNFRSF14, PD-L1, and combinations thereof.

Chemokine Receptor

In some embodiments, a cell of the present disclosure (e.g., an immunoresponsive cell) comprises one or more chimeric receptors (e.g., the EMCN-specific CARs described herein) and may further include one or more chemokine receptors. For example, transgenic expression of chemokine receptor CCR2b or CXCR2 in cells, such as T cells, enhances trafficking to CCL2-secreting or CXCL1- secreting solid tumors (Craddock et al, J Immunother. 2010 October; 33(8):780-8 and Kershaw et al. Hum Gene Ther. 2002 Nov. 1; 13(16): 1971-80). Without wishing to be bound by theory, it is believed that chemokine receptors expressed on chimeric receptor-expressing cells of the present disclosure may recognize chemokines secreted by tumors and improve targeting of the cell to the tumor, which may facilitate the infiltration of the cell to the tumor and enhance the antitumor efficacy of the cell. Chemokine receptors of the present disclosure may include a naturally occurring chemokine receptor, a recombinant chemokine receptor, or a chemokine-binding fragment thereof. Examples of suitable chemokine receptors that may expressed on a cell of the present disclosure include, without limitation, a CXC chemokine receptor, such as CXCR1, CXCR2, CXCR3, CXCR4, CXCR5, CXCR6, or CXCR7; a CC chemokine receptor, such as CCR1, CCR2, CCR3, CCR4, CCR5, CCR6, CCR7, CCR8, CCR9, CCR10, or CCR11; a CX3C chemokine receptor, such as CX3CR1; an XC chemokine receptor, such as XCR1; and chemokine-binding fragments thereof. In some embodiments, the chemokine receptor to be expressed on the cell is chosen based on the chemokines secreted by the tumor.

Chimeric Receptor Regulation

Some embodiments of the present disclosure relate to regulating one or more chimeric receptor activities of chimeric receptor-expressing cells of the present disclosure (e.g. the EMCN-specific CARs described herein). There are several ways chimeric receptor activities can be regulated. In some embodiments, a regulatable chimeric receptor, wherein one or more chimeric receptor activities can be controlled, may be desirable to optimize the safety and/or efficacy of the chimeric receptor therapy. For example, inducing apoptosis using a caspase fused to a dimerization domain (see, e.g., Di et al., N Engl. J. Med. 2011 Nov. 3; 365(18): 1673-1683) can be used as a safety switch in the chimeric receptor therapy. In some embodiments, a chimeric receptor-expressing cell of the present disclosure can also express an inducible Caspase-9 (iCaspase-9) that, upon administration of a dimerizer drug, such as rimiducid (IUPAC name: [(1R)-3-(3,4-dimethoxyphenyl)-1-[3-[2-[2-[[2-[3-[(1R)-3-(3,4-dimethoxyphenyl)-1-[(2S)-1-[(2S)-2-(3,4, 5-trimethoxyphenyl)butanoyl]piperidine-2-carbonyl] oxypropyl]phenoxy]acetyl]amino]ethylamino]-2-oxoethoxy]phenyl]propyl]            (2S)-1-[(2S)-2-(3,4,5-trimethoxyphenyl)butanoyl]piperidine-2-carboxylate), induces activation of the Caspase-9 and results in apoptosis of the cells. In some embodiments, the iCaspase-9 contains a binding domain that comprises a chemical inducer of dimerization (CID) that mediates dimerization in the presence of the CID, which results in inducible and selective depletion of the chimeric receptor-expressing cells.

Alternatively, in some embodiments a chimeric receptor of the present disclosure may be regulated by utilizing a small molecule or an antibody that deactivates or otherwise inhibits chimeric receptor activity. For example, an antibody may delete the chimeric receptor-expressing cells by inducing antibody dependent cell-mediated cytotoxicity (ADCC). In some embodiments, a chimeric receptor-expressing cell of the present disclosure may further express an antigen that is recognized by a molecule that is capable of inducing cell death by ADCC or complement-induced cell death. For example, a chimeric receptor-expressing cell of the present disclosure may further express a receptor capable of being targeted by an antibody or antibody fragment. Examples of suitable receptors that may be targeted by an antibody or antibody fragment include, without limitation, EpCAM, VEGFR, integrins (e.g., $\alpha\nu\beta$, $\alpha4$, $\alpha I^{3}/_{4}\beta3$, $\alpha4\beta7$, $\alpha5\beta1$, $\alpha\nu\beta$, $\alpha\nu$), members of the TNF receptor superfamily (e.g., TRAIL-R1 and TRAIL-R2), PDGF receptor, interferon receptor, folate receptor, GPNMB, ICAM-1, HLA-DR, CEA, CA-125, MUC1, TAG-72, IL-6 receptor, 5T4, GD2, GD3, CD2, CD3, CD4, CD5, CD11, CD11a/LFA-1, CD15, CD18/ITGB2, CD19, CD20, CD22, CD23/IgE Receptor, CD25, CD28, CD30, CD33, CD38, CD40, CD41, CD44, CD51, CD52, CD62L, CD74, CD80, CD125, CD147/basigin, CD152/CTLA-4, CD154/CD40L, CD195/CCR5, CD319/SLAMF7, and EGFR, and truncated versions thereof.

In some embodiments, a chimeric receptor-expressing cell of the present disclosure may also express a truncated epidermal growth factor receptor (EGFR) that lacks signaling capacity but retains an epitope that is recognized by molecules capable of inducing ADCC (e.g., WO2011/056894).

In some embodiments, a chimeric receptor-expressing cell of the present disclosure further includes a highly expressing compact marker/suicide gene that combines target epitopes from both CD32 and CD20 antigens in the chimeric receptor-expressing cell, which binds an anti-CD20 antibody (e.g., rituximab) resulting in selective depletion of the chimeric receptor-expressing cell by ADCC. Other methods for depleting chimeric receptor-expressing cells of the present disclosure my include, without limitation, administration of a monoclonal anti-CD52 antibody that selectively binds and targets the chimeric receptor-expressing cell for destruction by inducing ADCC. In some embodiments, the chimeric receptor-expressing cell can be selectively targeted using a chimeric receptor ligand, such as an anti-idiotypic antibody. In some embodiments, the anti-idiotypic antibody can cause effector cell activity, such as ADCC or ADC activity. In some embodiments, the chimeric receptor ligand can be further coupled to an agent that induces cell killing, such as a toxin. In some embodiments, a chimeric receptor-expressing cell of the present disclosure may further express a target protein recognized by a cell depleting agent of the present disclosure. In some embodiments, the target protein is CD20 and the cell depleting agent is an anti-CD20 antibody. In such embodiments, the cell depleting agent is administered once it is desirable to reduce or eliminate the chimeric receptor-expressing cell. In some embodiments, the cell depleting agent is an anti-CD52 antibody.

In some embodiments, a regulated chimeric receptor comprises a set of polypeptides, in which the components of a chimeric receptor of the present disclosure are partitioned on separate polypeptides or members. For example, the set of polypeptides may include a dimerization switch that, when in the presence of a dimerization molecule, can couple the polypeptides to one another to form a functional chimeric receptor.

EMCN-Specific Protein-Encoding Nucleic Acid Constructs

Certain aspects of the present disclosure relate to nucleic acids (e.g., isolated nucleic acids) encoding one or more EMCN-specific proteins of the present disclosure (e.g. the EMCN-specific CARs described herein). In some embodiments, the nucleic acid is an RNA construct, such as a messenger RNA (mRNA) transcript or a modified RNA. In some embodiments, the nucleic acid is a DNA construct.

In some embodiments, a nucleic acid of the present disclosure encodes a chimeric receptor that comprises one or more antigen-binding domain, where each domain binds to a target antigen (e.g., EMCN), a transmembrane domain, and one or more intracellular signaling domains. In some embodiments, the nucleic acid encodes a chimeric receptor that comprises an antigen-binding domain, a transmembrane domain, a primary signaling domain (e.g., CD3-zeta domain), and one or more costimulatory signaling domains. In some embodiments, the nucleic acid further comprises a nucleotide sequence encoding a spacer region. In some embodiments, the antigen-binding domain is connected to the transmembrane domain by the spacer region. In some embodiments, the spacer region comprises a nucleic acid sequence selected from any of the nucleic acid sequences listed in Table 3. In some embodiments, the nucleic acid further comprises a nucleotide sequence encoding a leader sequence.

The nucleic acids of the present disclosure may be obtained using any suitable recombinant methods known in the art, including, without limitation, by screening libraries from cells expressing the gene of interest, by deriving the gene of interest from a vector known to include the gene, or by isolating the gene of interest directly from cells and tissues containing the gene using standard techniques. Alternatively, the gene of interest may be produced synthetically.

In some embodiments, a nucleic acid of the present disclosure in comprised within a vector. In some embodiments, a nucleic acid of the present disclosure is expressed in a cell via transposons, a CRISPR/Cas9 system, a TALEN, or a zinc finger nuclease.

In some embodiments, expression of a nucleic acid encoding a chimeric receptor of the present disclosure may be achieved by operably linking the nucleic acid to a promoter and incorporating the construct into an expression vector. A suitable vector can replicate and integrate in eukaryotic cells. Typical cloning vectors contain transcription and translation terminators, initiation sequences, and promoters useful for regulating expression of the desired nucleic acid.

In some embodiments, expression constructs of the present disclosure may also be used for nucleic acid immunization and gene therapy, using standard gene delivery protocols (e.g., U.S. Pat. Nos. 5,399,346, 5,580,859, and 5,589,466). In some embodiments, a vector of the present disclosure is a gene therapy vector.

A nucleic acid of the present disclosure can be cloned into a number of types of vectors. For example, the nucleic acid can be cloned into a vector including, without limitation, a plasmid, a phagemid, a phage derivative, an animal virus, or a cosmid. In some embodiments, the vector may be an expression vector, a replication vector, a probe generation vector, or a sequencing vector.

In some embodiments, the plasmid vector comprises a transposon/transposase system to incorporate the nucleic acids of the present disclosure into the host cell genome. Methods of expressing proteins in immune cells using a transposon and transposase plasmid system are generally described in Chicaybam L, Hum Gene Ther. 2019 April; 30(4):511-522. doi: 10.1089/hum.2018.218; and Ptackova P, Cytotherapy. 2018 April; 20(4):507-520. doi: 10.1016/j.jcyt.2017.10.001, each of which are hereby incorporated by reference in their entirety. In some embodiments, the transposon system is the Sleeping Beauty transposon/transposase or the piggyBac transposon/transposase.

In some embodiments, an expression vector of the present disclosure may be provided to a cell in the form of a viral vector. Suitable viral vector systems are well known in the art. For example, viral vectors may be derived from retroviruses, adenoviruses, adeno-associated viruses, herpes viruses, and lentiviruses. In some embodiments, a vector of the present disclosure is a lentiviral vector. Lentiviral vectors are suitable for long-term gene transfer as such vectors allow long-term, stable integration of a transgene and its propagation in daughter cells. Lentiviral vectors are also advantageous over vectors derived from onco-retroviruses (e.g., murine leukemia viruses) in that lentiviral vectors can transduce non-proliferating cells. In some embodiments, a vector of the present disclosure is an adenoviral vector (A5/35). In some embodiments, a vector of the present disclosure contains an origin of replication functional in at least one organism, a promoter sequence, convenient restriction endonuclease sites, and one or more selectable markers (e.g., WO01/96584; WO01/29058; and U.S. Pat. No. 6,326, 193). A number of viral based systems have been developed for gene transfer into mammalian cells. A selected gene can be inserted into a vector and packaged in retroviral particles using techniques known in the art. The recombinant virus can then be isolated and delivered to mammalian cells either in vivo or ex vivo. A number of retroviral systems are known in the art.

In some embodiments, vectors of the present disclosure include additional promoter elements, such as enhancers that regulate the frequency of transcriptional initiation. Enhancers are typically located in a region that is 30 bp to 110 bp upstream of the start site, although a number of promoters have been shown to contain functional elements downstream of the start site as well. The spacing between promoter elements may be flexible, so that promoter function is preserved when elements are inverted or moved relative to one another. For example, in the thymidine kinase (tk) promoter the spacing between promoter elements can be increased to 50 bp apart before activity begins to decline. Depending on the promoter, individual elements may function either cooperatively or independently to activate transcription. Exemplary promoters may include, without limitation, the SFFV gene promoter, the EFS gene promoter, the CMV IE gene promoter, the EF1a promoter, the ubiquitin C promoter, and the phosphoglycerokinase (PGK) promoter.

In some embodiments, a promoter that is capable of expressing a nucleic acid of the present disclosure in a mammalian cell, such as an immunoresponsive cell of the present disclosure, is the EF1a promoter. The native EF1a promoter drives expression of the alpha subunit of the elongation factor-1 complex, which is responsible for the enzymatic delivery of aminoacyl tRNAs to the ribosome. The EF1a promoter has been widely used in mammalian expression plasmids and has been shown to be effective in driving chimeric receptor expression from nucleic acids cloned into a lentiviral vector.

In some embodiments, a promoter that is capable of expressing a nucleic acid of the present disclosure in a mammalian cell, such as an immunoresponsive cell of the present disclosure, is a constitutive promoter. For example, a suitable constitutive promoter is the immediate early cytomegalovirus (CMV) promoter. The CMV promoter is a strong constitutive promoter that is capable of driving high levels of expression of any polynucleotide sequence operatively linked to the promoter. Other suitable constitutive promoters include, without limitation, a ubiquitin C (UbiC) promoter, a simian virus 40 (SV40) early promoter, a mouse mammary tumor virus (MMTV) promoter, a human immunodeficiency virus (HIV) long terminal repeat (LTR) promoter, a MoMuLV promoter, an avian leukemia virus promoter, an Epstein-Barr virus immediate early promoter, a Rous sarcoma virus promoter, an actin promoter, a myosin promoter, an elongation factor-1a promoter, a hemoglobin promoter, and a creatine kinase promoter.

In some embodiments, a promoter that is capable of expressing a nucleic acid of the present disclosure in a mammalian cell, such as an immunoresponsive cell of the present disclosure, is an inducible promoter. Use of an inducible promoter may provide a molecular switch that is capable of inducing or repressing expression of a nucleic acid of the present disclosure when the promoter is operatively linked to the nucleic acid. Examples of inducible promoters include, without limitation, a metallothionine promoter, a glucocorticoid promoter, a progesterone promoter, and a tetracycline promoter.

In some embodiments, a vector of the present disclosure may further comprise a signal sequence to facilitate secretion, a polyadenylation signal and transcription terminator, an element allowing episomal replication, and/or elements allowing for selection.

In some embodiments, a vector of the present disclosure can further comprise a selectable marker gene and/or reporter gene to facilitate identification and selection of chimeric receptor-expressing cells from a population of cells that have been transduced with the vector. In some embodiments, the selectable marker may be encoded by a nucleic acid that is separate from the vector and used in a co-transfection procedure. Either selectable marker or reporter gene may be flanked with appropriate regulator sequences to allow expression in host cells. Examples of selectable markers include, without limitation, antibiotic-resistance genes, such as neo and the like.

In some embodiments, reporter genes may be used for identifying transduced cells and for evaluating the functionality of regulatory sequences. As disclosed herein, a reporter gene is a gene that is not present in or expressed by the recipient organism or tissue and that encodes a polypeptide whose expression results in an easily detectable property, such as enzymatic activity. Expression of the reporter gene can be assayed at a suitable time after the nucleic acid has been introduced into the recipient cells. Examples of reporter genes include, without limitation, genes encoding for luciferase, genes encoding for beta-galactosidase, genes encoding for chloramphenicol acetyl transferase, genes encoding for secreted alkaline phosphatase, and genes encoding for green fluorescent protein. Suitable expression systems are well known in the art and may be prepared using known techniques or obtained commercially. In some embodiments, a construct with a minimal 5' flanking region showing the highest level of expression of the reporter gene is identified as the promoter. Such promoter regions may be linked to a reporter gene and used to evaluate agents for the ability to modulate promoter-driven transcription.

In some embodiments, a vector comprising a nucleic acid sequence encoding a chimeric receptor of the present disclosure further comprises a second nucleic acid encoding a polypeptide that increases the activity of the chimeric receptor.

In embodiments where an EMCN-specific protein-expressing cell comprises two or more heterologous proteins (e.g., two or more chimeric receptors), a single nucleic acid may encode the two or more proteins under a single regulatory control element (e.g., promoter) or under separate regulatory control elements for each protein-encoding nucleotide sequence comprised in the nucleic acid. In some embodiments where an EMCN-specific protein-expressing cell comprises two or more heterologous proteins, each heterologous protein may be encoded by a separate nucleic acid. In some embodiments, each separate nucleic acid comprises its own control element (e.g., promoter). In some embodiments, a single nucleic acid encodes the two or more chimeric receptors and the chimeric receptor-encoding nucleotide sequences are in the same reading frame and are expressed as a single polypeptide chain. In such embodiments, the two or more chimeric receptors may be separated by one or more peptide cleavage sites, such as auto-cleavage sites or substrates for an intracellular protease. Suitable peptide cleavage sites may include, without limitation, a T2A peptide cleavage site, a P2A peptide cleavage site, an E2A peptide cleavage sire, and an F2A peptide cleavage site. In some embodiments, the two or more chimeric receptors comprise a T2A peptide cleavage site. In some embodiments, the two or more chimeric receptors comprise an E2A peptide cleavage site. In some embodiments, the two or more chimeric receptors comprise a T2A and an E2A peptide cleavage site.

Methods of introducing and expressing genes into a cell are well known in the art. For example, in some embodiments, an expression vector can be transferred into a host cell by physical, chemical, or biological means. Examples of physical means for introducing a nucleic acid into a host cell include, without limitation, calcium phosphate precipitation, lipofection, particle bombardment, microinjection, and electroporation. Examples of chemical means for introducing a nucleic acid into a host cell include, without limitation, colloidal dispersion systems, macromolecule complexes, nanocapsules, microspheres, beads, and lipid-based systems including oil-in-water emulsions, micelles, mixed micelles, and liposomes. Examples of biological means for introducing a nucleic acid into a host cell include, without limitation, the use of DNA and RNA vectors.

In some embodiments, liposomes may be used as a non-viral delivery system to introduce a nucleic acid or vector of the present disclosure into a host cell in vitro, ex vivo, or in vivo. In some embodiments, the nucleic acid may be associated with a lipid, for example by being encapsulated in the aqueous interior of a liposome, being interspersed within the lipid bilayer of a liposome, being attached to a liposome via a linking molecule that is associated with both the liposome and the nucleic acid, being entrapped in a liposome, being complexed with a liposome, being dispersed in a solution containing a lipid, being mixed with a lipid, being combined with a lipid, being contained as a suspension in a lipid, being contained or complexed with a micelle, or otherwise being associated with a lipid. As disclosed herein, lipid-associated nucleic acid or vector compositions are not limited to any particular structure in solution. In some embodiments, such compositions may be present in a bilayer structure, as micelles or with a "collapsed" structure. Such compositions may also be interspersed in a solution, forming aggregates that are not uniform in size or shape. As disclosed herein, lipids are fatty substances that may be naturally occurring or synthetic. In some embodiments, lipids can include the fatty droplets that naturally occur in the cytoplasm or the class of compounds that contain long-chain aliphatic hydrocarbons and their derivatives, such as fatty acids, alcohols, amines, amino alcohols, and aldehydes. Suitable lipids may be obtained from commercial sources and include, without limitation, dimyristyl phosphatidylcholine ("DMPC"), dicetylphosphate ("DCP"), cholesterol, and dimyristylphosphatidylglycerol ("DMPG"). Stock solutions of lipids in chloroform or chloroform/methanol can be stored at about –20° C. Chloroform is used as the solvent, as it is more readily evaporated than methanol. As used herein, a "liposome" may encompass a variety of single and multilamellar lipid vehicles formed by the generation of enclosed lipid bilayers or aggregates. In some embodiments, liposomes can be characterized as having vesicular structures with a phospholipid bilayer membrane and an inner aqueous medium. In some embodiments, multilamellar liposomes may have multiple lipid layers separated by aqueous medium. Multilamellar liposomes can form spontaneously when phospholipids are suspended in an excess of aqueous solution. In some embodiments, lipid components may undergo self-rearrangement before the formation of closed structures and can entrap water and dissolved solutes between the lipid bilayers. In some embodiments, the lipids may assume a micellar structure or merely exist as nonuniform aggregates of lipid molecules.

In some embodiments, a nucleic acid or vector of the present disclosure is introduced into a mammalian host cell, such as an immunoresponsive cell of the present disclosure. In some embodiments, the presence of a nucleic acid or vector of the present disclosure in a host cell may be confirmed by any suitable assay known in the art, including without limitation Southern blot assays, Northern blot assays, RT-PCR, PCR, ELISA assays, and Western blot assays.

In some embodiments, a nucleic acid or vector of the present disclosure is stably transduced into an immunoresponsive cell of the present disclosure. In some embodiments, cells that exhibit stable expression of the nucleic acid or vector express the encoded chimeric receptor for at least 1 week, at least 2 weeks, at least 3 weeks, at least 4 weeks, at least 5 weeks, at least 6 weeks, at least 7 weeks, at least 8 weeks, at least 3 months, at least 6 months, at least 9 months, or at least 12 months after transduction.

In embodiments where an EMCN-specific protein (e.g., chimeric receptor) of the present disclosure is transiently expressed in a cell, an EMCN-specific protein-encoding nucleic acid or vector of the present disclosure is transfected into an immunoresponsive cell of the present disclosure. In some embodiments the immunoresponsive cell expresses the EMCN-specific protein for about 4 days, about 5 days, about 6 days, about 7 days, about 8 days, about 9 days, about 10 days, about 11 days, about 12 days, about 13 days, about 14 days, or about 15 days after transfection.

In some embodiments, the nucleic acid construct encodes a bicistronically encoded chimeric antigen receptors. In some embodiments, the encoded bicistronic chimeric antigen receptors comprise an EMCN CAR (such as an EMCN inhibitory CAR) and a CAR specific for a second antigen (such as a tumor-targeting chimeric receptor).

In some embodiments, the nucleic acid construct encodes a bivalent chimeric antigen receptor. In some embodiments, the encoded bivalent chimeric antigen receptor comprises an EMCN antigen-binding domain and a second antigen-binding domain.

Pharmaceutical Compositions and Administration

Certain aspects of the present disclosure relate to compositions (e.g., pharmaceutical compositions) comprising one or more EMCN-specific proteins (e.g., chimeric receptors) of the present disclosure or immunoresponsive cells of the present disclosure that express such one or more EMCN-specific proteins. In some embodiments, compositions comprising EMCN-specific proteins (e.g., chimeric receptors) or genetically modified immunoresponsive cells that express such EMCN-specific proteins can be provided systemically or directly to a subject for the treatment of a proliferative disorder, such as a myeloid disorder. In certain embodiments, the composition is directly injected into an organ of interest (e.g., an organ affected by a disorder). Alternatively, the composition may be provided indirectly to the organ of interest, for example, by administration into the circulatory system (e.g., the tumor vasculature). Expansion and differentiation agents can be provided prior to, during, or after administration of the composition to increase production of T cells, NK cells, or CTL cells in vitro or in vivo.

Compositions comprising genetically modified cells of the present disclosure may be administered in any physiologically acceptable vehicle, for example intravascularly, although they may also be introduced into bone or other convenient sites where the genetically modified cells may find an appropriate site for regeneration and differentiation (e.g., thymus). In some embodiments, at least $1 \times 10^5$ cells may be administered, eventually reaching $1 \times 10^{10}$ or more cells. Compositions comprising genetically modified cells of the present disclosure can comprise a purified population of cells. Methods for determining the percentage of genetically modified cells in a population of cells are well known in the art and include, without limitation, fluorescence activated cell sorting (FACS). In some embodiments, the purity of genetically modified cells in a population of cells may be about 50%, about 55%, about 60%, or about 65%, about 70%, about 75%, about 80%, about 85%, about 90%, about 95%, about 97%, about 98%, about 99%, or more of the cells in the population of cells. Dosages can be readily adjusted by those skilled in the art (e.g., a decrease in purity may require an increase in dosage). The cells can be introduced by injection, catheter, or the like. In some embodiments, factors can also be included, for example, IL-2, IL-3, IL-6, IL-11, IL-7, IL-12, IL-15, IL-21, G-CSF, MCSF, GM-CSF, gamma-interferon, and erythropoietin.

In certain embodiments, the compositions are pharmaceutical compositions comprising genetically modified cells, such as immunoresponsive cells or their progenitors and a pharmaceutically acceptable carrier. Administration can be autologous or heterologous. For example, immunoresponsive cells, or progenitors can be obtained from one subject, and administered to the same subject or a different, compatible subject. In some embodiments, immunoresponsive cells of the present disclosure or their progeny may be derived from peripheral blood cells (e.g., in vivo, ex vivo, or in vitro derived) and may be administered via localized injection, including catheter administration, systemic injection, localized injection, intravenous injection, or parenteral administration. When administering a therapeutic composition of the present disclosure (e.g., a pharmaceutical composition containing a genetically modified cell of the present disclosure), it will generally be formulated in a unit dosage injectable form (solution, suspension, emulsion).

Formulations

Certain aspects of the present disclosure relate to formulations of compositions comprising EMCN-specific proteins (e.g., chimeric receptors) of the present disclosure or genetically modified cells (e.g., immunoresponsive cells of the present disclosure) expressing such proteins. In some embodiments, compositions of the present disclosure comprising genetically modified cells may be provided as sterile liquid preparations, including without limitation isotonic aqueous solutions, suspensions, emulsions, dispersions, and viscous compositions, which may be buffered to a selected pH. Liquid preparations are typically easier to prepare than gels, other viscous compositions, and solid compositions. Additionally, liquid compositions may be more convenient to administer, especially by injection. In some embodiments, viscous compositions can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (e.g., glycerol, propylene glycol, liquid polyethylene glycol, etc.) and suitable mixtures thereof.

In some embodiments, sterile injectable solutions can be prepared by incorporating genetically modified cells of the present disclosure in a sufficient amount of the appropriate solvent with various amounts of any other ingredients, as desired. Such compositions may be in admixture with a suitable carrier, diluent, or excipient such as sterile water, physiological saline, glucose, dextrose, or the like. In some embodiments, the compositions can also be lyophilized. The compositions can contain auxiliary substances such as wetting, dispersing agents, pH buffering agents, and antimicrobials depending upon the route of administration and the preparation desired.

In some embodiments, compositions of the present disclosure may further include various additives that may enhance the stability and sterility of the compositions. Examples of such additives include, without limitation, antimicrobial preservatives, antioxidants, chelating agents, and buffers. In some embodiments, microbial contamination may be prevented by the inclusions of any of various antibacterial and antifungal agents, including without limitation parabens, chlorobutanol, phenol, sorbic acid, and the like. Prolonged absorption of an injectable pharmaceutical formulation of the present disclosure can be brought about by the use of suitable agents that delay absorption, such as aluminum monostearate and gelatin.

In some embodiments, compositions of the present disclosure can be isotonic, i.e., having the same osmotic pressure as blood and lacrimal fluid. In some embodiments, the desired isotonicity may be achieved using, for example, sodium chloride, dextrose, boric acid, sodium tartrate, propylene glycol, or other inorganic or organic solutes.

In some embodiments, the components of the formulations of the present disclosure are selected to be chemically inert and to not affect the viability or efficacy of the genetically modified cells of the present disclosure.

One consideration concerning the therapeutic use of the genetically modified cells of the present disclosure is the quantity of cells needed to achieve optimal efficacy. In some embodiments, the quantity of cells to be administered will vary for the subject being treated. In certain embodiments, the quantity of genetically modified cells that are administered to a subject in need thereof may range from $1 \times 10^4$ cells to $1 \times 10^{10}$ cells. In some embodiments, the precise quantity of cells that would be considered an effective dose may be based on factors individual to each subject, including their size, age, sex, weight, and condition of the particular subject. Dosages can be readily ascertained by those skilled in the art based on the present disclosure and the knowledge in the art.

Heterologous Moieties and Modifications

In a further series of embodiments, the EMCN-specific proteins herein (e.g. an EMCN-specific chimeric protein including an antigen-binding domain having one or more of the amino acid sequences listed in Table A) include additional moieties and/or modifications.

Drug Conjugates

In various embodiments, the protein including the EMCN-specific antigen-binding domain as described herein is conjugated to a therapeutic agent (i.e. drug) to form an antibody-drug conjugate. Therapeutic agents include, but are not limited to, chemotherapeutic agents, imaging agents (e.g., radioisotopes), immune modulators (e.g., cytokines, chemokines, or checkpoint inhibitors), and toxins (e.g., cytotoxic agents). In certain embodiments, the therapeutic agents are attached to the antigen-binding domain through a linker peptide, as discussed in more detail herein.

Methods of preparing antibody-drug conjugates (ADCs) that can be adapted to conjugate drugs to the antigen-binding domains disclosed herein (e.g., having one or more of the amino acid sequences listed in Table A) are described, e.g., in U.S. Pat. No. 8,624,003 (pot method), U.S. Pat. No. 8,163,888 (one-step), U.S. Pat. No. 5,208,020 (two-step method), U.S. Pat. Nos. 8,337,856, 5,773,001, 7,829,531, 5,208,020, 7,745,394, WO 2017/136623, WO 2017/015502, WO 2017/015496, WO 2017/015495, WO 2004/010957, WO 2005/077090, WO 2005/082023, WO 2006/065533, WO 2007/030642, WO 2007/103288, WO 2013/173337, WO 2015/057699, WO 2015/095755, WO 2015/123679, WO 2015/157286, WO 2017/165851, WO 2009/073445, WO 2010/068759, WO 2010/138719, WO 2012/171020, WO 2014/008375, WO 2014/093394, WO 2014/093640, WO 2014/160360, WO 2015/054659, WO 2015/195925, WO 2017/160754, Storz (MAbs. 2015 November-December; 7(6): 989-1009), Lambert et al. (Adv Ther, 2017 34: 1015). Diamantis et al. (British Journal of Cancer, 2016, 114, 362-367), Carrico et al. (Nat Chem Biol, 2007. 3: 321-2), We et al. (Proc Natl Acad Sci USA, 2009. 106: 3000-5), Rabuka et al. (Curr Opin Chem Biol., 2011 14: 790-6), Hudak et al. (Angew Chem Int Ed Engl., 2012: 4161-5), Rabuka et al. (Nat Protoc., 2012 7:1052-67), Agarwal et al. (Proc Natl Acad Sci USA., 2013, 110: 46-51), Agarwal et al. (Bioconjugate Chem., 2013, 24: 846-851), Barfield et al. (Drug Dev. and D., 2014, 14:34-41), Drake et al. (Bioconjugate Chem., 2014, 25:1331-41), Liang et al. (J Am Chem Soc., 2014, 136:10850-3), Drake et al. (Curr Opin Chem Biol., 2015, 28:174-80), and York et al. (BMC Biotechnology, 2016, 16(1):23), each of which is hereby incorporated by reference in its entirety for all that it teaches.

Additional Binding Moieties

In various embodiments, the EMCN-specific chimeric protein includes an antigen-binding domain having one or more of the amino acid sequences listed in Table A and one or more additional binding moieties. In certain embodiments the binding moieties are antibody fragments or antibody formats including, but not limited to, full-length antibodies, Fab fragments, Fvs, scFvs, tandem scFvs, Diabodies, scDiabodies, DARTs, tandAbs, minibodies, camelid VHH, and other antibody fragments or formats known to those skilled in the art. Exemplary antibody and antibody fragment formats are described in detail in Brinkmann et al. (MABS, 2017, Vol. 9, No. 2, 182-212), herein incorporated by reference for all that it teaches.

In particular embodiments, the one or more additional binding moieties are attached to the C-terminus of one or more peptides of the EMCN-specific antigen-binding domain, such as the VH and/or VL, Fab heavy and/or light-chain fragment, or scFv. In particular embodiments, the one or more additional binding moieties are attached to the N-terminus of one or more peptides of the EMCN-specific antigen-binding domain, such as the VH and/or VL, Fab heavy and/or light-chain fragment, or scFv.

In certain embodiments, the one or more additional binding moieties are specific for a different antigen or epitope than EMCN. In certain embodiments, the one or more additional binding moieties are specific for EMCN.

In certain embodiments, the one or more additional binding moieties are attached to the antigen-binding domains described herein (e.g., having one or more of the amino acid sequences listed in Table A) using in vitro methods including, but not limited to, reactive chemistry (e.g., Click-chemistry) and affinity tagging systems. In certain embodiments, the one or more additional binding moieties are attached to the antigen-binding domains described herein (e.g., having one or more of the amino acid sequences listed in Table A) through Fc-mediated binding (e.g., Protein A/G). In certain embodiments, the one or more additional binding moieties are attached to the antigen-binding domains described herein (e.g., having one or more of the amino acid sequences listed in Table A) using recombinant DNA techniques, such as encoding the nucleotide sequence of the fusion product between the antigen-binding domains described herein and the additional binding moieties on the same expression vector (e.g., plasmid).

Functional/Reactive Groups

In various embodiments, the antigen-binding domains described herein (e.g., having one or more of the amino acid sequences listed in Table A) have modifications that comprise functional groups or chemically reactive groups that can be used in downstream processes, such as linking to additional moieties (e.g., drug conjugates and additional binding moieties) and downstream purification processes.

In certain embodiments, the modifications are chemically reactive groups including, but not limited to, reactive thiols (e.g., maleimide based reactive groups), reactive amines (e.g., N-hydroxysuccinimide based reactive groups), "click chemistry" groups (e.g. reactive alkyne groups), and aldehydes bearing formylglycine (FGly). In certain embodiments, the modifications are functional groups including, but not limited to, affinity peptide sequences (e.g., HA, HIS, FLAG, GST, MBP, and Strep systems etc.). In certain embodiments, the functional groups or chemically reactive groups have a cleavable peptide sequence. In particular embodiments, the cleavable peptide is cleaved by means including, but not limited to, photocleavage, chemical cleavage, protease cleavage, reducing conditions, and pH conditions. In particular embodiments, protease cleavage is carried out by intracellular proteases. In particular embodiments, protease cleavage is carried out by extracellular or membrane associated proteases. ADC therapies adopting protease cleavage are described in more detail in Choi et al. (Theranostics, 2012; 2(2): 156-178.), the entirety of which is hereby incorporated by reference for all it teaches.

Methods of Treatment

Certain aspects of the present disclosure relate to methods of using the proteins (e.g., chimeric receptors) and genetically modified cells of the present disclosure (e.g., immunoresponsive cells) that express such proteins (e.g., chimeric receptors) to treat subjects in need thereof. In some embodiments, the methods of the present disclosure are useful for treating cancer in a subject, such as a myeloid disorder. In some embodiments, the myeloid disorder is a myelodysplastic syndrome, a myeloproliferative neoplasm, a chronic myelomonocytic leukemia, acute myeloid leukemia (AML), acute myeloblastic leukemia, acute promyelocytic leukemia, acute myelomonocytic leukemia, chronic myelocytic leukemia, or polycythemia vera. In some embodiments, the myeloid disorder is AML. Other aspects of the present disclosure relate to use of the chimeric receptors and genetically modified cells of the present disclosure (e.g., immunoresponsive cells) that express such chimeric receptors in methods for treating a pathogen infection or other infectious disease in a subject, such as an immunocompromised human subject. In some embodiments, the methods of the present disclosure may comprise administering genetically modified cells of the present disclosure in an amount effective to achieve the desired effect, including without limitation palliation of an existing condition, prevention of a condition, treatment an existing condition, management of an existing condition, or prevention of recurrence or relapse of a condition. In some embodiments, the effective amount can be provided in one or a series of administrations of the genetically modified cells of the present disclosure (e.g., immunoresponsive cells). In some embodiments, an effective amount can be provided in a bolus or by continuous perfusion.

As disclosed herein, an "effective amount" or "therapeutically effective amount" is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the immunoresponsive cells administered.

For adoptive immunotherapy using antigen-specific cells (e.g., immunoresponsive cells such as T cells), cell doses in the range of about $1\times10^6$ to $1\times10^{10}$ cells (e.g., about $1\times10^9$ cells) are typically infused. Upon administration of the cells into the subject and subsequent differentiation, immunoresponsive cells are induced that are specifically directed against the specific antigen. In some embodiments, induction of immunoresponsive cells can include, without limitation, inactivation of antigen-specific cells such as by deletion or anergy. Inactivation is particularly useful to establish or reestablish tolerance such as in autoimmune disorders. The genetically modified cells can be administered by any method known in the art including, but not limited to, intravenous, subcutaneous, intranodal, intratumoral, intrathecal, intrapleural, intraperitoneal and directly to the thymus.

In some embodiments, methods of use encompass methods of inhibiting an immune response. Inhibiting an immune response can refer to preventing, attenuating, or inhibiting a cell-mediated immune response, such as, for example, induced by a chimeric receptor expressed on the surface of an immunomodulatory cell. In some embodiments, the methods include preventing, attenuating, or inhibiting activation of an activating chimeric receptor expressed on the surface of an immunomodulatory cell.

In some embodiments, a chimeric inhibitory receptor of the present disclosure is used to prevent, attenuate, inhibit, or suppress an immune response initiated by a tumor targeting chimeric receptor (e.g., an activating CAR). For example, an immunomodulatory cell expresses an inhibitory chimeric antigen that recognizes an antigen target 1 (e.g., a non-tumor antigen) and a tumor-targeting chimeric receptor that recognizes a different antigen target 2 (e.g., a tumor target). In this example, when the immunomodulatory cell contacts a target cell, the inhibitory and tumor targeting chimeric receptors may or may not bind to their cognate antigen. In a scenario of this example, where the target cell is a non-tumor cell that expresses both antigen target 1 and antigen target 2, both the inhibitory chimeric receptor and the tumor-targeting receptor can be activated. In such cases, the activation of the inhibitory chimeric receptor results in the prevention, attenuation, or inhibition of the tumor targeting chimeric receptor signaling and the immunomodulatory cell is not activated. Similarly, in exemplary instances where the target cell is a non-tumor cell that expresses only antigen target 1, only the inhibitory chimeric receptor can be activated. In contrast, in exemplary instances where the target cell is a tumor cell that expresses only antigen target 2, the inhibitory chimeric receptor cannot be activated while the tumor-targeting chimeric receptor can be activated, resulting in signal transduction that results in activation of the immunomodulatory cell.

Inhibition of an immune response initiated by a tumor targeting chimeric receptor can be an inhibition or reduction in the activation of the tumor targeting chimeric receptor, an inhibition or reduction in the signal transduction of a tumor targeting chimeric receptor, or an inhibition or reduction in the activation of the immunomodulatory cell. The inhibitory chimeric receptor can inhibit activation of the tumor targeting chimeric receptor, signal transduction by the tumor targeting chimeric receptor, or activation of the immunomodulatory cell by the tumor targeting chimeric receptor by about 1-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold or more as compared to the activation of the tumor targeting chimeric receptor, signal transduction, or activation of the immunomodulatory cell as compared to an immunomodulatory cell lacking an inhibitory chimeric receptor. In some embodiments, inhibition refers to a decrease or reduction of the activity of a tumor targeting chimeric receptor before or after it has been activated.

The immune response can be cytokine or chemokine production and secretion from an activated immunomodulatory cell. The immune response can be a cell-mediated immune response to a target cell.

In some embodiments, the chimeric inhibitory receptor is capable of suppressing cytokine production from an activated immunomodulatory cell. In some embodiments, the chimeric inhibitory receptor is capable of suppressing a cell-mediated immune response to a target cell, wherein the immune response is induced by activation of the immunomodulatory cell.

Therapeutic Treatment

In some embodiments, the methods of the present disclosure increase an immune response in a subject in need thereof. In some embodiments, the methods of the present disclosure include methods for treating and/or preventing a myeloid disorder in a subject. In some embodiments, the subject is a human. In some embodiments, suitable human subjects for therapy may comprise two treatment groups that can be distinguished by clinical criteria. Subjects with "advanced disease" or "high tumor burden" are those who bear a clinically measurable tumor. A clinically measurable tumor is one that can be detected on the basis of tumor mass (e.g., based on percentage of leukemic cells, by palpation, CAT scan, sonogram, mammogram or X-ray; positive biochemical or histopathologic markers on their own are insufficient to identify this population). In some embodiments, a pharmaceutical composition of the present disclosure is administered to these subjects to elicit an anti-tumor response, with the objective of palliating their condition. In some embodiments, reduction in tumor mass occurs as a result of administration of the pharmaceutical composition, but any clinical improvement will constitute a benefit. In some embodiments, clinical improvement includes decreased risk or rate of progression or reduction in pathological consequences of the tumor. In some embodiments, a second group of suitable human subjects are "adjuvant group" subjects. These subjects are individuals who have had a history of a myeloid disorder, but have been responsive to another mode of therapy. The prior therapy may have included, without limitation, surgical resection, radiotherapy, and/or traditional chemotherapy. As a result, these individuals have no clinically measurable tumor. However, they are suspected of being at risk for progression of the disease, either near the original tumor site, or by metastases. In some embodiments, this group can be further subdivided into high-risk and low-risk individuals. The subdivision can be made on the basis of features observed before or after the initial treatment. These features are known in the clinical arts, and are suitably defined for each different myeloid disorder. Features typical of high-risk subgroups are those in which the tumor has invaded neighboring tissues, or who show involvement of lymph nodes.

In any and all aspects of increasing an immune response as described herein, any increase or decrease or alteration of an aspect of characteristic(s) or function(s) is as compared to a cell not contacted with an immunoresponsive cell as described herein.

Increasing an immune response can be both enhancing an immune response or inducing an immune response. For instance, increasing an immune response encompasses both the start or initiation of an immune response, or ramping up or amplifying an on-going or existing immune response. In some embodiments, the treatment induces an immune response. In some embodiments, the induced immune response is an adaptive immune response. In some embodiments, the induced immune response is an innate immune response. In some embodiments, the treatment enhances an immune response. In some embodiments, the enhanced immune response is an adaptive immune response. In some embodiments, the enhanced immune response is an innate immune response. In some embodiments, the treatment increases an immune response. In some embodiments, the increased immune response is an adaptive immune response. In some embodiments, the increased immune response is an innate immune response.

In some embodiments, a further group of subjects are those having a genetic predisposition to a myeloid disorder, but that have not yet evidenced clinical signs of the myeloid disorder. For example, women testing positive for a genetic mutation associated with AML, but still of childbearing age, may benefit from receiving one or more of the cells of the present disclosure (e.g., immunoresponsive cells) in treatment prophylactically to prevent the occurrence of AML until it is suitable to perform preventive surgery. In some embodiments, the subjects can have an advanced form of disease, in which case the treatment objective can include mitigation or reversal of disease progression, and/or amelioration of side effects. In some embodiments, the subjects may have a history of the condition, for which they have already been treated, in which case the therapeutic objective may typically include a decrease or delay in the risk of recurrence.

Combination Therapies

In some embodiments, genetically modified cells of the present disclosure (e.g., immunoresponsive ells) expressing one or more proteins including an antigen-binding domain (e.g., scFv) of the present disclosure, such as a chimeric receptor of the present disclosure, may be used in combination with other known agents and therapies. In some embodiments, a combination therapy of the present disclosure comprises a genetically modified cells of the present disclosure that can be administered in combination with one or more additional therapeutic agents. In some embodiments, the genetically modified cell and the one or more additional therapeutic agents can be administered simultaneously, in the same or in separate compositions, or sequentially. For sequential administration, the genetically modified can be administered first, and the one or more additional agents can be administered second, or the order of administration can be reversed. In some embodiments, the genetically modified cells are further modified to express one or more additional therapeutic agents.

In some embodiments, a genetically modified cell of the present disclosure may be used in a treatment regimen in combination with surgery, chemotherapy, radiation, immunosuppressive agents (e.g., cyclosporin, azathioprine, methotrexate, mycophenolate, and FK506), antibodies, or other immunoablative agents (e.g., CAMPATH or anti-CD3 antibodies), cytoxin, fludarabme, cyclosporin, FK506, rapamycin, mycophenolic acid, steroids, FR901228, cytokines, irradiation, and peptide vaccines.

In some embodiments, a genetically modified cell of the present disclosure may be used in combination with a lymphodepleting agent. Suitable lymphodepleting agents reduce or decrease lymphocytes, e.g., B cell lymphocytes and/or T cell lymphocytes, prior to immunotherapy. Examples of suitable lymphodepleting agents include, without limitation, fludarabine, cyclophosphamide, corticosteroids, alemtuzumab, total body irradiation (TBI), and any combination thereof.

In some embodiments, a genetically modified cell of the present disclosure may be used in combination with a chemotherapeutic agent. Suitable chemotherapeutic agents include, without limitation, an anthracycline (e.g., doxorubicin), a *vinca* alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, tositumomab), an antimetabolite (e.g., folic acid antagonists, pyrimidine analogs, purine analogs and adenosine deaminase inhibitors, such as fludarabine), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide).

Examples of general chemotherapeutic agents suitable for use in combination therapies include, without limitation, anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idaniycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Examples of suitable alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®. Uracilmostaza®, Uramustin®, Uramustine®), chlormethine (Mustargen®), cyclophosphamide (Cytoxan®, Neosar®, Clafen®, Endoxan®, Procytox®, Rev Immune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamme (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Aitretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Examples of suitable mTOR inhibitors include, without limitation, temsirolimus, ridaforolimus (deferolimus), AP23573, MK8669, everolimus (Afimtor® or RADOOl), rapamycin (AY22989, Sirolmius®), and XL765.

Examples of suitable immunomodulators include, without limitation, afutuzumab, pegfilgrastim (Neulasta®), lenalidomide (CC-5013, Revlimid®), thalidomide (Thalomid®), actimid (CC4047), and IRX-2.

Examples of suitable anthracyclines include, without limitation, doxorubicin (Adriamycin® and Rubex®); bleomycin (Lenoxane®); daunorubicin (dauorubicin hydrochloride, daunomyem, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PES®); mitomycin C (Mutamycin®); geldanamycin; herbimycin; ravidomycin; and desacet lravidomycin.

Examples of suitable *vinca* alkaloids include, without limitation, vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbme®).

Examples of suitable proteosome inhibitors include, without limitation, bortezomib (Velcade®); carfilzomib; marizomib (NPI-0052); ixazomib citrate (MLN-9708); delanzomib (CEP-18770); and ONX-0912.

In some embodiments, a genetically modified cell of the present disclosure is administered in combination with a CD20 inhibitor, e.g., an anti-CD20 antibody, or fragment thereof. Exemplary anti-CD20 antibodies include, without limitation, rituximab, ofatumumab, ocrelizumab, veltuzumab, obinutuzumab, TRU-015 (Trubion Pharmaceuticals), ocaratuzumab, and Prol31921.

In some embodiments, a genetically modified cell of the present disclosure is administered in combination with an oncolytic virus. In some embodiments, oncolytic viruses are capable of selectively replicating in and triggering the death of or slowing the growth of a cancer cell. In some cases, oncolytic viruses have no effect or a minimal effect on non-cancer cells. Suitable oncolytic viruses include, without limitation, an oncolytic adenovirus, oncolytic Herpes Simplex Viruses, oncolytic retrovirus, oncolytic parvovirus, oncolytic vaccinia virus, oncolytic Sinbis virus, oncolytic influenza virus, or oncolytic RNA virus (e.g., oncolytic reovirus, oncolytic Newcastle Disease Virus (NDV), oncolytic measles virus, or oncolytic vesicular stomatitis virus (VSV)). In some embodiments, the oncolytic virus is a recombinant oncolytic virus.

In some embodiments, a genetically modified cell of the present disclosure is administered to a subject in combination with a protein tyrosine phosphatase inhibitor, e.g., a SHP-I inhibitor or a SHP-2 inhibitor. In one embodiment, a genetically modified cell of the present disclosure can be used in combination with a kinase inhibitor. Examples of suitable kinase inhibitors include, without limitation, CDK4 inhibitors, CDK4/6 inhibitors, BTK inhibitors, phosphatidylinositol 3-kinase (PI3K) inhibitors, mTOR inhibitors, MNK inhibitors, and anaplastic lymphoma kinase (ALK) inhibitors.

In some embodiments, a genetically modified cell of the present disclosure is administered to a subject in combination with a modulator of myeloid-derived suppressor cells (MDSCs). MDSCs accumulate in the periphery and at the tumor site of many solid tumors. These cells suppress T cell responses, thereby hindering the efficacy of chimeric receptor-expressing cell therapy. Without being bound by theory, it is believed that administration of a MDSC modulator enhances the efficacy of a genetically modified cell of the present disclosure. Examples of suitable modulators of MDSCs include, without limitation, MCS110 and BLZ945.

In some embodiments, a genetically modified cell of the present disclosure is administered to a subject in combination with an agent that inhibits or reduces the activity of immunosuppressive plasma cells. Immunosuppressive plasma cells have been shown to impede T cell-dependent immunogenic chemotherapy, such as oxaliplatin (Shalapour et al., Nature 2015, 521: 94-101). In one embodiment, immunosuppressive plasma cells can express one or more of IgA, interleukin (IL)-10, and PD-L1.

In some embodiments, a genetically modified cell of the present disclosure is administered to a subject in combination with an interleukin-15 (IL-15) polypeptide, an interleukin-15 receptor alpha (IL-I5Ra) polypeptide, or a combination of both an IL-15 polypeptide and an IL-15Ra polypeptide. In some embodiments, a genetically modified cell of the present disclosure is further modified to express an interleukin-15 (IL-15) polypeptide, an interleukin-15 receptor alpha (IL-I5Ra) polypeptide, or a combination of both an IL-15 polypeptide and an IL-15Ra polypeptide.

In some embodiments, a subject having a myeloid disorder (e.g., AML) is administered a genetically modified cell of the present disclosure in combination with an agent, e.g., cytotoxic or chemotherapy agent, a biologic therapy (e.g., antibody, e.g., monoclonal antibody, or cellular therapy), or an inhibitor (e.g., kinase inhibitor). In some embodiments, the subject is administered a genetically modified cell of the present disclosure in combination with a cytotoxic agent, e.g., CPX-351 (Celator Pharmaceuticals), cytarabme, daunorubicin, vosaroxin (Sunesis Pharmaceuticals), sapacitabine (Cyclacel Pharmaceuticals), idarubicin, or mitoxantrone. CPX-351 is a liposomal formulation comprising cytarabine and daunorubicin at a 5:1 molar ratio. In some embodiments, the subject is administered a chimeric receptor-expressing cell described herein in combination with a hypomethylating agent, e.g., a DNA methyltransferase inhibitor, e.g., azacytidine or decitabine. In some embodiments, the subject is administered a genetically modified cell of the present disclosure in combination with a biologic therapy, e.g., an antibody or cellular therapy, e.g., 225Aclintuzumab (Actimab-A; Actinium Pharmaceuticals), IPH2102 (Innate Pharma/Bristol Myers Squibb), SGN-CD33A (Seattle Genetics), or gemtuzumab ozogamicin (Mylotarg; Pfizer). In some embodiments, the subject is administered a genetically modified cell of the present disclosure in combination a FLT3 inhibitor, e.g., sorafenib (Bayer), midostaurin (Novartis), quizartinib (Daiichi Sankyo), crenoianib (Arog Pharmaceuticals), PLX3397 (Daiichi Sankyo), AKN-028 (Akinion Pharmaceuticals), or ASP2215 (Astelias). In some embodiments, the subject is administered a genetically modified cell of the present disclosure in combination with an isocitrate dehydrogenase (IDH) inhibitor, e.g., AG-221 (Celgene/Agios) or AG-120 (Agios/Celgene). In some embodiments, the subject is administered a genetically modified cell of the present disclosure in combination with a cell cycle regulator, e.g., inhibitor of polo-like kinase 1 (Plkl), e.g., volasertib (Boehringer Ingelheim); or an inhibitor of cyclin-dependent kinase 9 (Cdk9), e.g., alvocidib (Tolero Pharmaceuticals/Sanofi Aventis). In some embodiments, the subject is administered a genetically modified cell of the present disclosure in combination with a B cell receptor signaling network inhibitor, e.g., an inhibitor of B-cell lymphoma 2 (Bcl-2), e.g., venetoclax (Abbvie/Roche); or an inhibitor of Button's tyrosine kinase (Btk), e.g., ibrutinib (Pharmacyclics/Johnson & Johnson Janssen Pharmaceutical). In some embodiments, the subject is administered a genetically modified cell of the present disclosure in combination with an inhibitor of Miaminopeptidase; an inhibitor of histone deacetylase (HDAC), e.g., pracinostat (MEI Pharma); a multi-kinase inhibitor, e.g., rigosertib (Onconova Therapeutics/Baxter/SymBio); or a peptidic CXCR4 inverse agonist, e.g., BL-8040 (BioLineeRx).

In some embodiments, a subject can be administered an agent which enhances the activity or fitness of a genetically modified cell of the present disclosure. For example, the agent may inhibit a molecule that modulates or regulates, e.g., inhibits, T cell function. In some embodiments, the molecule that modulates or regulates T cell function is an inhibitory molecule. In some embodiments, inhibitory molecules, such as Programmed Death 1 (PD-1) can decrease the ability of the genetically modified cell to mount an immune effector response. Examples of suitable inhibitory molecules include, without limitation, PD-1, PD-L1, CTLA4, TIM3, CEACAM (e.g., CEACAM-1, CEACAM-3 and/or CEACAM-5), LAG3, VISTA, BTLA, TIGIT, LAIR1, CD 160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGF beta. Inhibition of a molecule that modulates or regulates, e.g., inhibits, T cell function, e.g., by inhibition at the DNA, RNA or protein level, can optimize the performance of genetically modified cells of the present disclosure. In some embodiments, an agent, e.g., an inhibitory nucleic acid, e.g., an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), can be used to inhibit expression of an inhibitory molecule in the genetically modified cell. In one embodiment, the inhibitor is an shRNA. In some embodiments, a genetically modified cell of the present disclosure may be further modified to express an inhibitory nucleic acid, e.g., an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), can be used to inhibit expression of an inhibitory molecule in the genetically modified cell.

In one embodiment, the agent that modulates or regulates, e.g., inhibits, T-cell function is inhibited within a genetically modified cell of the present disclosure. In such embodiments, a dsRNA molecule that inhibits expression of a molecule that modulates or regulates, e.g., inhibits, T-cell function is linked to the nucleic acid that encodes a component, e.g., all of the components, of a chimeric receptor of the present disclosure. In one embodiment, a nucleic acid molecule that encodes a dsRNA molecule that inhibits expression of the molecule that modulates or regulates, e.g., inhibits, T-cell function is operably linked to a promoter, e.g., a HI- or a U6-derived promoter such that the dsRNA molecule that inhibits expression of the molecule that modulates or regulates, e.g., inhibits, T-cell function is expressed, e.g., is expressed within a the genetically modified cell. In one embodiment the nucleic acid molecule that encodes a dsRNA molecule that inhibits expression of the molecule that modulates or regulates, e.g., inhibits, T-cell function is present on the same vector, e.g., a lentiviral vector, that comprises a nucleic acid molecule that encodes a component, e.g., all of the components, of the chimeric receptor. In such an embodiment the nucleic acid molecule that encodes a dsRNA molecule that inhibits expression of the molecule that modulates or regulates, e.g., inhibits, T-cell function is located on the vector, e.g., the lentiviral vector, 5'- or 3'- to the nucleic acid that encodes a component, e.g., all of the components, of the chimeric receptor. The nucleic acid molecule that encodes a dsRNA molecule that inhibits expression of the molecule that modulates or regulates, e.g., inhibits, T-cell function can be transcribed in the same or different direction as the nucleic acid that encodes a component, e.g., all of the components, of the chimeric receptor. In one embodiment the nucleic acid molecule that encodes a dsRNA molecule that inhibits expression of the molecule that modulates or regulates, e.g., inhibits, T-cell function is present on a vector other than the vector that comprises a nucleic acid molecule that encodes a component, e.g., all of the components, of the chimeric receptor. In one embodiment, the nucleic acid molecule that encodes a dsRNA molecule that inhibits expression of the molecule that modulates or regulates, e.g., inhibits, T-cell function it transiently expressed within the genetically modified cell. In one embodiment, the nucleic acid molecule that encodes a dsRNA molecule that inhibits expression of the molecule that modulates or regulates, e.g., inhibits, T-cell function is stably integrated into the genome of a genetically modified cell of the present disclosure.

In one embodiment, an agent that modulates or regulates, e.g., inhibits, T-cell function can be an antibody or antibody fragment that binds to an inhibitory molecule. For example, the agent can be an antibody or antibody fragment that binds to PD-1, PD-L1, PD-L2 or CTLA4. In one embodiment, the agent is an antibody or antibody fragment that binds to TIM3. In one embodiment, the agent is an antibody or antibody fragment that binds to LAG3.

In some embodiments, the agent which enhances the activity of the genetically modified cell is a CEACAM inhibitor (e.g., CEACAM-1, CEACAM-3, and/or CEACAM-5 inhibitor). In one embodiment, the inhibitor of CEACAM is an anti-CEACAM antibody molecule. In one embodiment, the agent which enhances activity of a genetically modified cell of the present disclosure is miR-17-92. In some embodiments, the agent which enhances the activity of the genetically modified cell is CD40L. In some embodiments, the agent which enhances the activity of the genetically modified cell is GM-CSF. In some embodiments, a genetically modified cell of the present disclosure is further modified to express an antibody or antibody fragment that binds to an inhibitory molecule of the present disclosure.

In one embodiment, the agent which enhances activity of a genetically modified cell of the present disclosure is a cytokine. Cytokines have important functions related to immunoresponsive cell expansion, differentiation, survival, and homeostats. Cytokines that can be administered to the subject receiving a genetically modified cell of the present disclosure include, without limitation, IL-2, IL-4, IL-7, IL-9, IIL-12, L-15, IL-18, and IL-21, or a combination thereof. The cytokine can be administered once a day or more than once a day, e.g., twice a day, three times a day, or four times a day. The cytokine can be administered for more than one day, e.g., the cytokine is administered for 2 days, 3 days, 4 days, 5 days, 6 days, 1 week, 2 weeks, 3 weeks, or 4 weeks. For example, the cytokine is administered once a day for 7 days. In some embodiments, a genetically modified cell of the present disclosure is further modified to express one or more cytokines, such as IL-2, IL-4, IL-7, IL-9, IL-12, L-15, IL-18, and IL-21.

In some embodiments, the cytokine can be administered simultaneously or concurrently with the genetically modified cells, e.g., administered on the same day. The cytokine may be prepared in the same pharmaceutical composition as the genetically modified cells, or may be prepared in a separate pharmaceutical composition. Alternatively, the cytokine can be administered shortly after administration of the genetically modified cells, e.g., 1 day, 2 days, 3 days, 4 days, 5 days, 6 days, or 7 days after administration of the genetically modified cells. In some embodiments where the cytokine is administered in a dosing regimen that occurs over more than one day, the first day of the cytokine dosing regimen can be on the same day as administration with the genetically modified cells, or the first day of the cytokine dosing regimen can be 1 day, 2 days, 3 days, 4 days, 5 days, 6 days, or 7 days after administration of the genetically modified cells. In one embodiment, on the first day, the genetically modified cells are administered to the subject, and on the second day, a cytokine is administered once a day for the next 7 days. In some embodiments, the cytokine is administered for a period of time after administration of the genetically modified cells, e.g., at least 2 weeks, 3 weeks, 4 weeks, 6 weeks, 8 weeks, 10 weeks, 12 weeks, 4 months, 5 months, 6 months, 7 months, 8 months, 9 months, 10 months, 11 months, or 1 year or more after administration of the genetically modified cells. In one embodiment, the cytokine is administered after assessment of the subject's response to the genetically modified cells.

Kits

Certain aspects of the present disclosure relate to kits for the treatment and/or prevention of a cancer (e.g., AML) or other diseases (e.g., immune-related or autoimmune disorders). In certain embodiments, the kit includes a therapeutic or prophylactic composition comprising an effective amount of one or more proteins including an antigen-binding domain (e.g., scFv) of the present disclosure, such as a chimeric receptor of the present disclosure, isolated nucleic acids of the present disclosure, vectors of the present disclosure, and/or cells of the present disclosure (e.g., immunoresponsive cells). In some embodiments, the kit comprises a sterile container. In some embodiments, such containers can be boxes, ampules, bottles, vials, tubes, bags, pouches, blister-packs, or other suitable container forms known in the art. The container may be made of plastic, glass, laminated paper, metal foil, or other materials suitable for holding medicaments.

In some embodiments, therapeutic or prophylactic composition is provided together with instructions for administering the therapeutic or prophylactic composition to a subject having or at risk of developing cancer (e.g., AML). In some embodiments, the instructions may include information about the use of the composition for the treatment and/or prevention of the disorder. In some embodiments, the instructions include, without limitation, a description of the therapeutic or prophylactic composition, a dosage schedule, an administration schedule for treatment or prevention of the disorder or a symptom thereof, precautions, warnings, indications, counter-indications, over-dosage information, adverse reactions, animal pharmacology, clinical studies, and/or references. In some embodiments, the instructions can be printed directly on the container (when present), or as a label applied to the container, or as a separate sheet, pamphlet, card, or folder supplied in or with the container.

EXEMPLARY EMBODIMENTS

1. A chimeric protein comprising an antigen-binding domain specific for endomucin (EMCN) and a heterologous molecule or moiety,
   wherein the antigen-binding domain comprises a heavy chain variable (VH) region and a light chain variable (VL) region, and
   wherein the VH comprises a heavy chain complementarity determining region 3 (CDR-H3) having the amino acid sequence of RIKD (SEQ ID NO: 4).

2. A chimeric protein comprising an antigen-binding domain specific for endomucin (EMCN) and a heterologous molecule or moiety,
   wherein the antigen-binding domain comprises a heavy chain variable (VH) region and a light chain variable (VL) region,
   wherein the VH comprises a heavy chain complementarity determining region 1 (CDR-H1), a heavy chain complementarity determining region 2 (CDR-H2), and a heavy chain complementarity determining region 3 (CDR-H3), and
   wherein the amino acid sequences of CDR-H1, CDR-H2, and CDR-H3 are contained within the VH region amino acid sequence of SEQ ID NO: 1, and optionally wherein the amino acid sequences of the CDR-H1, the CDR-H2, and the CDR-H3 of the reference antibody are defined based on the Kabat or Chothia numbering scheme.

3. A chimeric protein comprising an antigen-binding domain specific for endomucin (EMCN) and a heterologous molecule or moiety, wherein the antigen-binding domain comprises a heavy chain variable (VH) region and a light chain variable (VL) region, and wherein the VH comprises:

(a) a heavy chain complementarity determining region 1 (CDR-H1) having the amino acid sequence of GFSLSRY (SEQ ID NO: 2), a heavy chain complementarity determining region 2 (CDR-H2) having the amino acid sequence of WGNGN (SEQ ID NO: 3), and a heavy chain complementarity determining region 3 (CDR-H3) having the amino acid sequence of RIKD (SEQ ID NO: 4); or (b) a heavy chain complementarity determining region 1 (CDR-H1) having the amino acid sequence of RYDMH (SEQ ID NO: 102), a heavy chain complementarity determining region 2 (CDR-H2) having the amino acid sequence of VIWGNGNTHYHSALKS (SEQ ID NO: 103), and a heavy chain complementarity determining region 3 (CDR-H3) having the amino acid sequence of RIKD (SEQ ID NO: 4).

4. The chimeric protein of any one of embodiments 1-3, wherein the VL comprises a light chain complementarity determining region 1 (CDR-L1), a light chain complementarity determining region 2 (CDR-L2), and a light chain complementarity determining region 3 (CDR-L3), wherein the amino acid sequences of CDR-L1, CDR-L2, and CDR-L3 are contained within the VL region amino acid sequence of SEQ ID NO: 9.

5. The chimeric protein of any one of embodiments 1-4, wherein the VL comprises:

a light chain complementarity determining region 1 (CDR-L1) having the amino acid sequence of KSSQSLVASDENTYLN (SEQ ID NO: 10), a light chain complementarity determining region 2 (CDR-L2) having the amino acid sequence of QVSK-LDS (SEQ ID NO: 11), and a light chain complementarity determining region 3 (CDR-L3) having the amino acid sequence of LQGIHLPWT (SEQ ID NO: 12).

6. A chimeric protein comprising an antigen-binding domain specific for endomucin (EMCN) and a heterologous molecule or moiety, wherein the antigen-binding domain comprises a heavy chain variable (VH) region and a light chain variable (VL) region, wherein the VL comprises a light chain complementarity determining region 1 (CDR-L1), a light chain complementarity determining region 2 (CDR-L2), and a light chain complementarity determining region 3 (CDR-L3), and wherein the amino acid sequences of CDR-L1, CDR-L2, and CDR-L3 are contained within the VL region amino acid sequence of SEQ ID NO: 9.

7. A chimeric protein comprising an antigen-binding domain specific for endomucin (EMCN) and a heterologous molecule or moiety, wherein the antigen-binding domain comprises a heavy chain variable (VH) region and a light chain variable (VL) region, and wherein the VL comprises:

a light chain complementarity determining region 1 (CDR-L1) having the amino acid sequence of KSSQSLVASDENTYLN (SEQ ID NO: 10), a light chain complementarity determining region 2 (CDR-L2) having the amino acid sequence of QVSKLDS (SEQ ID NO: 11), and a light chain complementarity determining region 3 (CDR-L3) having the amino acid sequence of LQGIHLPWT (SEQ ID NO: 12).

8. The chimeric protein of embodiment 6 or embodiment 7, wherein the VH comprises a heavy chain complementarity determining region 1 (CDR-H1), a heavy chain complementarity determining region 2 (CDR-H2), and a heavy chain complementarity determining region 3 (CDR-H3), wherein the amino acid sequences of CDR-H1, CDR-H2, and CDR-H3 are contained within the VH region amino acid sequence of SEQ ID NO: 1.

9. The chimeric protein of any one of embodiments 6-8, wherein:

the VH comprises:

(a) a heavy chain complementarity determining region 1 (CDR-H1) having the amino acid sequence of GFSLSRY (SEQ ID NO: 2), a heavy chain complementarity determining region 2 (CDR-H2) having the amino acid sequence of WGNGN (SEQ ID NO: 3), and a heavy chain complementarity determining region 3 (CDR-H3) having the amino acid sequence of RIKD (SEQ ID NO: 4); or (b) a heavy chain complementarity determining region 1 (CDR-H1) having the amino acid sequence of RYDMH (SEQ ID NO: 102), a heavy chain complementarity determining region 2 (CDR-H2) having the amino acid sequence of VIWGNGNTHYHSALKS (SEQ ID NO: 103), and a heavy chain complementarity determining region 3 (CDR-H3) having the amino acid sequence of RIKD (SEQ ID NO: 4).

10. A chimeric protein comprising an antigen-binding domain specific for endomucin (EMCN) and a heterologous molecule or moiety, wherein the antigen-binding domain comprises a heavy chain variable (VH) region and a light chain variable (VL) region, wherein the VH comprises:

(a) a heavy chain complementarity determining region 1 (CDR-H1) having the amino acid sequence of GFSLSRY (SEQ ID NO: 2), a heavy chain complementarity determining region 2 (CDR-H2) having the amino acid sequence of WGNGN (SEQ ID NO: 3), and a heavy chain complementarity determining region 3 (CDR-H3) having the amino acid sequence of RIKD (SEQ ID NO: 4); or (b) a heavy chain complementarity determining region 1 (CDR-H1) having the amino acid sequence of RYDMH (SEQ ID NO: 102), a heavy chain complementarity determining region 2 (CDR-H2) having the amino acid sequence of VIWGNGNTHYHSALKS (SEQ ID NO: 103), and a heavy chain complementarity determining region 3 (CDR-H3) having the amino acid sequence of RIKD (SEQ ID NO: 4); and wherein the VL comprises:

> a light chain complementarity determining region 1 (CDR-L1) having the amino acid sequence of KSSQSLVASDENTYLN (SEQ ID NO: 10),
>
> a light chain complementarity determining region 2 (CDR-L2) having the amino acid sequence of QVSKLDS (SEQ ID NO: 11), and
>
> a light chain complementarity determining region 3 (CDR-L3) having the amino acid sequence of LQGIHLPWT (SEQ ID NO: 12).

11. The chimeric protein of any one of embodiments 1-10, wherein the VH region comprises an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO: 1.

12. The chimeric protein of any one of embodiments 1-11, wherein the VH region comprises the amino acid sequence of SEQ ID NO: 1.

13. The chimeric protein of any one of embodiments 1-12, wherein the VL region comprises an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO: 9.

14. The chimeric protein of any one of embodiments 1-12, wherein the VL region comprises the amino acid sequence of SEQ ID NO: 9.

15. A chimeric protein comprising an antigen-binding domain specific for endomucin (EMCN) and a heterologous molecule or moiety, > wherein the antigen-binding domain comprises a heavy chain variable (VH) region and a light chain variable (VL) region, and
>
> wherein the VH comprises an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO: 1.

16. The chimeric protein of embodiment 15, wherein the VH region comprises the amino acid sequence of SEQ ID NO: 1.

17. The chimeric of embodiment 15 or embodiment 16, wherein the VL region comprises an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO: 9.

18. The chimeric protein of embodiment 17, wherein the VL region comprises the amino acid sequence of SEQ ID NO: 9.

19. A chimeric protein comprising an antigen-binding domain specific for endomucin (EMCN) and a heterologous molecule or moiety, > wherein the antigen-binding domain comprises an antibody or antigen-binding fragment thereof,
>
> wherein the antibody or antigen-binding fragment thereof comprises a heavy chain variable (VH) region and a light chain variable (VL) region, and
>
> wherein the VL comprises an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO: 9.

20. The chimeric protein of embodiment 19, wherein the VL region comprises the amino acid sequence of SEQ ID NO: 9.

21. The chimeric protein of embodiment 19 or embodiment 20, wherein the VH region comprises the amino acid sequence of SEQ ID NO: 1.

22. A chimeric protein comprising an antigen-binding domain specific for endomucin (EMCN) and a heterologous molecule or moiety, > wherein the antigen-binding domain competes with a reference antibody or antigen-binding fragment thereof for binding to EMCN,
>
> wherein the reference antibody or antigen-binding fragment thereof comprises a heavy chain variable (VH) region and a light chain variable (VL) region,
>
> wherein the VH comprises:
>
>> a heavy chain complementarity determining region 1 (CDR-H1) having the amino acid sequence of GFSLSRY (SEQ ID NO: 2),
>>
>> a heavy chain complementarity determining region 2 (CDR-H2) having the amino acid sequence of WGNGN (SEQ ID NO: 3), and
>>
>> a heavy chain complementarity determining region 3 (CDR-H3) having the amino acid sequence of RIKD (SEQ ID NO: 4), and
>
> wherein the VL comprises:
>
>> a light chain complementarity determining region 1 (CDR-L1) having the amino acid sequence of KSSQSLVASDENTYLN (SEQ ID NO: 10),
>>
>> a light chain complementarity determining region 2 (CDR-L2) having the amino acid sequence of QVSKLDS (SEQ ID NO: 11), and
>>
>> a light chain complementarity determining region 3 (CDR-L3) having the amino acid sequence of LQGIHLPWT (SEQ ID NO: 12), and
>
> wherein the amino acid sequences of the CDR-H1, the CDR-H2, the CDR-H3, the CDR-L1, the CDR-L2, and the CDR-L3 of the reference antibody are defined based on the Chothia annotation and numbering scheme.

23. A chimeric protein comprising an antigen-binding domain specific for endomucin (EMCN) and a heterologous molecule or moiety, > wherein the antigen-binding domain binds essentially the same EMCN epitope as a reference antibody or antigen-binding fragment thereof,
>
> wherein the reference antibody or antigen-binding fragment thereof comprises a heavy chain variable (VH) region and a light chain variable (VL) region,
>
> wherein the VH comprises:
>
>> a heavy chain complementarity determining region 1 (CDR-H1) having the amino acid sequence of GFSLSRY (SEQ ID NO: 2),
>>
>> a heavy chain complementarity determining region 2 (CDR-H2) having the amino acid sequence of WGNGN (SEQ ID NO: 3), and
>>
>> a heavy chain complementarity determining region 3 (CDR-H3) having the amino acid sequence of RIKD (SEQ ID NO: 4), and
>
> wherein the VL comprises:
>
>> a light chain complementarity determining region 1 (CDR-L1) having the amino acid sequence of KSSQSLVASDENTYLN (SEQ ID NO: 10),
>>
>> a light chain complementarity determining region 2 (CDR-L2) having the amino acid sequence of QVSKLDS (SEQ ID NO: 11), and
>>
>> a light chain complementarity determining region 3 (CDR-L3) having the amino acid sequence of LQGIHLPWT (SEQ ID NO: 12),

73 wherein the amino acid sequences of the CDR-H1, the CDR-H2, the CDR-H3, the CDR-L1, the CDR-L2, and the CDR-L3 of the reference antibody are defined based on the Chothia annotation and numbering scheme.

24. A chimeric protein comprising an antigen-binding domain specific for endomucin (EMCN) and a heterologous molecule or moiety, wherein the antigen-binding domain binds an epitope of human EMCN that is the same as the EMCN epitope bound by a reference antibody or antigen-binding fragment thereof, wherein the reference antibody or antigen-binding fragment thereof comprises a heavy chain variable (VH) region and a light chain variable (VL) region, wherein the VH comprises:

a heavy chain complementarity determining region 1 (CDR-H1) having the amino acid sequence of GFSLSRY (SEQ ID NO: 2), a heavy chain complementarity determining region 2 (CDR-H2) having the amino acid sequence of WGNGN (SEQ ID NO: 3), and a heavy chain complementarity determining region 3 (CDR-H3) having the amino acid sequence of RIKD (SEQ ID NO: 4), and wherein the VL comprises:

a light chain complementarity determining region 1 (CDR-L1) having the amino acid sequence of KSSQSLVASDENTYLN (SEQ ID NO: 10), a light chain complementarity determining region 2 (CDR-L2) having the amino acid sequence of QVSKLDS (SEQ ID NO: 11), and a light chain complementarity determining region 3 (CDR-L3) having the amino acid sequence of LQGIHLPWT (SEQ ID NO: 12), wherein the amino acid sequences of the CDR-H1, the CDR-H2, the CDR-H3, the CDR-L1, the CDR-L2, and the CDR-L3 of the reference antibody are defined based on the Chothia annotation and numbering scheme.

25. The chimeric protein of any one of embodiments 22-24, wherein the VH region of the reference antibody or antigen-binding fragment thereof comprises the amino acid sequence of SEQ ID NO: 1.

26. The chimeric protein of any one of embodiments 22-25, wherein the VL region of the reference antibody or antigen-binding fragment thereof comprises the amino acid sequence of SEQ ID NO: 9.

27. The chimeric protein of any one of embodiments 1-26, wherein the antigen-binding domain comprises a F(ab) fragment, a F(ab') fragment, or a single chain variable fragment (scFV).

28. The chimeric protein of embodiment 27, wherein the antibody or antigen-binding fragment thereof comprises a single chain variable fragment (scFv).

29. The chimeric protein of any one of embodiments 1-28, wherein the VH and VL of the scFv are separated by a peptide linker.

30. The chimeric protein of any one of embodiments 1-29, wherein the antigen-binding domain comprises the structure VH-L-VL or VL-L-VH, wherein VH is the heavy chain variable domain, L is the peptide linker, and VL is the light chain variable domain.

31. The chimeric protein of embodiment 29 of embodiment 30, wherein the peptide linker comprises an amino acid sequence selected from the group consisting of: SEQ ID Nos:23-39.

32. The chimeric protein of embodiment 28 or embodiment 29, wherein the scFv comprises an amino acid sequence selected from the group consisting of: SEQ ID Nos: 17-22.

33. The chimeric protein of any one of embodiments 1-32, wherein the chimeric protein is an antibody-drug conjugate, and wherein the heterologous molecule or moiety comprises a therapeutic agent.

34. The chimeric protein of any one of embodiments 1-32, wherein the chimeric protein is a chimeric antigen receptor (CAR), and wherein the heterologous molecule or moiety comprises a polypeptide selected from the group consisting of: a transmembrane domain, one or more intracellular signaling domains, a hinge domain, a spacer region, one or more peptide linkers, and combinations thereof.

35. The chimeric protein of embodiment 34, wherein the CAR comprises a transmembrane domain.

36. The chimeric protein of embodiment 34 or embodiment 35, wherein the CAR comprises one or more intracellular signaling domains.

37. The chimeric protein of any one of embodiments 34-36, wherein the CAR is an activating CAR comprising one or more intracellular signaling domains that stimulate an immune response.

38. The chimeric protein of any one of embodiments 34-36, wherein the CAR is an inhibitory CAR comprising one or more intracellular inhibitory domains that inhibit an immune response.

39. The chimeric protein of embodiment 38, wherein the intracellular inhibitory domain comprises an enzymatic inhibitory domain.

40. The chimeric protein of embodiment 38, wherein the intracellular inhibitory domain comprises an intracellular inhibitory co-signaling domain.

41. The chimeric protein of any one of embodiments 35-40, wherein the CAR comprises a spacer region between the antigen-binding domain and the transmembrane domain.

42. The chimeric protein of embodiment 41, wherein the spacer region has an amino acid sequence selected from the group consisting of SEQ ID NOs:40-48.

43. A single chain variable fragment (scFv) specific for endomucin (EMCN), comprising a heavy chain variable (VH) region and a light chain variable (VL) region, wherein the VH comprises a heavy chain complementarity determining region 3 (CDR-H3) having the amino acid sequence of RIKD (SEQ ID NO: 4).

44. A single chain variable fragment (scFv) specific for endomucin (EMCN), wherein the antigen-binding domain comprises a heavy chain variable (VH) region and a light chain variable (VL) region, wherein the VH comprises a heavy chain complementarity determining region 1 (CDR-H1), a heavy chain complementarity determining region 2 (CDR-H2), and a heavy chain complementarity determining region 3 (CDR-H3), and wherein the amino acid sequences of CDR-H1, CDR-H2, and CDR-H3 are contained within the VH region amino acid sequence of SEQ ID NO: 1.

45. A single chain variable fragment (scFv) specific for endomucin (EMCN), wherein the antigen-binding domain comprises a heavy chain variable (VH) region and a light chain variable (VL) region, and wherein the VH comprises:

(a) a heavy chain complementarity determining region 1 (CDR-H1) having the amino acid sequence of GFSLSRY (SEQ ID NO: 2), a heavy chain complementarity determining region 2 (CDR-H2) having the amino acid sequence of WGNGN (SEQ ID NO: 3), and a heavy chain complementarity determining region 3 (CDR-H3) having the amino acid sequence of RIKD (SEQ ID NO: 4); or (b) a heavy chain complementarity determining region 1 (CDR-H1) having the amino acid sequence of RYDMH (SEQ ID NO: 102), a heavy chain complementarity determining region 2 (CDR-H2) having the amino acid sequence of VIWGNGNTHYHSALKS (SEQ ID NO: 103), and a heavy chain complementarity determining region 3 (CDR-H3) having the amino acid sequence of RIKD (SEQ ID NO: 4).

46. The scFv of any one of embodiments 43-45, wherein the VL comprises a light chain complementarity determining region 1 (CDR-L1), a light chain complementarity determining region 2 (CDR-L2), and a light chain complementarity determining region 3 (CDR-L3), wherein the amino acid sequences of CDR-L1, CDR-L2, and CDR-L3 are contained within the VL region amino acid sequence of SEQ ID NO: 9.

47. The scFv of any one of embodiments 43-46, wherein the VL comprises:

a light chain complementarity determining region 1 (CDR-L1) having the amino acid sequence of KSSQSLVASDENTYLN (SEQ ID NO: 10), a light chain complementarity determining region 2 (CDR-L2) having the amino acid sequence of QVSK-LDS (SEQ ID NO: 11), and a light chain complementarity determining region 3 (CDR-L3) having the amino acid sequence of LQGIHLPWT (SEQ ID NO: 12).

48. A single chain variable fragment (scFv) specific for endomucin (EMCN), wherein the antigen-binding domain comprises a heavy chain variable (VH) region and a light chain variable (VL) region, wherein the VL comprises a light chain complementarity determining region 1 (CDR-L1), a light chain complementarity determining region 2 (CDR-L2), and a light chain complementarity determining region 3 (CDR-L3), and wherein the amino acid sequences of CDR-L1, CDR-L2, and CDR-L3 are contained within the VL region amino acid sequence of SEQ ID NO: 9.

49. A single chain variable fragment (scFv) specific for endomucin (EMCN), wherein the antigen-binding domain comprises a heavy chain variable (VH) region and a light chain variable (VL) region, and wherein the VL comprises:

a light chain complementarity determining region 1 (CDR-L1) having the amino acid sequence of KSSQSLVASDENTYLN (SEQ ID NO: 10), a light chain complementarity determining region 2 (CDR-L2) having the amino acid sequence of QVSKLDS (SEQ ID NO: 11), and a light chain complementarity determining region 3 (CDR-L3) having the amino acid sequence of LQGIHLPWT (SEQ ID NO: 12).

50. The scFv of embodiment 48 or embodiment 49, wherein the VH comprises a heavy chain complementarity determining region 1 (CDR-H1), a heavy chain complementarity determining region 2 (CDR-H2), and a heavy chain complementarity determining region 3 (CDR-H3), wherein the amino acid sequences of CDR-H1, CDR-H2, and CDR-H3 are contained within the VH region amino acid sequence of SEQ ID NO: 1.

51. The scFv of any one of embodiments 48-50, wherein the VH comprises:

(a) a heavy chain complementarity determining region 1 (CDR-H1) having the amino acid sequence of GFSLSRY (SEQ ID NO: 2), a heavy chain complementarity determining region 2 (CDR-H2) having the amino acid sequence of WGNGN (SEQ ID NO: 3), and a heavy chain complementarity determining region 3 (CDR-H3) having the amino acid sequence of RIKD (SEQ ID NO: 4); or (b) a heavy chain complementarity determining region 1 (CDR-H1) having the amino acid sequence of RYDMH (SEQ ID NO: 102), a heavy chain complementarity determining region 2 (CDR-H2) having the amino acid sequence of VIWGNGNTHYHSALKS (SEQ ID NO: 103), and a heavy chain complementarity determining region 3 (CDR-H3) having the amino acid sequence of RIKD (SEQ ID NO: 4)

52. A single chain variable fragment (scFv) specific for endomucin (EMCN), wherein the antigen-binding domain comprises a heavy chain variable (VH) region and a light chain variable (VL) region, wherein the VH comprises:

(a) a heavy chain complementarity determining region 1 (CDR-H1) having the amino acid sequence of GFSLSRY (SEQ ID NO: 2), a heavy chain complementarity determining region 2 (CDR-H2) having the amino acid sequence of WGNGN (SEQ ID NO: 3), and a heavy chain complementarity determining region 3 (CDR-H3) having the amino acid sequence of RIKD (SEQ ID NO: 4); or (b) a heavy chain complementarity determining region 1 (CDR-H1) having the amino acid sequence of RYDMH (SEQ ID NO: 102), a heavy chain complementarity determining region 2 (CDR-H2) having the amino acid sequence of VIWGNGNTHYHSALKS (SEQ ID NO: 103), and a heavy chain complementarity determining region 3 (CDR-H3) having the amino acid sequence of RIKD (SEQ ID NO: 4), and wherein the VL comprises:

a light chain complementarity determining region 1 (CDR-L1) having the amino acid sequence of KSSQSLVASDENTYLN (SEQ ID NO: 10), a light chain complementarity determining region 2 (CDR-L2) having the amino acid sequence of QVSKLDS (SEQ ID NO: 11), and a light chain complementarity determining region 3 (CDR-L3) having the amino acid sequence of LQGIHLPWT (SEQ ID NO: 12).

53. The scFv of any one of embodiments 43-52, wherein the VH region comprises an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO: 1.

54. The scFv of any one of embodiments 43-53, wherein the VH region comprises the amino acid sequence of SEQ ID NO: 1.

55. The scFv of any one of embodiments 43-54, wherein the VL region comprises an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO: 9.

56. The scFv of any one of embodiments 43-55, wherein the VL region comprises the amino acid sequence of SEQ ID NO: 9.

57. A single chain variable fragment (scFv) specific for endomucin (EMCN),
 wherein the antigen-binding domain comprises a heavy chain variable (VH) region and a light chain variable (VL) region, and
 wherein the VH comprises an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO: 1.

58. The scFv of embodiment 57, wherein the VH region comprises the amino acid sequence of SEQ ID NO: 1.

59. The scFv of embodiment 57 or embodiment 58, wherein the VL region comprises an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO: 9.

60. The scFv of embodiment 59, wherein the VL region comprises the amino acid sequence of SEQ ID NO: 9.

61. A single chain variable fragment (scFv) comprising an antigen-binding domain specific for endomucin (EMCN),
 wherein the antigen-binding domain comprises an antibody or antigen-binding fragment thereof,
 wherein the antibody or antigen-binding fragment thereof comprises a heavy chain variable (VH) region and a light chain variable (VL) region, and
 wherein the VL comprises an amino acid sequence with at least 90%, at least 91%, at least 92%, at least 93%, at least 94%, at least 95%, at least 96%, at least 97%, at least 98%, at least 99%, or 100% identity to the amino acid sequence of SEQ ID NO: 9.

62. The scFv of embodiment 61, wherein the VL region comprises the amino acid sequence of SEQ ID NO: 9.

63. The scFv of embodiment 61 or embodiment 62, wherein the VH region comprises the amino acid sequence of SEQ ID NO: 1.

64. The scFv of any one of embodiments 43-63, wherein the scFv comprises an amino acid sequence selected from the group consisting of: SEQ ID NOs: 17-22.

65. A single chain variable fragment (scFv) comprising an antigen-binding domain specific for endomucin (EMCN),
 wherein the antigen-binding domain competes with a reference antibody or antigen-binding fragment thereof for binding to EMCN,
 wherein the reference antibody or antigen-binding fragment thereof comprises a heavy chain variable (VH) region and a light chain variable (VL) region,
 wherein the VH comprises:
  a heavy chain complementarity determining region 1 (CDR-H1) having the amino acid sequence of GFSLSRY (SEQ ID NO: 2), a heavy chain complementarity determining region 2 (CDR-H2) having the amino acid sequence of WGNGN (SEQ ID NO: 3), and
  a heavy chain complementarity determining region 3 (CDR-H3) having the amino acid sequence of RIKD (SEQ ID NO: 4), and
 wherein the VL comprises:
  a light chain complementarity determining region 1 (CDR-L1) having the amino acid sequence of KSSQSLVASDENTYLN (SEQ ID NO: 10),
  a light chain complementarity determining region 2 (CDR-L2) having the amino acid sequence of QVSKLDS (SEQ ID NO: 11), and
  a light chain complementarity determining region 3 (CDR-L3) having the amino acid sequence of LQGIHLPWT (SEQ ID NO: 12),
 wherein the amino acid sequences of the CDR-H1, the CDR-H2, the CDR-H3, the CDR-L1, the CDR-L2, and the CDR-L3 of the reference antibody are defined based on the Chothia annotation and numbering scheme.

66. A single chain variable fragment (scFv) comprising an antigen-binding domain specific for endomucin (EMCN),
 wherein the antigen-binding domain binds essentially the same EMCN epitope as a reference antibody or antigen-binding fragment thereof,
 wherein the reference antibody or antigen-binding fragment thereof comprises a heavy chain variable (VH) region and a light chain variable (VL) region,
 wherein the VH comprises:
  a heavy chain complementarity determining region 1 (CDR-H1) having the amino acid sequence of GFSLSRY (SEQ ID NO: 2),
  a heavy chain complementarity determining region 2 (CDR-H2) having the amino acid sequence of WGNGN (SEQ ID NO: 3), and
  a heavy chain complementarity determining region 3 (CDR-H3) having the amino acid sequence of RIKD (SEQ ID NO: 4), and
 wherein the VL comprises:
  a light chain complementarity determining region 1 (CDR-L1) having the amino acid sequence of KSSQSLVASDENTYLN (SEQ ID NO: 10),
  a light chain complementarity determining region 2 (CDR-L2) having the amino acid sequence of QVSKLDS (SEQ ID NO: 11), and
  a light chain complementarity determining region 3 (CDR-L3) having the amino acid sequence of LQGIHLPWT (SEQ ID NO: 12),
 wherein the amino acid sequences of the CDR-H1, the CDR-H2, the CDR-H3, the CDR-L1, the CDR-L2, and the CDR-L3 of the reference antibody are defined based on the Chothia annotation and numbering scheme.

67. A single chain variable fragment (scFv) comprising an antigen-binding domain specific for endomucin (EMCN),
 wherein the antigen-binding domain binds an epitope of human EMCN that is the same as the EMCN epitope bound by a reference antibody or antigen-binding fragment thereof,
 wherein the reference antibody or antigen-binding fragment thereof comprises a heavy chain variable (VH) region and a light chain variable (VL) region,
 wherein the VH comprises:
  a heavy chain complementarity determining region 1 (CDR-H1) having the amino acid sequence of GFSLSRY (SEQ ID NO: 2), a heavy chain complementarity determining region 2 (CDR-H2) having the amino acid sequence of WGNGN (SEQ ID NO: 3), and a heavy chain complementarity determining region 3 (CDR-H3) having the amino acid sequence of RIKD (SEQ ID NO: 4), and wherein the VL comprises:

a light chain complementarity determining region 1 (CDR-L1) having the amino acid sequence of KSSQSLVASDENTYLN (SEQ ID NO: 10), a light chain complementarity determining region 2 (CDR-L2) having the amino acid sequence of QVSKLDS (SEQ ID NO: 11), and wherein the amino acid sequences of the CDR-H1, the CDR-H2, the CDR-H3, the CDR-L1, the CDR-L2, and the CDR-L3 of the reference antibody are defined based on the Chothia annotation and numbering scheme.

68. The scFv of any one of embodiments 65-67, wherein the VH region of the reference antibody or antigen-binding fragment thereof comprises the amino acid sequence of SEQ ID NO: 1.

69. The scFv of any one of embodiments 65-68, wherein the VL region of the reference antibody or antigen-binding fragment thereof comprises the amino acid sequence of SEQ ID NO: 9.

70. A composition comprising the chimeric protein of any one of embodiments 1-42 and a pharmaceutically acceptable carrier, pharmaceutically acceptable excipient, or a combination thereof.

71. A composition comprising the scFv of any one of embodiments 43-69 and a pharmaceutically acceptable carrier, pharmaceutically acceptable excipient, or a combination thereof.

72. An engineered nucleic acid encoding the chimeric protein of any one of embodiments 1-42.

73. An engineered nucleic acid encoding the scFv of any one of embodiments 43-69.

74. An expression vector comprising the engineered nucleic acid of embodiment 72.

75. An expression vector comprising the engineered nucleic acid of embodiment 73.

76. A composition comprising the engineered nucleic acid of embodiment 72 or the expression vector of embodiment 74, and a pharmaceutically acceptable carrier, pharmaceutically acceptable excipient, or a combination thereof.

77. A composition comprising the engineered nucleic acid of embodiment 73 or the expression vector of embodiment 75, and a pharmaceutically acceptable carrier, pharmaceutically acceptable excipient, or a combination thereof.

78. A method of making an engineered cell, comprising transducing an isolated cell or population of cells with the engineered nucleic acid of embodiment 72 or the expression vector of embodiment 74.

79. A method of making an engineered cell, comprising transducing an isolated cell or population of cells with the engineered nucleic acid of embodiment 73 or the expression vector of embodiment 75.

80. An engineered cell produced by the method of embodiment 78.

81. An engineered cell produced by the method of embodiment 79.

82. An isolated cell comprising the engineered nucleic acid of embodiment 72, the expression vector of embodiment 74, or the composition of embodiment 76.

83. An isolated cell comprising the engineered nucleic acid of embodiment 73, the expression vector of embodiment 75, or the composition of embodiment 77.

84. A population of engineered cells expressing the engineered nucleic acid of embodiment 72, the expression vector of embodiment 74.

85. A population of engineered cells expressing the engineered nucleic acid of embodiment 73, the expression vector of embodiment 75.

86. An isolated cell comprising the chimeric protein of any one of embodiments 1-42.

87. An isolated cell comprising the scFv of any one of embodiments 43-69.

88. A population of engineered cells expressing the chimeric protein of any one of embodiments 1-42.

89. A population of engineered cells expressing the scFv of any one of embodiments 43-69.

90. The cell or population of cells of any one of embodiments 80, 82, 84, 86, and 88, wherein the chimeric protein is recombinantly expressed.

91. The cell or population of cells of any one of embodiments 81, 83, 85, 87, and 89, wherein the scFv is recombinantly expressed.

92. The cell or population of cells of any one of embodiments 80, 82, 84, 86, 88 and 90, wherein the chimeric protein is expressed from a vector or a selected locus from the genome of the cell.

93. The cell or population of cells of any one of embodiments 81, 83, 85, 87, 89, and 91, wherein the chimeric protein is expressed from a vector or a selected locus from the genome of the cell.

94. The cell or population of cells of any one of embodiments 80, 82, 84, 86, 88, 90, and 92, wherein the cell or population of cells further comprises one or more tumor-targeting chimeric receptors expressed on the cell surface.

95. The cell or population of cells of embodiment 94, wherein each of the one or more tumor-targeting chimeric receptors is a chimeric antigen receptor (CAR) or an engineered T cell receptor.

96. The cell or population of cells of embodiment 94 or 95, wherein the cell or population of cells comprises a first tumor targeting chimeric receptor targeting a first tumor-associated antigen, and a second tumor targeting chimeric receptor targeting a second tumor-associated antigen.

97. The cell or population of cells of embodiment 96, wherein the first tumor-associated antigen comprises CD33 and the second tumor-associated antigen comprises FLT3.

98. The cell or population of cells of embodiment 94 or 95, wherein the one or more tumor-targeting chimeric receptors comprises a tumor-targeting chimeric receptor that targets CD33 and FLT3.

99. The cell or population of cells of any one of embodiments 80, 82, 84, 86, 88, 90, 92, and 94-98, wherein the cell or population of cells is selected from the group consisting of: a T cell, a CD8+ T cell, a CD4+ T cell, a gamma-delta T cell, a cytotoxic T lymphocyte (CTL), a regulatory T cell, a viral-specific T cell, a Natural Killer T (NKT) cell, a Natural Killer (NK) cell, a B cell, a tumor-infiltrating lymphocyte (TIL), an innate lymphoid cell, a mast cell, an eosinophil, a basophil, a neutrophil, a myeloid cell, a macrophage, a monocyte, a dendritic cell, an erythrocyte, a platelet cell, a human embryonic stem cell (ESC), an ESC-derived cell, a pluripotent stem cell, a mesenchymal stromal cell (MSC), an induced pluripotent stem cell (iPSC), and an iPSC-derived cell.

100. The cell or population of cells of any one of embodiments 80, 82, 84, 86, 88, 90, 92, and 94-98, wherein the cell or population of cells is an NK cell.

101. The cell or population of cells of any one of embodiments 80, 82, 84, 86, 88, 90, 92, and 94-100, wherein the cell is autologous.

102. The cell or population of cells of any one of embodiments 80, 82, 84, 86, 88, 90, 92, and 94-100, wherein the cell is allogeneic.

103. A pharmaceutical composition comprising an effective amount of the cell or population of engineered cells of any one of embodiments 80, 82, 84, 86, 88, 90, 92, and 94-102 and a pharmaceutically acceptable carrier, pharmaceutically acceptable excipient, or a combination thereof.

104. A pharmaceutical composition comprising an effective amount of genetically modified cells expressing the chimeric protein of any one of embodiments 1-42 and a pharmaceutically acceptable carrier, pharmaceutically acceptable excipient, or a combination thereof.

105. The pharmaceutical composition of embodiment 103 or embodiment 104, which is for treating and/or preventing a tumor.

106. A method of treating a subject in need thereof, the method comprising administering a therapeutically effective dose of the composition of embodiment 70 or embodiment 76, or any of the cells of any one of embodiments 80, 82, 84, 86, 88, 90, 92, and 94-102, or the composition of embodiment 103 or embodiment 104.

107. A method of stimulating a cell-mediated immune response to a tumor cell in a subject, the method comprising administering to a subject having a tumor a therapeutically effective dose of the composition of embodiment 70 or embodiment 76, or any of the cells of any one of embodiments 80, 82, 84, 86, 88, 90, 92, and 94-102, or the composition of embodiment 103 or embodiment 104.

108. A method of inhibiting a cell-mediated immune response to a tumor cell in a subject, the method comprising administering to a subject having a tumor a therapeutically effective dose of the composition of embodiment 70 or embodiment 76, or any of the cells of any one of embodiments 80, 82, 84, 86, 88, 90, 92, and 94-102, or the composition of embodiment 103 or embodiment 104.

109. The method of embodiment 108 comprising administering to the subject any of the cell of any one of embodiments 80, 82, 84, 86, 88, 90, 92, and 94-102, wherein the isolated cell or population of cells express the chimeric protein comprising the inhibitory CAR of embodiment 38.

110. A method of treating a subject having a tumor, the method comprising administering a therapeutically effective dose of the composition of embodiment 76 or embodiment 76, or any of the cells of any one of embodiments 80, 82, 84, 86, 88, 90, 92, and 94-102, or the composition of embodiment 103 or embodiment 104.

111. The method of any one of embodiments 106-107 and 110, wherein the chimeric protein comprises an inhibitory CAR of any one of embodiments 38-40, and the cell or population of cells further express one or more tumor-targeting chimeric receptors.

112. The method of embodiment 111, wherein the method results in reduced off-target effects as compared to a method of administering an equivalent composition including a cell or population of cells comprising the one or more tumor-targeting chimeric receptors but lacking the inhibitory CAR.

113. A kit for treating and/or preventing a tumor, comprising the chimeric protein of any one of embodiments 1-42.

114. The kit of embodiment 113, wherein the kit further comprises written instructions for using the chimeric protein for producing one or more antigen-specific cells for treating and/or preventing a tumor in a subject.

115. A kit for treating and/or preventing a tumor, comprising the cell or population of cells of any one of embodiments 80, 82, 84, 86, 88, 90, 92, and 94-102.

116. The kit of embodiment 115, wherein the kit further comprises written instructions for using the cell for treating and/or preventing a tumor in a subject.

117. A kit for treating and/or preventing a tumor, comprising the engineered nucleic acid of embodiment 72.

118. The kit of embodiment 117, wherein the kit further comprises written instructions for using the nucleic acid for producing one or more antigen-specific cells for treating and/or preventing a tumor in a subject.

119. A kit for treating and/or preventing a tumor, comprising the vector of embodiment 74.

120. The kit of embodiment 119, wherein the kit further comprises written instructions for using the vector for producing one or more antigen-specific cells for treating and/or preventing a tumor in a subject.

121. A kit for treating and/or preventing a tumor, comprising the composition of any one of embodiments 74, 76, and 103-105.

122. The kit of embodiment 121, wherein the kit further comprises written instructions for using the composition for treating and/or preventing a tumor in a subject.

EXAMPLES

The following are examples of methods and compositions of the present disclosure. It is understood that various other embodiments may be practiced, given the general description provided herein.

Below are examples of specific embodiments for carrying out the claimed subject matter of the present disclosure. The examples are offered for illustrative purposes only and are not intended to limit the scope of the present disclosure in any way. Efforts have been made to ensure accuracy with respect to numbers used (e.g., amounts, temperatures, etc.), but some experimental error and deviation should, of course, be allowed for.

Example 1: Anti-EMCN Antibody Sequence Determination

Methods

Antibody Sequencing

Rat anti-human EMCN monoclonal antibody clone Ab1 was sequenced. Briefly, samples containing each of the immunoglobulin chains were digested by various enzymes then analyzed by LC-MS/MS. Peptides were characterized from LC-MS/MS data using de novo peptide sequencing and then assembled into antibody sequences.

Results

The Ab1 anti-EMCN antibody was peptide sequenced. LC-MS/MS data of multiple enzyme digestions were mapped to the assembled antibody sequences. In the heavy chain and light chain, 100% of amino acid residues were covered by at least 5 peptide scans, with significant supporting fragment ions (data not shown).

Sequencing results for the light-chain and heavy-chain variable regions are shown in FIG. 1 and FIG. 2, respectively, with the Chothia annotation and numbering scheme. The framework and complementarity determining regions (CDRs) are annotated according to the Chothia annotation and numbering scheme as well as the Kabat annotation and numbering scheme. Sequences are presented in Table A. Given Leucine (L) and Isoleucine (I) have same residue mass, determination of the two amino acids was determined by additional analysis.

TABLE A

| Anti-EMCN Antibody (Ab1) Sequences | | |
|---|---|---|
| Amino Acid Sequence | SEQ ID NO: | Description |
| QVQLKESGPGLVQPSQTLSLTCTVSGFSLSRYDMHWV RQPPGQGLEWMGVIWGNGNTHYHSALKSRLSISRDTS KSQVFLKMNSLQTEDTAIYFCTLRIKDWGPGTMVTVSS | 1 | anti-EMCN antibody Ab1 heavy chain variable (VH) region |
| GFSLSRY | 2 | anti-EMCN antibody Ab1 heavy chain complementarity determining region 1 (CDR-H1) sequence based on Chothia numbering |
| RYDMH | 102 | anti-EMCN antibody Ab1 heavy chain complementarity determining region 1 (CDR-H1) sequence based on Kabat numbering |
| WGNGN | 3 | anti-EMCN antibody Ab1 heavy chain complementarity determining region 2 (CDR-H2) sequence based on Chothia numbering |
| VIWGNGNTHYHSALKS | 103 | anti-EMCN antibody Ab1 heavy chain complementarity determining region 2 (CDR-H2) sequence based on Kabat numbering |
| RIKD | 4 | anti-EMCN antibody Ab1 heavy chain complementarity determining region 3 (CDR-H3) sequence based on Chothia and Kabat numbering |
| QVQLKESGPGLVQPSQTLSLTCTVS | 5 | anti-EMCN antibody Ab1 heavy chain framework region 1 (HFR1) sequence based on Chothia numbering |
| QVQLKESGPGLVQPSQTLSLTCTVSGFSLS | 104 | anti-EMCN antibody Ab1 heavy chain framework region 1 (HFR1) sequence based on Kabat numbering |
| DMHWVRQPPGQGLEWMGVI | 6 | anti-EMCN antibody Ab1 heavy chain framework region 2 (HFR2) sequence based on Chothia numbering |
| WVRQPPGQGLEWMG | 105 | anti-EMCN antibody Ab1 heavy chain framework region 2 (HFR2) sequence based on Kabat numbering |
| THYHSALKSRLSISRDTSKSQVFLKMNSLQTEDTAIYFC TL | 7 | anti-EMCN antibody Ab1 heavy chain framework region 3 (HFR3) sequence based on Chothia numbering |
| RLSISRDTSKSQVFLKMNSLQTEDTAIYFCTL | 106 | anti-EMCN antibody Ab1 heavy chain framework region 3 (HFR3) sequence based on Kabat numbering |
| WGPGTMVTVSS | 8 | anti-EMCN antibody Ab1 heavy chain framework region 4 (HFR4) sequence based on Chothia and Kabat numbering |

TABLE A-continued

Anti-EMCN Antibody (Ab1) Sequences

| Amino Acid Sequence | SEQ ID NO: | Description |
|---|---|---|
| DIVMTQTPPSLSVALGQSVSISCKSSQSLVASDENTYLN WLLQSPGRSPKRLIYQVSKLDSGVPDRFSGSGSEKDFT LKISRVEAEDLGVYYCLQGIHLPWTFGGGTKLELK | 9 | anti-EMCN antibody Ab1 light chain variable (VL) region |
| KSSQSLVASDENTYLN | 10 | anti-EMCN antibody Ab1 light chain complementarity determining region 1 (CDR-L1) sequence based on Chothia and Kabat numbering |
| QVSKLDS | 11 | anti-EMCN antibody Ab1 light chain complementarity determining region 2 (CDR-L2) sequence based on Chothia and Kabat numbering |
| LQGIHLPWT | 12 | anti-EMCN antibody Ab1 light chain complementarity determining region 3 (CDR-L3) sequence based on Chothia and Kabat numbering |
| DIVMTQTPPSLSVALGQSVSISC | 13 | anti-EMCN antibody Ab1 light chain framework region 1 (LFR1) sequence based on Chothia and Kabat numbering |
| WLLQSPGRSPKRLIY | 14 | anti-EMCN antibody Ab1 light chain framework region 2 (LFR2) sequence based on Chothia and Kabat numbering |
| GVPDRFSGSGSEKDFTLKISRVEAEDLGVYYC | 15 | anti-EMCN antibody Ab1 light chain framework region 3 (LFR3) sequence based on Chothia and Kabat numbering |
| FGGGTKLELK | 16 | anti-EMCN antibody Ab1 light chain framework region 4 (LFR4) sequence based on Chothia and Kabat numbering |

Example 2: Generation of EMCN Target Cells

Methods

Lentiviral Production

A lentiviral vector encoding human endomucin (Origene Cat. No. RC215698L4; Lenti ORF clone of Human endomucin (EMCN), transcript variant 1, mGFP) was used to generate EMCN expressing cell lines. Lentivirus was produced using: Lenti-X 293T packaging cell line (Clontech, Cat #632180); LX293T Complete growth medium, without antibiotics; DMEM, hi-glucose; 1 mM Sodium Pyruvate; 10% FBS, heat-inactivated; Opti-Mem I Reduced Serum Media (Gibco/Thermo Fisher; Cat #31985); FuGene HD (Promega, Cat #E2311); Envelope, Packaging, and Transfer Vector plasmids; VSV-G-pseudotyped envelope vector (pMD2.G); Packaging vector that contains Gag, Pol, Rev, and Tat that can be used with 2nd and 3rd generation transfer vectors (psMAX2). 293T(FT) cells from 90% confluent 10 cm dishes were lifted and dispensed at 1:3 dilution late in the afternoon the day before transfection and incubated cells as normal overnight at 37° C., 5% CO2 (cells should be 60-85% confluent the next day at time of transfection).

A transfection reaction was prepped for each 10 cm dish according to the protocol below:

1. Prep transfection reaction for each 10 cm dish in a separate 1.7 mL tube.
2. Add 900 uL Opti-Mem I at RT.
3. Add 9 ug vector backbone (containing gene of interest) per reaction.
4. Add 8 ug packaging vector per reaction.
5. Add 1 ug envelope vector per reaction (pMD2.G).
6. Mix thoroughly by quickly vortexing for 3 seconds.
7. Add 55 uL Fugene HD per reaction.
8. Mix by quickly pipetting up and down 20-30 times.
9. Let sit at RT for 10 min (allowing DNA complexes to form).
10. Slowly add mixture in dropwise manner around the dish, then mix by gently rocking back-forth and up-down for 5-10 seconds (do not swirl).
11. Place dish into virus incubator.

Viral supernatants were harvested on days 2 and 3 using a serological pipette. Cellular debris was removed using a Millipore steriflip 0.45 um filters. A Lenti-X Concentrator (Cat. Nos. 631231 & 631232) was used according to the protocol: 1) Combine 1 volume of Lenti-X Concentrator with 3 volumes of clarified supernatant. Mix by gentle inversion; 2) Incubate mixture on ice or at 4° C. for 30 minutes to overnight; (3) Centrifuge sample at 1,500×g for 45 minutes at 4° C.; (4) Carefully remove and discard supernatant, taking care not to disturb the pellet; (5) Gently resuspend the pellet in ⅒ to ⅟₁₀₀th of the original volume using sterile PBS+0.1% BSA.

Lentiviral Transduction

The Molm13 cell line was obtained from AddexBio (Cat. No. C0003003) and the SEM cell line was obtained from the German Collection of Microorganisms and Cell Culture GmbH (DSMZ No. ACC 546).

Lentiviral transduction of cell lines was performed according to the protocol below:

1. Plate 0.5-1 million cells (500 uL) in a 24-well plate for each cell line and condition (in RPMI+1% FBS)
2. Transduce 400K virus to each cell line except No Virus transduction control
3. Transfer virus (stored in −80 C) to a 1.5 mL eppendorf tube
4. Add 2.5 uL of LentiBlast-A to virus tube and mix well. Add 2.5 uL LentiBlast-B and mix well
5. Set centrifuge to 32 C, 4000×rpm for 10 min. to warm up
6. Add virus to cells in the plate and mix 10×
7. Parafilm wrap the outside of plates
8. Set plate in centrifuge for 1 hr. at 800×g, 32 C
9. After spin, add an extra 500 uL of 1% FBS RPMI media to wells
10. Place in 37° C. incubator overnight
11. Add 3 mL fresh complete media (10% FBS+RPMI) and transfer to a 6-well plate the next day Puromycin Selection Transduced cells were selected in 0.5-3.33 μg/mL Puromycin in 10% FBS+RPMI media. Puromycin was added 5. Wash 1× with FACS buffer and resuspend in 200 uL FACS buffer before acquiring on the Cytoflex flow cytometer.

Results

Figure 3B:
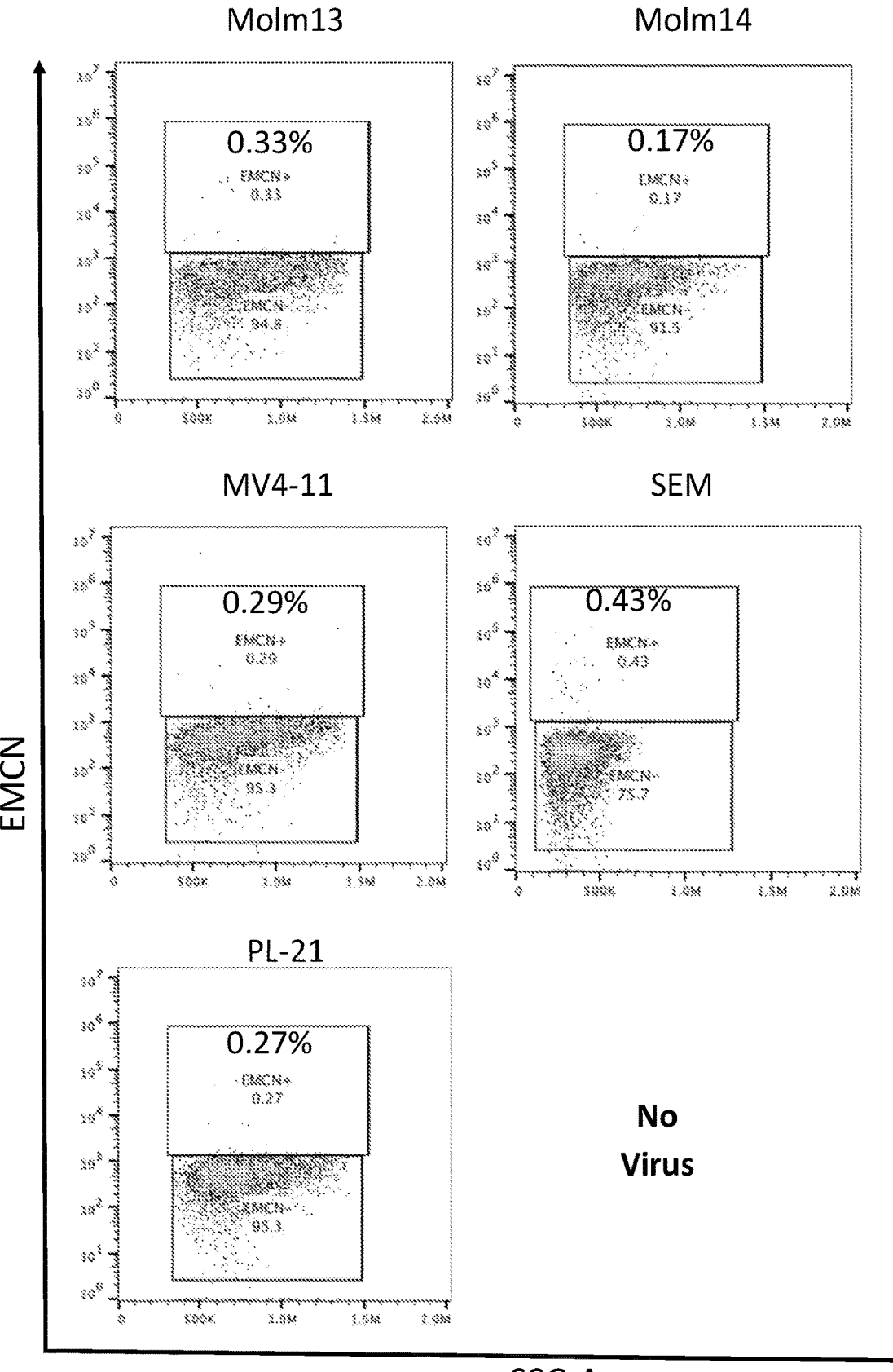
FIG. 3B. No Virus transduction control cell lines showing baseline EMCN expression.
Figure 3C:
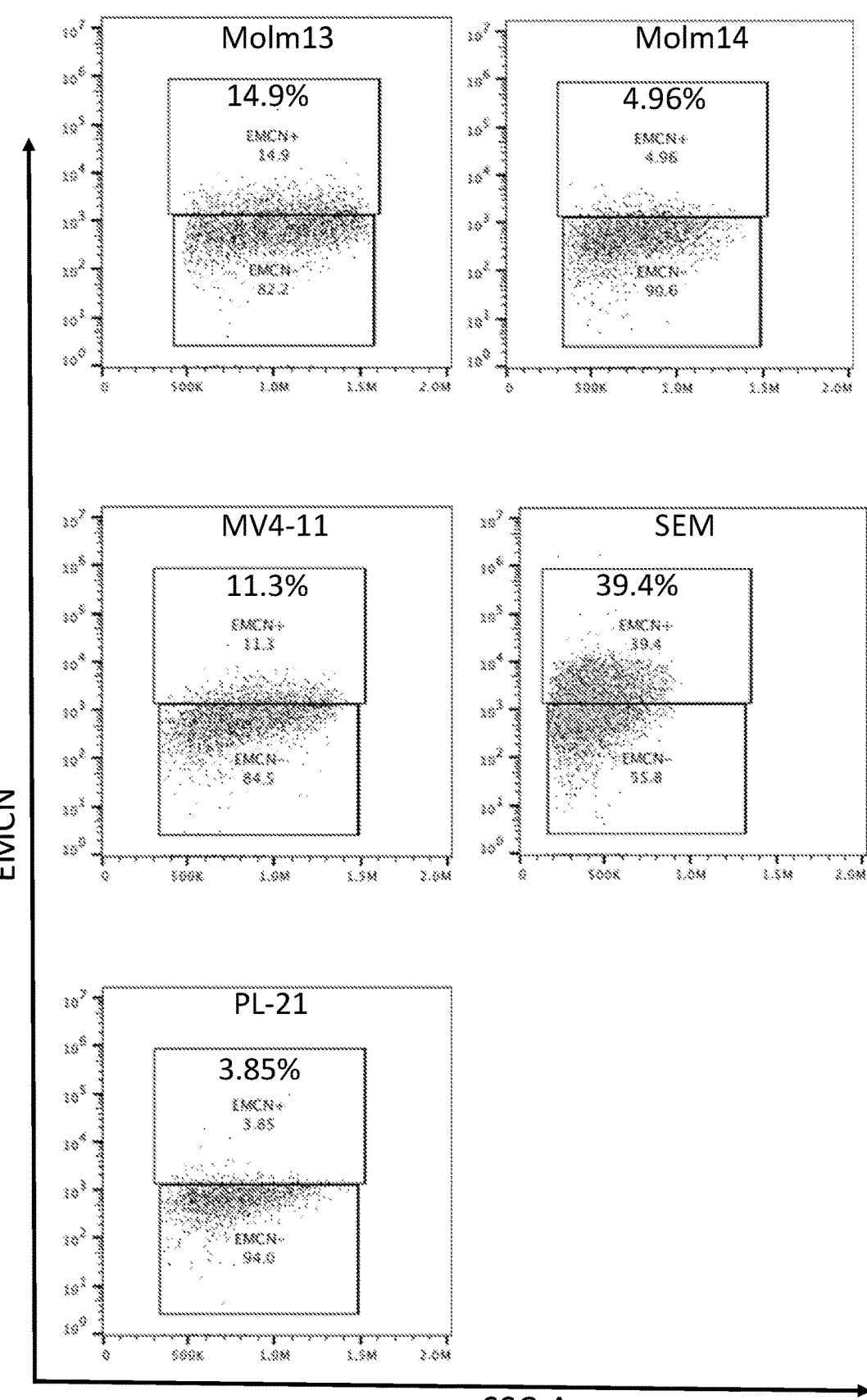
FIG. 3C. Transduced cell lines showing EMCN expression on Day 3 following transduction.

EMCN expressing cell lines were generated. Specifically, cells lines known to express potential cancer targets of interest for CAR meditated killing (e.g., FLT3 (CD135) and CD33 (SIGLEC3)). Following lentiviral transduction and drug-selection, engineered cells were evaluated for EMCN expression by flow cytometry. The gating strategy for establishing EMCN expression baseline was established using a secondary-only control (FIG. 3A). As shown in FIG. 3B, none of the No Virus transduction control cell lines demonstrated EMCN expression. As shown in FIG. 3C, transduced cell lines demonstrated low levels of expression on Day 3 following transduction.

Figure 4A:
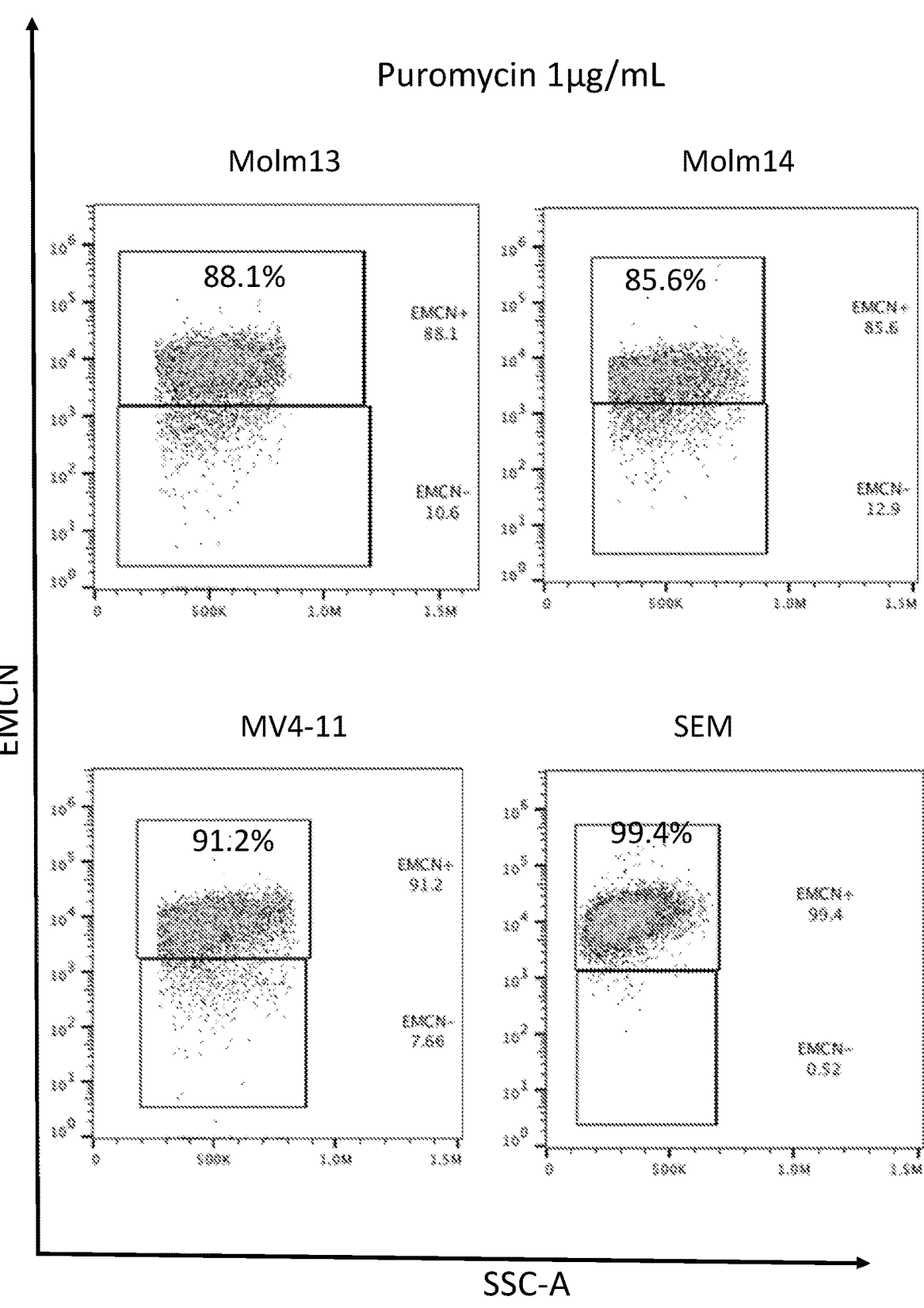
FIG. 4A. Transduced cell lines showing EMCN expression on Day 24 post-transduction following 21 days of drug selection with 1 µg/mL Puromycin.
Figure 4B:
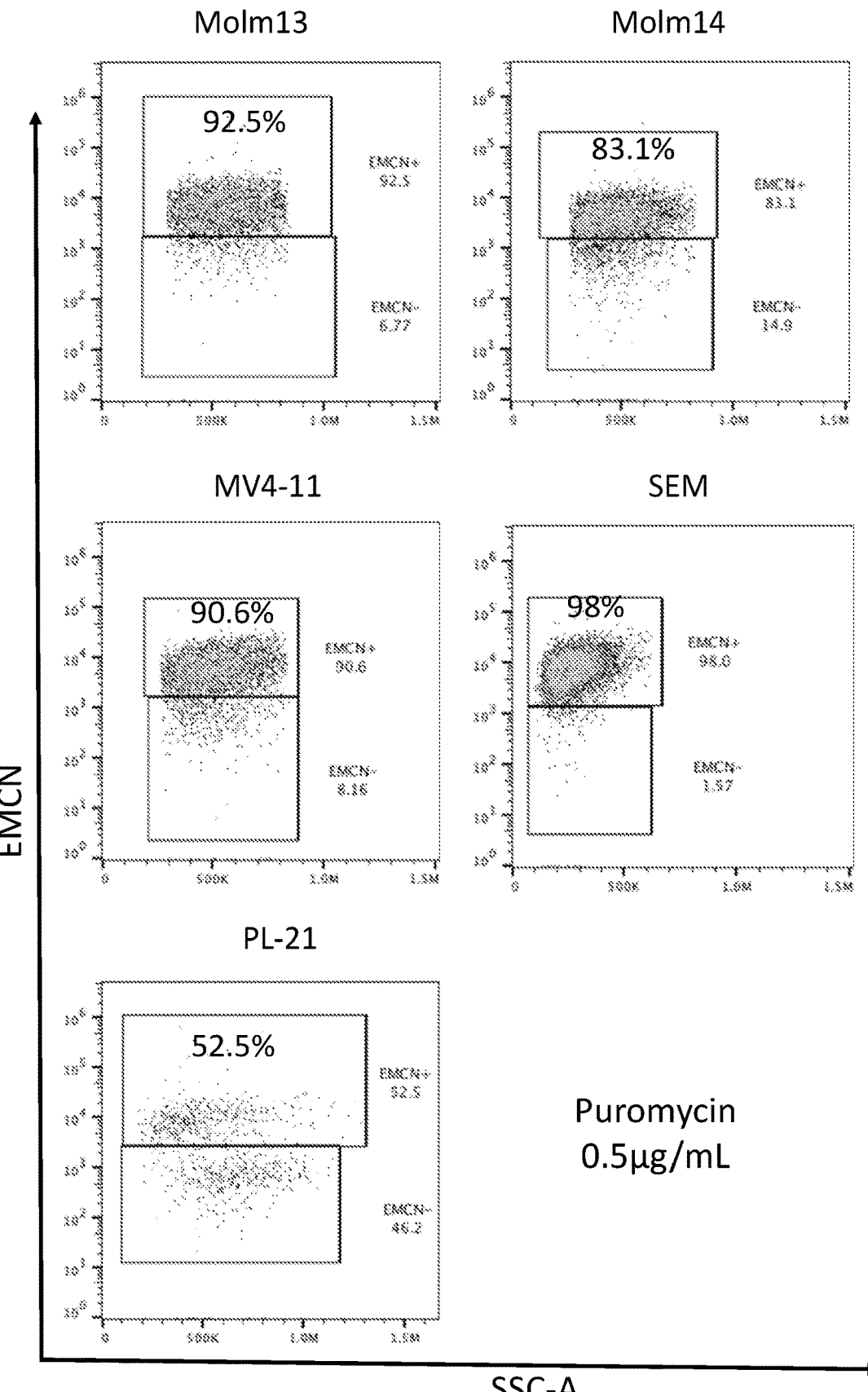
FIG. 4B. Transduced cell lines showing EMCN expression on Day 24 post-transduction following 21 days of drug selection with 0.5 µg/mL Puromycin.

Transduced cells were then drug-selected for 21 days (Day 24 post transduction). As shown in FIG. 4A and FIG. 4B, engineered Molm13, Molm14, MV4-11, and SEM cells demonstrated between 83-99% of cells expressing EMCN by flow cytometry following culturing with 1 μg/mL Puromycin or 0.5 μg/mL Puromycin, respectively. Transduced PL-21 selected in 0.5 μg/mL Puromycin demonstrated greater than 50% of cells expressing EMCN (PL-21 were not viable following selection with 1 μg/mL Puromycin).

Figure 5:
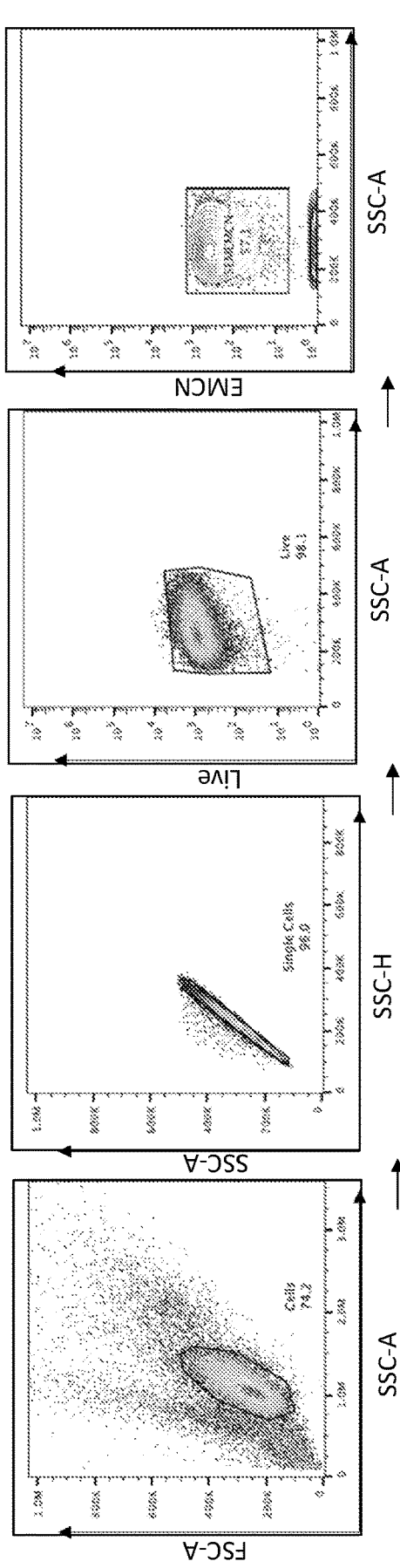
FIG. 5. Gating strategy for establishing EMCN expression baseline for analysis of cells engineered to express EMCN.

The expression profile of the engineered cells was further assessed. The gating strategy for establishing EMCN expression baseline was established using a secondary-only control (FIG. 5). As shown in Table B, Molm13, and SEM cells engineered to express EMCN all demonstrated EMCN expression above controls, while also demonstrating maintained expression of cancer targets FLT3 and CD33.

TABLE B

| | Mean fluorescence intensity (MFI)* of cell lines engineered to express EMCN | | | | | |
|---|---|---|---|---|---|---|
| | FLT3 expression | | CD33 expression | | EMCN expression | |
| Cell Lines | (—) control | FLT3 | (—) control | CD33 | (—) control | EMCN |
| MOLM13-WT | 53.4 | 3768 | 697 | 189032 | 52.1 | 133 |
| MOLM13-EMCN | 28.0 | 1749 | 193 | 138194 | 42.5 | 6269 |
| SEM-WT | 28.9 | 51314 | 287 | 1350 | 27.0 | 48.8 |
| SEM-EMCN | 15.4 | 59184 | 70.2 | 729 | 18.3 | 6472 |

MFI = Mean fluorescence intensity = geometric mean;
Geometric mean calculated by FlowJo software flow cytometry software;
(—) control = unstained sample three days after transduction and refreshed every 2-4 days. Cells were monitored during selection for EMCN expression by flow cytometry. Puromycin selection began 3 days post-transduction, and was then maintained during in vitro culturing of the cells.

Staining for FACS Analysis

Antibody staining of transduced cells and/or puromycin selected cells was performed according to the protocol below:

1. Aliquot 500 uL of cells into each condition (Secondary only and EMCN staining)
2. Spin once, aspirate supernatants, resuspend in L/D mix and stain on ice, covered, for 30 mins. 1:1000 L/D Aqua Fixability Dye
3. Wash 1× with FACS buffer and resuspend in Primary stain (1:100) or FACS buffer for 1 hr on ice
4. Wash 1× with FACS buffer and resuspend all samples in Secondary stain (1:5000) for 30 mins. on ice Example 3: Anti-EMCN Activating CAR Evaluation Methods Lentiviral Cloning and Production CAR constructs were cloned into a lentiviral vector. Lentivirus was produced using the Lenti-X 293T system, as described above. The antigen specificity and domain organization for the CAR constructs examined are described in Table C below, and scFv amino acid sequences and nucleotide sequences are presented in Table D and Table E, respectively.

TABLE C

| CAR Constructs (Activating) | |
|---|---|
| Construct | Description |
| SB00819 | FLT3 CAR |
| SB01052 | CD33 CAR |

TABLE C-continued

| CAR Constructs (Activating) | |
|---|---|
| Construct | Description |
| SB02405 | CD8ss-Flag-EMCN Ab1 scFv (VH-(G4S)3-VL)-CD28 hinge/CD28 TM/CD28 ICD-CD3z |
| SB02406 | CD8ss-Flag-EMCN Ab1 scFv (VL-(G4S)3-VH)-CD28 hinge/CD28 TM/CD28 ICD-CD3z |
| SB02407 | CD8ss-Flag-EMCN Ab1 scFv (VH-(Whitlow)-VL)-CD28 hinge/CD28 TM/CD28 ICD-CD3z |

TABLE C-continued

| CAR Constructs (Activating) | |
|---|---|
| Construct | Description |
| SB02408 | CD8ss-Flag-EMCN Ab1 scFv (VL-(Whitlow)-VH)-CD28 hinge/CD28 TM/CD28 ICD-CD3z |
| SB02409 | CD8ss-Flag-EMCN Ab1 scFv (VH-(G4S)-VL)-CD28 hinge/CD28 TM/CD28 ICD-CD3z |
| SB02410 | CD8ss-Flag-EMCN Ab1 scFv (VL-(G4S)-VH)-CD28 hinge/CD28 TM/CD28 ICD-CD3z |

TABLE D

CAR scFv Amino Acid Sequences

| scFv | Amino Acid Sequence (bold italic designates linker sequence) | SEQ ID NO: |
|---|---|---|
| SB2405 | QVQLKESGPGLVQPSQTLSLTCTVSGFSLSRYDMHWVRQPPGQGLEWM GVIWGNGNTHYHSALKSRLSISRDTSKSQVFLKMNSLQTEDTAIYFCT LRIKDWGPGTMVTVSS*GGGGSGGGGSGGGGS*DIVMTQTPPSLSVALGQ SVSISCKSSQSLVASDENTYLNWLLQSPGRSPKRLIYQVSKLDSGVPD RFSGSGSEKDFTLKISRVEAEDLGVYYCLQGIHLPWTFGGGTKLELK | 17 |
| SB2406 | DIVMTQTPPSLSVALGQSVSISCKSSQSLVASDENTYLNWLLQSPGRSPK RLIYQVSKLDSGVPDRFSGSGSEKDFTLKISRVEAEDLGVYYCLQGIHLP WTFGGGTKLELK*GGGGSGGGGSGGGGS*QVQLKESGPGLVQPSQTLSLT CTVSGFSLSRYDMHWVRQPPGQGLEWMGVIWGNGNTHYHSALKSRLSI SRDTSKSQVFLKMNSLQTEDTAIYFCTLRIKDWGPGTMVTVSS | 18 |
| SB2407 | QVQLKESGPGLVQPSQTLSLTCTVSGFSLSRYDMHWVRQPPGQGLEWM GVIWGNGNTHYHSALKSRLSISRDTSKSQVFLKMNSLQTEDTAIYFCTLR IKDWGPGTMVTVSS*GSTSGSGKPGSGEGSTKG*DIVMTQTPPSLSVALGQS VSISCKSSQSLVASDENTYLNWLLQSPGRSPKRLIYQVSKLDSGVPDRFS GSGSEKDFTLKISRVEAEDLGVYYCLQGIHLPWTFGGGTKLELK | 19 |
| SB2408 | DIVMTQTPPSLSVALGQSVSISCKSSQSLVASDENTYLNWLLQSPGRSPK RLIYQVSKLDSGVPDRFSGSGSEKDFTLKISRVEAEDLGVYYCLQGIHLP WTFGGGTKLELK*GSTSGSGKPGSGEGSTK*GQVQLKESGPGLVQPSQTLS LTCTVSGFSLSRYDMHWVRQPPGQGLEWMGVIWGNGNTHYHSALKSR LSISRDTSKSQVFLKMNSLQTEDTAIYFCTLRIKDWGPGTMVTVSS | 20 |
| SB2409 | QVQLKESGPGLVQPSQTLSLTCTVSGFSLSRYDMHWVRQPPGQGLEWM GVIWGNGNTHYHSALKSRLSISRDTSKSQVFLKMNSLQTEDTAIYFCTLR IKDWGPGTMVTVSS*GGGGS*DIVMTQTPPSLSVALGQSVSISCKSSQSLVA SDENTYLNWLLQSPGRSPKRLIYQVSKLDSGVPDRFSGSGSEKDFTLKI SRVEAEDLGVYYCLQGIHLPWTFGGGTKLELK | 21 |
| SB2410 | DIVMTQTPPSLSVALGQSVSISCKSSQSLVASDENTYLNWLLQSPGRSPK RLIYQVSKLDSGVPDRFSGSGSEKDFTLKISRVEAEDLGVYYCLQGIHLP WTFGGGTKLELK*GGGGS*QVQLKESGPGLVQPSQTLSLTCTVSGFSLSRY DMHWVRQPPGQGLEWMGVIWGNGNTHYHSALKSRLSISRDTSKSQVFL KMNSLQTEDTAIYFCTLRIKDWGPGTMVTVSS | 22 |

TABLE E

CAR scFv Nucleotide Sequences

| scFv | Nucleotide Sequence | SEQ ID NO: |
|---|---|---|
| SB2405 | CAGGTGCAGCTGAAAGAGTCTGGACCTGGACTGGTGCAGCCCAGCCA AACACTGAGCCTGACCTGTACCGTGTCCGGCTTCAGCCTGAGCAGAT ACGACATGCACTGGGTCCGACAGCCTCCAGGACAAGGCTTGGAATGG ATGGGCGTGATCTGGGGCAACGGCAACACACACTATCACAGCGCCCT GAAGTCCCGGCTGAGCATCAGCAGAGATACCAGCAAGAGCCAGGTGT TCCTGAAGATGAACTCCCTCCAGACCGAGGACACCGCCATCTATTTCT GCACCCTGCGGATCAAGGATTGGGGCCCTGGCACAATGGTCACCGTT TCTAGCGGAGGCGGAGGATCTGGTGGCGGAGGAAGTGGCGGAGGCG GTTCTGATATCGTGATGACCCAGACACCTCCTAGCCTGTCTGTGGCTC TGGGCCAGTCTGTGTCCATCAGCTGCAAGAGCAGCCAGTCTCTGGTG GCCAGCGACGAGAACACCTACCTGAATTGGCTGCTGCAAAGCCCCGG CAGAAGCCCCAAGAGACTGATCTACCAGGTGTCCAAGCTGGACAGCG GCGTGCCCGATAGATTTTCTGGCAGCGGCAGCGAGAAGGACTTCACC | 58 |

TABLE E-continued

CAR scFv Nucleotide Sequences

| scFv | Nucleotide Sequence | SEQ ID NO: |
|------|---------------------|------------|
| | CTGAAGATCTCCAGAGTGGAAGCCGAGGACCTGGGCGTGTACTACTG TCTGCAAGGCATCCATCTGCCTTGGACCTTTGGAGGCGGCACAAAGCT GGAACTGAAGGCCGCT | |
| SB2406 | GACATCGTGATGACCCAGACACCTCCTAGCCTGTCTGTGGCTCTGGGC CAGTCTGTGTCCATCAGCTGCAAGAGCAGCCAGTCTCTGGTGGCCAG CGACGAGAACACCTACCTGAATTGGCTGCTGCAAAGCCCCGGCGAA GCCCCAAGAGACTGATCTACCAGGTGTCCAAGCTGGACAGCGGCGTG CCCGATAGATTTTCTGGCAGCGGCTCCGAGAAGGACTTCACCCTGAA GATCAGCAGAGTGGAAGCCGAGGACCTGGGCGTGTACTACTGTCTGC AAGGCATCCATCTGCCTTGGACCTTTGGCGGAGGCACAAAGCTGGAA CTGAAAGGCGGCGGAGGAGGAAGCGGAGGCGGAGGATCTGGTGGTGGTG GATCTCAGGTGCAGCTGAAAGAGTCTGGCCCTGGACTGGTGCAGCCT AGCCAAACACTGAGCCTGACCTGTACCGTGTCCGGCTTCAGCCTGAG CAGATACGACATGCACTGGGTCCGACAGCCTCCAGGACAAGGCTTGG AATGGATGGGCGTGATCTGGGGCAACGGCAACACACTATCACAGC GCCCTGAAGTCCCGGCTGAGCATCTCCAGAGATACCAGCAAGAGCCA GGTGTTCCTGAAGATGAACTCCCTCCAGACCGAGGACACCGCCATCT ATTTCTGCACCCTGCGGATCAAGGATTGGGGCCCTGGCACAATGGTC ACCGTGTCTAGCGCCGCT | 59 |
| SB2407 | CAGGTGCAGCTGAAAGAGTCTGGACCTGGACTGGTGCAGCCCAGCCA AACACTGAGCCTGACCTGTACCGTGTCCGGCTTCAGCCTGAGCAGAT ACGACATGCACTGGGTCCGACAGCCTCCAGGACAAGGCTTGGAATGG ATGGGCGTGATCTGGGGCAACGGCAACACACTATCACAGCGCCCT GAAGTCCCGGCTGAGCATCAGCAGAGATACCAGCAAGAGCCAGGTGT TCCTGAAGATGAACTCCCTCCAGACCGAGGACACCGCCATCTATTTCT GCACCCTGCGGATCAAGGATTGGGGCCCTGGCACAATGGTCACCGTG TCTAGCGGCAGCACAAGCGGCTCTGGAAAACCTGGATCTGGCGAGGG CTCTACCAAGGGCGACATCGTGATGACCCAGACACCTCCTTCTCTGTC TGTGGCCCTGGGCCAGTCTGTGTCCATCAGCTGTAAAAGCAGCCAGTC TCTGGTGGCCAGCGACGAGAACACCTACCTGAATTGGCTGCTGCAAA GCCCCGGCAGAAGCCCCAAGAGACTGATCTACCAGGTGTCCAAGCTG GACAGCGGCGTGCCCGATAGATTTTCTGGCAGCGGCAGCGAGAAGGA CTTCACCCTGAAGATCTCCAGAGTGGAAGCCGAGGACCTGGGCGTGT ACTACTGTCTGCAAGGCATCCATCTGCCTTGGACCTTTGGCGGAGGCA CAAAGCTGGAACTGAAGGCCGCT | 60 |
| SB2408 | GACATCGTGATGACCCAGACACCTCCTAGCCTGTCTGTGGCTCTGGGC CAGTCTGTGTCCATCAGCTGCAAGAGCAGCCAGTCTCTGGTGGCCAG CGACGAGAACACCTACCTGAATTGGCTGCTGCAAAGCCCCGGCAGAA GCCCCAAGAGACTGATCTACCAGGTGTCCAAGCTGGACAGCGGCGTG CCCGATAGATTTTCTGGCAGCGGCTCCGAGAAGGACTTCACCCTGAA GATCAGCAGAGTGGAAGCCGAGGACCTGGGCGTGTACTACTGTCTGC AAGGCATCCATCTGCCTTGGACCTTTGGCGGAGGCACAAAGCTGGAA CTGAAGGGCAGCACAAGCGGCTCTGGCAAACCTGGATCTGGCGAGGG CTCTACCAAGGGCCAGGTGCAGCTGAAAGAGTCTGGCCCTGGACTGG TGCAGCCTAGCCAAACACTGAGCCTGACCTGTACCGTGTCCGGCTTCA GCCTGAGCAGATACGACATGCACTGGGTCCGACAGCCTCCAGGACAA GGCTTGGAATGGATGGGCGTGATCTGGGGCAACGGCAACACACTA TCACAGCGCCCTGAAGTCCCGGCTGAGCATCTCCAGAGATACCAGCA AGAGCCAGGTGTTCCTGAAGATGAACTCCCTCCAGACCGAGGACACC GCCATCTATTTCTGCACCCTGCGGATCAAGGATTGGGGCCCTGGCACA ATGGTCACCGTGTCTAGCGCCGCT | 61 |
| SB2409 | CAGGTGCAGCTGAAAGAGTCTGGACCTGGACTGGTGCAGCCCAGCCA AACACTGAGCCTGACCTGTACCGTGTCCGGCTTCAGCCTGAGCAGAT ACGACATGCACTGGGTCCGACAGCCTCCAGGACAAGGCTTGGAATGG ATGGGCGTGATCTGGGGCAACGGCAACACACTATCACAGCGCCCT GAAGTCCCGGCTGAGCATCAGCAGAGATACCAGCAAGAGCCAGGTGT TCCTGAAGATGAACTCCCTCCAGACCGAGGACACCGCCATCTATTTCT GCACCCTGCGGATCAAGGATTGGGGCCCTGGCACAATGGTCACCGTT TCTAGTGGTGGCGGAGGCAGCGACATCGTGATGACACAGACACCTCC AAGCCTGTCTGTGGCCCTGGGACAGTCCGTGTCTATCAGCTGCAAGA GCAGCCAGTCTCTGGTGGCCAGCGACGAGAACACCTACCTGAATTGG CTGCTGCAAAGCCCCGGCAGAAGCCCCAAGAGACTGATCTACCAGGT GTCCAAGCTGGACAGCGGCGTGCCCGATAGATTTTCTGGCAGCGGCA GCGAGAAGGACTTCACCCTGAAGATCTCCAGAGTGGAAGCCGAGGAC CTGGGCGTGTACTACTGTCTGCAAGGCATCCATCTGCCTTGGACCTTT GGAGGCGGCACAAAGCTGGAACTGAAGGCCGCT | 62 |
| SB2410 | GACATCGTGATGACCCAGACACCTCCTAGCCTGTCTGTGGCTCTGGGC CAGTCTGTGTCCATCAGCTGCAAGAGCAGCCAGTCTCTGGTGGCCAG CGACGAGAACACCTACCTGAATTGGCTGCTGCAAAGCCCCGGCAGAA | 63 |

TABLE E-continued

CAR scFv Nucleotide Sequences

| scFv | Nucleotide Sequence | SEQ ID NO: |
|------|---------------------|------------|
| | GCCCCAAGAGACTGATCTACCAGGTGTCCAAGCTGGACAGCGGCGTG<br>CCCGATAGATTTTCTGGCAGCGGCTCCGAGAAGGACTTCACCCTGAA<br>GATCAGCAGAGTGGAAGCCGAGGACCTGGGCGTGTACTACTGTCTGC<br>AAGGCATCCATCTGCCTTGGACCTTTGGCGGAGGCACAAAGCTGGAA<br>CTGAAAGGCGGCGGAGGATCCCAGGTGCAGCTGAAAGAATCTGGCCC<br>TGGACTGGTGCAGCCCAGCCAAACACTGAGCCTGACCTGTACCGTGT<br>CCGGCTTCAGCCTGAGCAGATACGACATGCACTGGGTCCGACAGCCT<br>CCAGGACAAGGCTTGGAATGGATGGGCGTGATCTGGGGCAACGGCAA<br>CACACACTATCACAGCGCCCTGAAGTCCCGGCTGAGCATCTCCAGAG<br>ATACCAGCAAGAGCCAGGTGTTCCTGAAGATGAACTCCCTCCAGACC<br>GAGGACACCGCCATCTATTTCTGCACCCTGCGGATCAAGGATTGGGG<br>CCCTGGCACAATGGTCACCGTGTCTAGCGCCGCT | |

T-Cell Assays

Primary T cells were isolated from human donor PBMCs and frozen. Prior to transduction, T cells were thawed and activated with Human T-Activator CD3/CD28 Dynabeads and cultured in CTS OpTmizer T Cell Expansion medium with IL-2 overnight. Next, T cells were transduced with a CAR lentivirus containing a selected CAR vector by removing a portion of the media and adding drop-wise the appropriate amount of lentiviral supernatant then gently mixed by pipetting. The cells were placed in an incubator overnight and the next day additional media was added to dilute the virus. The cells were then cultured as normal. Day 4 post-transduction, CAR expression was assessed via antibody staining and flow cytometry.

For functional assays, on day 9 after transduction the T cells and target cells were mixed together and co-cultured (ET ratio: 1:1, 96-well plate, 200 ul total medium volume). To distinguish targets cells and T cells, target cells were stained with CellTrace Violet dye.

For cytotoxicity assays, cells were collected after an 18-hour co-incubation and stained with Sytox Red cell viability dye to distinguish live/dead target cells. T cell cytotoxicity against the target cells was assessed by flow cytometry (analysis performed using FlowJo software) and presented as percent killing normalized to a No Virus transduction T cell control.

Results

CAR T cells specific for FLT3, CD33, or various constructs for EMCN were generated. Each receptor included a cytoplasmic signaling domain such that binding to a target antigen should stimulate an immune response, such as cytokine production and/or target cell killing. For EMCN-specific CAR constructs, different VH and VL orientations together with various scFv linkers (G4S, (G4S)3, and Whitlow) were also assessed.

Figure 6A:
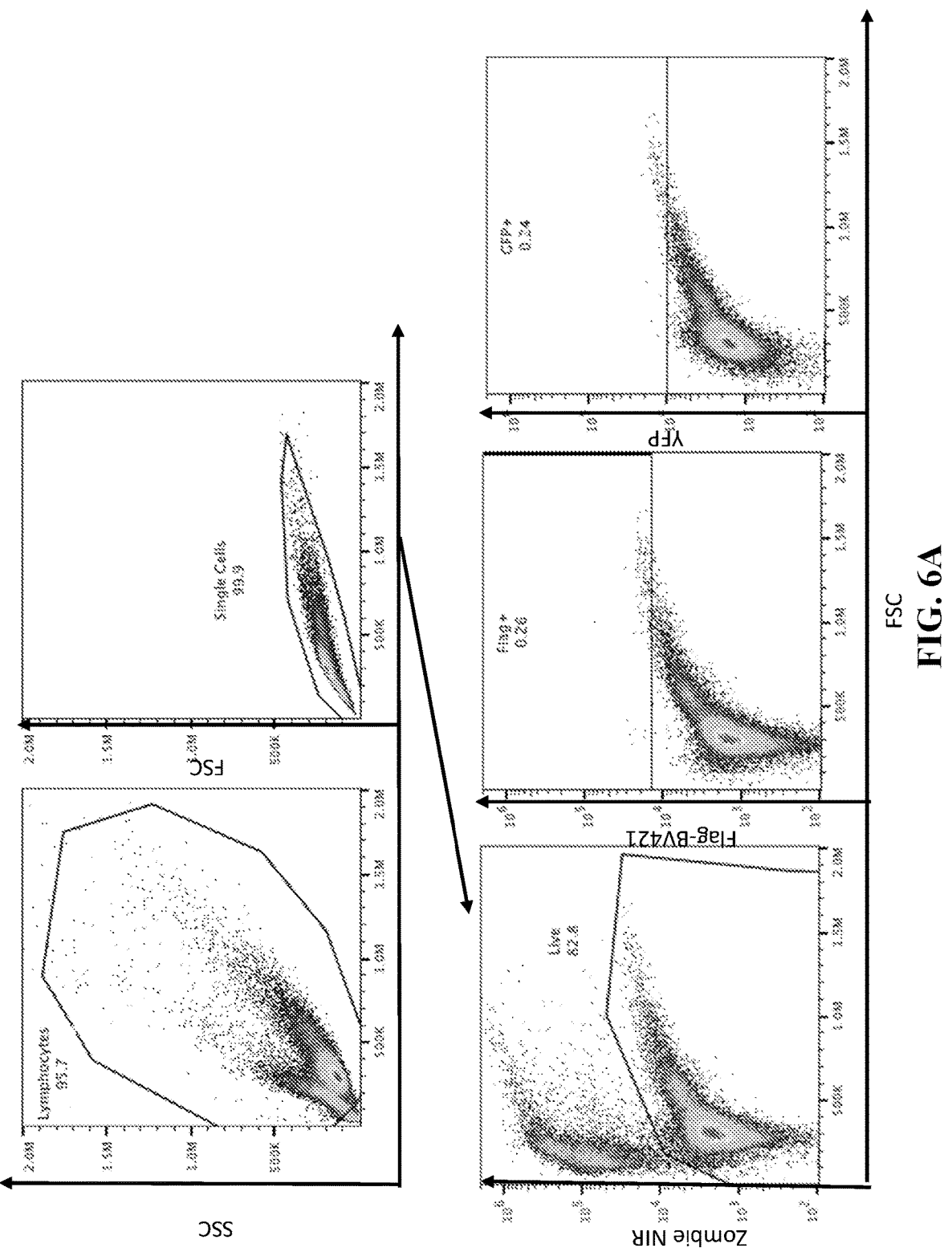
FIG. 6A. Gating strategy for establishing the CAR expression baseline was established using a No Virus transduction control.
Figure 6B:
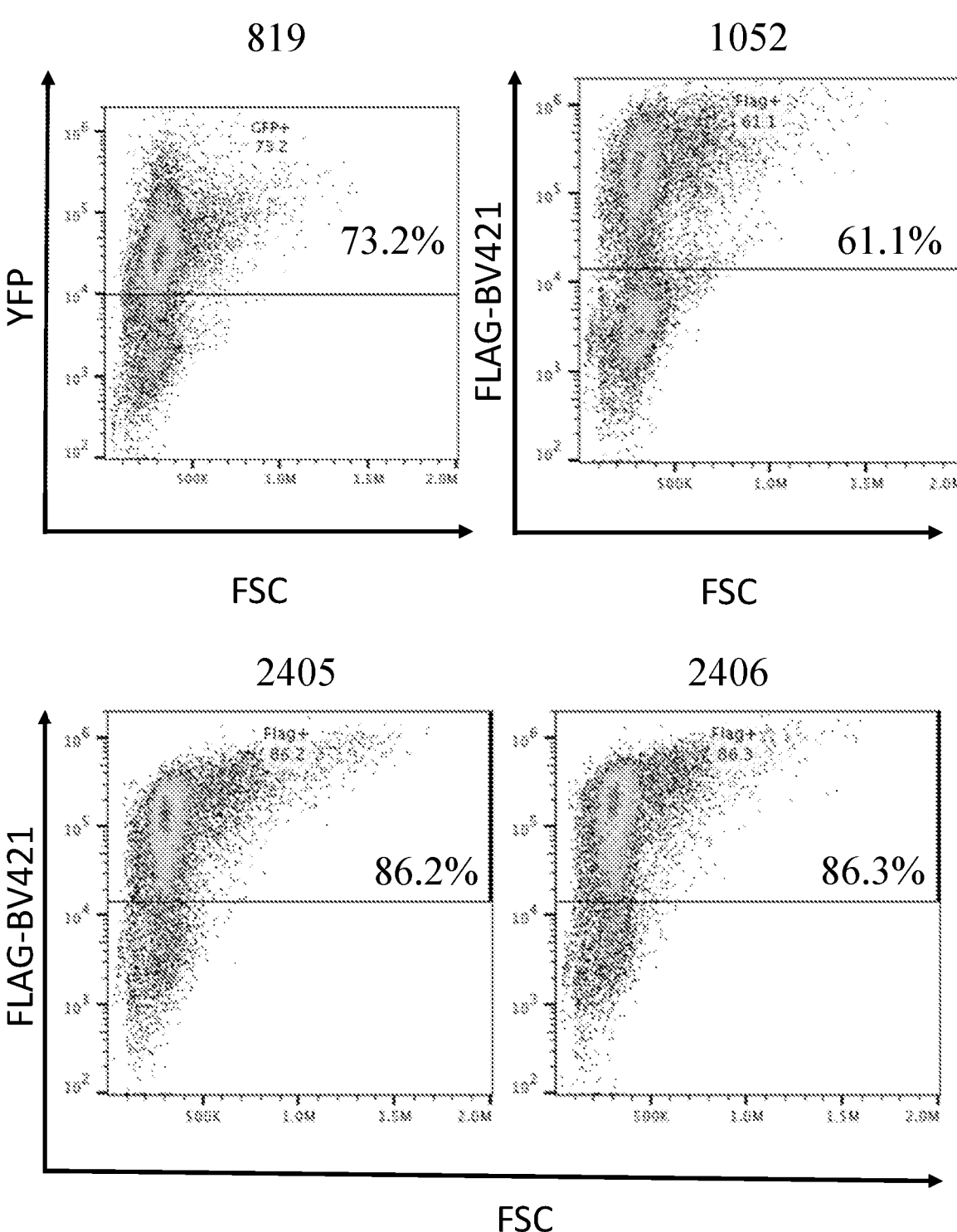
FIG. 6B. CAR expression of transduced cells for CAR constructs SB00819, SB01052, SB02405, and SB02406.
Figure 6C:
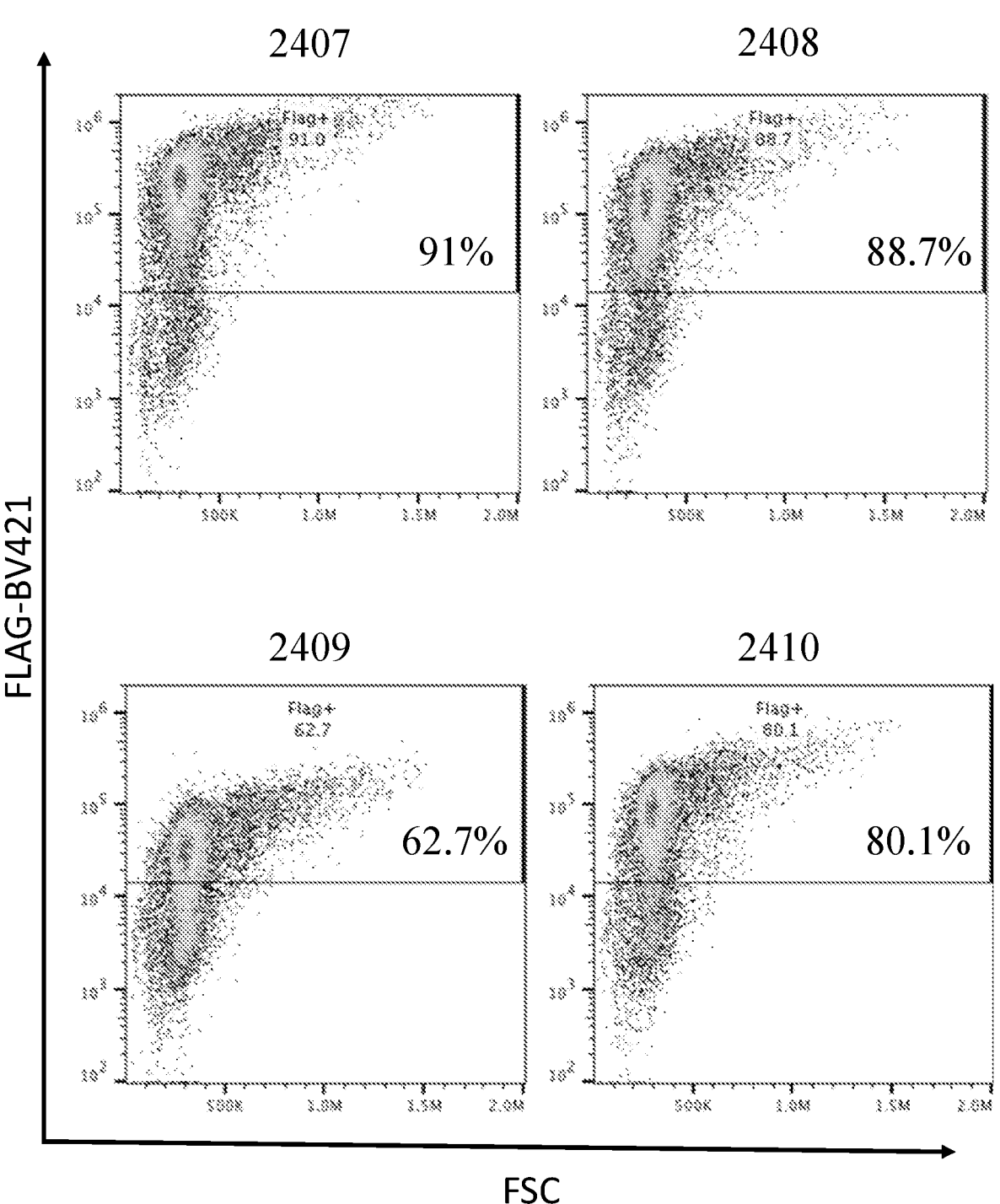
FIG. 6C. CAR expression of transduced cells for CAR constructs SB02407, SB02408, SB02409, and SB02410.

Following lentiviral transduction of primary human T cells, the engineered cells were assessed for CAR expression. The gating strategy for establishing the CAR expression baseline was established using a No Virus transduction control (FIG. 6A). As shown in FIG. 6B and FIG. 6C, CAR expression was observed on between 61-91% of transduced cells.

Figure 7A:
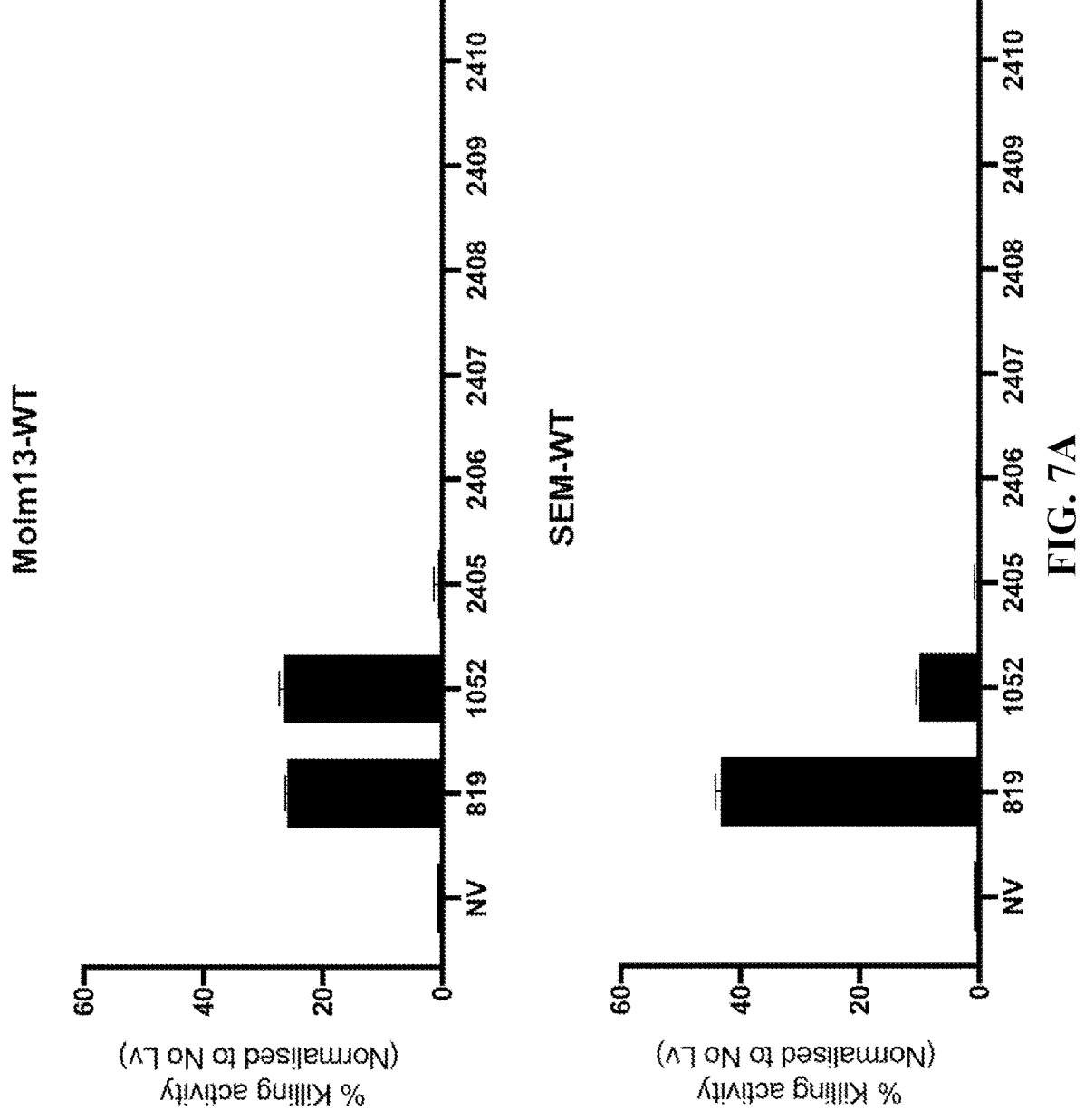
FIG. 7A, Percent killing (normalized to a No Virus transduction T cell control) following co-incubation of FLT3-specific or CD33-specific CAR T cells with parental Molm13 (top panel) or SEM (bottom panel).
Figure 7B:
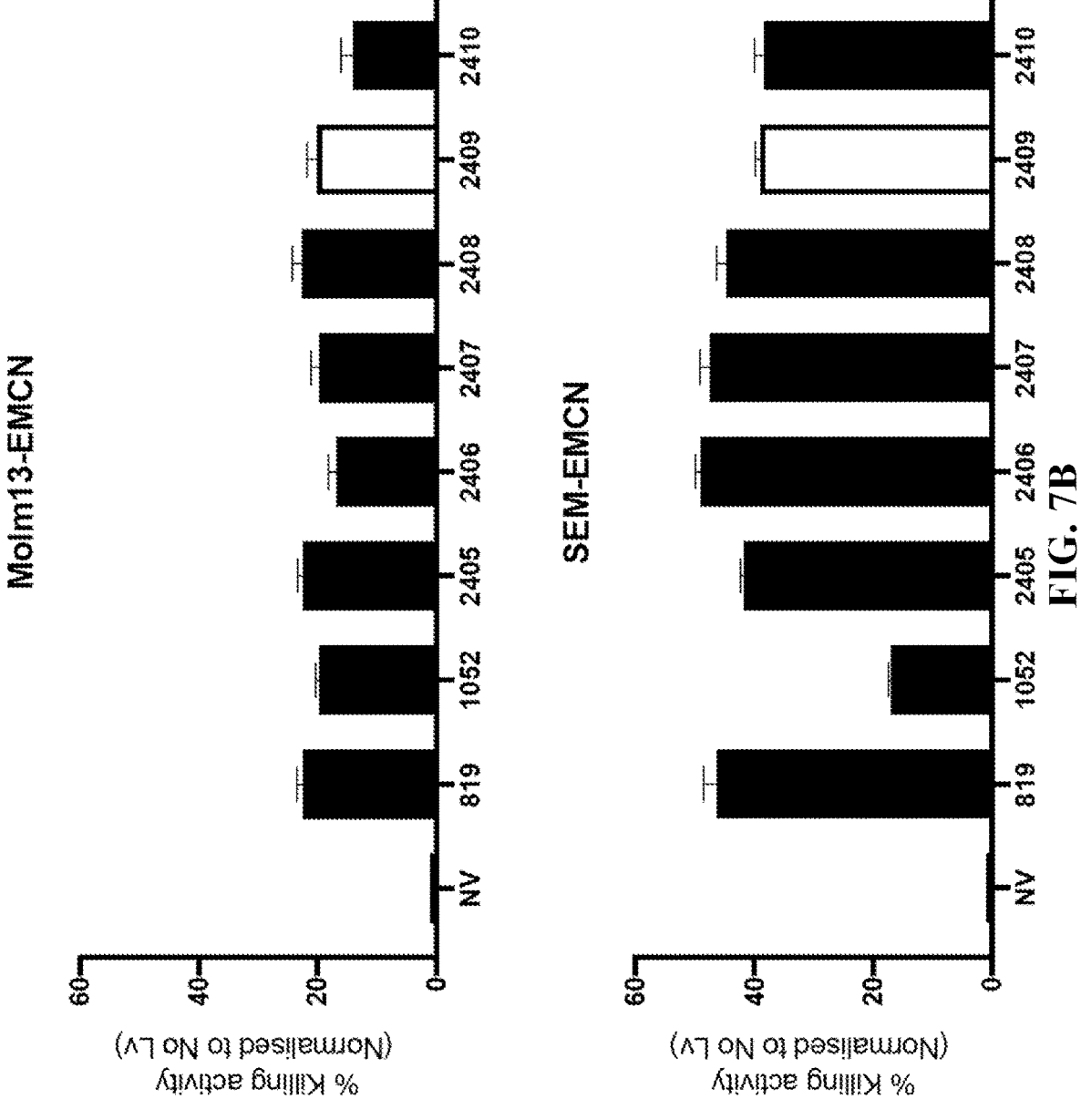
FIG. 7B. Percent killing (normalized to a No Virus transduction T cell control) following co-incubation of FLT3-specific or CD33-specific CAR T cells with Molm13 (top panel) or SEM (bottom panel) target cells engineered to express EMCN.

The various CAR T cells were then assessed for functional activity. Each of the CAR T cells was co-incubated with Molm13 target cells, SEM target cells, Molm13 target cells engineered to express EMCN, or SEM target cells engineered to express EMCN. Parental and engineered Molm13 and SEM cell lines natively express FLT3 and CD33, as demonstrated above (see FIG. 5C and FIG. 5D). Co-incubation of FLT3-specific or CD33-specific CAR T cells with parental Molm13 (FIG. 7A; top panel) or SEM (FIG. 7A; bottom panel) target cells led to target cell killing (second and third columns, respectively), while co-incubation with EMCN-specific CAR T cells did not demonstrate detectable levels of target cell killing (columns 4-9). In contrast, co-incubation of CAR T cells with Molm13 (FIG. 7B; top panel) or SEM (FIG. 7B; bottom panel) target cells engineered to express EMCN led to target cell killing for both FLT3-specific or CD33-specific CAR T cells (second and third columns, respectively), as well as EMCN-specific CAR T cells (columns 4-9). Thus, CAR T cells engineered with an EMCN-specific CAR demonstrated target-specific functional activity for all constructs tested.

Example 4: Anti-EMCN NOT-Gate CAR Evaluation

Methods

Lentiviral Cloning and Production

CAR constructs are cloned into a lentiviral vector. Lentivirus is produced using the Lenti-X 293T system, as described above. The antigen specificity and domain organization for the CAR constructs examined are described in Table F below.

TABLE F

CAR Constructs (Activating and Inhibitory)

| Construct | Description |
|-----------|-------------|
| SB00819 | FLT3 CAR#1 |
| SB01052 | CD33 CAR |
| SB02005 | FLT3 CAR#2 |
| SB02405 | CD8ss-Flag-EMCN Ab1 scFv (VH-(G4S)3-VL)-CD28 hinge/CD28 TM/CD28 ICD-CD3z |
| SB02406 | CD8ss-Flag-EMCN Ab1 scFv (VL-(G4S)3-VH)-CD28 hinge/CD28 TM/CD28 ICD-CD3z |
| SB02645 | EMCN iCAR #1 |
| SB02646 | EMCN iCAR #2 |
| SB02647 | EMCN iCAR #3 |
| SB02648 | EMCN iCAR #4 |
| SB02649 | EMCN iCAR #5 |
| SB02650 | EMCN iCAR #6 |
| SB02651 | EMCN iCAR #7 |
| SB02652 | EMCN iCAR #8 |

TABLE F-continued

| CAR Constructs (Activating and Inhibitory) | |
| --- | --- |
| Construct | Description |
| SB02686 | EMCN iCAR #9 |
| SB02687 | EMCN iCAR #10 |
| SB02688 | EMCN iCAR #11 |
| SB02760 | EMCN iCAR #12 |
| SB02761 | EMCN iCAR #13 |
| SB02762 | EMCN iCAR #14 |

T-Cell Assays

Primary T cells are isolated from human donor PBMCs and frozen. Prior to transduction, T cells are thawed and activated with Human T-Activator CD3/CD28 Dynabeads and are cultured in CTS OpTmizer T Cell Expansion medium with IL-2 overnight. Next, T cells are transduced with CAR lentiviruses containing a selected EMCN-specific inhibitory CAR vector together with CAR lentiviruses containing either a FLT3-specific or CD33-specific activating CAR vector by removing a portion of the media and adding drop-wise the appropriate amount of lentiviral supernatant then gently mixed by pipetting. The cells were placed in an incubator overnight and the next day additional media was added to dilute the virus. The cells were then cultured as normal. Day 4 post-transduction, CAR expression was assessed via antibody staining and flow cytometry.

For functional assays, T cells and target cells are co-cultured on day 9 after transduction (ET ratio: 1:1, 96-well plate, 200 ul total medium volume). To distinguish targets cells and T cells, target cells are stained with CellTrace Violet dye.

For cytokine production assays, supernatant is collected after a 5 or 18-hour co-culture and stored at −80 degree for evaluation by Luminex assay.

For cytotoxicity assays, cells are collected after an 18-hour co-incubation and stained with Sytox Red cell viability dye to distinguish live/dead target cells. Cytotoxicity is assessed by flow cytometry (FlowJo) and presented as percent killing normalized to a No Virus transduction T cell control.

Results

CAR T cells specific for EMCN and FLT3 or specific for EMCN and CD33 are generated. FLT3 and CD33 CARs include a cytoplasmic signaling domain such that binding to a target antigen should stimulate an immune response, such as cytokine production and/or target cell killing. EMCN CARs include an inhibitory cytoplasmic domain such that binding to a target antigen should inhibit an immune response, such as that stimulated by the FLT3-specific or CD33-specific CARs binding to their respective targets. Such a system is referred to as a "NOT gate." For EMCN-specific CAR constructs, different VH and VL orientations together with various scFv linkers (G4S, (G4S)3, and Whitlow) are also assessed.

Following lentiviral transduction of primary human T cells, the engineered cells are assessed and confirmed for CAR co-expression. The various CAR T cells are then assessed for functional activity. Co-incubation of CAR T cells with parental Molm13 or SEM target cells leads to target cell killing. In contrast, co-incubation of CAR T cells with Molm13 or SEM target cells engineered to express EMCN leads to reduced or eliminated target cell killing relative to killing of parental target cells. Thus, CAR T cells engineered with an EMCN-specific CAR with an inhibitory cytoplasmic domain demonstrates the ability to reduce or minimize killing of EMCN-expressing cells establishing an effective NOT gate system to avoid undesired killing of EMCN-positive cells.

Example 5: Assessment of Various Chimeric Inhibitory Receptors In Reducing NK Cell Activation Methods and Materials Individual iCAR and aCAR constructs were packaged into lentiviral particles and used to transduce primary NK cells after 10 d expansion with K562 feeder cells with 500 U/mL IL-2 and 20 ng/uL IL-15. Virus amounts were set by p24 titer (750,000 pg per transduction). iCAR constructs contained puroR cassettes, so puromycin was added to NK cell cultures from day 4 to 7 post transduction, at which time expression was assessed by flow cytometry and NK cells were transferred to a microwell plate for killing assays with 12,500 NK cells and 50,000 total tumor cells. NK cells were cultured with (1) tumor cells expressing aCAR antigen FLT3 only, (2) tumor cells expressing both aCAR antigen FLT3 and iCAR antigen EMCN, or (3) both tumor cell types mixed. After 16-18 hrs, cultures were analyzed by flow cytometry and remaining live targets cells of each type were counted. aCAR-mediated killing (basal subtracted) of a given NK cell type was quantified by first calculating total killing (reduction of targets compared to a target-only condition), and then subtracting total killing by control (iCAR-only) NK cells. iCAR-mediated protection was quantified as the change in aCAR-mediated killing between targets with or without iCAR antigen. Killing assay supernatant was analyzed for TNFa secretion, and aCAR and iCAR performance metrics were calculated analogously to killing. For expression analysis, iCARs were stained with a V5-Alexafluor 647 and aCARs with aFLAG-BV-421. Cells were assigned to 4 quadrants based on iCAR+/− and aCAR+/− expression states, allowing us to assess "% aCAR+iCAR+" and "% not aCAR+iCAR−" (aCAR+iCAR− are ungated and potentially toxic CAR-NK cells and are to be avoided). To further analyze expression level, we measured median fluorescence intensity (MFI) of aCAR and iCAR of the aCAR+iCAR+ subpopulation, which we normalized by the MFI of untransduced NK cells in the respective fluorescence channels. For each iCAR, 1-3 biological replicates were performed (shown as different points with the same marker type). X and Y error lines (where applicable): +/−standard error of the mean.

The anti-EMCN iCAR constructs assessed used the formats shown in Table G with reference to the intracellular domain. The anti-FLT3 aCAR construct assessed is also shown in Table G.

TABLE G

Chimeric inhibitory receptors and tumor-targeting chimeric receptor sequences

| SEQ ID NO | Name | Sequence |
|---|---|---|
| 89 | Anti-EMCN-CD8 hinge-KIR2DL1 TM-KIR2DL1 iCAR (CD8 SS bold) | MALPVTALLLPLALLLHAARPQVQLKESGPGLVQPSQTLSLTCTVSGF SLSRYDMHWVRQPPGQGLEWMGVIWGNGNTHYHSALKSRLSISRDTSK SQVFLKMNSLQTEDTAIYFCTLRIKDWGPGTMVTVSSGGGGSGGGGSG GGGSDIVMTQTPPSLSVALGQSVSISCKSSQSLVASDENTYLNWLLQSPG RSPKRLIYQVSKLDSGVPDRFSGSGSEKDFTLKISRVEAEDLGVYYCLQG IHLPWTFGGGTKLELKGKPIPNPLLGLDSTNGAATTTPAPRPPTPAPTIAL QPLSLRPEACRPAAGGAVHTRGLDFACDILIGTSVVIILFILLFFLLHRWCS NKKNAAVMDQESAGNRTANSEDSDEQDPQEVTYTQLNHCVFTQRKITR PSQRPKTPPTDIIVYTELPNAESRSKVVSCP |
| 90 | Anti-EMCN-CD8 hinge-LIR1 TM-KLRG1 iCAR (CD8 SS bold) | MALPVTALLLPLALLLHAARPQVQLKESGPGLVQPSQTLSLTCTVSGF SLSRYDMHWVRQPPGQGLEWMGVIWGNGNTHYHSALKSRLSISRDTSK SQVFLKMNSLQTEDTAIYFCTLRIKDWGPGTMVTVSSGGGGSGGGGSG GGGSDIVMTQTPPSLSVALGQSVSISCKSSQSLVASDENTYLNWLLQSPG RSPKRLIYQVSKLDSGVPDRFSGSGSEKDFTLKISRVEAEDLGVYYCLQG IHLPWTFGGGTKLELKGKPIPNPLLGLDSTNGAATTTPAPRPPTPAPTIAL QPLSLRPEACRPAAGGAVHTRGLDFACDVIGILVAVILLLLLLLLLFLIMT DSVIYSMLELPTATQAQNDYGPQQKSSSSRPSCSCLGSG |
| 91 | Anti-EMCN-CD8 hinge-KLRG1 TM-KLRG1 iCAR (CD8 SS bold) | MALPVTALLLPLALLLHAARPQVQLKESGPGLVQPSQTLSLTCTVSGF SLSRYDMHWVRQPPGQGLEWMGVIWGNGNTHYHSALKSRLSISRDTSK SQVFLKMNSLQTEDTAIYFCTLRIKDWGPGTMVTVSSGGGGSGGGGSG GGGSDIVMTQTPPSLSVALGQSVSISCKSSQSLVASDENTYLNWLLQSPG RSPKRLIYQVSKLDSGVPDRFSGSGSEKDFTLKISRVEAEDLGVYYCLQG IHLPWTFGGGTKLELKGKPIPNPLLGLDSTNGAATTTPAPRPPTPAPTIAL QPLSLRPEACRPAAGGAVHTRGLDFACDVAIALGLLTAVLLSVLLYQWI MTDSVIYSMLELPTATQAQNDYGPQQKSSSSRPSCSCLGSG |
| 92 | Anti-EMCN-CD8 hinge-LAIR1 TM-LAIR1 ICAR (CD8 SS bold) | MALPVTALLLPLALLLHAARPQVQLKESGPGLVQPSQTLSLTCTVSGF SLSRYDMHWVRQPPGQGLEWMGVIWGNGNTHYHSALKSRLSISRDTSK SQVFLKMNSLQTEDTAIYFCTLRIKDWGPGTMVTVSSGGGGSGGGGSG GGGSDIVMTQTPPSLSVALGQSVSISCKSSQSLVASDENTYLNWLLQSPG RSPKRLIYQVSKLDSGVPDRFSGSGSEKDFTLKISRVEAEDLGVYYCLQG IHLPWTFGGGTKLELKGKPIPNPLLGLDSTNGAATTTPAPRPPTPAPTIAL QPLSLRPEACRPAAGGAVHTRGLDFACDILIGVSVVFLFCLLLLVLFCLH RQNQIKQGPPRSKDEEQKPQQRPDLAVDVLERTADKATVNGLPEKDRET DTSALAAGSSQEVTYAQLDHWALTQRTARAVSPQSTKPMAESITYAAV ARH |
| 93 | Anti-EMCN-CD8 hinge-LIR2 TM-LIR2 ICAR (CD8 SS bold) | MALPVTALLLPLALLLHAARPQVQLKESGPGLVQPSQTLSLTCTVSGF SLSRYDMHWVRQPPGQGLEWMGVIWGNGNTHYHSALKSRLSISRDTSK SQVFLKMNSLQTEDTAIYFCTLRIKDWGPGTMVTVSSGGGGSGGGGSG GGGSDIVMTQTPPSLSVALGQSVSISCKSSQSLVASDENTYLNWLLQSPG RSPKRLIYQVSKLDSGVPDRFSGSGSEKDFTLKISRVEAEDLGVYYCLQG IHLPWTFGGGTKLELKGKPIPNPLLGLDSTNGAATTTPAPRPPTPAPTIAL QPLSLRPEACRPAAGGAVHTRGLDFACDVIGILVAVVLLLLLLLLLLFLILR HRRQGKHWTSTQRKADFQHPAGAVGPEPTDRGLQWRSSPAADAQEEN LYAAVKDTQPEDGVEMDTRAAASEAPQDVTYAQLHSLTLRRKATEPPP SQEREPPAEPSIYATLAIH |
| 94 | Anti-EMCN-CD8 hinge-LIR3 TM-LIR3 iCAR (CD8 SS bold) | MALPVTALLLPLALLLHAARPQVQLKESGPGLVQPSQTLSLTCTVSGF SLSRYDMHWVRQPPGQGLEWMGVIWGNGNTHYHSALKSRLSISRDTSK SQVFLKMNSLQTEDTAIYFCTLRIKDWGPGTMVTVSSGGGGSGGGGSG GGGSDIVMTQTPPSLSVALGQSVSISCKSSQSLVASDENTYLNWLLQSPG RSPKRLIYQVSKLDSGVPDRFSGSGSEKDFTLKISRVEAEDLGVYYCLQG IHLPWTFGGGTKLELKGKPIPNPLLGLDSTNGAATTTPAPRPPTPAPTIAL QPLSLRPEACRPAAGGAVHTRGLDFACDVLIGVSVAFVLLLFLLLFLLLR RQRHSKHRTSDQRKTDFQRPAGAAETEPKDRGLLRRSSPAADVQEENLY AAVKDTQSEDRVELDSQSPHDEDPQAVTYAPVKHSSPRREMASPPSSLS GEFLDTKDRQVEEDRQMDTEAAASEASQDVTYAQLHSLTLRRKATEPPP SQEGEPPAEPSIYATLAIH |
| 95 | Anti-EMCN-CD8 hinge-LIR5 TM-LIR5 iCAR (CD8 SS bold) | MALPVTALLLPLALLLHAARPQVQLKESGPGLVQPSQTLSLTCTVSGF SLSRYDMHWVRQPPGQGLEWMGVIWGNGNTHYHSALKSRLSISRDTSK SQVFLKMNSLQTEDTAIYFCTLRIKDWGPGTMVTVSSGGGGSGGGGSG GGGSDIVMTQTPPSLSVALGQSVSISCKSSQSLVASDENTYLNWLLQSPG RSPKRLIYQVSKLDSGVPDRFSGSGSEKDFTLKISRVEAEDLGVYYCLQG IHLPWTFGGGTKLELKGKPIPNPLLGLDSTNGAATTTPAPRPPTPAPTIAL QPLSLRPEACRPAAGGAVHTRGLDFACDVLIGVLVVSILLLSLLLFLLLQ HWRQGKHRTLAQRQADFQRPPGAAEPEPKDGGLQRRSSPAADVQGENF CAAVKNTQPEDGVEMDTRQSPHDEDPQAVTYAKVKHSRPRREMASPPS PLSGEFLDTKDRQAEEDRQMDTEAAASEAPQDVTYAQLHSFTLRQKAT EPPPSQEGASPAEPSVYATLAIH |

TABLE G-continued

Chimeric inhibitory receptors and tumor-targeting chimeric receptor sequences

| SEQ ID NO | Name | Sequence |
|---|---|---|
| 96 | Anti-EMCN-CD8 hinge-SIGLEC-2 TM- SIGLEC-2 iCAR (CD8 SS bold) | MALPVTALLLPLALLLHAARPQVQLKESGPGLVQPSQTLSLTCTVSGF SLSRYDMHWVRQPPGQGLEWMGVIWGNGNTHYHSALKSRLSISRDTSK SQVFLKMNSLQTEDTAIYFCTLRIKDWGPGTMVTVSSGGGGSGGGGSG GGGSDIVMTQTPPSLSVALGQSVSISCKSSQSLVASDENTYLNWLLQSPG RSPKRLIYQVSKLDSGVPDRFSGSGSEKDFTLKISRVEAEDLGVYYCLQG IHLPWTFGGGTKLELKGKPIPNPLLGLDSTNGAATTTPAPRPPTPAPTIAL QPLSLRPEACRPAAGGAVHTRGLDFACDVAVGLGSCLAILILAICGLKLQ RRWKRTQSQQGLQENSSGQSFFVRNKKVRRAPLSEGPHSLGCYNPMME DGISYTTLRFPEMNIPRTGDAESSEMQRPPPDCDDTVTYSALHKRQVGD YENVIPDFPEDEGIHYSELIQFGVGERPQAQENVDYVILKH |
| 97 | Anti-EMCN-CD8 hinge-SIGLEC-10 TM- SIGLEC-10 iCAR (CD8 SS bold) | MALPVTALLLPLALLLHAARPQVQLKESGPGLVQPSQTLSLTCTVSGF SLSRYDMHWVRQPPGQGLEWMGVIWGNGNTHYHSALKSRLSISRDTSK SQVFLKMNSLQTEDTAIYFCTLRIKDWGPGTMVTVSSGGGGSGGGGSG GGGSDIVMTQTPPSLSVALGQSVSISCKSSQSLVASDENTYLNWLLQSPG RSPKRLIYQVSKLDSGVPDRFSGSGSEKDFTLKISRVEAEDLGVYYCLQG IHLPWTFGGGTKLELKGKPIPNPLLGLDSTNGAATTTPAPRPPTPAPTIAL QPLSLRPEACRPAAGGAVHTRGLDFACDGAFLGIGITALLFLCLALIIMKI LPKRRTQTETPRPRFSRHSTILDYINVVPTAGPLAQKRNQKATPNSPRTPL PPGAPSPESKKNQKKQYQLPSFPEPKSSTQAPESQESQEELHYATLNFPG VRPRPEARMPKGTQADYAEVKFQ |
| 98 | Anti-EMCN scFv nucleotide sequence with (G4S)3 linker | CAGGTGCAGCTGAAAGAGTCTGGACCTGGACTGGTGCAGCCCAGCCA AACACTGAGCCTGACCTGTACCGTGTCCGGCTTCAGCCTGAGCAGAT ACGACATGCACTGGGTCCGACAGCCTCCAGGACAAGGCTTGGAATGG ATGGGCGTGATCTGGGGCAACGGCAACACACACTATCACAGCGCCCT GAAGTCCCGGCTGAGCATCAGCAGAGATACCAGCAAGAGCCAGGTG TTCCTGAAGATGAACAGCCTGCAGACCGAGGACACCGCCATCTATTT CTGCACCCTGCGGATCAAGGATTGGGGCCCTGGCACAATGGTCACCG TTTCTAGCGGAGGCGGAGGATCTGGTGGCGGAGGAAGTGGCGGAGG CGGTTCTGATATCGTGATGACCCAGACACCTCCTAGCCTGTCTGTGGC TCTGGGCCAGTCTGTGTCCATCAGCTGCAAGAGCAGCCAGAGCCTGG TGGCCTCCGACGAGAACACCTACCTGAATTGGCTGCTGCAGAGCCCC GGCAGAAGCCCCAAGAGACTGATCTACCAGGTGTCCAAGCTGGACA GCGGCGTGCCCGATAGATTTTCTGGCAGCGGCAGCGAGAAGGACTTC ACCCTGAAGATCTCCAGAGTGGAAGCCGAGGACCTGGGCGTGTACTA CTGTCTGCAAGGCATCCATCTGCCTTGGACCTTTGGAGGCGGCACAA AGCTGGAACTGAAA |
| 99 | anti-FLT3 scFv | EVQLVQSGAEVKKPGSSVKVSCKASGGTFSSYAISWVRQAPGQGLEWM GGIIPIFGTANYAQKFQGRVTITADKSTSTAYMELSSLRSEDTAVYYCAT FALFGFREQAFDIWGQGTTVTVSSGGGGSGGGGSGGGGSDIQMTQSPSS LSASVGDRVTITCRASQSISSYLNWYQQKPGKAPKLLIYAASSLQSGVPS RFSGSGSGTDFTLTISSLQPEDLATYYCQQSYSTPFTFGPGTKVDIK |
| 100 | anti-FLT3-CD28/CD3 ζ aCAR (IgK signal sequence bold; AGGS-Flag italic) | METDTLLLWVLLLWVPGSTG*AGGSDYKDDDDKGGS*EVQLVQSGAEV KKPGSSVKVSCKASGGTFSSYAISWVRQAPGQGLEWMGGIIPIFGTANY AQKFQGRVTITADKSTSTAYMELSSLRSEDTAVYYCATFALFGFREQAF DIWGQGTTVTVSSGGGGSGGGGSGGGGSDIQMTQSPSSLSASVGDRVTI TCRASQSISSYLNWYQQKPGKAPKLLIYAASSLQSGVPSRFSGSGSGTDF TLTISSLQPEDLATYYCQQSYSTPFTFGPGTKVDIKTTTPAPRPPTPAPTIA LQPLSLRPEACRPAAGGAVHTRGLDFACDFWVLVVVGGVLACYSLLVT VAFIIFWVRSKRSRLLHSDYMNMTPRRPGPTRKHYQPYAPPRDFAAYRS RVKFSRSADAPAYKQGQNQLYNELNLGRREEYDVLDKRRGRDPEMGG KPRRKNPQEGLYNELQKDKMAEAYSEIGMKGERRRGKGHDGLYQGLS TATKDTYDALHMQALPPR |
| 101 | SS (IgK)-Flag-anti-FLT3-CD28/CD3 ζ aCAR nucleotide sequence (with Kozak bold italics) | *GCCGCCACC*ATGGAAACCGACACACTGCTGCTGTGGGTGCTGCTTCTT TGGGTGCCCGGATCTACAGGTGCCGGCGGAAGCGACTACAAGGACG ACGATGACAAAGGCGGCAGCGAGGTTCAACTGGTACAAAGCGGAGC CGAGGTAAAGAAACCAGGGAGTAGCGTCAAAGTGTCCTGCAAAGCC TCAGGCGGCACATTCAGTAGCTATGCTATTTCATGGGTACGCCAAGC ACCAGGACAGGGGCTGGAGTGGATGGGCGGGATTATCCCCATCTTCG GTACGGCAAACTATGCACAAAAGTTCCAGGGACGAGTCACCATCACG GCTGATAAGTCCACCTCCACCGCCTATATGGAGCTGAGTTCCCTTCGG AGCGAGGATACTGCTGTGTATTATTGTGCCACGTTCGCACTGTTCGGT TTTCGGGAGCAGGCGTTTGATATTTGGGGACAAGGCACAACGGTCAC GGTCAGTTCAGGCGGAGGGGGATCAGGGGGTGGGGGGTCAGGTGGC GGTGGAAGTGACATTCAGATGACCCAGAGTCCCTCTTCATTGAGTGC GAGCGTCGGTGATCGGGTTACGATAACCTGTAGGGCCTCCCAAAGTA TATCATCATATTTGAACTGGTACCAACAGAAACCTGGGAAAGCGCCG AAGCTCCTTATCTATGCTGCCAGCTCTTTGCAAAGCGGTGTGCCCTCA CGGTTCTCCGGTAGTGGGTCCGGGACCGACTTCACTTTGACCATCAGC AGCCTTCAGCCAGAGGATCTTGCCACTTATTACTGCCAGCAATCTTAT |

TABLE G-continued

_Chimeric inhibitory receptors and tumor-targeting chimeric receptor sequences_

| SEQ ID NO | Name | Sequence |
|---|---|---|
| | | AGCACACCGTTTACATTCGGTCCAGGCACAAAGGTAGACATTAAGAC CACCACACCAGCTCCTAGACCTCCAACTCCTGCTCCTACAATCGCCCT GCAGCCACTGAGTCTGAGGCCAGAGGCTTGTAGACCTGCTGCAGGCG GAGCCGTGCATACAAGAGGACTGGATTTCGCCTGCGACTTCTGGGTG CTCGTGGTTGTTGGCGGAGTGCTGGCCTGTTACAGCCTGCTGGTTACC GTGGCCTTCATCATCTTTTGGGTCCGAAGCAAGCGGAGCCGGCTGCT GCACAGCGATTACATGAACATGACCCCTCGGAGGCCCGGACCTACCA GAAAGCACTACCAGCCTTACGCTCCTCCTAGAGATTTCGCCGCCTACC GGTCCAGAGTGAAGTTCAGCAGATCCGCCGATGCTCCCGCCTATAAG CAGGGCCAGAACCAGCTGTACAACGAGCTGAACCTGGGGAGAAGAG AAGAGTACGACGTGCTGGACAAGCGGAGAGGCAGAGATCCTGAAAT GGGCGGCAAGCCCAGACGGAAGAATCCTCAAGAGGGCCTGTATAAT GAGCTGCAGAAAGACAAGATGGCCGAGGCCTACAGCGAGATCGGAA TGAAGGGCGAGCGCAGAAGAGGCAAGGGACACGATGGACTGTACCA GGGACTGAGCACCGCCACCAAGGATACCTATGACGCCCTGCACATGC AGGCCCTGCCTCCAAGATAA |

Results

NK cells were engineered to express activating chimeric antigen receptors (aCARS) and inhibitory chimeric antigen receptors (iCARs) having various inhibitory domain formats derived from different inhibitory receptors. NK cells were virally transduced with aCAR only or in combination with iCARs having the various inhibitory domains indicated.

Figure 8:
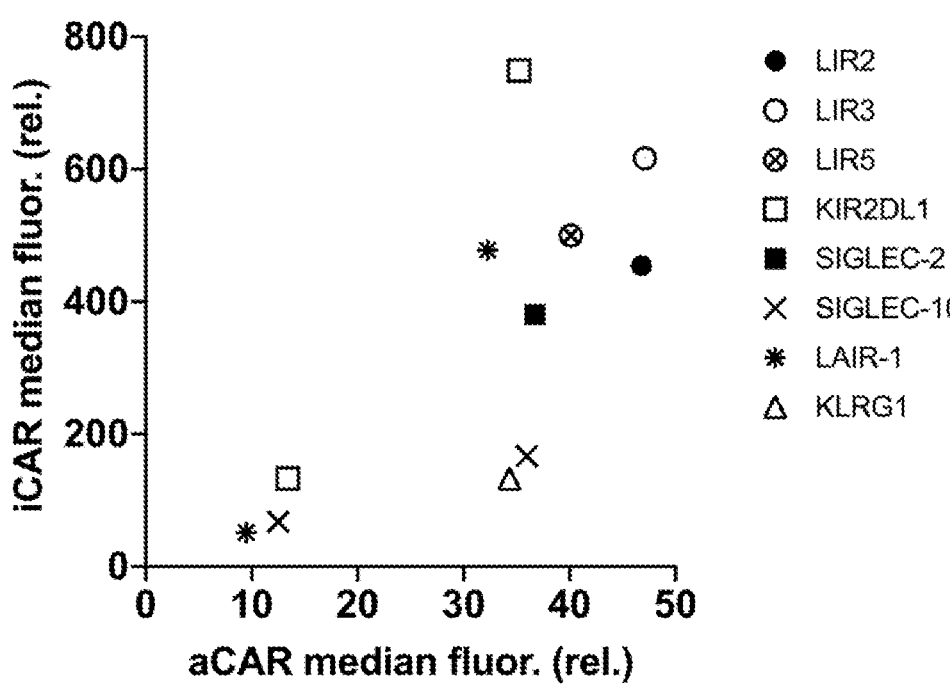
FIG. 8 shows expression profiles of an anti-FLT3 aCAR and various iCAR formats with an anti-EMCN binding domain, including co-expression, following transduction of NK cells as assessed by flow cytometry. Between 1 and 3 biological replicates per condition (indicated as separate points).
Figure 8:
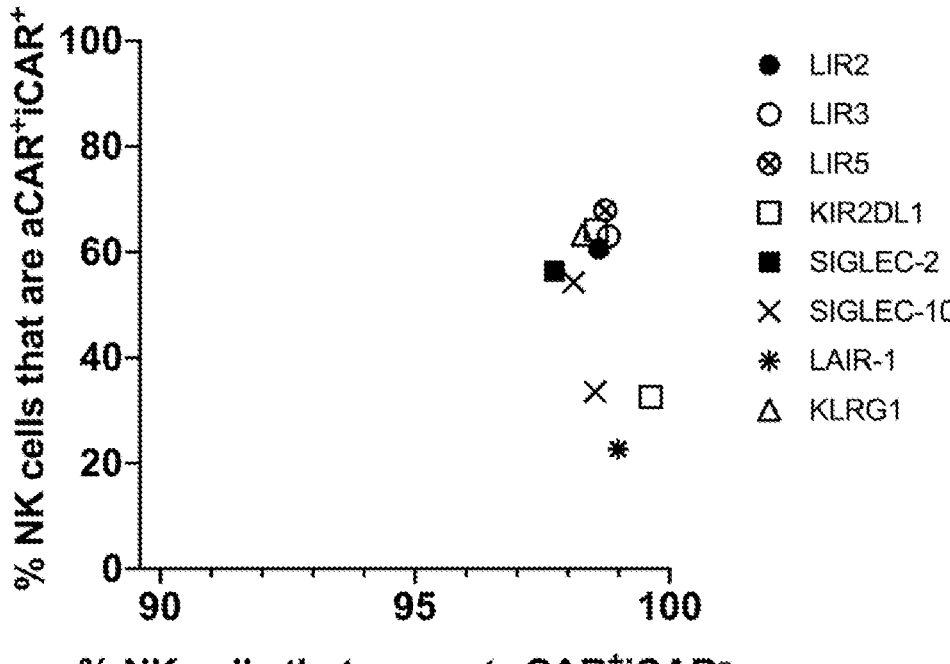

Engineered NK cells were assessed for CAR expression. As shown in FIG. 8, among aCAR+iCAR+NK cells (top panel), anti-FLT3 aCAR expression was generally greater than 10-fold above background and the anti-EMCN iCAR was generally greater than 100-fold. LIR family constructs demonstrated notably high expression relative to other constructs. The profile of CAR expressing populations was also assessed (bottom panel) and demonstrated the total population contained fewer than 5% aCAR+iCAR- cells and had varying percentages of aCAR+iCAR+ populations for the various iCAR formats, with KLRG1, LIR2, LIR3, LIR5, and SIGLEC-2 formats having consistently greater than 50% of cells being aCAR+iCAR+. Again, LIR family iCARs notably generally demonstrated a greater proportion of aCAR+iCAR+ cells relative to other constructs.

Figure 9:
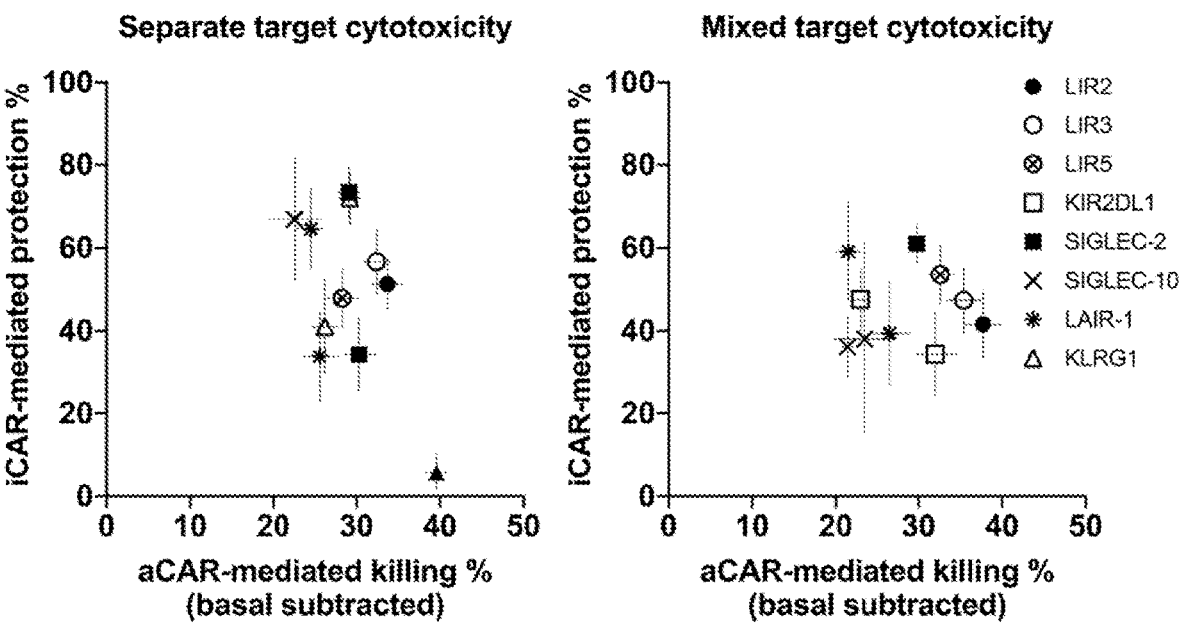
FIG. 9 shows NK cell mediated killing (top panels) and cytokine secretion (bottom panel). Shown are for the various NK cells engineered to co-express an anti-FLT3 aCAR and the indicated anti-EMCN iCARs. "Separate"=each type of SEM cell presented separately (top left panel). "Mixed"=both types of SEM cells mixed together in the same culture (top right panel). Between 1 and 3 biological replicates per condition (indicated as separate points). 3 technical replicates per measurement, X and Y SEM plotted where relevant. KLRG1 is not shown where its iCAR protection is negative.
Figure 9:
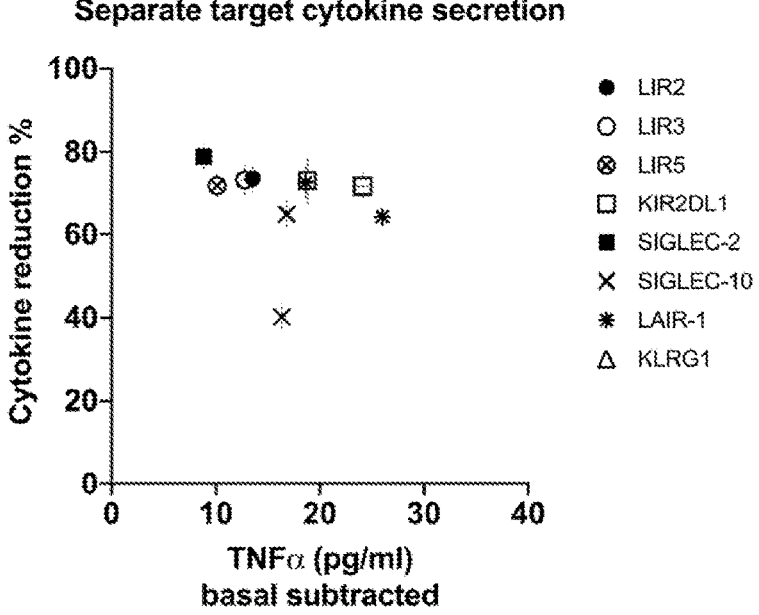

Next, anti-EMCN iCAR reduction of anti-FLT3 aCAR-induced NK cell mediated killing of target cells and NK cell cytokine production was assessed. Reduction was determined for each of the target SEM cells separately ("Separate": aCAR antigen FLT3 only SEM cells and aCAR/iCAR antigen FLT3/EMCN co-expressing SEM cells separately) or in the context of a mixed population of target and non-target cells ("Mixed": aCAR antigen FLT3 only SEM cells and aCAR/iCAR antigen FLT3/EMCN co-expressing SEM cells together in the same culture). As shown in FIG. 9, NK cells expressing LIR2, LIR3, LIR5, KIR2DL1, LAIR1, and SIGLEC-2 anti-EMCN iCAR formats demonstrated consistent aCAR-mediated performance in killing (top panels) and iCAR-mediated protection in both killing (top panels) and cytokine reduction (bottom panel), with SIGLEC-10 and KLRG1 constructs varying more in their performance.

The results demonstrate NK cells were successfully engineered to co-express aCARs and iCARs, in particular anti-EMCN iCARS, successfully kill target cells and produce cytokines in the absence of an iCAR ligand in an aCAR ligand dependent manner, and successfully reduce NK-mediated killing and cytokine production in an iCAR ligand (anti-EMCN) dependent manner.

Example 6: Assessment of Protection of Healthy HSPC Populations by an EMCN iCAR

Methods and Materials

Human hematopoietic stem and progenitor cells (HSPCs) express both CD33 and EMCN, and thus, the ability of an anti-endomucin (aEMCN)-targeting inhibitory CAR (iCAR) to protect HSPCs from anti-CD33 activating CAR killing is assessed. Human CD34+ bone marrow-derived hemaotopietic stem and progenitor cells were sourced from AllCells. Viability dye and antibodies for flow cytometry, including lineage cocktail, CD34, CD38, and CD45RA, were purchased from BD biosciences or Biolegend. NK cells were purified in house from donors using CD3 depletion and CD56 positive selection. NK cells were expanded by co-culturing with K562 cells expressing membrane tethered IL-15 and IL-21. NK cells were transduced using synthetic constructs encoding CARs in a gamma retroviral backbone by spinduction on retronectin-coated plates. To prepare the CAR-encoding retroviruses, GP2 packaging cells were transfected with the synthetic constructs. aCARs were second generation CARs with an anti-CD33 antigen-binding domain, and iCARs were constructed analogously but with two inhibitory intracellular domains instead of an activating intracellular domain. An off-target inhibitory CAR (iCAR) used as a control included an anti-HER2 binding domain. The anti-EMCN iCAR included an anti-EMCN scFV of SEQ ID NO: 17, a CD8 hinge, a LIR1 transmembrane domain, a first intracellular domain of LIR1, and a second intracellular domain of KIR3DL1.

Figure 10:
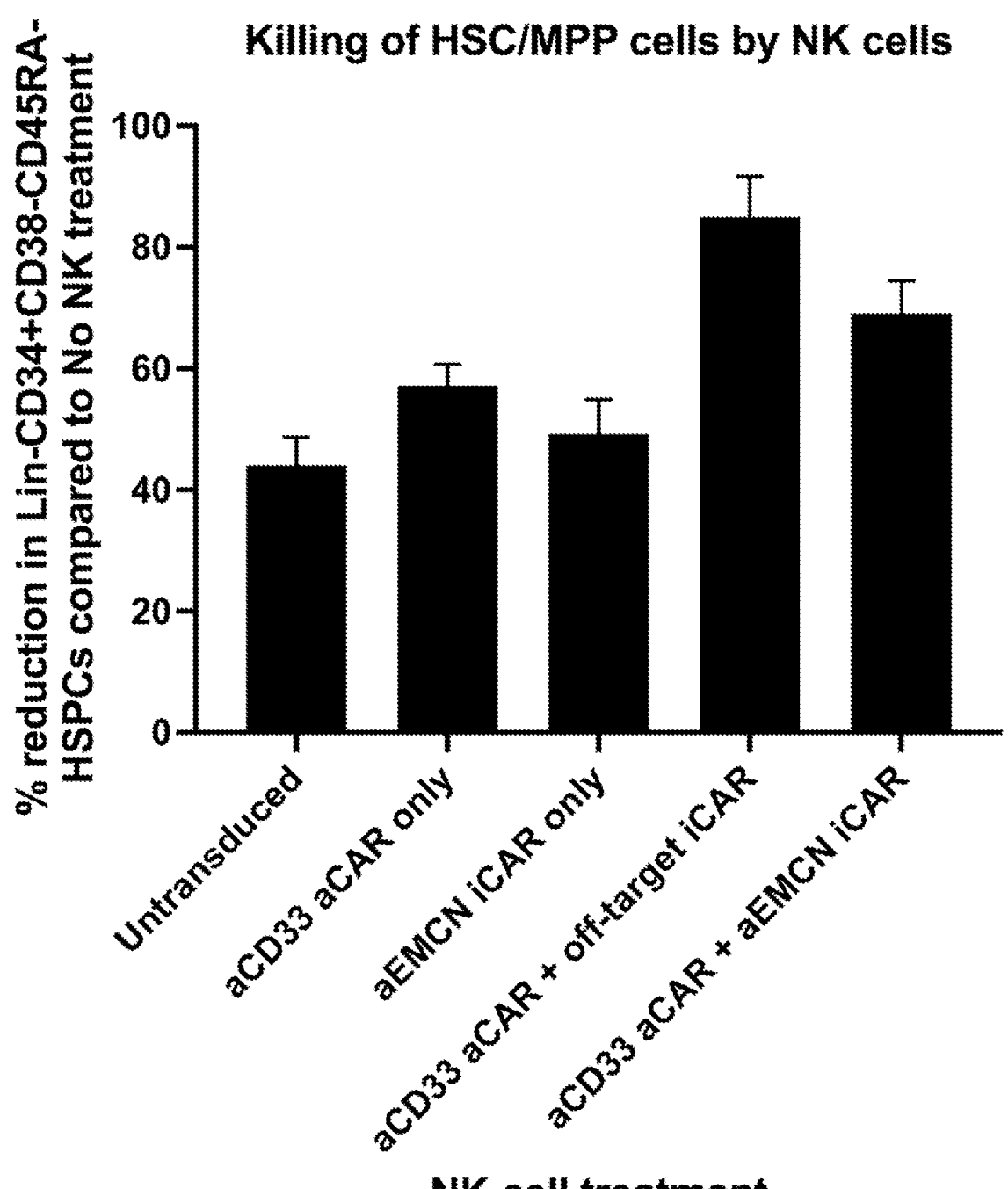
FIG. 10 shows percent killing of hematopoietic stem and progenitor cells (HSPCs) co-cultured with NK cells expressing various chimeric antigen receptors.

HSPCs were thawed and washed once with RPMI. CAR-expressing NK cells were washed once with RPMI and then arrayed in various combinations with HSPCs at 4:1 E:T ratio in microwell plates and incubated overnight at 37 degrees C. with $\kappa$% $CO_2$. Assay plates were centrifuged, stained with the antibody cocktail and viability dye, and analyzed by flow cytometry. A fixed volume from every well was acquired and the counts of the various subpopulations in each volume were tallied and used to calculate killing relative to a condition with no NK cells (FIG. 10).

Results

Killing of HSPCs by CAR-transduced NK cells was assessed and compared to killing by untransduced NK cells. As shown in FIG. 10, co-culture with αCD33 aCAR NK cells resulted in more killing of HSPCs than co-culture with aEMCN iCAR NK cells. Additionally, co-culture with NK cells expressing an aCD33 aCAR and an iCAR specific to an off-target antigen (not expressed by HSPCs) resulted in more killing than co-culture with NK cells expressing an αCD33 aCAR and an αEMCN iCAR. Although the dual-CAR transduced NK cell conditions resulted in elevated baseline killing, the NK cells expressing an aEMCN iCAR and an αCD33 aCAR resulted in reduced killing of HSPCs as compared to NK cells expressing an off-target iCAR and an αCD33 aCAR, indicating αEMCN iCAR-mediated protection of HSPCs.

Example 7: Assessment of aEMCN iCAR Activity In Vivo

The ability of an anti-endomucin (aEMCN)-targeting iCAR to protect EMCN-expressing cells is assessed in a mouse model. A B cell precursor leukemia cell line (NALM6) cells are used as target cells and are genetically modified to express either FLT3 (the activating antigen) only ("cancer model cell") or both FLT3 and EMCN (the safety antigen) together ("healthy model cell"). The mouse model consists of Jax hIL-15 mice (NSG background) injected with a 1:1 mixture of these two NALM6 cell types (5e5 cells total) via tail vein route. Mice are divided into 3 groups of 6 mice, each of which receiving one of 3 NK cell treatments, including (Group A) No NK cells (PBS control), (Group B) NK cells expressing aFLT3 aCAR, or (Group C) NK cells expressing both aFLT3 aCAR and aEMCN iCAR. Peripheral blood are collected from these mice weekly and prepared for flow cytometry analysis with red blood cell lysis and staining with antibodies and viability dyes to discriminate NALM6 cells that do or do not express the safety antigen. Although NK cells in Group B express the aCAR and reduce target cell number, both NK cells in Groups A and B do not have the iCAR or recognize the safety antigen, so in both groups the % of target cells that express EMCN remain at 50% as initially injected. However, NK cells in Group C recognize the safety antigen on the EMCN+ NALM6 subpopulation, reducing the NK cell-mediated killing of the target cells. The results demonstrate successful NOT gate circuit function based on an elevation in the % of target cells in peripheral blood that are EMCN+ as compared to the two control groups.

INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

EQUIVALENTS

While various specific embodiments have been illustrated and described, the above specification is not restrictive. It will be appreciated that various changes can be made without departing from the spirit and scope of the present disclosure(s). Many variations will become apparent to those skilled in the art upon review of this specification.

OTHER SEQUENCES

Other sequences related to the present disclosure are presented below:

| Sequence | SEQ ID NO: | Description |
|---|---|---|
| GGAGGCGGAGGATCTGGTGGCGGAG GAAGTGGCGGAGGCGGTTCT | 64 | (G4S)₃ linker nucleic acid |
| GGTGGTGGTGGCAGTGGTGGCGGTG GCTCAGGTGGCGGCGGATCAGGCGG TGGTGGTTCTGGCGGCGGTGGATCT | 65 | (G4S)₅ linker nucleic acid |
| MALPVTALLLPLALLLHAARPEVQL VQSGAEVKKPGSSVKVSCKASGGTF SSYAISWVRQAPGQGLEWMGGIIPI FGTANYAQKFQGRVTITADKSTSTA YMELSSLRSEDTAVYYCATFALFGF REQAFDIWGQGTTVTVSSGGGGSGG GGSGGGGSDIQMTQSPSSLSASVGD RVTITCRASQSISSYLNWYQQKPGK APKLLIYAASSLQSGVPSRFSGSGS GTDFTLTISSLQPEDLATYYCQQSY STPFTFGPGTKVDIKTTTPAPRPPT PAPTIALQPLSLRPEACRPAAGGAV HTRGLDFACDIYIWAPLAGTCGVLL LSLVITKRGRKKLLYIFKQPFMRPV QTTQEEDGCSCRFPEEEEGGCELRV KFSRSADAPAYKQGQNQLYNELNLG RREEYDVLDKRRGRDPEMGGKPRRK NPQEGLYNELQKDKMAEAYSEIGMK GERRRGKGHDGLYQGLSTATKDTYD ALHMQALPPRGSSGTGMVSKGEELF TGVVPILVELDGDVNGHKFSVSGEG EGDATYGKLTLKLICTTGKLPVPWP TLVTTLGYGLQCFARYPDHMKQHDF FKSAMPEGYVQERTIFFKDDGNYKT RAEVKFEGDTLVNRIELKGIDFKED GNILGHKLEYNYNSHNVYITADKQK NGIKANFKIRHNIEDGGVQLADHYQ QNTPIGDGPVLLPDNHYLSYQSALS KDPNEKRDHMVLLEFVTAAGITLGM DELYK | 66 | SB00819 Cassette |
| METDTLLLWVLLLWVPGSTGAGGSD YKDDDDKGGSQVQLVQSGAEVKKPG SSVKVSCKASGYTFTDYNMHWVRQA PGQGLEWIGYIYPYNGGTGYNQKFK SKATITADESTNTAYMELSSLRSED TAVYYCARGRPAMDYWGQGTLVTVS SGGGGSGGGGSGGGGSDIQMTQSPS SLSASVGDRVTITCRASESVDNYGI SFMNWFQQKPGKAPKLLIYAASNQG SGVPSRFSGSGSGTDFTLTISSLQP DDFATYYCQQSKEVPWTFGQGTKVE IKSGAAAIEVMYPPPYLDNEKSNGT IIHVKGKHLCPSPLFPGPSKPFWVL VVVGGVLACYSLLVTVAFIIFWVRS KRSRLLHSDYMNMTPRRPGPTRKHY QPYAPPRDFAAYRSRVKFSRSADAP AYKQGQNQLYNELNLGRREEYDVLD KRRGRDPEMGGKPRRKNPQEGLYNE LQKDKMAEAYSEIGMKGERRRGKGH DGLYQGLSTATKDTYDALHMQALPP R | 67 | SB01052 Cassette |
| MALPVTALLLPLALLLHAARPAGGS DYKDDDDKGGSQVQLKESGPGLVQP SQTLSLTCTVSGFSLSRYDMHWVRQ PPGQGLEWMGVIWGNGNTHYHSALK SRLSISRDTSKSQVFLKMNSLQTED TAIYFCTLRIKDWGPGTMVTVSSGG GGSGGGGSGGGGSDIVMTQTPPSLS VALGQSVSISCKSSQSLVASDENTY | 68 | SB02645 Cassette |

| Sequence | SEQ ID NO: | Description |
|---|---|---|

LNWLLQSPGRSPKRLIYQVSKLDSG
VPDRFSGSGSEKDFTLKISRVEAED
LGVYYCLQGIHLPWTFGGGTKLELK
TTTPAPRPPTPAPTIALQPLSLRPE
ACRPAAGGAVHTRGLDFACDLLPLG
GLPLLITTCFCLFCCLRRHQGKQNE
LSDTAGREINLVDAHLKSEQTEAST
RQNSQVLLSETGIYDNDPDLCFRMQ
EGSEVYSNPCLEENKPGIVYASLNH
SVIGPNSRLARNVKEAPTEYASICV
RS*

MALPVTALLLPLALLLHAARPAGGS  69  SB02646 Cassette
DYKDDDDKGGSQVQLKESGPGLVQP
SQTLSLTCTVSGFSLSRYDMHWVRQ
PPGQGLEWMGVIWGNGNTHYHSALK
SRLSISRDTSKSQVFLKMNSLQTED
TAIYFCTLRIKDWGPGTMVTVSSGG
GGSGGGGSGGGGSDIVMTQTPPSLS
VALGQSVSISCKSSQSLVASDENTY
LNWLLQSPGRSPKRLIYQVSKLDSG
VPDRFSGSGSEKDFTLKISRVEAED
LGVYYCLQGIHLPWTFGGGTKLELK
TTTPAPRPPTPAPTIALQPLSLRPE
ACRPAAGGAVHTRGLDFACDLLPLG
GLPLLITTCFCLFCCLRRHQGKQNE
LSDTAGREINLVDAHLKSEQTEAST
RQNSQVLLSETGIYDNDPDLCFRMQ
EGSEVYSNPCLEENKPGIVYASLNH
SVIGPNSRLARNVKEAPTEYASICV
RSGSGATNFSLLKQAGDVEENPGPM
TEYKPTVRLATRDDVPRAVRTLAAA
FADYPATRHTVDPDRHIERVTELQE
LFLTRVGLDIGKVWVADDGAAVAVW
TTPESVEAGAVFAEIGPRMAELSGS
RLAAQQQMEGLLAPHRPKEPAWFLA
TVGVSPDHQGKGLGSAVVLPGVEAA
ERAGVPAFLETSAPRNLPFYERLGF
TVTADVEVPEGPRTWCMTRKPGA*

MALPVTALLLPLALLLHAARPAGGS  70  SB02647 Cassette
DYKDDDDKGGSQVQLKESGPGLVQP
SQTLSLTCTVSGFSLSRYDMHWVRQ
PPGQGLEWMGVIWGNGNTHYHSALK
SRLSISRDTSKSQVFLKMNSLQTED
TAIYFCTLRIKDWGPGTMVTVSSGG
GGSGGGGSGGGGSDIVMTQTPPSLS
VALGQSVSISCKSSQSLVASDENTY
LNWLLQSPGRSPKRLIYQVSKLDSG
VPDRFSGSGSEKDFTLKISRVEAED
LGVYYCLQGIHLPWTFGGGTKLELK
TTTPAPRPPTPAPTIALQPLSLRPE
ACRPAAGGAVHTRGLDFACDVIGIL
VAVILLLLLLLLLLFLILRHRRQGKH
WTSTQRKADFQHPAGAVGPEPTDRG
LQWRSSPAADAQEENLYAAVKHTQP
EDGVEMDTRSPHDEDPQAVTYAEVK
HSRPRREMASPPSPLSGEFLDTKDR
QAEEDRQMDTEAAASEAPQDVTYAQ
LHSLTLRREATEPPPSQEGPSPAVP
SIYATLAIH*

MALPVTALLLPLALLLHAARPAGGS  71  SB02648 Cassette
DYKDDDDKGGSQVQLKESGPGLVQP
SQTLSLTCTVSGFSLSRYDMHWVRQ
PPGQGLEWMGVIWGNGNTHYHSALK
SRLSISRDTSKSQVFLKMNSLQTED
TAIYFCTLRIKDWGPGTMVTVSSGG
GGSGGGGSGGGGSDIVMTQTPPSLS
VALGQSVSISCKSSQSLVASDENTY
LNWLLQSPGRSPKRLIYQVSKLDSG
VPDRFSGSGSEKDFTLKISRVEAED
LGVYYCLQGIHLPWTFGGGTKLELK
TTTPAPRPPTPAPTIALQPLSLRPE
ACRPAAGGAVHTRGLDFACDVIGIL
VAVILLLLLLLLLLFLILRHRRQGKH WTSTQRKADFQHPAGAVGPEPTDRG
LQWRSSPAADAQEENLYAAVKHTQP
EDGVEMDTRSPHDEDPQAVTYAEVK
HSRPRREMASPPSPLSGEFLDTKDR
QAEEDRQMDTEAAASEAPQDVTYAQ
LHSLTLRREATEPPPSQEGPSPAVP
SIYATLAIHGSGATNFSLLKQAGDV
EENPGPMTEYKPTVRLATRDDVPRA
VRTLAAAFADYPATRHTVDPDRHIE
RVTELQELFLTRVGLDIGKVWVADD
GAAVAVWTTPESVEAGAVFAEIGPR
MAELSGSRLAAQQQMEGLLAPHRPK
EPAWFLATVGVSPDHQGKGLGSAVV
LPGVEAAERAGVPAFLETSAPRNLP
FYERLGFTVTADVEVPEGPRTWCMT
RKPGA*

MALPVTALLLPLALLLHAARPAGGS  72  SB02649 Cassette
DYKDDDDKGGSDIVMTQTPPSLSVA
LGQSVSISCKSSQSLVASDENTYLN
WLLQSPGRSPKRLIYQVSKLDSGVP
DRFSGSGSEKDFTLKISRVEAEDLG
VYYCLQGIHLPWTFGGGTKLELKGG
GGSGGGGSGGGGSQVQLKESGPGLV
QPSQTLSLTCTVSGFSLSRYDMHWV
RQPPGQGLEWMGVIWGNGNTHYHSA
LKSRLSISRDTSKSQVFLKMNSLQT
EDTAIYFCTLRIKDWGPGTMVTVSS
TTTPAPRPPTPAPTIALQPLSLRPE
ACRPAAGGAVHTRGLDFACDLLPLG
GLPLLITTCFCLFCCLRRHQGKQNE
LSDTAGREINLVDAHLKSEQTEAST
RQNSQVLLSETGIYDNDPDLCFRMQ
EGSEVYSNPCLEENKPGIVYASLNH
SVIGPNSRLARNVKEAPTEYASICV
RS*

MALPVTALLLPLALLLHAARPAGGS  73  SB02650 Cassette
DYKDDDDKGGSQVQLKESGPGLVQP
SQTLSLTCTVSGFSLSRYDMHWVRQ
PPGQGLEWMGVIWGNGNTHYHSALK
SRLSISRDTSKSQVFLKMNSLQTED
TAIYFCTLRIKDWGPGTMVTVSSGG
GGSGGGGSGGGGSDIVMTQTPPSLS
VALGQSVSISCKSSQSLVASDENTY
LNWLLQSPGRSPKRLIYQVSKLDSG
VPDRFSGSGSEKDFTLKISRVEAED
LGVYYCLQGIHLPWTFGGGTKLELK
TTTPAPRPPTPAPTIALQPLSLRPE
ACRPAAGGAVHTRGLDFACDLLPLG
GLPLLITTCFCLFCCLRRHQGKQNE
LSDTAGREINLVDAHLKSEQTEAST
RQNSQVLLSETGIYDNDPDLCFRMQ
EGSEVYSNPCLEENKPGIVYASLNH
SVIGPNSRLARNVKEAPTEYASICV
RSLRHRRQGKHWTSTQRKADFQHPA
GAVGPEPTDRGLQWRSSPAADAQEE
NLYAAVKHTQPEDGVEMDTRSPHDE
DPQAVTYAEVKHSRPRREMASPPSP
LSGEFLDTKDRQAEEDRQMDTEAAA
SEAPQDVTYAQLHSLTLRREATEPP
PSQEGPSPAVPSIYATLAIH*

MALPVTALLLPLALLLHAARPAGGS  74  SB02651 Cassette
DYKDDDDKGGSDIVMTQTPPSLSVA
LGQSVSISCKSSQSLVASDENTYLN
WLLQSPGRSPKRLIYQVSKLDSGVP
DRFSGSGSEKDFTLKISRVEAEDLG
VYYCLQGIHLPWTFGGGTKLELKGG
GGSGGGGSGGGGSQVQLKESGPGLV
QPSQTLSLTCTVSGFSLSRYDMHWV
RQPPGQGLEWMGVIWGNGNTHYHSA
LKSRLSISRDTSKSQVFLKMNSLQT
EDTAIYFCTLRIKDWGPGTMVTVSS
TTTPAPRPPTPAPTIALQPLSLRPE
ACRPAAGGAVHTRGLDFACDVIGIL -continued -continued

| Sequence | SEQ ID NO: | Description |
|---|---|---|
| VAVILLLLLLLLLLFLILRHRRQGKH WTSTQRKADFQHPAGAVGPEPTDRG LQWRSSPAADAQEENLYAAVKHTQP EDGVEMDTRSPHDEDPQAVTYAEVK HSRPRREMASPPSPLSGEFLDTKDR QAEEDRQMDTEAAASEAPDVTYAQ LHSLTLRREATEPPPSQEGPSPAVP SIYATLAIH* | | |
| MALPVTALLLPLALLLHAARPAGGS DYKDDDDKGGSQVQLKESGPGLVQP SQTLSLTCTVSGFSLSRYDMHWVRQ PPGQGLEWMGVIWGNGNTHYHSALK SRLSISRDTSKSQVFLKMNSLQTED TAIYFCTLRIKDWGPGTMVTVSSGG GGSGGGGSGGGGSDIVMTQTPPSLS VALGQSVSISCKSSQSLVASDENTY LNWLLQSPGRSPKRLIYQVSKLDSG VPDRFSGSGSEKDFTLKISRVEAED LGVYYCLQGIHLPWTFGGGTKLELK TTTPAPRPPTPAPTIALQPLSLRPE ACRPAAGGAVHTRGLDFACDVIGIL VAVILLLLLLLLLLFLILRHRRQGKH WTSTQRKADFQHPAGAVGPEPTDRG LQWRSSPAADAQEENLYAAVKHTQP EDGVEMDTRSPHDEDPQAVTYAEVK HSRPRREMASPPSPLSGEFLDTKDR QAEEDRQMDTEAAASEAPDVTYAQ LHSLTLRREATEPPPSQEGPSPAVP SIYATLAIHRRHQGKQNELSDTAGR EINLVDAHLKSEQTEASTRQNSQVL LSETGIYDNDPDLCFRMQEGSEVYS NPCLEENKPGIVYASLNHSVIGPNS RLARNVKEAPTEYASICVRS* | 75 | SB02652 Cassette |
| MALPVTALLLPLALLLHAARPAGGS DYKDDDDKGGSQVQLKESGPGLVQP SQTLSLTCTVSGFSLSRYDMHWVRQ PPGQGLEWMGVIWGNGNTHYHSALK SRLSISRDTSKSQVFLKMNSLQTED TAIYFCTLRIKDWGPGTMVTVSSGG GGSDIVMTQTPPSLSVALGQSVSIS CKSSQSLVASDENTYLNWLLQSPGR SPKRLIYQVSKLDSGVPDRFSGSGS EKDFTLKISRVEAEDLGVYYCLQGI HLPWTFGGGTKLELKTTTPAPRPPT PAPTIALQPLSLRPEACRPAAGGAV HTRGLDFACDLLPLGGLPLLITTCF CLFCCLRRHQGKQNELSDTAGREIN LVDAHLKSEQTEASTRQNSQVLLSE TGIYDNDPDLCFRMQEGSEVYSNPC LEENKPGIVYASLNHSVIGPNSRLA RNVKEAPTEYASICVRS* | 76 | SB02686 Cassette |
| MALPVTALLLPLALLLHAARPAGGS DYKDDDDKGGSQVQLKESGPGLVQP SQTLSLTCTVSGFSLSRYDMHWVRQ PPGQGLEWMGVIWGNGNTHYHSALK SRLSISRDTSKSQVFLKMNSLQTED TAIYFCTLRIKDWGPGTMVTVSSGG GGSDIVMTQTPPSLSVALGQSVSIS CKSSQSLVASDENTYLNWLLQSPGR SPKRLIYQVSKLDSGVPDRFSGSGS EKDFTLKISRVEAEDLGVYYCLQGI HLPWTFGGGTKLELKTTTPAPRPPT PAPTIALQPLSLRPEACRPAAGGAV HTRGLDFACDVIGILVAVILLLLLL LLLLFLILRHRRQGKHWTSTQRKADF QHPAGAVGPEPTDRGLQWRSSPAAD AQEENLYAAVKHTQPEDGVEMDTRS PHDEDPQAVTYAEVKHSRPRREMAS PPSPLSGEFLDTKDRQAEEDRQMDT EAAASEAPQDVTYAQLHSLTLRREA TEPPPSQEGPSPAVPSIYATLAIH* | 77 | SB02687 Cassette |

| Sequence | SEQ ID NO: | Description |
|---|---|---|
| MALPVTALLLPLALLLHAARPAGGS DYKDDDDKGGSQVQLKESGPGLVQP SQTLSLTCTVSGFSLSRYDMHWVRQ PPGQGLEWMGVIWGNGNTHYHSALK SRLSISRDTSKSQVFLKMNSLQTED TAIYFCTLRIKDWGPGTMVTVSSGG GGSDIVMTQTPPSLSVALGQSVSIS CKSSQSLVASDENTYLNWLLQSPGR SPKRLIYQVSKLDSGVPDRFSGSGS EKDFTLKISRVEAEDLGVYYCLQGI HLPWTFGGGTKLELKTTTPAPRPPT PAPTIALQPLSLRPEACRPAAGGAV HTRGLDFACDVIGILVAVILLLLLL LLLLFLILRHRRQGKHWTSTQRKADF QHPAGAVGPEPTDRGLQWRSSPAAD AQEENLYAAVKHTQPEDGVEMDTRS PHDEDPQAVTYAEVKHSRPRREMAS PPSPLSGEFLDTKDRQAEEDRQMDT EAAASEAPQDVTYAQLHSLTLRREA TEPPPSQEGPSPAVPSIYATLAIHR RHQGKQNELSDTAGREINLVDAHLK SEQTEASTRQNSQVLLSETGIYDND PDLCFRMQEGSEVYSNPCLEENKPG IVYASLNHSVIGPNSRLARNVKEAP TEYASICVRS* | 78 | SB02688 Cassette |
| MALPVTALLLPLALLLHAARPAGGS DYKDDDDKGGSQVQLKESGPGLVQP SQTLSLTCTVSGFSLSRYDMHWVRQ PPGQGLEWMGVIWGNGNTHYHSALK SRLSISRDTSKSQVFLKMNSLQTED TAIYFCTLRIKDWGPGTMVTVSSGS TSGSGKPGSGEGSTKGDIVMTQTPP SLSVALGQSVSISCKSSQSLVASDE NTYLNWLLQSPGRSPKRLIYQVSKL DSGVPDRFSGSGSEKDFTLKISRVE AEDLGVYYCLQGIHLPWTFGGGTKL ELKTTTPAPRPPTPAPTIALQPLSL RPEACRPAAGGAVHTRGLDFACDLL PLGGLPLLITTCFCLFCCLRRHQGK QNELSDTAGREINLVDAHLKSEQTE ASTRQNSQVLLSETGIYDNDPDLCF RMQEGSEVYSNPCLEENKPGIVYAS LNHSVIGPNSRLARNVKEAPTEYAS ICVRS* | 79 | SB02760 Cassette |
| MALPVTALLLPLALLLHAARPAGGS DYKDDDDKGGSQVQLKESGPGLVQP SQTLSLTCTVSGFSLSRYDMHWVRQ PPGQGLEWMGVIWGNGNTHYHSALK SRLSISRDTSKSQVFLKMNSLQTED TAIYFCTLRIKDWGPGTMVTVSSGS TSGSGKPGSGEGSTKGDIVMTQTPP SLSVALGQSVSISCKSSQSLVASDE NTYLNWLLQSPGRSPKRLIYQVSKL DSGVPDRFSGSGSEKDFTLKISRVE AEDLGVYYCLQGIHLPWTFGGGTKL ELKTTTPAPRPPTPAPTIALQPLSL RPEACRPAAGGAVHTRGLDFACDVI GILVAVILLLLLLLLLLFLILRHRRQ GKHWTSTQRKADFQHPAGAVGPEPT DRGLQWRSSPAADAQEENLYAAVKH TQPEDGVEMDTRSPHDEDPQAVTYA EVKHSRPRREMASPPSPLSGEFLDT KDRQAEEDRQMDTEAAASEAPQDVT YAQLHSLTLRREATEPPPSQEGPSP AVPSIYATLAIH* | 80 | SB02761 Cassette |
| MALPVTALLLPLALLLHAARPAGGS DYKDDDDKGGSQVQLKESGPGLVQP SQTLSLTCTVSGFSLSRYDMHWVRQ PPGQGLEWMGVIWGNGNTHYHSALK SRLSISRDTSKSQVFLKMNSLQTED TAIYFCTLRIKDWGPGTMVTVSSGS TSGSGKPGSGEGSTKGDIVMTQTPP | 81 | SB02762 Cassette |

-continued                                  -continued

| Sequence | SEQ ID NO: Description |
|----------|------------------------|
| SLSVALGQSVSISCKSSQSLVASDE | |
| NTYLNWLLQSPGRSPKRLIYQVSKL | |
| DSGVPDRFSGSGSEKDFTLKISRVE | |
| AEDLGVYYCLQGIHLPWTFGGGTKL | |
| ELKTTTPAPRPPTPAPTIALQPLSL | |
| RPEACRPAAGGAVHTRGLDFACDVI | |
| GILVAVILLLLLLLLLFLILRHRRQ | |
| GKHWTSTQRKADFQHPAGAVGPEPT | |
| DRGLQWRSSPAADAQEENLYAAVKH | |
| TQPEDGVEMDTRSPHDEDPQAVTYA | |

| Sequence | SEQ ID NO: Description |
|----------|------------------------|
| EVKHSRPRREMASPPSPLSGEFLDT | |
| KDRQAEEDRQMDTEAAASEAPQDVT | |
| YAQLHSLTLRREATEPPPSQEGPSP | |
| AVPSIYATLAIHRRHQGKQNELSDT | |
| AGREINLVDAHLKSEQTEASTRQNS | |
| QVLLSETGIYDNDPDLCFRMQEGSE | |
| VYSNPCLEENKPGIVYASLNHSVIG | |
| PNSRLARNVKEAPTEYASICVRS* | |

SEQUENCE LISTING

Sequence total quantity: 111

| | |
|---|---|
| SEQ ID NO: 1 | moltype = AA  length = 112 |
| FEATURE | Location/Qualifiers |
| REGION | 1..112 |
| | note = Description of Artificial Sequence: Synthetic |
| | polypeptide |
| source | 1..112 |
| | mol_type = protein |
| | organism = synthetic construct |

SEQUENCE: 1
QVQLKESGPG LVQPSQTLSL TCTVSGFSLS RYDMHWVRQP PGQGLEWMGV IWGNGNTHYH  60
SALKSRLSIS RDTSKSQVFL KMNSLQTEDT AIYFCTLRIK DWGPGTMVTV SS         112

| | |
|---|---|
| SEQ ID NO: 2 | moltype = AA  length = 7 |
| FEATURE | Location/Qualifiers |
| REGION | 1..7 |
| | note = Description of Artificial Sequence: Synthetic peptide |
| source | 1..7 |
| | mol_type = protein |
| | organism = synthetic construct |

SEQUENCE: 2
GFSLSRY                                                             7

| | |
|---|---|
| SEQ ID NO: 3 | moltype = AA  length = 5 |
| FEATURE | Location/Qualifiers |
| REGION | 1..5 |
| | note = Description of Artificial Sequence: Synthetic peptide |
| source | 1..5 |
| | mol_type = protein |
| | organism = synthetic construct |

SEQUENCE: 3
WGNGN                                                               5

| | |
|---|---|
| SEQ ID NO: 4 | moltype = AA  length = 4 |
| FEATURE | Location/Qualifiers |
| REGION | 1..4 |
| | note = Description of Artificial Sequence: Synthetic peptide |
| source | 1..4 |
| | mol_type = protein |
| | organism = synthetic construct |

SEQUENCE: 4
RIKD                                                                4

| | |
|---|---|
| SEQ ID NO: 5 | moltype = AA  length = 25 |
| FEATURE | Location/Qualifiers |
| REGION | 1..25 |
| | note = Description of Artificial Sequence: Synthetic peptide |
| source | 1..25 |
| | mol_type = protein |
| | organism = synthetic construct |

SEQUENCE: 5
QVQLKESGPG LVQPSQTLSL TCTVS                                          25

| | |
|---|---|
| SEQ ID NO: 6 | moltype = AA  length = 19 |
| FEATURE | Location/Qualifiers |
| REGION | 1..19 |
| | note = Description of Artificial Sequence: Synthetic peptide |
| source | 1..19 |
| | mol_type = protein |
| | organism = synthetic construct |

-continued

```
SEQUENCE: 6
DMHWVRQPPG QGLEWMGVI                                                      19

SEQ ID NO: 7              moltype = AA  length = 41
FEATURE                   Location/Qualifiers
REGION                    1..41
                          note = Description of Artificial Sequence: Synthetic
                           polypeptide
source                    1..41
                          mol_type = protein
                          organism = synthetic construct
SEQUENCE: 7
THYHSALKSR LSISRDTSKS QVFLKMNSLQ TEDTAIYFCT L                             41

SEQ ID NO: 8              moltype = AA  length = 11
FEATURE                   Location/Qualifiers
REGION                    1..11
                          note = Description of Artificial Sequence: Synthetic peptide
source                    1..11
                          mol_type = protein
                          organism = synthetic construct
SEQUENCE: 8
WGPGTMVTVS S                                                             11

SEQ ID NO: 9              moltype = AA  length = 112
FEATURE                   Location/Qualifiers
REGION                    1..112
                          note = Description of Artificial Sequence: Synthetic
                           polypeptide
source                    1..112
                          mol_type = protein
                          organism = synthetic construct
SEQUENCE: 9
DIVMTQTPPS LSVALGQSVS ISCKSSQSLV ASDENTYLNW LLQSPGRSPK RLIYQVSKLD   60
SGVPDRFSGS GSEKDFTLKI SRVEAEDLGV YYCLQGIHLP WTFGGGTKLE LK           112

SEQ ID NO: 10             moltype = AA  length = 16
FEATURE                   Location/Qualifiers
REGION                    1..16
                          note = Description of Artificial Sequence: Synthetic peptide
source                    1..16
                          mol_type = protein
                          organism = synthetic construct
SEQUENCE: 10
KSSQSLVASD ENTYLN                                                        16

SEQ ID NO: 11             moltype = AA  length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 11
QVSKLDS                                                                  7

SEQ ID NO: 12             moltype = AA  length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 12
LQGIHLPWT                                                                9

SEQ ID NO: 13             moltype = AA  length = 23
FEATURE                   Location/Qualifiers
REGION                    1..23
                          note = Description of Artificial Sequence: Synthetic peptide
source                    1..23
                          mol_type = protein
                          organism = synthetic construct
SEQUENCE: 13
DIVMTQTPPS LSVALGQSVS ISC                                                23

SEQ ID NO: 14             moltype = AA  length = 15
FEATURE                   Location/Qualifiers
REGION                    1..15
```

```
                          note = Description of Artificial Sequence: Synthetic peptide
source                    1..15
                          mol_type = protein
                          organism = synthetic construct
SEQUENCE: 14
WLLQSPGRSP KRLIY                                                         15

SEQ ID NO: 15             moltype = AA  length = 32
FEATURE                   Location/Qualifiers
REGION                    1..32
                          note = Description of Artificial Sequence: Synthetic
                           polypeptide
source                    1..32
                          mol_type = protein
                          organism = synthetic construct
SEQUENCE: 15
GVPDRFSGSG SEKDFTLKIS RVEAEDLGVY YC                                      32

SEQ ID NO: 16             moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 16
FGGGTKLELK                                                               10

SEQ ID NO: 17             moltype = AA  length = 239
FEATURE                   Location/Qualifiers
REGION                    1..239
                          note = Description of Artificial Sequence: Synthetic
                           polypeptide
source                    1..239
                          mol_type = protein
                          organism = synthetic construct
SEQUENCE: 17
QVQLKESGPG LVQPSQTLSL TCTVSGFSLS RYDMHWVRQP PGQGLEWMGV IWGNGNTHYH  60
SALKSRLSIS RDTSKSQVFL KMNSLQTEDT AIYFCTLRIK DWGPGTMVTV SSGGGGSGGG  120
GSGGGGSDIV MTQTPPSLSV ALGQSVSISC KSSQSLVASD ENTYLNWLLQ SPGRSPKRLI  180
YQVSKLDSGV PDRFSGSGSE KDFTLKISRV EAEDLGVYYC LQGIHLPWTF GGGTKLELK    239

SEQ ID NO: 18             moltype = AA  length = 239
FEATURE                   Location/Qualifiers
REGION                    1..239
                          note = Description of Artificial Sequence: Synthetic
                           polypeptide
source                    1..239
                          mol_type = protein
                          organism = synthetic construct
SEQUENCE: 18
DIVMTQTPPS LSVALGQSVS ISCKSSQSLV ASDENTYLNW LLQSPGRSPK RLIYQVSKLD  60
SGVPDRFSGS GSEKDFTLKI SRVEAEDLGV YYCLQGIHLP WTFGGGTKLE LKGGGGSGGG  120
GSGGGGSQVQ LKESGPGLVQ PSQTLSLTCT VSGFSLSRYD MHWVRQPPGQ GLEWMGVIWG  180
NGNTHYHSAL KSRLSISRDT SKSQVFLKMN SLQTEDTAIY FCTLRIKDWG PGTMVTVSS   239

SEQ ID NO: 19             moltype = AA  length = 242
FEATURE                   Location/Qualifiers
REGION                    1..242
                          note = Description of Artificial Sequence: Synthetic
                           polypeptide
source                    1..242
                          mol_type = protein
                          organism = synthetic construct
SEQUENCE: 19
QVQLKESGPG LVQPSQTLSL TCTVSGFSLS RYDMHWVRQP PGQGLEWMGV IWGNGNTHYH  60
SALKSRLSIS RDTSKSQVFL KMNSLQTEDT AIYFCTLRIK DWGPGTMVTV SSGSTSGSGK  120
PGSGEGSTKG DIVMTQTPPS LSVALGQSVS ISCKSSQSLV ASDENTYLNW LLQSPGRSPK  180
RLIYQVSKLD SGVPDRFSGS GSEKDFTLKI SRVEAEDLGV YYCLQGIHLP WTFGGGTKLE  240
LK                                                               242

SEQ ID NO: 20             moltype = AA  length = 242
FEATURE                   Location/Qualifiers
REGION                    1..242
                          note = Description of Artificial Sequence: Synthetic
                           polypeptide
source                    1..242
                          mol_type = protein
                          organism = synthetic construct
```

-continued

```
SEQUENCE: 20
DIVMTQTPPS LSVALGQSVS ISCKSSQSLV ASDENTYLNW LLQSPGRSPK RLIYQVSKLD    60
SGVPDRFSGS GSEKDFTLKI SRVEAEDLGV YYCLQGIHLP WTFGGGTKLE LKGSTSGSGK   120
PGSGEGSTKG QVQLKESGPG LVQPSQTLSL TCTVSGFSLS RYDMHWVRQP PGQGLEWMGV   180
IWGNGNTHYH SALKSRLSIS RDTSKSQVFL KMNSLQTEDT AIYFCTLRIK DWGPGTMVTV   240
SS                                                                 242

SEQ ID NO: 21           moltype = AA  length = 229
FEATURE                 Location/Qualifiers
REGION                  1..229
                        note = Description of Artificial Sequence: Synthetic
                         polypeptide
source                  1..229
                        mol_type = protein
                        organism = synthetic construct
SEQUENCE: 21
QVQLKESGPG LVQPSQTLSL TCTVSGFSLS RYDMHWVRQP PGQGLEWMGV IWGNGNTHYH    60
SALKSRLSIS RDTSKSQVFL KMNSLQTEDT AIYFCTLRIK DWGPGTMVTV SSGGGGGSDIV   120
MTQTPPSLSV ALGQSVSISC KSSQSLVASD ENTYLNWLLQ SPGRSPKRLI YQVSKLDSGV   180
PDRFSGSGSE KDFTLKISRV EAEDLGVYYC LQGIHLPWTF GGGTKLELK              229

SEQ ID NO: 22           moltype = AA  length = 229
FEATURE                 Location/Qualifiers
REGION                  1..229
                        note = Description of Artificial Sequence: Synthetic
                         polypeptide
source                  1..229
                        mol_type = protein
                        organism = synthetic construct
SEQUENCE: 22
DIVMTQTPPS LSVALGQSVS ISCKSSQSLV ASDENTYLNW LLQSPGRSPK RLIYQVSKLD    60
SGVPDRFSGS GSEKDFTLKI SRVEAEDLGV YYCLQGIHLP WTFGGGTKLE LKGGGGSQVQ   120
LKESGPGLVQ PSQTLSLTCT VSGFSLSRYD MHWVRQPPGQ GLEWMGVIWG NGNTHYHSAL   180
KSRLSISRDT SKSQVFLKMN SLQTEDTAIY FCTLRIKDWG PGTMVTVSS              229

SEQ ID NO: 23           moltype =    length =
SEQUENCE: 23
000

SEQ ID NO: 24           moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 24
GGSGGS                                                               6

SEQ ID NO: 25           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 25
GGSGGSGGS                                                            9

SEQ ID NO: 26           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 26
GGSGGSGGSG GS                                                       12

SEQ ID NO: 27           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 27
GGSGGSGGSG GSGGS                                                    15
```

```
SEQ ID NO: 28            moltype = AA   length = 4
FEATURE                  Location/Qualifiers
REGION                   1..4
                         note = Description of Artificial Sequence: Synthetic peptide
source                   1..4
                         mol_type = protein
                         organism = synthetic construct
SEQUENCE: 28
GGGS                                                                    4

SEQ ID NO: 29            moltype = AA   length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 29
GGGSGGGS                                                                8

SEQ ID NO: 30            moltype = AA   length = 12
FEATURE                  Location/Qualifiers
REGION                   1..12
                         note = Description of Artificial Sequence: Synthetic peptide
source                   1..12
                         mol_type = protein
                         organism = synthetic construct
SEQUENCE: 30
GGGSGGGSGG GS                                                           12

SEQ ID NO: 31            moltype = AA   length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 31
GGGSGGGSGG GSGGGS                                                       16

SEQ ID NO: 32            moltype = AA   length = 20
FEATURE                  Location/Qualifiers
REGION                   1..20
                         note = Description of Artificial Sequence: Synthetic peptide
source                   1..20
                         mol_type = protein
                         organism = synthetic construct
SEQUENCE: 32
GGGSGGGSGG GSGGGSGGGS                                                   20

SEQ ID NO: 33            moltype = AA   length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 33
GGGGS                                                                   5

SEQ ID NO: 34            moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 34
GGGGSGGGGS                                                              10

SEQ ID NO: 35            moltype = AA   length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 35
GGGGSGGGGS GGGGS                                                        15
```

```
SEQ ID NO: 36          moltype = AA   length = 20
FEATURE                Location/Qualifiers
REGION                 1..20
                       note = Description of Artificial Sequence: Synthetic peptide
source                 1..20
                       mol_type = protein
                       organism = synthetic construct
SEQUENCE: 36
GGGGSGGGGS GGGGSGGGGS                                             20

SEQ ID NO: 37          moltype = AA   length = 25
FEATURE                Location/Qualifiers
REGION                 1..25
                       note = Description of Artificial Sequence: Synthetic peptide
source                 1..25
                       mol_type = protein
                       organism = synthetic construct
SEQUENCE: 37
GGGGSGGGGS GGGGSGGGGS GGGGS                                       25

SEQ ID NO: 38          moltype = AA   length = 18
FEATURE                Location/Qualifiers
REGION                 1..18
                       note = Description of Artificial Sequence: Synthetic peptide
source                 1..18
                       mol_type = protein
                       organism = synthetic construct
SEQUENCE: 38
GSTSGSGKPG SGEGSTKG                                               18

SEQ ID NO: 39          moltype = AA   length = 20
FEATURE                Location/Qualifiers
REGION                 1..20
                       note = Description of Artificial Sequence: Synthetic peptide
source                 1..20
                       mol_type = protein
                       organism = synthetic construct
SEQUENCE: 39
EAAAKEAAAK EAAAKEAAAK                                             20

SEQ ID NO: 40          moltype = AA   length = 42
FEATURE                Location/Qualifiers
REGION                 1..42
                       note = Description of Artificial Sequence: Synthetic
                        polypeptide
source                 1..42
                       mol_type = protein
                       organism = synthetic construct
SEQUENCE: 40
AAAIEVMYPP PYLDNEKSNG TIIHVKGKHL CPSPLFPGPS KP          42

SEQ ID NO: 41          moltype = AA   length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 41
ESKYGPPCPS CP                                                     12

SEQ ID NO: 42          moltype = AA   length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 42
ESKYGPPAPS AP                                                     12

SEQ ID NO: 43          moltype = AA   length = 12
FEATURE                Location/Qualifiers
REGION                 1..12
                       note = Description of Artificial Sequence: Synthetic peptide
source                 1..12
                       mol_type = protein
                       organism = synthetic construct
```

```
SEQUENCE: 43
ESKYGPPCPP CP                                                                    12

SEQ ID NO: 44           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 44
EPKSCDKTHT CP                                                                    12

SEQ ID NO: 45           moltype = AA  length = 86
FEATURE                 Location/Qualifiers
REGION                  1..86
                        note = Description of Artificial Sequence: Synthetic
                         polypeptide
source                  1..86
                        mol_type = protein
                        organism = synthetic construct
SEQUENCE: 45
AAAFVPVFLP AKPTTTPAPR PPTPAPTIAS QPLSLRPEAC RPAAGGAVHT RGLDFACDIY  60
IWAPLAGTCG VLLLSLVITL YCNHRN                                        86

SEQ ID NO: 46           moltype = AA  length = 132
FEATURE                 Location/Qualifiers
REGION                  1..132
                        note = Description of Artificial Sequence: Synthetic
                         polypeptide
source                  1..132
                        mol_type = protein
                        organism = synthetic construct
SEQUENCE: 46
ACPTGLYTHS GECCKACNLG EGVAQPCGAN QTVCEPCLDS VTFSDVVSAT EPCKPCTECV  60
GLQSMSAPCV EADDAVCRCA YGYYQDETTG RCEACRVCEA GSGLVFSCQD KQNTVCEECP 120
DGTYSDEADA EC                                                     132

SEQ ID NO: 47           moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 47
ACPTGLYTHS GECCKACNLG EGVAQPCGAN QTVC                               34

SEQ ID NO: 48           moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 48
AVGQDTQEVI VVPHSLPFKV                                               20

SEQ ID NO: 49           moltype = DNA  length = 126
FEATURE                 Location/Qualifiers
misc_feature            1..126
                        note = Description of Artificial Sequence: Synthetic
                         polynucleotide
source                  1..126
                        mol_type = other DNA
                        organism = synthetic construct
SEQUENCE: 49
gcagcagcta tcgaggtgat gtatcctccg ccctacctgg ataatgaaaa gagtaatggg  60
actatcattc atgtaaaagg gaagcatctt tgtccttctc ccctttttccc cggtccgtct 120
aaacct                                                            126

SEQ ID NO: 50           moltype = DNA  length = 36
FEATURE                 Location/Qualifiers
misc_feature            1..36
                        note = Description of Artificial Sequence: Synthetic
                         oligonucleotide
source                  1..36
                        mol_type = other DNA
```

-continued

```
                        organism = synthetic construct
SEQUENCE: 50
gaaagcaagt acggtccacc ttgccctagc tgtccg                                        36

SEQ ID NO: 51           moltype = DNA  length = 36
FEATURE                 Location/Qualifiers
misc_feature            1..36
                        note = Description of Artificial Sequence: Synthetic
                         oligonucleotide
source                  1..36
                        mol_type = other DNA
                        organism = synthetic construct
SEQUENCE: 51
gaatccaagt acggcccccc agcgcctagt gcccca                                        36

SEQ ID NO: 52           moltype = DNA  length = 36
FEATURE                 Location/Qualifiers
misc_feature            1..36
                        note = Description of Artificial Sequence: Synthetic
                         oligonucleotide
source                  1..36
                        mol_type = other DNA
                        organism = synthetic construct
SEQUENCE: 52
gaatctaaat atggcccgcc atgcccgcct tgccca                                        36

SEQ ID NO: 53           moltype = DNA  length = 36
FEATURE                 Location/Qualifiers
misc_feature            1..36
                        note = Description of Artificial Sequence: Synthetic
                         oligonucleotide
source                  1..36
                        mol_type = other DNA
                        organism = synthetic construct
SEQUENCE: 53
gaaccgaagt cttgtgataa aactcatacg tgcccg                                        36

SEQ ID NO: 54           moltype = DNA  length = 258
FEATURE                 Location/Qualifiers
misc_feature            1..258
                        note = Description of Artificial Sequence: Synthetic
                         polynucleotide
source                  1..258
                        mol_type = other DNA
                        organism = synthetic construct
SEQUENCE: 54
gctgctgctt tcgtacccgt gttcctccct gctaagccta cgactacccc cgcaccgaga   60
ccacccacgc cagcacccac gattgctagc cagcccctta gtttgcgacc agaagcttgt  120
cggcctgctg ctggtggcgc ggtacatacc cgcggccttg attttgcttg cgatatatat  180
atctgggcgc ctctggccgg aacatgcggg gtcctcctcc tttctctggt tattactctc  240
tactgtaatc acaggaat                                                258

SEQ ID NO: 55           moltype = DNA  length = 396
FEATURE                 Location/Qualifiers
misc_feature            1..396
                        note = Description of Artificial Sequence: Synthetic
                         polynucleotide
source                  1..396
                        mol_type = other DNA
                        organism = synthetic construct
SEQUENCE: 55
gcctgcccga ccgggctcta cactcatagc ggggaatgtt gtaaggcatg taacttgggt   60
gagggcgtcg cacagccctg cggagctaac caaacagtgt gcgaaccctg cctcgatagt  120
gtgacgttct ctgatgttgt atcagctaca gagccttgca aaccatgtac tgagtgcgtt  180
ggacttcagt caatgagcgc tccatgtgtg gaggcagatg atgcggtctg tcgatgtgct  240
tacggatact accaagacga dacaacaggg cggtgcgagg cctgtagagt ttgtgaggcg  300
ggctccgggc tggtgttttc atgtcaagac aagcaaaata cggtctgtga agagtgccct  360
gatggcacct actcagacga agcagatgca gaatgc                            396

SEQ ID NO: 56           moltype = DNA  length = 102
FEATURE                 Location/Qualifiers
misc_feature            1..102
                        note = Description of Artificial Sequence: Synthetic
                         polynucleotide
source                  1..102
                        mol_type = other DNA
                        organism = synthetic construct
SEQUENCE: 56
gcctgccctade caggactcta cacgcatagc ggtgagtgtt gtaaagcatg caacctcggg   60
```

```
gaaggtgtag cccagccatg cggggctaac caaaccgttt gc                            102

SEQ ID NO: 57          moltype = DNA  length = 60
FEATURE                Location/Qualifiers
misc_feature           1..60
                       note = Description of Artificial Sequence: Synthetic
                       oligonucleotide
source                 1..60
                       mol_type = other DNA
                       organism = synthetic construct
SEQUENCE: 57
gctgtgggcc aggacacgca ggaggtcatc gtggtgccac actccttgcc ctttaaggtg   60

SEQ ID NO: 58          moltype = DNA  length = 723
FEATURE                Location/Qualifiers
misc_feature           1..723
                       note = Description of Artificial Sequence: Synthetic
                       polynucleotide
source                 1..723
                       mol_type = other DNA
                       organism = synthetic construct
SEQUENCE: 58
caggtgcagc tgaaagagtc tggacctgga ctggtgcagc ccagccaaac actgagcctg   60
acctgtaccg tgtccggctt cagcctgagc agatacgaca tgcactgggt ccgacagcct   120
ccaggacaag gcttggaatg gatgggcgtg atctgggcca cggcaacac acactatcac    180
agcgccctga gtcccggct gagcatcagc agagatacca gcaagagcca ggtgttcctg    240
aagatgaact ccctccagac cgaggacacc gccatctatt tctgcaccct gcggatcaag    300
gattggggcc ctggcacaat ggtcaccgtt tctagcggag gcggaggatc tggtggcgga    360
ggaagtggcg gaggcggttc tgatatcgtg atgacccaga cacctcctag cctgtctgtg    420
gctctgggcc agtctgtgtc catcagctgc aagagcagcc agtctctggt ggccagcgac    480
gagaacacct acctgaattg gctgctgcaa agcccccggc gaagccccaa gagactgatc    540
taccaggtgt ccaagctgga cagcggccgtg cccgatagat tttctggcag cggcagcgag   600
aaggacttca ccctgaagat ctccagagtg gaagccgagg acctgggcgt gtactactgt    660
ctgcaaggca tccatctgcc ttggaccttt ggaggcggca caaagctgga actgaaggcc    720
gct                                                                    723

SEQ ID NO: 59          moltype = DNA  length = 723
FEATURE                Location/Qualifiers
misc_feature           1..723
                       note = Description of Artificial Sequence: Synthetic
                       polynucleotide
source                 1..723
                       mol_type = other DNA
                       organism = synthetic construct
SEQUENCE: 59
gacatcgtga tgacccagac acctcctagc ctgtctgtgg ctctgggcca gtctgtgtcc   60
atcagctgca agagcagcca gtctctggtg gccagcgacg agaacaccta cctgaattgg    120
ctgctgcaaa gcccccggcag aagccccaag agactgatct accaggtgtc caagctggac    180
agcggcgtgc ccgatagatt ttctggcagc ggctccgaga aggacttcac cctgaagatc    240
agcagagtgg aagccgagga cctgggcgtg tactactgtc tgcaaggcat ccatctgcct    300
tggaccttg gcggaggcac aaagctggaa ctgaaaggcc gcggaggaag cggaggcgga    360
ggatctggtg gtggtggatc tcaggtgcag ctgaaagagt ctggccctgg actggtgcag    420
cctagccaaa cactgagcct gacctgtacc gtgtccggct tcagcctgag cagatacgac    480
atgcactggg tccgacagcc tccaggacaa ggcttggaat ggatgggcgt gatctggggc    540
aacggcaaca cacactatca cagcgccctg aagtcccggc tgagcatctc cagagatacc    600
agcaagagcc aggtgttcct gaagatgaac tccctccaga ccgaggacac cgccatctat    660
ttctgcaccc tgcggatcaa ggattggggc cctggcacaa tggtcaccgt gtctagcgcc    720
gct                                                                    723

SEQ ID NO: 60          moltype = DNA  length = 732
FEATURE                Location/Qualifiers
misc_feature           1..732
                       note = Description of Artificial Sequence: Synthetic
                       polynucleotide
source                 1..732
                       mol_type = other DNA
                       organism = synthetic construct
SEQUENCE: 60
caggtgcagc tgaaagagtc tggacctgga ctggtgcagc ccagccaaac actgagcctg   60
acctgtaccg tgtccggctt cagcctgagc agatacgaca tgcactgggt ccgacagcct   120
ccaggacaag gcttggaatg gatgggcgtg atctggggca cggcaacac acactatcac    180
agcgccctga gtcccggct gagcatcagc agagatacca gcaagagcca ggtgttcctg    240
aagatgaact ccctccagac cgaggacacc gccatctatt tctgcaccct gcggatcaag    300
gattggggcc ctggcacaat ggtcaccgtg tctagcggca gcaagcggg ctctggaaaa    360
cctggatctg gcgagggctc taccaagggc gacatcgtga tgacccagac acctccttct    420
ctgtctgtgg ccctgggcca gtctgtgtcc atcagctgta aaagcagcca gtctctggtg    480
gccagcgacg agaacaccta cctgaattgg ctgctgcaaa gccccggcag aagccccaag    540
agactgatct accaggtgtc caagctggac agcggcgtgc ccgatagatt ttctggcagc    600
ggcagcgaga aggacttcac cctgaagatc tccagagtgg aagccgagga cctgggcgtg    660
```

-continued

```
tactactgtc tgcaaggcat ccatctgcct tggacctttg gcggaggcac aaagctggaa   720
ctgaaggccg ct                                                       732

SEQ ID NO: 61          moltype = DNA  length = 732
FEATURE                Location/Qualifiers
misc_feature           1..732
                       note = Description of Artificial Sequence: Synthetic
                       polynucleotide
source                 1..732
                       mol_type = other DNA
                       organism = synthetic construct
SEQUENCE: 61
gacatcgtga tgacccagac acctcctagc ctgtctgtgg ctctgggcca gtctgtgtcc   60
atcagctgca agagcagcca gtctctggtg gccagcgacg agaacaccta cctgaattgg   120
ctgctgcaaa gccccggcag aagccccaag agactgatct accaggtgtc caagctggac   180
agcggcgtgc ccgatagatt ttctggcagc ggctccgaga aggacttcac cctgaagatc   240
agcagagtgg aagccgagga cctgggcgtg tactactgtc tgcaaggcat ccatctgcct   300
tggacctttg gcggaggcac aaagctggaa ctgaagggcg gcacaagcgg ctctggcaaa   360
cctggatctg gcgagggctc taccaaaggc caggtgcagc tgaaagagtc tggccctgga   420
ctggtgcagc ctagccaaac actgagcctg acctgtaccg tgtccggctt cagcctgagc   480
agatacgaca tgcactgggt ccgacagcct ccaggacaag gcttggaatg gatgggcgtg   540
atctggggca acggcaacac acactatcac agcgccctga gtcccggct gagcatctcc   600
agagatacca gcaagagcca ggtgttcctg aagatgaact ccctccagac cgaggacacc   660
gccatctatt tctgcaccct gcggatcaag gattggggcc ctggcacaat ggtcaccgtg   720
tctagcgccg ct                                                       732

SEQ ID NO: 62          moltype = DNA  length = 693
FEATURE                Location/Qualifiers
misc_feature           1..693
                       note = Description of Artificial Sequence: Synthetic
                       polynucleotide
source                 1..693
                       mol_type = other DNA
                       organism = synthetic construct
SEQUENCE: 62
caggtgcagc tgaaagagtc tggacctgga ctggtgcagc ccagccaaac actgagcctg   60
acctgtaccg tgtccggctt cagcctgagc agatacgaca tgcactgggt ccgacagcct   120
ccaggacaag gcttggaatg gatgggcgtg atctggggca acggcaacac acactatcac   180
agcgccctga gtcccggct gagcatcagc agagatacca gcaagagcca ggtgttcctg   240
aagatgaact ccctccagac cgaggacacc gccatctatt tctgcaccct gcggatcaag   300
gattggggcc ctggcacaat ggtcaccgtt tctagtggtg gcggaggcag cgacatcgtg   360
atgacacaga cacctccaag cctgtctgtg gccctgggac agtccgtgtc tatcagctgc   420
aagagcagcc agtctctggt ggccagcgac gagaacacct acctgaattg gctgctgcaa   480
agccccggca gaagccccaa gagactgatc taccaggtgt ccaagctgga cagcggcgtg   540
cccgatagat tttctggcag cggcagcgag aaggacttca ccctgaagat ctccagagtg   600
gaagccgagg acctgggcgt gtactactgt ctgcaaggca tccatctgcc ttggaccttt   660
ggaggcggca caaagctgga actgaaggcc gct                                693

SEQ ID NO: 63          moltype = DNA  length = 693
FEATURE                Location/Qualifiers
misc_feature           1..693
                       note = Description of Artificial Sequence: Synthetic
                       polynucleotide
source                 1..693
                       mol_type = other DNA
                       organism = synthetic construct
SEQUENCE: 63
gacatcgtga tgacccagac acctcctagc ctgtctgtgg ctctgggcca gtctgtgtcc   60
atcagctgca agagcagcca gtctctggtg gccagcgacg agaacaccta cctgaattgg   120
ctgctgcaaa gccccggcag aagccccaag agactgatct accaggtgtc caagctggac   180
agcggcgtgc ccgatagatt ttctggcagc ggctccgaga aggacttcac cctgaagatc   240
agcagagtgg aagccgagga cctgggcgtg tactactgtc tgcaaggcat ccatctgcct   300
tggacctttg gcggaggcac aaagctggaa ctgaaaggcg gcggaggatc caggtgcag   360
ctgaaagaat ctggccctgg actggtgcag cccagccaaa cactgagcct gacctgtacc   420
gtgtccggct tcagcctgag cagatacgac atgcactggg tccgacagcc tccaggacaa   480
ggcttggaat ggatgggcgt gatctggggc aacggcaaca cacactatca cagcgccctg   540
aagtcccggc tgagcatctc cagagatacc agcaagagcc aggtgttcct gaagatgaac   600
tccctccaga ccgaggacac cgccatctat ttctgcaccc tgcggatcaa ggattggggc   660
cctggcacaa tggtcaccgt gtctagcgcc gct                                693

SEQ ID NO: 64          moltype = DNA  length = 45
FEATURE                Location/Qualifiers
misc_feature           1..45
                       note = Description of Artificial Sequence: Synthetic
                       oligonucleotide
source                 1..45
                       mol_type = other DNA
                       organism = synthetic construct
SEQUENCE: 64
```

-continued

```
ggaggcggag gatctggtgg cggaggaagt ggcggaggcg gttct                     45

SEQ ID NO: 65                moltype = DNA   length = 75
FEATURE                      Location/Qualifiers
misc_feature                 1..75
                             note = Description of Artificial Sequence: Synthetic
                             oligonucleotide
source                       1..75
                             mol_type = other DNA
                             organism = synthetic construct
SEQUENCE: 65
ggtggtggtg gcagtggtgg cggtggctca ggtggcggcg gatcaggcgg tggtggttct     60
ggcggcggtg gatct                                                      75

SEQ ID NO: 66                moltype = AA   length = 730
FEATURE                      Location/Qualifiers
REGION                       1..730
                             note = Description of Artificial Sequence: Synthetic
                             polypeptide
source                       1..730
                             mol_type = protein
                             organism = synthetic construct
SEQUENCE: 66
MALPVTALLL PLALLLHAAR PEVQLVQSGA EVKKPGSSVK VSCKASGGTF SSYAISWVRQ     60
APGQGLEWMG GIIPIFGTAN YAQKFQGRVT ITADKSTSTA YMELSSLRSE DTAVYYCATF    120
ALFGFREQAF DIWGQGTTVT VSSGGGGSGG GGSGGGGSDI QMTQSPSSLS ASVGDRVTIT    180
CRASQSISSY LNWYQQKPGK APKLLIYAAS SLQSGVPSRF SGSGSGTDFT LTISSLQPED    240
LATYYCQQSY STPFTFGPGT KVDIKTTTPA PRPPTPAPTI ALQPLSLRPE ACRPAAGGAV    300
HTRGLDFACD IYIWAPLAGT CGVLLLSLVI TKRGRKKLLY IFKQPFMRPV QTTQEEDGCS    360
CRFPEEEEGG CELRVKFSRS ADAPAYKQGQ NQLYNELNLG RREEYDVLDK RRGRDPEMGG    420
KPRRKNPQEG LYNELQKDKM AEAYSEIGMK GERRRGKGHD GLYQGLSTAT KDTYDALHMQ    480
ALPPRGSSGT GMVSKGEELF TGVVPILVEL DGDVNGHKFS VSGEGEGDAT YGKLTLKLIC    540
TTGKLPVPWP TLVTTLGYGL QCFARYPDHM KQHDFFKSAM PEGYVQERTI FFKDDGNYKT    600
RAEVKFEGDT LVNRIELKGI DFKEDGNILG HKLEYNYNSH NVYITADKQK NGIKANFKIR    660
HNIEDGGVQL ADHYQQNTPI GDGPVLLPDN HYLSYQSALS KDPNEKRDHM VLLEFVTAAG    720
ITLGMDELYK                                                           730

SEQ ID NO: 67                moltype = AA   length = 501
FEATURE                      Location/Qualifiers
REGION                       1..501
                             note = Description of Artificial Sequence: Synthetic
                             polypeptide
source                       1..501
                             mol_type = protein
                             organism = synthetic construct
SEQUENCE: 67
METDTLLLWV LLLWVPGSTG AGGSDYKDDD DKGGSQVQLV QSGAEVKKPG SSVKVSCKAS     60
GYTFTDYNMH WVRQAPGQGL EWIGYIYPYN GGTGYNQKFK SKATITADES TNTAYMELSS    120
LRSEDTAVYY CARGRPAMDY WGQGTLVTVS SGGGGSGGGG SGGGGSDIQM TQSPSSLSAS    180
VGDRVTITCR ASESVDNYGI SFMNWFQQKP GKAPKLLIYA ASNQGSGVPS RFSGSGSGTD    240
FTLTISSLQP DDFATYYCQQ SKEVPWTFGQ GTKVEIKSGA AAIEVMYPPP YLDNEKSNGT    300
IIHVKGKHLC PSPLFPGPSK PFWVLVVVGG VLACYSLLVT VAFIIFWVRS KRSRLLHSDY    360
MNMTPRRPGP TRKHYQPYAP PRDFAAYRSR VKFSRSADAP AYKQGQNQLY NELNLGRREE    420
YDVLDKRRGR DPEMGGKPRR KNPQEGLYNE LQKDKMAEAY SEIGMKGERR RGKGHDGLYQ    480
GLSTATKDTY DALHMQALPP R                                              501

SEQ ID NO: 68                moltype = AA   length = 452
FEATURE                      Location/Qualifiers
REGION                       1..452
                             note = Description of Artificial Sequence: Synthetic
                             polypeptide
source                       1..452
                             mol_type = protein
                             organism = synthetic construct
SEQUENCE: 68
MALPVTALLL PLALLLHAAR PAGGSDYKDD DDKGGSQVQL KESGPGLVQP SQTLSLTCTV     60
SGFSLSRYDM HWVRQPPGQG LEWMGVIWGN GNTHYHSALK SRLSISRDTS KSQVFLKMNS    120
LQTEDTAIYF CTLRIKDWGP GTMVTVSSGG GGSGGGGSGG GGSDIVMTQT PPSLSVALGQ    180
SVSISCKSSQ SLVASDENTY LNWLLQSPGR SPKRLIYQVS KLDSGVPDRF SGSGSEKDFT    240
LKISRVEAED LGVYYCLQGI HLPWTFGGGT KLELKTTTPA PRPPTPAPTI ALQPLSLRPE    300
ACRPAAGGAV HTRGLDFACD LLPLGGLPLL ITTCFCLFCC LRRHQGKQNE LSDTAGREIN    360
LVDAHLKSEQ TEASTRQNSQ VLLSETGIYD NDPDLCFRMQ EGSEVYSNPC LEENKPGIVY    420
ASLNHSVIGN NSRLARNVKE APTEYASICV RS                                  452

SEQ ID NO: 69                moltype = AA   length = 673
FEATURE                      Location/Qualifiers
REGION                       1..673
                             note = Description of Artificial Sequence: Synthetic
                             polypeptide
```

```
source                     1..673
                           mol_type = protein
                           organism = synthetic construct
SEQUENCE: 69
MALPVTALLL PLALLLHAAR PAGGSDYKDD DDKGGSQVQL KESGPGLVQP SQTLSLTCTV    60
SGFSLSRYDM HWVRQPPGQG LEWMGVIWGN GNTHYHSALK SRLSISRDTS KSQVFLKMNS   120
LQTEDTAIYF CTLRIKDWGP GTMVTVSSGG GGSGGGGSGG GGSDIVMTQT PPSLSVALGQ   180
SVSISCKSSQ SLVASDENTY LNWLLQSPGR SPKRLIYQVS KLDSGVPDRF SGSGSEKDFT   240
LKISRVEAED LGVYYCLQGI HLPWTFGGGT KLELKTTTPA PRPPTPAPTI ALQPLSLRPE   300
ACRPAAGGAV HTRGLDFACD LLPLGGLPLL ITTCFCLFCC LRRHQGKQNE LSDTAGREIN   360
LVDAHLKSEQ TEASTRQNSQ VLLSETGIYD NDPDLCFRMQ EGSEVYSNPC LEENKPGIVY   420
ASLNHSVIGP NSRLARNVKE APTEYASICV RSGSGATNFS LLKQAGDVEE NPGPMTEYKP   480
TVRLATRDDV PRAVRTLAAA FADYPATRHT VDPDRHIERV TELQELFLTR VGLDIGKVWV   540
ADDGAAVAVW TTPESVEAGA VFAEIGPRMA ELSGSRLAAQ QQMEGLLAPH RPKEPAWFLA   600
TVGVSPDHQG KGLGSAVVLP GVEAAERAGV PAFLETSAPR NLPFYERLGF TVTADVEVPE   660
GPRTWCMTRK PGA                                                      673

SEQ ID NO: 70              moltype = AA   length = 509
FEATURE                    Location/Qualifiers
REGION                     1..509
                           note = Description of Artificial Sequence: Synthetic
                            polypeptide
source                     1..509
                           mol_type = protein
                           organism = synthetic construct
SEQUENCE: 70
MALPVTALLL PLALLLHAAR PAGGSDYKDD DDKGGSQVQL KESGPGLVQP SQTLSLTCTV    60
SGFSLSRYDM HWVRQPPGQG LEWMGVIWGN GNTHYHSALK SRLSISRDTS KSQVFLKMNS   120
LQTEDTAIYF CTLRIKDWGP GTMVTVSSGG GGSGGGGSGG GGSDIVMTQT PPSLSVALGQ   180
SVSISCKSSQ SLVASDENTY LNWLLQSPGR SPKRLIYQVS KLDSGVPDRF SGSGSEKDFT   240
LKISRVEAED LGVYYCLQGI HLPWTFGGGT KLELKTTTPA PRPPTPAPTI ALQPLSLRPE   300
ACRPAAGGAV HTRGLDFACD VIGILVAVIL LLLLLLLLFL ILRHRRQGKH WTSTQRKADF   360
QHPAGAVGPE PTDRGLQWRS SPAADAQEEN LYAAVKHTQP EDGVEMDTRS PHDEDPQAVT   420
YAEVKHSRPR REMASPPSPL SGEFLDTKDR QAEEDRQMDT EAAASEAPQD VTYAQLHSLT   480
LRREATEPPP SQEGPSPAVP SIYATLAIH                                     509

SEQ ID NO: 71              moltype = AA   length = 730
FEATURE                    Location/Qualifiers
REGION                     1..730
                           note = Description of Artificial Sequence: Synthetic
                            polypeptide
source                     1..730
                           mol_type = protein
                           organism = synthetic construct
SEQUENCE: 71
MALPVTALLL PLALLLHAAR PAGGSDYKDD DDKGGSQVQL KESGPGLVQP SQTLSLTCTV    60
SGFSLSRYDM HWVRQPPGQG LEWMGVIWGN GNTHYHSALK SRLSISRDTS KSQVFLKMNS   120
LQTEDTAIYF CTLRIKDWGP GTMVTVSSGG GGSGGGGSGG GGSDIVMTQT PPSLSVALGQ   180
SVSISCKSSQ SLVASDENTY LNWLLQSPGR SPKRLIYQVS KLDSGVPDRF SGSGSEKDFT   240
LKISRVEAED LGVYYCLQGI HLPWTFGGGT KLELKTTTPA PRPPTPAPTI ALQPLSLRPE   300
ACRPAAGGAV HTRGLDFACD VIGILVAVIL LLLLLLLLFL ILRHRRQGKH WTSTQRKADF   360
QHPAGAVGPE PTDRGLQWRS SPAADAQEEN LYAAVKHTQP EDGVEMDTRS PHDEDPQAVT   420
YAEVKHSRPR REMASPPSPL SGEFLDTKDR QAEEDRQMDT EAAASEAPQD VTYAQLHSLT   480
LRREATEPPP SQEGPSPAVP SIYATLAIHG SGATNFSLLK QAGDVEENPG PMTEYKPTVR   540
LATRDDVPRA VRTLAAAFAD YPATRHTVDP DRHIERVTEL QELFLTRVGL DIGKVWVADD   600
GAAVAVWTTP ESVEAGAVFA EIGPRMAELS GSRLAAQQQM EGLLAPHRPK EPAWFLATVG   660
VSPDHQGKGL GSAVVLPGVE AAERAGVPAF LETSAPRNLP FYERLGFTVT ADVEVPEGPR   720
TWCMTRKPGA                                                         730

SEQ ID NO: 72              moltype = AA   length = 452
FEATURE                    Location/Qualifiers
REGION                     1..452
                           note = Description of Artificial Sequence: Synthetic
                            polypeptide
source                     1..452
                           mol_type = protein
                           organism = synthetic construct
SEQUENCE: 72
MALPVTALLL PLALLLHAAR PAGGSDYKDD DDKGGSDIVM TQTPPSLSVA LGQSVSISCK    60
SSQSLVASDE NTYLNWLLQS PGRSPKRLIY QVSKLDSGVP DRFSGSGSEK DFTLKISRVE   120
AEDLGVYYCL QGIHLPWTFG GGTKLELKGG GGSGGGGSGG GGSQVQLKES GPGLVQPSQT   180
LSLTCTVSGF SLSRYDMHWV RQPPGQGLEW MGVIWGNGNT HYHSALKSRL SISRDTSKSQ   240
VFLKMNSLQT EDTAIYFCTL RIKDWGPGTM VTVSSTTTPA PRPPTPAPTI ALQPLSLRPE   300
ACRPAAGGAV HTRGLDFACD LLPLGGLPLL ITTCFCLFCC LRRHQGKQNE LSDTAGREIN   360
LVDAHLKSEQ TEASTRQNSQ VLLSETGIYD NDPDLCFRMQ EGSEVYSNPC LEENKPGIVY   420
ASLNHSVIGP NSRLARNVKE APTEYASICV RS                                 452

SEQ ID NO: 73              moltype = AA   length = 620
FEATURE                    Location/Qualifiers
```

-continued

```
REGION                      1..620
                            note = Description of Artificial Sequence: Synthetic
                             polypeptide
source                      1..620
                            mol_type = protein
                            organism = synthetic construct
SEQUENCE: 73
MALPVTALLL PLALLLHAAR PAGGSDYKDD DDKGGSQVQL KESGPGLVQP SQTLSLTCTV    60
SGFSLSRYDM HWVRQPPGQG LEWMGVIWGN GNTHYHSALK SRLSISRDTS KSQVFLKMNS   120
LQTEDTAIYF CTLRIKDWGP GTMVTVSSGG GGSGGGGSGG GGSDIVMTQT PPSLSVALGQ   180
SVSISCKSSQ SLVASDENTY LNWLLQSPGR SPKRLIYQVS KLDSGVPDRF SGSGSEKDFT   240
LKISRVEAED LGVYYCLQGI HLPWTFGGGT KLELKTTTPA PRPPTPAPTI ALQPLSLRPE   300
ACRPAAGGAV HTRGLDFACD LLPLGGLPLL ITTCFCLFCC LRRHQGKQNE LSDTAGREIN   360
LVDAHLKSEQ TEASTRQNSQ VLLSETGIYD NDPDLCFRMQ EGSEVYSNPC LEENKPGIVY   420
ASLNHSVIGP NSRLARNVKE APTEYASICV RSLRHRRQGK HWTSTQRKAD FQHPAGAVGP   480
EPTDRGLQWR SSPAADAQEE NLYAAVKHTQ PEDGVEMDTR SPHDEDPQAV TYAEVKHSRP   540
RREMASPPSP LSGEFLDTKD RQAEEDRQMD TEAAASEAPQ DVTYAQLHSL TLRREATEPP   600
PSQEGPSPAV PSIYATLAIH                                               620

SEQ ID NO: 74               moltype = AA   length = 509
FEATURE                     Location/Qualifiers
REGION                      1..509
                            note = Description of Artificial Sequence: Synthetic
                             polypeptide
source                      1..509
                            mol_type = protein
                            organism = synthetic construct
SEQUENCE: 74
MALPVTALLL PLALLLHAAR PAGGSDYKDD DDKGGSDIVM TQTPPSLSVA LGQSVSISCK    60
SSQSLVASDE NTYLNWLLQS PGRSPKRLIY QVSKLDSGVP DRFSGSGSEK DPTLKISRVE   120
AEDLGVYYCL QGIHLPWTFG GGTKLELKGG GGSGGGGSGG GGSQVQLKES GPGLVQPSQT   180
LSLTCTVSGF SLSRYDMHWV RQPPGQGLEW MGVIWGNGNT HYHSALKSRL SISRDTSKSQ   240
VFLKMNSLQT EDTAIYFCTL RIKDWGPGTM VTVSSTTTPA PRPPTPAPTI ALQPLSLRPE   300
ACRPAAGGAV HTRGLDFACD VIGILVAVIL LLLLLLLFL ILRHRRQGKH WTSTQRKADF   360
QHPAGAVGPE PTDRGLQWRS SPAADAQEEN LYAAVKHTQP EDGVEMDTRS PHDEDPQAVT   420
YAEVKHSRPR REMASPPSPL SGEFLDTKDR QAEEDRQMDT EAAASEAPQD VTYAQLHSLT   480
LRREATEPPP SQEGPSPAVP SIYATLAIH                                     509

SEQ ID NO: 75               moltype = AA   length = 620
FEATURE                     Location/Qualifiers
REGION                      1..620
                            note = Description of Artificial Sequence: Synthetic
                             polypeptide
source                      1..620
                            mol_type = protein
                            organism = synthetic construct
SEQUENCE: 75
MALPVTALLL PLALLLHAAR PAGGSDYKDD DDKGGSQVQL KESGPGLVQP SQTLSLTCTV    60
SGFSLSRYDM HWVRQPPGQG LEWMGVIWGN GNTHYHSALK SRLSISRDTS KSQVFLKMNS   120
LQTEDTAIYF CTLRIKDWGP GTMVTVSSGG GGSGGGGSGG GGSDIVMTQT PPSLSVALGQ   180
SVSISCKSSQ SLVASDENTY LNWLLQSPGR SPKRLIYQVS KLDSGVPDRF SGSGSEKDFT   240
LKISRVEAED LGVYYCLQGI HLPWTFGGGT KLELKTTTPA PRPPTPAPTI ALQPLSLRPE   300
ACRPAAGGAV HTRGLDFACD VIGILVAVIL LLLLLLLLFL ILRHRRQGKH WTSTQRKADF   360
QHPAGAVGPE PTDRGLQWRS SPAADAQEEN LYAAVKHTQP EDGVEMDTRS PHDEDPQAVT   420
YAEVKHSRPR REMASPPSPL SGEFLDTKDR QAEEDRQMDT EAAASEAPQD VTYAQLHSLT   480
LRREATEPPP SQEGPSPAVP SIYATLAIHR RHQGKQNELS DTAGREINLV DAHLKSEQTE   540
ASTRQNSQVL LSETGIYDND PDLCFRMQEG SEVYSNPCLE ENKPGIVYAS LNHSVIGPNS   600
RLARNVKEAP TEYASICVRS                                               620

SEQ ID NO: 76               moltype = AA   length = 442
FEATURE                     Location/Qualifiers
REGION                      1..442
                            note = Description of Artificial Sequence: Synthetic
                             polypeptide
source                      1..442
                            mol_type = protein
                            organism = synthetic construct
SEQUENCE: 76
MALPVTALLL PLALLLHAAR PAGGSDYKDD DDKGGSQVQL KESGPGLVQP SQTLSLTCTV    60
SGFSLSRYDM HWVRQPPGQG LEWMGVIWGN GNTHYHSALK SRLSISRDTS KSQVFLKMNS   120
LQTEDTAIYF CTLRIKDWGP GTMVTVSSGG GGSDIVMTQT PPSLSVALGQ SVSISCKSSQ   180
SLVASDENTY LNWLLQSPGR SPKRLIYQVS KLDSGVPDRF SGSGSEKDFT LKISRVEAED   240
LGVYYCLQGI HLPWTFGGGT KLELKTTTPA PRPPTPAPTI ALQPLSLRPE ACRPAAGGAV   300
HTRGLDFACD LLPLGGLPLL ITTCFCLFCC LRRHQGKQNE LSDTAGREIN LVDAHLKSEQ   360
TEASTRQNSQ VLLSETGIYD NDPDLCFRMQ EGSEVYSNPC LEENKPGIVY ASLNHSVIGP   420
NSRLARNVKE APTEYASICV RS                                            442

SEQ ID NO: 77               moltype = AA   length = 499
FEATURE                     Location/Qualifiers
```

```
REGION                   1..499
                         note = Description of Artificial Sequence: Synthetic
                          polypeptide
source                   1..499
                         mol_type = protein
                         organism = synthetic construct
SEQUENCE: 77
MALPVTALLL PLALLLHAAR PAGGSDYKDD DDKGGSQVQL KESGPGLVQP SQTLSLTCTV    60
SGFSLSRYDM HWVRQPPGQG LEWMGVIWGN GNTHYHSALK SRLSISRDTS KSQVFLKMNS   120
LQTEDTAIYF CTLRIKDWGP GTMVTVSSGG GGSDIVMTQT PPSLSVALGQ SVSISCKSSQ   180
SLVASDENTY LNWLLQSPGR SPKRLIYQVS KLDSGVPDRF SGSGSEKDFT LKISRVEAED   240
LGVYYCLQGI HLPWTFGGGT KLELKTTTPA PRPPTPAPTI ALQPLSLRPE ACRPAAGGAV   300
HTRGLDFACD VIGILVAVIL LLLLLLLLFL ILRHRRQGKH WTSTQRKADF QHPAGAVGPE   360
PTDRGLQWRS SPAADAQEEN LYAAVKHTQP EDGVEMDTRS PHDEDPQAVT YAEVKHSRPR   420
REMASPPSPL SGEFLDTKDR QAEEDRQMDT EAAASEAPQD VTYAQLHSLT LRREATEPPP   480
SQEGPSPAVP SIYATLAIH                                               499

SEQ ID NO: 78            moltype = AA  length = 610
FEATURE                  Location/Qualifiers
REGION                   1..610
                         note = Description of Artificial Sequence: Synthetic
                          polypeptide
source                   1..610
                         mol_type = protein
                         organism = synthetic construct
SEQUENCE: 78
MALPVTALLL PLALLLHAAR PAGGSDYKDD DDKGGSQVQL KESGPGLVQP SQTLSLTCTV    60
SGFSLSRYDM HWVRQPPGQG LEWMGVIWGN GNTHYHSALK SRLSISRDTS KSQVFLKMNS   120
LQTEDTAIYF CTLRIKDWGP GTMVTVSSGG GGSDIVMTQT PPSLSVALGQ SVSISCKSSQ   180
SLVASDENTY LNWLLQSPGR SPKRLIYQVS KLDSGVPDRF SGSGSEKDFT LKISRVEAED   240
LGVYYCLQGI HLPWTFGGGT KLELKTTTPA PRPPTPAPTI ALQPLSLRPE ACRPAAGGAV   300
HTRGLDFACD VIGILVAVIL LLLLLLLLFL ILRHRRQGKH WTSTQRKADF QHPAGAVGPE   360
PTDRGLQWRS SPAADAQEEN LYAAVKHTQP EDGVEMDTRS PHDEDPQAVT YAEVKHSRPR   420
REMASPPSPL SGEFLDTKDR QAEEDRQMDT EAAASEAPQD VTYAQLHSLT LRREATEPPP   480
SQEGPSPAVP SIYATLAIHR RHQGKQNELS DTAGREINLV DAHLKSEQTE ASTRQNSQVL   540
LSETGIYDND PDLCFRMQEG SEVYSNPCLE ENKPGIVYAS LNHSVIGPNS RLARNVKEAP   600
TEYASICVRS                                                         610

SEQ ID NO: 79            moltype = AA  length = 455
FEATURE                  Location/Qualifiers
REGION                   1..455
                         note = Description of Artificial Sequence: Synthetic
                          polypeptide
source                   1..455
                         mol_type = protein
                         organism = synthetic construct
SEQUENCE: 79
MALPVTALLL PLALLLHAAR PAGGSDYKDD DDKGGSQVQL KESGPGLVQP SQTLSLTCTV    60
SGFSLSRYDM HWVRQPPGQG LEWMGVIWGN GNTHYHSALK SRLSISRDTS KSQVFLKMNS   120
LQTEDTAIYF CTLRIKDWGP GTMVTVSSGS TSGSGKPGSG EGSTKGDIVM TQTPPSLSVA   180
LGQSVSISCK SSQSLVASDE NTYLNWLLQS PGRSPKRLIY QVSKLDSGVP DRFSGSGSEK   240
DFTLKISRVE AEDLGVYYCL QGIHLPWTFG GGTKLELKTT TPAPRPPTPA PTIALQPLSL   300
RPEACRPAAG GAVHTRGLDF ACDLLPLGGL PLLITTCFCL FCCLRRHQGK QNELSDTAGR   360
EINLVDAHLK SEQTEASTRQ NSQVLLSETG IYDNDPDLCF RMQEGSEVYS NPCLEENKPG   420
IVYASLNHSV IGPNSRLARN VKEAPTEYAS ICVRS                             455

SEQ ID NO: 80            moltype = AA  length = 512
FEATURE                  Location/Qualifiers
REGION                   1..512
                         note = Description of Artificial Sequence: Synthetic
                          polypeptide
source                   1..512
                         mol_type = protein
                         organism = synthetic construct
SEQUENCE: 80
MALPVTALLL PLALLLHAAR PAGGSDYKDD DDKGGSQVQL KESGPGLVQP SQTLSLTCTV    60
SGFSLSRYDM HWVRQPPGQG LEWMGVIWGN GNTHYHSALK SRLSISRDTS KSQVFLKMNS   120
LQTEDTAIYF CTLRIKDWGP GTMVTVSSGS TSGSGKPGSG EGSTKGDIVM TQTPPSLSVA   180
LGQSVSISCK SSQSLVASDE NTYLNWLLQS PGRSPKRLIY QVSKLDSGVP DRFSGSGSEK   240
DFTLKISRVE AEDLGVYYCL QGIHLPWTFG GGTKLELKTT TPAPRPPTPA PTIALQPLSL   300
RPEACRPAAG GAVHTRGLDF ACDVIGILVA VILLLLLLLL LFLILRHRRQ GKHWTSTQRK   360
ADFQHPAGAV GPEPTDRGLQ WRSSPAADAQ EENLYAAVKH TQPEDGVEMD TRSPHDEDPQ   420
AVTYAEVKHS RPRREMASPP SPLSGEFLDT KDRQAEEDRQ MDTEAAASEA PQDVTYAQLH   480
SLTLRREATE PPPSQEGPSP AVPSIYATLA IH                                512

SEQ ID NO: 81            moltype = AA  length = 623
FEATURE                  Location/Qualifiers
REGION                   1..623
                         note = Description of Artificial Sequence: Synthetic
```

-continued

```
                         polypeptide
source                   1..623
                         mol_type = protein
                         organism = synthetic construct
SEQUENCE: 81
MALPVTALLL PLALLLHAAR PAGGSDYKDD DDKGGSQVQL KESGPGLVQP SQTLSLTCTV   60
SGFSLSRYDM HWVRQPPGQG LEWMGVIWGN GNTHYHSALK SRLSISRDTS KSQVFLKMNS  120
LQTEDTAIYF CTLRIKDWGP GTMVTVSSGS TSGSGKPGSG EGSTKGDIVM TQTPPSLSVA  180
LGQSVSISCK SSQSLVASDE NTYLNWLLQS PGRSPKRLIY QVSKLDSGVP DRFSGSGSEK  240
DFTLKISRVE AEDLGVYYCL QGIHLPWTFG GGTKLELKTT TPAPRPPTPA PTIALQPLSL  300
RPEACRPAAG GAVHTRGLDF ACDVIGILVA VILLLLLLLL LFLILRHRRQ GKHWTSTQRK  360
ADFQHPAGAV GPEPTDRGLQ WRSSPAADAQ EENLYAAVKH TQPEDGVEMD TRSPHDEDPQ  420
AVTYAEVKHS RPRREMASPP SPLSGEFLDT KDRQAEEDRQ MDTEAAASEA PQDVTYAQLH  480
SLTLRREATE PPPSQEGPSP AVPSIYATLA IHRRHQGKQN ELSDTAGREI NLVDAHLKSE  540
QTEASTRQNS QVLLSETGIY DNDPDLCFRM QEGSEVYSNP CLEENKPGIV YASLNHSVIG  600
PNSRLARNVK EAPTEYASIC VRS                                          623

SEQ ID NO: 82            moltype = AA  length = 21
FEATURE                  Location/Qualifiers
REGION                   1..21
                         note = Description of Artificial Sequence: Synthetic peptide
source                   1..21
                         mol_type = protein
                         organism = synthetic construct
SEQUENCE: 82
IYIWAPLAGT CGVLLLSLVI T                                             21

SEQ ID NO: 83            moltype = AA  length = 27
FEATURE                  Location/Qualifiers
REGION                   1..27
                         note = Description of Artificial Sequence: Synthetic peptide
source                   1..27
                         mol_type = protein
                         organism = synthetic construct
SEQUENCE: 83
IYIWAPLAGT CGVLLLSLVI TLYCNHR                                       27

SEQ ID NO: 84            moltype = AA  length = 28
FEATURE                  Location/Qualifiers
REGION                   1..28
                         note = Description of Artificial Sequence: Synthetic peptide
source                   1..28
                         mol_type = protein
                         organism = synthetic construct
SEQUENCE: 84
IYIWAPLAGT CGVLLLSLVI TLYCNHRN                                      28

SEQ ID NO: 85            moltype = AA  length = 45
FEATURE                  Location/Qualifiers
REGION                   1..45
                         note = Description of Artificial Sequence: Synthetic
                          polypeptide
source                   1..45
                         mol_type = protein
                         organism = synthetic construct
SEQUENCE: 85
TTTPAPRPPT PAPTIALQPL SLRPEACRPA AGGAVHTRGL DFACD                   45

SEQ ID NO: 86            moltype = AA  length = 66
FEATURE                  Location/Qualifiers
REGION                   1..66
                         note = Description of Artificial Sequence: Synthetic
                          polypeptide
source                   1..66
                         mol_type = protein
                         organism = synthetic construct
SEQUENCE: 86
ALSNSIMYFS HFVPVFLPAK PTTTPAPRPP TPAPTIASQP LSLRPEACRP AAGGAVHTRG   60
LDFACD                                                             66

SEQ ID NO: 87            moltype = AA  length = 55
FEATURE                  Location/Qualifiers
REGION                   1..55
                         note = Description of Artificial Sequence: Synthetic
                          polypeptide
source                   1..55
                         mol_type = protein
                         organism = synthetic construct
SEQUENCE: 87
```

```
FVPVFLPAKP TTTPAPRPPT PAPTIALQPL SLRPEACRPA AGGAVHTRGL DFACD         55

SEQ ID NO: 88            moltype = AA   length = 12
FEATURE                  Location/Qualifiers
REGION                   1..12
                         note = Description of Artificial Sequence: Synthetic peptide
source                   1..12
                         mol_type = protein
                         organism = synthetic construct
SEQUENCE: 88
GGCKJSGGCK JS                                                       12

SEQ ID NO: 89            moltype = AA   length = 426
FEATURE                  Location/Qualifiers
REGION                   1..426
                         note = Description of Artificial Sequence: Synthetic
                          polypeptide
source                   1..426
                         mol_type = protein
                         organism = synthetic construct
SEQUENCE: 89
MALPVTALLL PLALLLHAAR PQVQLKESGP GLVQPSQTLS LTCTVSGFSL SRYDMHWVRQ    60
PPGQGLEWMG VIWGNGNTHY HSALKSRLSI SRDTSKSQVF LKMNSLQTED TAIYFCTLRI   120
KDWGPGTMVT VSSGGGGSGG GGSGGGGSDI VMTQTPPSLS VALGQSVSIS CKSSQSLVAS   180
DENTYLNWLL QSPGRSPKRL IYQVSKLDSG VPDRFSGSGS EKDFTLKISR VEAEDLGVYY   240
CLQGIHLPWT FGGGTKLELK GKPIPNPLLG LDSTNGAATT TPAPRPPTPA PTIALQPLSL   300
RPEACRPAAG GAVHTRGLDF ACDILIGTSV VIILFILLFF LLHRWCSNKK NAAVMDQESA   360
GNRTANSEDS DEQDPQEVTY TQLNHCVFTQ RKITRPSQRP KTPPTDIIVY TELPNAESRS   420
KVVSCP                                                             426

SEQ ID NO: 90            moltype = AA   length = 385
FEATURE                  Location/Qualifiers
REGION                   1..385
                         note = Description of Artificial Sequence: Synthetic
                          polypeptide
source                   1..385
                         mol_type = protein
                         organism = synthetic construct
SEQUENCE: 90
MALPVTALLL PLALLLHAAR PQVQLKESGP GLVQPSQTLS LTCTVSGFSL SRYDMHWVRQ    60
PPGQGLEWMG VIWGNGNTHY HSALKSRLSI SRDTSKSQVF LKMNSLQTED TAIYFCTLRI   120
KDWGPGTMVT VSSGGGGSGG GGSGGGGSDI VMTQTPPSLS VALGQSVSIS CKSSQSLVAS   180
DENTYLNWLL QSPGRSPKRL IYQVSKLDSG VPDRFSGSGS EKDFTLKISR VEAEDLGVYY   240
CLQGIHLPWT FGGGTKLELK GKPIPNPLLG LDSTNGAATT TPAPRPPTPA PTIALQPLSL   300
RPEACRPAAG GAVHTRGLDF ACDVIGILVA VILLLLLLLL LFLIMTDSVI YSMLELPTAT   360
QAQNDYGPQQ KSSSSRPSCS CLGSG                                        385

SEQ ID NO: 91            moltype = AA   length = 385
FEATURE                  Location/Qualifiers
REGION                   1..385
                         note = Description of Artificial Sequence: Synthetic
                          polypeptide
source                   1..385
                         mol_type = protein
                         organism = synthetic construct
SEQUENCE: 91
MALPVTALLL PLALLLHAAR PQVQLKESGP GLVQPSQTLS LTCTVSGFSL SRYDMHWVRQ    60
PPGQGLEWMG VIWGNGNTHY HSALKSRLSI SRDTSKSQVF LKMNSLQTED TAIYFCTLRI   120
KDWGPGTMVT VSSGGGGSGG GGSGGGGSDI VMTQTPPSLS VALGQSVSIS CKSSQSLVAS   180
DENTYLNWLL QSPGRSPKRL IYQVSKLDSG VPDRFSGSGS EKDFTLKISR VEAEDLGVYY   240
CLQGIHLPWT FGGGTKLELK GKPIPNPLLG LDSTNGAATT TPAPRPPTPA PTIALQPLSL   300
RPEACRPAAG GAVHTRGLDF ACDVAIALGL LTAVLLSVLL YQWIMTDSVI YSMLELPTAT   360
QAQNDYGPQQ KSSSSRPSCS CLGSG                                        385

SEQ ID NO: 92            moltype = AA   length = 445
FEATURE                  Location/Qualifiers
REGION                   1..445
                         note = Description of Artificial Sequence: Synthetic
                          polypeptide
source                   1..445
                         mol_type = protein
                         organism = synthetic construct
SEQUENCE: 92
MALPVTALLL PLALLLHAAR PQVQLKESGP GLVQPSQTLS LTCTVSGFSL SRYDMHWVRQ    60
PPGQGLEWMG VIWGNGNTHY HSALKSRLSI SRDTSKSQVF LKMNSLQTED TAIYFCTLRI   120
KDWGPGTMVT VSSGGGGSGG GGSGGGGSDI VMTQTPPSLS VALGQSVSIS CKSSQSLVAS   180
DENTYLNWLL QSPGRSPKRL IYQVSKLDSG VPDRFSGSGS EKDFTLKISR VEAEDLGVYY   240
CLQGIHLPWT FGGGTKLELK GKPIPNPLLG LDSTNGAATT TPAPRPPTPA PTIALQPLSL   300
RPEACRPAAG GAVHTRGLDF ACDILIGVSV VFLFCLLLLV LFCLHRQNQI KQGPPRSKDE   360
```

-continued

```
EQKPQQRPDL AVDVLERTAD KATVNGLPEK DRETDTSALA AGSSQEVTYA QLDHWALTQR  420
TARAVSPQST KPMAESITYA AVARH                                           445

SEQ ID NO: 93              moltype = AA  length = 460
FEATURE                    Location/Qualifiers
REGION                     1..460
                           note = Description of Artificial Sequence: Synthetic
                            polypeptide
source                     1..460
                           mol_type = protein
                           organism = synthetic construct
SEQUENCE: 93
MALPVTALLL PLALLLHAAR PQVQLKESGP GLVQPSQTLS LTCTVSGFSL SRYDMHWVRQ  60
PPGQGLEWMG VIWGNGNTHY HSALKSRLSI SRDTSKSQVF LKMNSLQTED TAIYFCTLRI  120
KDWGPGTMVT VSSGGGGSGG GGSGGGGSDI VMTQTPPSLS VALGQSVSIS CKSSQSLVAS  180
DENTYLNWLL QSPGRSPKRL IYQVSKLDSG VPDRFSGSGS EKDFTLKISR VEAEDLGVYY  240
CLQGIHLPWT FGGGTKLELK GKPIPNPLLG LDSTNGAATT TPAPRPPTPA PTIALQPLSL  300
RPEACRPAAG GAVHTRGLDF ACDVIGILVA VVLLLLLLLL LFLILRHRRQ GKHWTSTQRK  360
ADFQHPAGAV GPEPTDRGLQ WRSSPAADAQ EENLYAAVKD TQPEDGVEMD TRAAASEAPQ  420
DVTYAQLHSL TLRRKATEPP PSQEREPPAE PSIYATLAIH                          460

SEQ ID NO: 94              moltype = AA  length = 511
FEATURE                    Location/Qualifiers
REGION                     1..511
                           note = Description of Artificial Sequence: Synthetic
                            polypeptide
source                     1..511
                           mol_type = protein
                           organism = synthetic construct
SEQUENCE: 94
MALPVTALLL PLALLLHAAR PQVQLKESGP GLVQPSQTLS LTCTVSGFSL SRYDMHWVRQ  60
PPGQGLEWMG VIWGNGNTHY HSALKSRLSI SRDTSKSQVF LKMNSLQTED TAIYFCTLRI  120
KDWGPGTMVT VSSGGGGSGG GGSGGGGSDI VMTQTPPSLS VALGQSVSIS CKSSQSLVAS  180
DENTYLNWLL QSPGRSPKRL IYQVSKLDSG VPDRFSGSGS EKDFTLKISR VEAEDLGVYY  240
CLQGIHLPWT FGGGTKLELK GKPIPNPLLG LDSTNGAATT TPAPRPPTPA PTIALQPLSL  300
RPEACRPAAG GAVHTRGLDF ACDVLIGVSV AFVLLLFLLL FLLLRRQRHS KHRTSDQRKT  360
DFQRPAGAAE TEPKDRGLLR RSSPAADVQE ENLYAAVKDT QSEDRVELDS QSPHDEDPQA  420
VTYAPVKHSS PRREMASPPS SLSGEFLDTK DRQVEEDRQM DTEAAASEAS QDVTYAQLHS  480
LTLRRKATEP PPSQEGEPPA EPSIYATLAI H                                  511

SEQ ID NO: 95              moltype = AA  length = 512
FEATURE                    Location/Qualifiers
REGION                     1..512
                           note = Description of Artificial Sequence: Synthetic
                            polypeptide
source                     1..512
                           mol_type = protein
                           organism = synthetic construct
SEQUENCE: 95
MALPVTALLL PLALLLHAAR PQVQLKESGP GLVQPSQTLS LTCTVSGFSL SRYDMHWVRQ  60
PPGQGLEWMG VIWGNGNTHY HSALKSRLSI SRDTSKSQVF LKMNSLQTED TAIYFCTLRI  120
KDWGPGTMVT VSSGGGGSGG GGSGGGGSDI VMTQTPPSLS VALGQSVSIS CKSSQSLVAS  180
DENTYLNWLL QSPGRSPKRL IYQVSKLDSG VPDRFSGSGS EKDFTLKISR VEAEDLGVYY  240
CLQGIHLPWT FGGGTKLELK GKPIPNPLLG LDSTNGAATT TPAPRPPTPA PTIALQPLSL  300
RPEACRPAAG GAVHTRGLDF ACDVLIGVLV VSILLLSLLL FLLLQHWRQG KHRTLAQRQA  360
DFQRPPGAAE PEPKDGGLQR RSSPAADVQG ENFCAAVKNT QPEDGVEMDT RQSPHDEDPQ  420
AVTYAKVKHS RPRREMASPP SPLSGEFLDT KDRQAEEDRQ MDTEAAASEA PQDVTYAQLH  480
SFTLRQKATE PPPSQEGASP AEPSVYATLA IH                                 512

SEQ ID NO: 96              moltype = AA  length = 483
FEATURE                    Location/Qualifiers
REGION                     1..483
                           note = Description of Artificial Sequence: Synthetic
                            polypeptide
source                     1..483
                           mol_type = protein
                           organism = synthetic construct
SEQUENCE: 96
MALPVTALLL PLALLLHAAR PQVQLKESGP GLVQPSQTLS LTCTVSGFSL SRYDMHWVRQ  60
PPGQGLEWMG VIWGNGNTHY HSALKSRLSI SRDTSKSQVF LKMNSLQTED TAIYFCTLRI  120
KDWGPGTMVT VSSGGGGSGG GGSGGGGSDI VMTQTPPSLS VALGQSVSIS CKSSQSLVAS  180
DENTYLNWLL QSPGRSPKRL IYQVSKLDSG VPDRFSGSGS EKDFTLKISR VEAEDLGVYY  240
CLQGIHLPWT FGGGTKLELK GKPIPNPLLG LDSTNGAATT TPAPRPPTPA PTIALQPLSL  300
RPEACRPAAG GAVHTRGLDF ACDVAVGLGS CLAILILAIC GLKLQRRWKR TQSQQGLQEN  360
SSGQSFFVRN KKVRRAPLSE GPHSLGCYNP MMEDGISYTT LRFPEMNIPR TGDAESSEMQ  420
RPPPDCDDTV TYSALHKRQV GDYENVIPDF PEDEGIHYSE LIQFGVGERP QAQENVDYVI  480
LKH                                                                  483

SEQ ID NO: 97              moltype = AA  length = 470
```

-continued

```
FEATURE              Location/Qualifiers
REGION               1..470
                     note = Description of Artificial Sequence: Synthetic
                      polypeptide
source               1..470
                     mol_type = protein
                     organism = synthetic construct
SEQUENCE: 97
MALPVTALLL PLALLLHAAR PQVQLKESGP GLVQPSQTLS LTCTVSGFSL SRYDMHWVRQ   60
PPGQGLEWMG VIWGNGNTHY HSALKSRLSI SRDTSKSQVF LKMNSLQTED TAIYFCTLRI  120
KDWGPGTMVT VSSGGGGSGG GGSGGGGSDI VMTQTPPSLS VALGQSVSIS CKSSQSLVAS  180
DENTYLNWLL QSPGRSPKRL IYQVSKLDSG VPDRFSGSGS EKDFTLKISR VEAEDLGVYY  240
CLQGIHLPWT FGGGTKLELK GKPIPNPLLG LDSTNGAATT TPAPRPPTPA PTIALQPLSL  300
RPEACRPAAG GAVHTRGLDF ACDGAFLGIG ITALLFLCLA LIIMKILPKR RTQTETPRPR  360
FSRHSTILDY INVVPTAGPL AQKRNQKATP NSPRTPLPPG APSPESKKNQ KKQYQLPSFP  420
EPKSSTQAPE SQESQEELHY ATLNFPGVRP RPEARMPKGT QADYAEVKFQ             470

SEQ ID NO: 98       moltype = DNA   length = 717
FEATURE              Location/Qualifiers
misc_feature         1..717
                     note = Description of Artificial Sequence: Synthetic
                      polynucleotide
source               1..717
                     mol_type = other DNA
                     organism = synthetic construct
SEQUENCE: 98
caggtgcagc tgaaagagtc tggacctgga ctggtgcagc ccagccaaac actgagcctg   60
acctgtaccg tgtccggctt cagcctgagc agatacgaca tgcactgggt ccgacagcct  120
ccaggacaag gcttggaatg gatgggcgtg atctggggca acggcaacac acactatcac  180
agcgccctga gtcccggct gagcatcagc agagatacca gcaagagcca ggtgttcctg   240
aagatgaaca gcctgcagac cgaggacacc gccatctatt tctgcaccct gcggatcaag  300
gattggggcc ctggcacaat ggtcaccgtt tctagcggag gcggaggatc tggtggcgga  360
ggaagtggcg gaggcggttc tgatatcgtg atgacccaga cacctcctag cctgtctgtg  420
gctctgggcc agtctgtgtc catcagctgc aagagcagcc agagcctggt ggcctccgac  480
gagaacaacct acctgaattg gctgctgcag agccccggca agagccccaa ggagactgatc  540
taccaggtgt ccaagctgga cagcggcgtg cccgatagat tttctggcag cggcagcgag  600
aaggacttca ccctgaagat ctccagagtg gaagccgagg acctgggcgt gtactactgt  660
ctgcaaggca tccatctgcc ttggaccttt ggaggcggca caaagctgga actgaaa     717

SEQ ID NO: 99       moltype = AA   length = 244
FEATURE              Location/Qualifiers
REGION               1..244
                     note = Description of Artificial Sequence: Synthetic
                      polypeptide
source               1..244
                     mol_type = protein
                     organism = synthetic construct
SEQUENCE: 99
EVQLVQSGAE VKKPGSSVKV SCKASGGTFS SYAISWVRQA PGQGLEWMGG IIPIFGTANY   60
AQKFQGRVTI TADKSTSTAY MELSSLRSED TAVYYCATFA LFGFREQAFD IWGQGTTVTV  120
SSGGGGSGGG GSGGGGSDIQ MTQSPSSLSA SVGDRVTITC RASQSISSYL NWYQQKPGKA  180
PKLLIYAASS LQSGVPSRFS GSGSGTDFTL TISSLQPEDL ATYYCQQSYS TPFTFGPGTK  240
VDIK                                                               244

SEQ ID NO: 100      moltype = AA   length = 504
FEATURE              Location/Qualifiers
REGION               1..504
                     note = Description of Artificial Sequence: Synthetic
                      polypeptide
source               1..504
                     mol_type = protein
                     organism = synthetic construct
SEQUENCE: 100
METDTLLLWV LLLWVPGSTG AGGSDYKDDD DKGGSEVQLV QSGAEVKKPG SSVKVSCKAS   60
GGTFSSYAIS WVRQAPGQGL EWMGGIIPIF GTANYAQKFQ GRVTITADKS TSTAYMELSS  120
LRSEDTAVYY CATFALFGFR EQAFDIWGQG TTVTVSSGGG GSGGGGSGGG GSDIQMTQSP  180
SSLSASVGDR VTITCRASQS ISSYLNWYQQ KPGKAPKLLI YAASSLQSGV PSRFSGSGSG  240
TDFTLTISSL QPEDLATYYC QQSYSTPFTF GPGTKVDIKT TTPAPRPPTP APTIALQPLS  300
LRPEACRPAA GGAVHTRGLD FACDFWVLVV VGGVLACYSL LVTVAFIIFW VRSKRSLLLH  360
SDYMNMTPRR PGPTRKHYQP YAPPRDFAAY RSRVKFSRSA DAPAYKQGQN QLYNELNLGR  420
REEYDVLDKR RGRDPEMGGK PRRKNPQEGL YNELQKDKMA EAYSEIGMKG ERRRGKGHDG  480
LYQGLSTATK DTYDALHMQA LPPR                                         504

SEQ ID NO: 101      moltype = DNA   length = 1524
FEATURE              Location/Qualifiers
misc_feature         1..1524
                     note = Description of Artificial Sequence: Synthetic
                      polynucleotide
source               1..1524
```

-continued

```
                          mol_type = other DNA
                          organism = synthetic construct
SEQUENCE: 101
gccgccacca tggaaaccga cacactgctg ctgtgggtgc tgcttctttg ggtgcccgga   60
tctacaggtg ccggcggaag cgactacaag gacgacgatg acaaaggcgg cagcgaggtt  120
caactggtac aaagcggagc cgaggtaaag aaaccaggga gtagcgtcaa agtgtcctgc  180
aaagcctcag gcggcacatt cagtagctat gctatttcat gggtacgcca agcaccagga  240
cagggggctgg agtggatggg cgggattatc cccatcttcg gtacggcaaa ctatgcacaa  300
aagttccagg gacgagtcac catcacggct gataagtcca cctccaccgc ctatatggag  360
ctgagttccc ttcggagcga ggatactgct gtgtattatt gtgccacgtt cgcactgttc  420
ggttttcggg agcaggcgtt tgatatttgg ggacaaggca caacggtcac ggtcagttca  480
ggcggagggg gatcaggggg tggggggtca ggtggcggtg gaagtgacat tcagatgacc  540
cagagtccct cttcattgag tgcgagcgtc ggtgatcggg ttacgataac ctgtagggcc  600
tcccaaagta tatcatcata tttgaactgg taccaacaga aactgggaaa agcgccgaag  660
ctccttatct atgctgccag ctctttgcaa agcggtgtgc cctcacggtt ctccggtagt  720
gggtccggga ccgacttcac tttgaccatc agcagccttc agccagagga tcttgccact  780
tattactgcc agcaatctta tagcacaccg tttacattcg gtccaggcac aaaggtagac  840
attaagacca ccacaccagc tcctacacct ccaactcctg ctcctacaat cgccctgcag  900
ccactgagtc tgaggccaga ggcttgtaga cctgctgcag gcggagccgt gcatacaaga  960
ggactggatt tcgcctgcga cttctgggtg ctcgtggttg ttggcggagt gctggcctgt 1020
tacagcctgc tggttaccgt ggccttcatc atcttttggg tccgaagcaa gcggagccgg 1080
ctgctgcaca gcgattacat gaacatgacc cctcggaggc ccggacctac cagaaagcac 1140
taccagcctt acgctcctcc tagagatttc gccgcctacc ggtccagagt gaagttcagc 1200
agatccgccg atgctcccgc ctataagcag ggccagaacc agctgtacaa cgagctgaac 1260
ctggggagaa gagaagagta cgacgtgctg gacaagcgga gaggcagaga tcctgaaatg 1320
ggcggcaagc ccagacggaa gaatcctcaa gagggcctgt ataatgagct gcagaaagac 1380
aagatggccg aggcctacag cgagatcgga atgaaggcg agcgcagaag aggcaaggga 1440
cacgatggac tgtaccaggg actgagcacc gccaccaagg ataccatga cgccctgcac 1500
atgcaggccc tgcctccaag ataa                                         1524

SEQ ID NO: 102          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 102
RYDMH                                                               5

SEQ ID NO: 103          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 103
VIWGNGNTHY HSALKS                                                   16

SEQ ID NO: 104          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 104
QVQLKESGPG LVQPSQTLSL TCTVSGFSLS                                    30

SEQ ID NO: 105          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 105
WVRQPPGQGL EWMG                                                     14

SEQ ID NO: 106          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
```

-continued

```
SEQUENCE: 106
RLSISRDTSK SQVFLKMNSL QTEDTAIYFC TL                               32

SEQ ID NO: 107          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 107
GGGGS                                                            5

SEQ ID NO: 108          moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 108
GGGS                                                             4

SEQ ID NO: 109          moltype = AA  length = 5
FEATURE                 Location/Qualifiers
REGION                  1..5
                        note = Description of Artificial Sequence: Synthetic
                         polypeptide
source                  1..5
                        mol_type = protein
                        organism = synthetic construct
REGION                  5
                        note = The entire sequence of amino acids 1-5 can be
                         repeated one to six times.
SEQUENCE: 109
GGGGS                                                            5

SEQ ID NO: 110          moltype = AA  length = 5
FEATURE                 Location/Qualifiers
source                  1..5
                        mol_type = protein
                        organism = synthetic construct
REGION                  5
                        note = The entire sequence of amino acids 1-5 can be
                         repeated one to ten times
SEQUENCE: 110
GGGGS                                                            5

SEQ ID NO: 111          moltype = AA  length = 4
FEATURE                 Location/Qualifiers
source                  1..4
                        mol_type = protein
                        organism = synthetic construct
REGION                  4
                        note = The entire sequence of amino acids 1-5 can be
                         repeated one to ten times
SEQUENCE: 111
GGGS                                                             4
```

What is claimed is:

1. A chimeric protein comprising an antigen-binding domain specific for endomucin (EMCN) and a heterologous molecule or moiety, wherein the antigen-binding domain comprises a heavy chain variable (VH) region and a light chain variable (VL) region, wherein (a) the VH comprises:

a heavy chain complementarity determining region 1 (CDR-H1) having the amino acid sequence of RYDMH (SEQ ID NO: 102), a heavy chain complementarity determining region 2 (CDR-H2) having the amino acid sequence of VIWGNGNTHYHSALKS (SEQ ID NO: 103), and a heavy chain complementarity determining region 3 (CDR-H3) having the amino acid sequence of RIKD (SEQ ID NO: 4), and the VL comprises:

a light chain complementarity determining region 1 (CDR-L1) having the amino acid sequence of KSSQSLVASDENTYLN (SEQ ID NO: 10), a light chain complementarity determining region 2 (CDR-L2) having the amino acid sequence of QVSKLDS (SEQ ID NO: 11), and a light chain complementarity determining region 3 (CDR-L3) having the amino acid sequence of LQGIHLPWT (SEQ ID NO: 12), and wherein the amino acid sequences of the CDR-H1, the CDR-H2, the CDR-H3, the CDR-L1, the CDR-L2, and the CDR-L3 of the reference antibody are defined based on the Kabat numbering scheme; or (b) the VH comprises:

a heavy chain complementarity determining region 1 (CDR-H1) having the amino acid sequence of GFSLSRY (SEQ ID NO: 2), a heavy chain complementarity determining region 2 (CDR-H2) having the amino acid sequence of WGNGN (SEQ ID NO: 3), and a heavy chain complementarity determining region 3 (CDR-H3) having the amino acid sequence of RIKD (SEQ ID NO: 4), and the VL comprises:

a light chain complementarity determining region 1 (CDR-L1) having the amino acid sequence of KSSQSLVASDENTYLN (SEQ ID NO: 10), a light chain complementarity determining region 2 (CDR-L2) having the amino acid sequence of QVSKLDS (SEQ ID NO: 11), and a light chain complementarity determining region 3 (CDR-L3) having the amino acid sequence of LQGIHLPWT (SEQ ID NO: 12), and wherein the amino acid sequences of the CDR-H1, the CDR-H2, the CDR-H3, the CDR-L1, the CDR-L2, and the CDR-L3 of the reference antibody are defined based on the Chothia numbering scheme; or (c) the VH comprises:

a heavy chain complementarity determining region 1 (CDR-H1) contained within the VH region amino acid sequence of SEQ ID NO: 1, a heavy chain complementarity determining region 2 (CDR-H2) contained within the VH region amino acid sequence of SEQ ID NO: 1, and a heavy chain complementarity determining region 3 (CDR-H3) contained within the VH region amino acid sequence of SEQ ID NO: 1, and the VL comprises:

a light chain complementarity determining region 1 (CDR-L1) are contained within the VL region amino acid sequence of SEQ ID NO: 9, a light chain complementarity determining region 2 (CDR-L2) are contained within the VL region amino acid sequence of SEQ ID NO: 9, and a light chain complementarity determining region 3 (CDR-L3) are contained within the VL region amino acid sequence of SEQ ID NO: 9, and optionally wherein the amino acid sequences of the CDR-H1, the CDR-H2, the CDR-H3, the CDR-L1, the CDR-L2, and the CDR-L3 of the reference antibody are defined based on the Kabat or Chothia numbering scheme.

2. The chimeric protein of claim 1, wherein the VH region comprises the amino acid sequence of SEQ ID NO: 1.

3. The chimeric protein of claim 1, wherein the VL region comprises the amino acid sequence of SEQ ID NO: 9.

4. The chimeric protein of claim 1, wherein the antigen-binding domain comprises a single chain variable fragment (scFv).

5. The chimeric protein of claim 4, wherein the VH and VL of the scFv are separated by a peptide linker.

6. The chimeric protein of claim 5, wherein the antigen-binding domain comprises the structure VH-L-VL or VL-L-VH, wherein VH is the heavy chain variable domain, L is the peptide linker, and VL is the light chain variable domain.

7. The chimeric protein of claim 4, wherein the scFv comprises an amino acid sequence selected from the group consisting of: SEQ ID Nos: 17-22.

8. The chimeric protein of claim 1, wherein the chimeric protein is a chimeric antigen receptor (CAR), and wherein the heterologous molecule or moiety comprises a polypeptide selected from the group consisting of: a transmembrane domain, one or more intracellular signaling domains, a hinge domain, a spacer region, one or more peptide linkers, and combinations thereof.

9. The chimeric protein of claim 8, wherein the CAR is an inhibitory CAR comprising one or more intracellular inhibitory domains that inhibit an immune response.

10. The chimeric protein of claim 9, wherein the intracellular inhibitory domain comprises an enzymatic inhibitory domain or an intracellular inhibitory co-signaling domain.

11. An engineered nucleic acid encoding the chimeric protein of claim 1.

12. An expression vector comprising the engineered nucleic acid of claim 11.

13. An isolated cell or a population of engineered cells comprising the engineered nucleic acid of claim 11.

14. The cell or population of cells of claim 13, wherein the cell or population of cells further comprises one or more tumor-targeting chimeric receptors expressed on the cell surface.

15. The cell or population of cells of claim 14, wherein each of the one or more tumor-targeting chimeric receptors is a chimeric antigen receptor (CAR) or an engineered T cell receptor.

16. The cell or population of cells of claim 13, wherein the cell or population of cells is selected from the group consisting of: a T cell, a CD8+ T cell, a CD4+ T cell, a gamma-delta T cell, a cytotoxic T lymphocyte (CTL), a regulatory T cell, a viral-specific T cell, a Natural Killer T (NKT) cell, a Natural Killer (NK) cell, a B cell, a tumor-infiltrating lymphocyte (TIL), an innate lymphoid cell, a mast cell, an eosinophil, a basophil, a neutrophil, a myeloid cell, a macrophage, a monocyte, a dendritic cell, an erythrocyte, a platelet cell, a human embryonic stem cell (ESC), an ESC-derived cell, a pluripotent stem cell, a mesenchymal stromal cell (MSC), an induced pluripotent stem cell (iPSC), and an iPSC-derived cell.

17. A pharmaceutical composition comprising an effective amount of the cell or population of engineered cells of claim 13 and a pharmaceutically acceptable carrier, pharmaceutically acceptable excipient, or a combination thereof.

18. A method of stimulating a cell-mediated immune response to a tumor cell in a subject, the method comprising administering to a subject having a tumor a therapeutically effective dose of the cell or population of cells of claim 13.

19. A method of treating a subject having a tumor, the method comprising administering a therapeutically effective dose of the cell or population of cells of claim 13.

* * * * *